US010238378B2

(12) United States Patent
Bonutti et al.

(10) Patent No.: US 10,238,378 B2
(45) Date of Patent: Mar. 26, 2019

(54) TISSUE FIXATION SYSTEM AND METHOD

(71) Applicant: P Tech, LLC, Effingham, IL (US)

(72) Inventors: Peter M. Bonutti, Manalapan, FL (US); Glen A. Phillips, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 71 days.

(21) Appl. No.: 15/163,425

(22) Filed: May 24, 2016

(65) Prior Publication Data

US 2017/0049487 A1    Feb. 23, 2017

Related U.S. Application Data

(63) Continuation of application No. 12/576,992, filed on Oct. 9, 2009, which is a continuation-in-part of
(Continued)

(51) Int. Cl.
A61B 17/04    (2006.01)
A61F 2/44    (2006.01)
(Continued)

(52) U.S. Cl.
CPC ...... *A61B 17/0401* (2013.01); *A61B 17/0218* (2013.01); *A61B 17/0469* (2013.01); *A61B 17/0482* (2013.01); *A61B 17/0483* (2013.01); *A61B 17/0487* (2013.01); *A61B 17/1637* (2013.01); *A61B 17/1671* (2013.01); *A61B 17/1675* (2013.01); *A61B 17/17* (2013.01); *A61B 17/683* (2013.01); *A61B 17/7053* (2013.01); *A61B 17/842* (2013.01); *A61B 17/8869* (2013.01); *A61B 17/00491* (2013.01); *A61B 17/0467* (2013.01);
(Continued)

(58) Field of Classification Search
CPC ............ A61B 17/1757; A61B 17/1789; A61B 17/1792
USPC .... 606/79–90, 139–150, 157, 228–233, 247, 606/248, 279; 623/13.11–13.17
See application file for complete search history.

(56) References Cited

U.S. PATENT DOCUMENTS 319,296 A    6/1885    Molesworth
668,878 A    2/1901    Jensen
(Continued)

FOREIGN PATENT DOCUMENTS

CA    2641580    8/2007
CA    2680827    9/2008
(Continued)

OTHER PUBLICATIONS

ISR—International Search Report for WO/2008/116203, published Dec. 24, 2008 for PCT/US08/57948.
(Continued)

Primary Examiner — Matthew Lawson
(74) Attorney, Agent, or Firm — Stinson Leonard Street LLP

(57) ABSTRACT

Methods and devices for stabilizing spinal anatomical structures. Some example methods may include introducing a curved segment of an elongate fastener placement rod adjacent to a bone, providing a fastener at the leading end of the curved segment, and/or securing the fastener in place with respect to the bone.

18 Claims, 63 Drawing Sheets

Related U.S. Application Data application No. 11/358,311, filed on Feb. 21, 2006, now Pat. No. 9,173,647, and a continuation-in-part of application No. 11/258,795, filed on Oct. 26, 2005, and a continuation of application No. 11/202,294, filed on Oct. 5, 2005, now Pat. No. 9,463,012.

(60) Provisional application No. 60/655,140, filed on Feb. 22, 2005, provisional application No. 60/622,095, filed on Oct. 26, 2004.

(51) Int. Cl.
| | | |
|---|---|---|
| A61B 17/02 | (2006.01) | |
| A61B 17/68 | (2006.01) | |
| A61B 17/70 | (2006.01) | |
| A61B 17/84 | (2006.01) | |
| A61B 17/88 | (2006.01) | |
| A61B 17/17 | (2006.01) | |
| A61B 17/16 | (2006.01) | |
| A61B 17/29 | (2006.01) | |
| A61F 2/08 | (2006.01) | |
| A61F 2/28 | (2006.01) | |
| A61F 2/30 | (2006.01) | |
| A61B 17/00 | (2006.01) | |
| A61B 17/06 | (2006.01) | |
| A61B 90/00 | (2016.01) | |

(52) U.S. Cl.
CPC ....... A61B 17/0485 (2013.01); A61B 17/1615 (2013.01); A61B 17/1757 (2013.01); A61B 2017/00004 (2013.01); A61B 2017/00477 (2013.01); A61B 2017/00818 (2013.01); A61B 2017/00876 (2013.01); A61B 2017/00893 (2013.01); A61B 2017/00898 (2013.01); A61B 2017/0404 (2013.01); A61B 2017/0409 (2013.01); A61B 2017/0417 (2013.01); A61B 2017/0464 (2013.01); A61B 2017/0488 (2013.01); A61B 2017/0496 (2013.01); A61B 2017/06176 (2013.01); A61B 2017/2926 (2013.01); A61B 2090/064 (2016.02); A61F 2/08 (2013.01); A61F 2/28 (2013.01); A61F 2/442 (2013.01); A61F 2002/2817 (2013.01); A61F 2002/30062 (2013.01); A61F 2002/30677 (2013.01); A61F 2002/444 (2013.01); A61F 2002/4435 (2013.01); A61F 2210/0004 (2013.01); A61F 2310/00293 (2013.01); A61F 2310/00359 (2013.01)

(56) References Cited

U.S. PATENT DOCUMENTS

| | | | |
|---|---|---|---|
| 668,879 | A | 2/1901 | Miller |
| 702,789 | A | 6/1902 | Gibson |
| 862,712 | A | 8/1907 | Collins |
| 2,121,193 | A | 12/1932 | Hanicke |
| 2,187,852 | A | 8/1936 | Friddle |
| 2,178,840 | A | 11/1939 | Lorenian |
| 2,199,025 | A | 4/1940 | Conn |
| 2,235,419 | A | 3/1941 | Callahan |
| 2,248,054 | A | 7/1941 | Becker |
| 2,270,188 | A | 1/1942 | Longfellow |
| 2,518,276 | A | 8/1950 | Braward |
| 2,557,669 | A | 6/1951 | Lloyd |
| 2,566,499 | A | 9/1951 | Richter |
| 2,621,653 | A | 12/1952 | Briggs |
| 2,725,053 | A | 11/1955 | Bambara |
| 2,830,587 | A | 4/1958 | Everett |
| 3,204,635 | A | 9/1965 | Voss |
| 3,347,234 | A | 10/1967 | Voss |
| 3,367,809 | A | 2/1968 | Soloff |
| 3,391,690 | A | 7/1968 | Armao |
| 3,477,429 | A | 11/1969 | Sampson |
| 3,513,848 | A | 5/1970 | Winston |
| 3,518,993 | A | 7/1970 | Blake |
| 3,577,991 | A | 5/1971 | Wilkinson |
| 3,596,292 | A | 8/1971 | Erb |
| 3,608,539 | A | 9/1971 | Miller |
| 3,625,220 | A | 12/1971 | Engelsher |
| 3,648,705 | A | 3/1972 | Lary |
| 3,653,388 | A | 4/1972 | Tenckhoff |
| 3,656,476 | A | 4/1972 | Swinney |
| 3,657,056 | A | 4/1972 | Winston |
| 3,678,980 | A | 7/1972 | Guttshall |
| 3,709,218 | A | 1/1973 | Halloran |
| 3,711,347 | A | 1/1973 | Wagner |
| 3,760,808 | A | 9/1973 | Bleuer |
| 3,788,318 | A | 1/1974 | Kim |
| 3,789,852 | A | 2/1974 | Kim |
| 3,802,438 | A | 4/1974 | Wolvek |
| 3,807,394 | A | 4/1974 | Attenborough |
| 3,809,075 | A | 5/1974 | Matles |
| 3,811,449 | A | 5/1974 | Gravlee |
| 3,825,010 | A | 7/1974 | McDonald |
| 3,833,003 | A | 9/1974 | Taricco |
| 3,835,849 | A | 9/1974 | McGuire |
| 3,842,824 | A | 10/1974 | Neufeld |
| 3,857,396 | A | 12/1974 | Hardwick |
| 3,867,932 | A | 2/1975 | Huene |
| 3,875,652 | A | 4/1975 | Arnold |
| 3,898,992 | A | 8/1975 | Balamuth |
| 3,918,442 | A | 11/1975 | Nikolaev |
| 3,968,800 | A | 7/1976 | Vilasi |
| 4,023,559 | A | 5/1977 | Gaskell |
| 4,064,566 | A | 12/1977 | Fletcher |
| 4,089,071 | A | 5/1978 | Kainberz |
| 4,156,574 | A | 5/1979 | Boben |
| 4,164,794 | A | 8/1979 | Spector |
| 4,171,544 | A | 10/1979 | Hench |
| 4,183,102 | A | 1/1980 | Guiset |
| 4,199,864 | A | 4/1980 | Ashman |
| 4,200,939 | A | 5/1980 | Oser |
| 4,210,148 | A | 7/1980 | Stivala |
| 4,213,816 | A | 7/1980 | Morris |
| 4,235,233 | A | 11/1980 | Mouwen |
| 4,235,238 | A | 11/1980 | Ogui |
| 4,257,411 | A | 3/1981 | Cho |
| 4,265,231 | A | 5/1981 | Scheller |
| 4,281,649 | A | 8/1981 | Derweduwen |
| 4,291,698 | A | 9/1981 | Fuchs |
| 4,309,488 | A | 1/1982 | Heide |
| 4,320,762 | A | 3/1982 | Bentov |
| 4,351,069 | A | 9/1982 | Ballintyn |
| 4,364,381 | A | 12/1982 | Sher |
| 4,365,356 | A | 12/1982 | Broemer |
| 4,388,921 | A | 6/1983 | Sutter |
| 4,395,798 | A | 8/1983 | McVey |
| 4,409,974 | A | 10/1983 | Freedland |
| 4,414,166 | A | 11/1983 | Charlson |
| 4,437,191 | A | 3/1984 | Van der Zat |
| 4,437,362 | A | 3/1984 | Hurst |
| 4,444,180 | A | 4/1984 | Schneider |
| 4,448,194 | A | 5/1984 | DiGiovanni |
| 4,456,005 | A | 6/1984 | Lichty |
| 4,461,281 | A | 7/1984 | Carson |
| 4,493,317 | A | 1/1985 | Klaue |
| 4,495,664 | A | 1/1985 | Bianquaert |
| 4,501,031 | A | 2/1985 | McDaniel |
| 4,504,268 | A | 3/1985 | Herlitze |
| 4,506,681 | A | 3/1985 | Mundell |
| 4,514,125 | A | 4/1985 | Stol |
| 4,526,173 | A | 7/1985 | Sheehan |
| 4,532,926 | A | 8/1985 | O'Holla |
| 4,535,772 | A | 8/1985 | Sheehan |
| 4,547,327 | A | 10/1985 | Bruins |
| 4,556,350 | A | 12/1985 | Bernhardt |
| 4,566,138 | A | 1/1986 | Lewis |
| 4,589,868 | A | 5/1986 | Dretler |
| 4,590,928 | A | 5/1986 | Hunt |

(56) References Cited

U.S. PATENT DOCUMENTS

| | | |
|---|---|---|
| 4,597,379 A | 7/1986 | Kihn |
| 4,599,085 A | 7/1986 | Riess |
| 4,601,893 A | 7/1986 | Cardinal |
| 4,606,335 A | 8/1986 | Wedeen |
| 4,621,640 A | 11/1986 | Mulhollan |
| 4,630,609 A | 12/1986 | Chin |
| 4,632,100 A | 12/1986 | Somers |
| 4,632,101 A | 12/1986 | Freedland |
| 4,645,503 A | 2/1987 | Lin |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,685,458 A | 8/1987 | Leckrone |
| 4,691,741 A | 9/1987 | Affa |
| 4,705,040 A | 11/1987 | Mueller |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,743,257 A | 5/1988 | Tormala |
| 4,749,585 A | 6/1988 | Greco |
| 4,750,492 A | 6/1988 | Jacobs |
| 4,768,507 A | 9/1988 | Fischell |
| 4,772,286 A | 9/1988 | Goble |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hlavacek |
| 4,817,591 A | 4/1989 | Klaue |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill |
| 4,899,744 A | 2/1990 | Fujitsuka |
| 4,901,721 A | 2/1990 | Hakki |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green |
| 4,935,026 A | 6/1990 | Drews |
| 4,935,028 A | 6/1990 | Drews |
| 4,945,625 A | 8/1990 | Winston |
| 4,946,468 A | 8/1990 | Li |
| 4,950,285 A | 8/1990 | Wilk |
| 4,954,126 A | 9/1990 | Wallsten |
| 4,955,910 A | 9/1990 | Bolesky |
| 4,957,498 A | 9/1990 | Caspari |
| 4,961,741 A | 10/1990 | Hayhurst |
| 4,963,151 A | 10/1990 | Ducheyne |
| 4,966,583 A | 10/1990 | Debbas |
| 4,968,315 A | 11/1990 | Gattuma |
| 4,968,317 A | 11/1990 | Tormala |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,129 A | 8/1991 | Hayhurst |
| 5,046,513 A | 9/1991 | Gattuma |
| 5,047,055 A | 9/1991 | Bao |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,102,421 A | 4/1992 | Anspach |
| 5,108,399 A | 4/1992 | Eitenmuller |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,385 A | 1/1993 | Sontag |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,493 A | 6/1993 | Raad |
| 5,219,359 A | 6/1993 | McQuilkin |
| 5,226,899 A | 7/1993 | Lee |
| 5,234,006 A | 8/1993 | Eaton |
| 5,234,425 A | 8/1993 | Fogarty |
| 5,234,443 A | 8/1993 | Phan |

(56) References Cited

U.S. PATENT DOCUMENTS

| | | |
|---|---|---|
| 5,236,438 A | 8/1993 | Wilk |
| 5,236,445 A | 8/1993 | Hayhurst |
| 5,242,902 A | 9/1993 | Murphy |
| 5,254,113 A | 10/1993 | Wilk |
| 5,258,007 A | 11/1993 | Spetzler |
| 5,258,015 A | 11/1993 | Li |
| 5,258,016 A | 11/1993 | Di Poto |
| 5,261,886 A | 11/1993 | Chesterfield |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Haber |
| 5,282,832 A | 2/1994 | Toso |
| 5,290,281 A | 3/1994 | Tschakaloff |
| 5,304,119 A | 4/1994 | Balaban |
| 5,306,280 A | 4/1994 | Bregen |
| 5,306,301 A | 4/1994 | Graf |
| 5,315,741 A | 5/1994 | Dubberke |
| 5,318,588 A | 6/1994 | Horzewski |
| 5,320,611 A | 6/1994 | Bonutti |
| 5,324,308 A | 6/1994 | Pierce |
| 5,328,480 A | 7/1994 | Melker |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot |
| 5,330,486 A | 7/1994 | Wilk |
| 5,336,231 A | 8/1994 | Adair |
| 5,336,240 A | 8/1994 | Metzler |
| 5,339,799 A | 8/1994 | Kami |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,366,480 A | 11/1994 | Corriveaau |
| 5,370,646 A | 12/1994 | Reese |
| 5,370,660 A | 12/1994 | Weinstein |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,173 A | 2/1995 | Wilk |
| 5,395,308 A | 3/1995 | Fox |
| 5,397,311 A | 3/1995 | Walker |
| 5,400,805 A | 3/1995 | Warren |
| 5,403,312 A | 4/1995 | Yates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Shikhman |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr |
| 5,447,503 A | 9/1995 | Miller |
| 5,449,372 A | 9/1995 | Schmaltz |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donell |
| 5,464,426 A | 11/1995 | Bonutti |
| 5,464,427 A | 11/1995 | Curtis |
| 5,470,337 A | 11/1995 | Moss |
| 5,472,444 A | 12/1995 | Huebner |
| 5,474,554 A | 12/1995 | Ku |
| 5,478,351 A | 12/1995 | Meade |
| 5,478,353 A | 12/1995 | Yoon |
| 5,480,403 A | 1/1996 | Lee |
| 5,486,197 A | 1/1996 | Le |
| 5,487,844 A | 1/1996 | Fujita |
| 5,488,958 A | 2/1996 | Topel |
| 5,496,292 A | 3/1996 | Burnham |
| 5,496,318 A | 3/1996 | Howland |
| 5,496,335 A | 3/1996 | Thomason |
| 5,496,348 A | 3/1996 | Bonutti |
| 5,500,000 A | 3/1996 | Feagin |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,522,844 A | 6/1996 | Johnson |
| 5,522,845 A | 6/1996 | Wenstrom |
| 5,522,846 A | 6/1996 | Bonutti |
| 5,527,341 A | 6/1996 | Gogolewski |
| 5,527,342 A | 6/1996 | Pietrzak |
| 5,527,343 A | 6/1996 | Bonutti |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,718 A | 7/1996 | Bartlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,545,630 A | 8/1996 | Bonutti |
| 5,549,631 A | 8/1996 | Bonutti |
| 5,556,402 A | 9/1996 | Xu |
| 5,569,252 A | 10/1996 | Justin |
| 5,569,305 A | 10/1996 | Bonutti |
| 5,569,306 A | 10/1996 | Thal |
| 5,573,517 A | 11/1996 | Bonutti |
| 5,573,538 A | 11/1996 | Laboureau |
| 5,573,542 A | 11/1996 | Stevens |
| 5,575,801 A | 11/1996 | Habermeyer |
| 5,578,046 A | 11/1996 | Liu |
| 5,580,344 A | 12/1996 | Hasson |
| 5,584,835 A | 12/1996 | Greenfield |
| 5,584,839 A | 12/1996 | Gieringer |
| 5,584,860 A | 12/1996 | Goble |
| 5,584,862 A | 12/1996 | Bonutti |
| 5,591,206 A | 1/1997 | Moufarrege |
| 5,593,422 A | 1/1997 | Muijs Van De Moer |
| 5,593,425 A | 1/1997 | Bonutti |
| 5,593,625 A | 1/1997 | Riebel |
| 5,601,557 A | 2/1997 | Hayhurst |
| 5,601,558 A | 2/1997 | Torrie |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin |
| 5,620,461 A | 4/1997 | Muijs Van De Moer |
| 5,626,612 A | 5/1997 | Bartlett |
| 5,626,614 A | 5/1997 | Hart |
| 5,626,718 A | 5/1997 | Philippe |
| 5,630,824 A | 5/1997 | Hart |
| 5,634,926 A | 6/1997 | Jobe |
| 5,628,751 A | 7/1997 | Sander |
| 5,643,274 A | 7/1997 | Sander |
| 5,643,293 A | 7/1997 | Kogasaka |
| 5,643,295 A | 7/1997 | Yoon |
| 5,643,321 A | 7/1997 | McDevitt |
| 5,645,553 A | 7/1997 | Kolesa |
| 5,645,597 A | 7/1997 | Krapiva |
| 5,645,599 A | 7/1997 | Samani |
| 5,649,955 A | 7/1997 | Hashimoto |
| 5,649,963 A | 7/1997 | McDevitt |
| 5,651,377 A | 7/1997 | O'Donnell |
| 5,658,313 A | 8/1997 | Thal |
| 5,660,225 A | 8/1997 | Saffran |
| 5,662,658 A | 9/1997 | Wenstrom |
| 5,665,089 A | 9/1997 | Dall |
| 5,665,109 A | 9/1997 | Yoon |
| 5,667,513 A | 9/1997 | Torrie |

(56) References Cited

U.S. PATENT DOCUMENTS

| | | |
|---|---|---|
| 5,669,917 A | 9/1997 | Sauer |
| 5,674,240 A | 10/1997 | Bonutti |
| 5,681,310 A | 10/1997 | Yuan |
| 5,681,333 A | 10/1997 | Burkhart |
| 5,681,351 A | 10/1997 | Jamiolkowski |
| 5,681,352 A | 10/1997 | Clancy |
| 5,685,820 A | 11/1997 | Riek |
| 5,688,283 A | 11/1997 | Knapp |
| 5,690,654 A | 11/1997 | Ovil |
| 5,690,655 A | 11/1997 | Hart |
| 5,690,676 A | 11/1997 | Di Poto |
| 5,693,055 A | 12/1997 | Zahiri |
| 5,697,950 A | 12/1997 | Fucci |
| 5,702,397 A | 12/1997 | Gonle |
| 5,702,462 A | 12/1997 | Oberlander |
| 5,707,395 A | 1/1998 | Li |
| 5,713,903 A | 2/1998 | Sander |
| 5,713,921 A | 2/1998 | Bonutti |
| 5,718,717 A | 2/1998 | Bonutti |
| 5,720,747 A | 2/1998 | Burke |
| 5,725,541 A | 3/1998 | Anspach |
| 5,725,556 A | 3/1998 | Moser |
| 5,725,582 A | 3/1998 | Bevan |
| 5,730,747 A | 3/1998 | Ek |
| 5,733,306 A | 3/1998 | Bonutti |
| 5,720,753 A | 4/1998 | Sander |
| 5,735,875 A | 4/1998 | Bonutti |
| 5,735,877 A | 4/1998 | Pagedas |
| 5,735,899 A | 4/1998 | Schwartz |
| 5,741,282 A | 4/1998 | Anspach |
| 5,752,952 A | 5/1998 | Adamson |
| 5,752,974 A | 5/1998 | Rhee |
| 5,755,809 A | 5/1998 | Cohen |
| 5,762,458 A | 6/1998 | Wang |
| 5,766,221 A | 6/1998 | Benderev |
| 5,769,894 A | 6/1998 | Ferragamo |
| 5,772,672 A | 6/1998 | Toy |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |
| 5,792,096 A | 8/1998 | Rentmeester |
| 5,797,931 A | 8/1998 | Bito |
| 5,800,537 A | 9/1998 | Bell |
| 5,807,403 A | 9/1998 | Beyar |
| 5,810,849 A | 9/1998 | Kontos Slavros |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | SHarkey |
| 5,824,009 A | 10/1998 | Fukuda |
| 5,830,125 A | 11/1998 | Scribner |
| 5,836,897 A | 11/1998 | Sakural |
| 5,839,899 A | 11/1998 | Robinson |
| 5,843,084 A | 12/1998 | Hart |
| 5,843,178 A | 12/1998 | Vanney |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige |
| 5,868,749 A | 2/1999 | Reed |
| 5,874,235 A | 2/1999 | Chan |
| 5,879,372 A | 3/1999 | Bartlett |
| 5,891,166 A | 4/1999 | Scervinsky |
| 5,891,168 A | 4/1999 | Thal |
| 5,893,880 A | 4/1999 | Egan |
| 5,897,574 A | 4/1999 | Bonutti |
| 5,899,911 A | 5/1999 | Carter |
| 5,899,921 A | 5/1999 | Caspari |
| 5,906,579 A | 5/1999 | Vander Salm |
| 5,906,625 A | 5/1999 | Bito |
| 5,908,429 A | 6/1999 | Yoon |
| 5,911,721 A | 6/1999 | Nicholson |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund |
| 5,921,986 A | 7/1999 | BOnutti |
| 5,925,064 A | 7/1999 | Meyers |
| 5,928,244 A | 7/1999 | Tovey |
| 5,928,267 A | 7/1999 | Bonutti |
| 5,931,838 A | 8/1999 | Vito |
| 5,931,869 A | 8/1999 | Boucher |
| 5,940,942 A | 8/1999 | Fong |
| 5,941,900 A | 8/1999 | Bonutti |
| 5,941,901 A | 8/1999 | Egan |
| 5,944,750 A | 8/1999 | Tanner |
| 5,945,002 A | 9/1999 | Bonutti |
| 5,947,982 A | 9/1999 | Duran |
| 5,948,000 A | 9/1999 | Larsen |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto |
| 5,961,499 A | 10/1999 | Bonutti |
| 5,961,521 A | 10/1999 | Roger |
| 5,961,554 A | 10/1999 | Janson |
| 5,964,765 A | 10/1999 | Fenton |
| 5,964,769 A | 10/1999 | Wagner |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri |
| 5,989,282 A | 11/1999 | Bonutti |
| 5,993,458 A | 11/1999 | Vaitekunas |
| 5,993,477 A | 11/1999 | Vaitekunas |
| 6,007,567 A | 12/1999 | Bonutti |
| 6,007,580 A | 12/1999 | Lehto |
| 6,010,525 A | 1/2000 | Bonutti |
| 6,010,526 A | 1/2000 | Sandstrom |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher |
| 6,056,751 A | 5/2000 | Fenton |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti |
| 6,059,827 A | 5/2000 | Fenton |
| 6,063,095 A | 5/2000 | Wang |
| 6,066,151 A | 5/2000 | Miyawaki |
| 6,066,160 A | 5/2000 | Colvin |
| 6,066,166 A | 5/2000 | Bischoff |
| 6,068,637 A | 5/2000 | Popov |
| 6,068,648 A | 5/2000 | Cole |
| 6,077,277 A | 6/2000 | Mollenauer |
| 6,077,292 A | 6/2000 | Bonutti |
| 6,080,161 A | 6/2000 | Eaves |
| 6,080,192 A | 6/2000 | Demopulos |
| 6,083,522 A | 7/2000 | Chu |
| 6,086,593 A | 7/2000 | Bonutti |
| 6,086,608 A | 7/2000 | Ek |
| 6,090,072 A | 7/2000 | Kratoska |
| 6,099,531 A | 8/2000 | Bonutti |
| 6,099,537 A | 8/2000 | Sugai |
| 6,099,550 A | 8/2000 | Yoon |
| 6,099,552 A | 8/2000 | Adams |
| 6,102,850 A | 8/2000 | Wang |
| 6,106,545 A | 8/2000 | Egan |
| 6,117,160 A | 9/2000 | Bonutti |
| 6,120,536 A | 9/2000 | Ding |
| 6,125,574 A | 10/2000 | Ganaja |
| 6,126,677 A | 10/2000 | Ganaja |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle |

(56) References Cited

U.S. PATENT DOCUMENTS

| | | |
|---|---|---|
| 6,159,224 A | 12/2000 | Yoon |
| 6,159,234 A | 12/2000 | Bonutti |
| 6,171,299 B1 | 1/2001 | Bonutti |
| 6,171,307 B1 | 1/2001 | Bonutti |
| 6,174,324 B1 | 1/2001 | Egan |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer |
| 6,190,401 B1 | 2/2001 | Green |
| 6,200,322 B1 | 3/2001 | Branch |
| 6,217,591 B1 | 4/2001 | Egan |
| 6,224,593 B1 | 5/2001 | Ryan |
| 6,224,630 B1 | 5/2001 | Bao |
| 6,228,086 B1 | 5/2001 | Wahl |
| 6,231,592 B1 | 5/2001 | Bonutti |
| 6,238,395 B1 | 5/2001 | Bonutti |
| 6,238,396 B1 | 5/2001 | Bonutti |
| 6,258,091 B1 | 7/2001 | Sevrain |
| 6,264,675 B1 | 7/2001 | Brotz |
| 6,267,761 B1 | 7/2001 | Ryan |
| 6,273,717 B1 | 8/2001 | Hahn |
| 6,280,474 B1 | 8/2001 | Cassidy |
| 6,286,746 B1 | 9/2001 | Egan |
| 6,287,325 B1 | 9/2001 | Bonutti |
| 6,293,961 B2 | 9/2001 | Schwartz |
| 6,306,159 B1 | 10/2001 | Schwartz |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich |
| 6,348,056 B1 | 2/2002 | Bates |
| 6,358,271 B1 | 3/2002 | Egan |
| 6,364,897 B1 | 4/2002 | Bonutti |
| 6,368,325 B1 | 4/2002 | McKinley |
| 6,368,343 B1 | 4/2002 | Bonutti |
| 6,371,957 B1 | 4/2002 | Amrein |
| 6,409,742 B1 | 6/2002 | Fulton |
| 6,409,743 B1 | 6/2002 | Fenton |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer |
| 6,447,516 B1 | 9/2002 | Bonutti |
| 6,450,985 B1 | 9/2002 | Schoelling |
| 6,461,360 B1 | 10/2002 | Adams |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel |
| 6,527,774 B2 | 3/2003 | Lieberman |
| 6,530,933 B1 | 3/2003 | Yeung |
| 6,535,764 B2 | 3/2003 | Imran |
| 6,544,267 B1 | 4/2003 | Cole |
| 6,545,390 B1 | 4/2003 | Hahn |
| 6,547,792 B1 | 4/2003 | Tsuji |
| 6,551,304 B1 | 4/2003 | Whalen |
| 6,551,343 B1 | 4/2003 | Tormala |
| 6,554,852 B1 | 4/2003 | Oberlander |
| 6,557,426 B2 | 5/2003 | Reinemann |
| 6,558,390 B2 | 5/2003 | Cragg |
| 6,568,313 B2 | 5/2003 | Fukui |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,592,609 B1 | 7/2003 | Bonutti |
| 6,594,517 B1 | 7/2003 | Nevo |
| 6,585,764 B2 | 8/2003 | Wright |
| 6,602,293 B1 | 8/2003 | Biermann |
| 6,605,090 B1 | 8/2003 | Trieu |
| 6,610,080 B2 | 8/2003 | Morgan |
| 6,618,910 B1 | 9/2003 | Pontaoe |
| 6,620,195 B2 * | 9/2003 | Goble ............. A61B 17/1714 606/310 |
| 6,623,487 B1 | 9/2003 | Goshert |
| 6,626,944 B1 | 9/2003 | Taylor |
| 6,623,488 B1 | 10/2003 | Weaver |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer |
| 6,645,227 B2 | 11/2003 | Fallin |
| 6,666,877 B2 | 12/2003 | Morgan |
| 6,669,705 B2 | 12/2003 | Westhaver |
| 6,679,888 B2 | 1/2004 | Green |
| 6,679,917 B2 * | 1/2004 | Ek ................. A61B 17/0401 623/20.14 |
| 6,685,750 B1 | 2/2004 | Plos |
| 6,699,240 B2 | 3/2004 | Fracischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li |
| 6,770,078 B2 | 8/2004 | Bonutti |
| 6,780,198 B1 | 8/2004 | Gregoire |
| 6,786,989 B2 | 9/2004 | Torriani |
| 6,796,003 B1 | 9/2004 | Marvel |
| 6,818,010 B2 | 11/2004 | Eichhorn |
| 6,823,871 B2 | 11/2004 | Schmieding |
| 6,830,589 B2 | 12/2004 | Erickson |
| 6,860,885 B2 | 3/2005 | Bonutti |
| 6,878,167 B2 | 4/2005 | Ferree |
| 6,890,334 B2 | 5/2005 | Brace |
| 6,893,434 B2 | 5/2005 | Fenton |
| 6,899,722 B2 | 5/2005 | Bonutti |
| 6,913,666 B1 | 7/2005 | Aeschlimann |
| 6,916,321 B2 | 7/2005 | TenHuisen |
| 6,921,264 B2 | 7/2005 | Mayer |
| 6,923,824 B2 | 8/2005 | Morgan |
| 6,932,835 B2 | 8/2005 | Bonutti |
| 6,942,684 B2 | 9/2005 | Bonutti |
| 6,944,111 B2 | 9/2005 | Nakamura |
| 6,955,540 B2 | 10/2005 | Mayer |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan |
| 7,094,251 B2 | 8/2006 | Bonutti |
| 7,104,996 B2 | 9/2006 | Bonutti |
| 7,128,763 B1 | 10/2006 | Blatt |
| 7,018,380 B2 | 12/2006 | Cole |
| 7,147,652 B2 | 12/2006 | Bonutti |
| 7,160,405 B2 | 1/2007 | Aeschlimann |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian |
| 7,250,051 B2 | 7/2007 | Francischelli |
| 7,252,685 B2 | 8/2007 | Bindseil |
| 7,273,497 B2 | 9/2007 | Ferree |
| 7,326,200 B2 | 2/2008 | Trieu |
| 7,329,263 B2 | 2/2008 | Bonutti |
| 7,335,205 B2 | 2/2008 | Aeschlimann |
| 7,377,930 B2 | 5/2008 | Loughran |
| 7,429,266 B2 | 9/2008 | Bonutti |
| 7,445,634 B2 | 11/2008 | Trieu |
| 7,481,825 B2 | 1/2009 | Bonutti |

(56) References Cited

U.S. PATENT DOCUMENTS

| | | |
|---|---|---|
| 7,481,831 B2 | 1/2009 | Bonutti |
| 7,510,895 B2 | 3/2009 | Rateman |
| 7,597,705 B2 | 10/2009 | Forsberg |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,041,114 B2 | 10/2011 | Rother et al. |
| 8,128,669 B2 | 3/2012 | Bonutti |
| 8,140,982 B2 | 3/2012 | Hamilton |
| 8,147,514 B2 | 4/2012 | Bonutti |
| 8,162,977 B2 | 4/2012 | Bonutti |
| 8,771,314 B2 | 7/2014 | Crombie |
| 8,845,699 B2 | 9/2014 | Bonutti |
| 2001/0002440 A1 | 5/2001 | Bonutti |
| 2001/0008971 A1 | 7/2001 | Schwartz |
| 2001/0009250 A1 | 7/2001 | Hermanh |
| 2001/0041916 A1 | 11/2001 | Bonutti |
| 2001/0056287 A1 | 12/2001 | Bonutti |
| 2002/0016593 A1 | 2/2002 | Hearn |
| 2002/0016633 A1 | 2/2002 | Lin |
| 2002/0019649 A1 | 2/2002 | Sikora |
| 2002/0026244 A1 | 2/2002 | Trieu |
| 2002/0029067 A1 | 3/2002 | Bonutti |
| 2002/0029083 A1 | 3/2002 | Zucherman |
| 2002/0029084 A1 | 3/2002 | Paul |
| 2002/0045902 A1 | 4/2002 | Bonutti |
| 2002/0058966 A1 | 5/2002 | Tormala |
| 2002/0062153 A1 | 5/2002 | Paul |
| 2002/0087189 A1 | 7/2002 | Bonutti |
| 2002/0091391 A1* | 7/2002 | Cole ............... A61B 17/0401 606/916 |
| 2002/0103495 A1 | 8/2002 | Cole |
| 2002/0120269 A1 | 8/2002 | Lange |
| 2002/0120270 A1 | 8/2002 | Trieu |
| 2002/0123750 A1 | 9/2002 | Eisermann |
| 2002/0161439 A1 | 10/2002 | Strobel |
| 2002/0183762 A1 | 12/2002 | Anderson |
| 2002/0188301 A1 | 12/2002 | Dallara |
| 2003/0039196 A1 | 2/2003 | Nakamura |
| 2003/0040758 A1 | 2/2003 | Wang |
| 2003/0065361 A1 | 4/2003 | Dreyfuss |
| 2003/0065391 A1* | 4/2003 | Re ............... A61B 17/1714 623/13.14 |
| 2003/0083667 A1 | 5/2003 | Ralph |
| 2003/0097148 A1 | 5/2003 | Valimaa |
| 2003/0105474 A1 | 6/2003 | Bonutti |
| 2003/0125749 A1 | 7/2003 | Yuan |
| 2003/0158555 A1 | 8/2003 | Sanders |
| 2003/0158582 A1 | 8/2003 | Bonutti |
| 2003/0167072 A1 | 8/2003 | Oberlander |
| 2003/0118518 A1 | 9/2003 | HYahn |
| 2003/0181800 A1 | 9/2003 | Bonutti |
| 2003/0195514 A1 | 10/2003 | Trieu |
| 2003/0195530 A1 | 10/2003 | Thill |
| 2003/0195565 A1 | 10/2003 | Bonutti |
| 2003/0204204 A1 | 10/2003 | Bonutti |
| 2003/0208203 A1 | 11/2003 | Lim |
| 2003/0216742 A1 | 11/2003 | Wetzler |
| 2003/0225438 A1 | 12/2003 | Bonutti |
| 2003/0229361 A1 | 12/2003 | Jackson |
| 2004/0010287 A1 | 1/2004 | Bonutti |
| 2004/0024459 A1 | 2/2004 | Ferree |
| 2004/0030341 A1 | 2/2004 | Aeschlimann |
| 2004/0034357 A1 | 2/2004 | Beane |
| 2004/0039392 A1 | 2/2004 | Trieu |
| 2004/0049207 A1 | 3/2004 | Goldfarb |
| 2004/0097939 A1 | 5/2004 | Bonutti |
| 2004/0098050 A1 | 5/2004 | Foerster |
| 2004/0102788 A1 | 5/2004 | Huebner |
| 2004/0116963 A1 | 6/2004 | Lattouf |
| 2004/0138703 A1 | 7/2004 | Alleyne |
| 2004/0138705 A1 | 7/2004 | Heino |
| 2004/0143268 A1* | 7/2004 | Falahee ............... A61B 17/1757 606/247 |
| 2004/0143334 A1 | 7/2004 | Ferree |
| 2004/0167548 A1 | 8/2004 | BOnutti |
| 2004/0172063 A1 | 9/2004 | Li |
| 2004/0186471 A1 | 9/2004 | Trieu |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti |
| 2005/0033362 A1 | 2/2005 | Grafton |
| 2005/0033366 A1 | 2/2005 | Cole |
| 2005/0038514 A1 | 2/2005 | Helm |
| 2005/0043733 A1 | 2/2005 | Eisermann |
| 2005/0043796 A1 | 2/2005 | Grant |
| 2005/0065409 A1 | 3/2005 | de la Torre |
| 2005/0070765 A1 | 3/2005 | Abdelgany |
| 2005/0071012 A1 | 3/2005 | Serhan |
| 2005/0075644 A1 | 4/2005 | DiPoto |
| 2005/0090827 A1 | 4/2005 | Gedebou |
| 2005/0096699 A1 | 5/2005 | Wixey |
| 2005/0113928 A1 | 5/2005 | Cragg |
| 2005/0125072 A1 | 6/2005 | Kolb |
| 2005/0126680 A1 | 6/2005 | Aeschlimann |
| 2005/0143745 A1* | 6/2005 | Hodorek ............ A61B 17/1659 606/87 |
| 2005/0143826 A1 | 6/2005 | Zucherman |
| 2005/0149024 A1 | 7/2005 | Ferrante |
| 2005/0149029 A1 | 7/2005 | Bonutti |
| 2005/0197537 A1 | 9/2005 | Bonadio |
| 2005/0203521 A1 | 9/2005 | Bonutti |
| 2005/0216059 A1 | 9/2005 | Bonutti et al. |
| 2005/0216087 A1 | 9/2005 | Zucherman |
| 2005/0222620 A1 | 10/2005 | Bonutti |
| 2005/0234459 A1* | 10/2005 | Falahee ............... A61B 17/1757 606/323 |
| 2005/0234460 A1 | 10/2005 | Miller |
| 2005/0240190 A1 | 10/2005 | Gall |
| 2005/0240227 A1 | 10/2005 | Bonutti |
| 2005/0246021 A1 | 11/2005 | Ringeisen |
| 2005/0256582 A1 | 11/2005 | Ferree |
| 2005/0261684 A1 | 11/2005 | Shaolian |
| 2005/0267481 A1 | 12/2005 | Carl |
| 2005/0267534 A1 | 12/2005 | Bonutti |
| 2005/0283246 A1 | 12/2005 | Cauthen |
| 2006/0009846 A1 | 1/2006 | Trieu |
| 2006/0009855 A1 | 1/2006 | Goble |
| 2006/0015101 A1 | 1/2006 | Warburton |
| 2006/0015108 A1 | 1/2006 | Bonutti |
| 2006/0024357 A1 | 2/2006 | Carpenter |
| 2006/0026244 A1 | 2/2006 | Watson |
| 2006/0064095 A1 | 3/2006 | Senn |
| 2006/0089646 A1 | 4/2006 | Bonutti |
| 2006/0122600 A1 | 6/2006 | Cole |
| 2006/0122704 A1 | 6/2006 | Vresilovic |
| 2006/0142799 A1 | 6/2006 | BOnutti |
| 2006/0167495 A1 | 7/2006 | Bonutti |
| 2006/0189982 A1 | 8/2006 | Lange |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235413 A1 | 10/2006 | Denham |
| 2006/0235470 A1 | 10/2006 | Bonutti |
| 2006/0241695 A1 | 10/2006 | Bonutti |
| 2006/0264953 A1 | 11/2006 | Falahee |
| 2006/0265009 A1 | 11/2006 | Bonutti |
| 2006/0265011 A1 | 11/2006 | Bonutti |
| 2007/0032825 A1 | 2/2007 | Bonutti |
| 2007/0088362 A1 | 4/2007 | Bonutti |
| 2007/0118129 A1 | 5/2007 | Fraser |
| 2007/0198555 A1 | 8/2007 | Friedman |
| 2007/0233092 A1 | 10/2007 | Falahee |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | BOnutti |
| 2008/0039873 A1 | 2/2008 | Bonutti |
| 2008/0046090 A1 | 2/2008 | Paul |
| 2008/0097448 A1 | 4/2008 | Binder |
| 2008/0108897 A1 | 5/2008 | Bonutti |

(56) References Cited

U.S. PATENT DOCUMENTS

| | | |
|---|---|---|
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall |
| 2008/0275453 A1* | 11/2008 | Lafosse ............. A61B 17/1778 606/96 |
| 2009/0024161 A1 | 1/2009 | Bonutti |
| 2009/0093684 A1 | 4/2009 | Scharer |
| 2009/0138014 A1 | 5/2009 | Bonutti |
| 2009/0194969 A1 | 8/2009 | Bearey |
| 2010/0211120 A1 | 2/2010 | Bonutti |
| 2011/0060375 A1 | 3/2011 | Bonutti |
| 2011/0295253 A1 | 12/2011 | Bonutti |
| 2012/0165841 A1 | 6/2012 | Bonutti |
| 2012/0191140 A1 | 7/2012 | Bonutti |
| 2012/0215233 A1 | 8/2012 | Bonutti |

FOREIGN PATENT DOCUMENTS

| | | |
|---|---|---|
| CA | 2698057 | 3/2009 |
| DE | 1903316 | 10/1964 |
| DE | 1903016 | 8/1970 |
| DE | 3517204 | 11/1986 |
| DE | 3722538 | 1/1989 |
| DE | 9002844 U1 | 12/1990 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 199112779 | 9/1991 |
| WO | 199323094 | 11/1993 |
| WO | 1994008642 | 4/1994 |
| WO | 1995016398 | 6/1995 |
| WO | 1995031941 | 11/1995 |
| WO | 1996014802 | 5/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2009124215 | 10/2009 |
| WO | 2010099222 | 2/2010 |

OTHER PUBLICATIONS

IPER—International Preliminary Report on Patentability for WO/2008/116203, published Sep. 22, 2009 for PCT/US08/57948.
Written Opinion for WO/2008/116203, dated Oct. 23, 2008 for PCT/US08/57948.
IPR—International Publication WO2009/029908, published May 3, 2009 for PCT/US08/74941.
ISR—International Search Report for WO2009/029908, published May 3, 2009 for PCT/US08/74941.
IPER—International Preliminary Report on Patentability for WO2009/029908 published Mar. 2, 2010 for PCT/US08/74941.
Written Opinion for WO2009/029908, dated Feb. 28, 2010 for PCT/US08/74941.
International Search Report and Written Opinion for PCT/US2010/02563 completed Apr. 13, 2010.
Petition for Inter Partes Review of U.S. Pat. No. 5,980,559, IPR 2013-00603, Filing Date Sep. 24, 2013.
Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , Journal of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J_ of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.

(56) References Cited

OTHER PUBLICATIONS

Guide to Ultrasound Plastic Assembly, Ultrasonic Division Publication, (c) 1995.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510k, Summary for Arthrex Inc. 's Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64-2-1998.
Packer et al, Repair of Acute Scapho-Lunate Dissociation Facilitated by the "TAG" Suture Anchor, Journal of Hand Surgery (British and European Volume, 1994) 198: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb.), 1998: pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.

Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of NorthAmerica: Total Shoulder Arthroplasty, vol. 29 No. 3, Jul. 1998 p. 403-413.
Murphy et al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Non-Final Office Action dated Dec. 29, 2014 relating to U.S. Appl. No. 11/358,311, 8 pgs.
Final Office Action dated Jun. 9, 2014 relating to U.S. Appl. No. 11/358,311, 11 pgs.
Final Office Action dated Dec. 17, 2013 relating to U.S. Appl. No. 11/358,311, 8 pgs.
Non-Final Office Action dated Jul. 26, 2013 relating to U.S. Appl. No. 11/358,311, 7 pgs.
Final Office Action dated Oct. 18, 2012 relating to U.S. Appl. No. 11/358,311, 9 pgs.
Non-Final Office Action dated Mar. 20, 2012 relating to U.S. Appl. No. 11/358,311, 8 pgs.
Final Office Action dated Jan. 18, 2011 relating to U.S. Appl. No. 11/358,311, 12 pgs.
Non-Final Office Action dated May 14, 2010 relating to U.S. Appl. No. 11/358,311, 12 pgs.
Final Office Action dated Oct. 2, 2009 relating to U.S. Appl. No. 11/358,311, 12 pgs.
Non-Final Office Action dated Apr. 8, 2008 relating to U.S. Appl. No. 11/358,311, 13 pgs.
PTC Notification of Transmittal of the International Search Report and the Written Opinion of the International Searching Authority, or the Declaration, Application No. PCT/US2010/052018, dated Dec. 1, 2010, 18 pages.
Non-Final Office Action dated Mar. 27, 2015 relating to U.S. Appl. No. 11/258,795, 13 pages.
Final Office Action dated May 16, 2014 relating to U.S. Appl. No. 11/258,795, 13 pages.
Non-Final Office Action dated Nov. 8, 2013 relating to U.S. Appl. No. 11/258,795, 15 pages.
Final Office Action dated Dec. 20, 2011 relating to U.S. Appl. No. 11/258,795, 12 pages.
Non-Final Office Action dated Apr. 26, 2011 relating to U.S. Appl. No. 11/258,795, 12 pages.
Final Office Action dated Mar. 2, 2010 relating to U.S. Appl. No. 11/258,795, 11 pages.
Non-Final Office Action dated Sep. 19, 2008 relating to U.S. Appl. No. 11/258,795, 6 pages.
Final Office Action dated Mar. 3, 2015 relating to U.S. Appl. No. 12/872,140, 6 pages.
Non-Final Office Action dated Jun. 9, 2014 relating to U.S. Appl. No. 12/872,140, 12 pages.
Final Office Action dated Nov. 6, 2012 relating to U.S. Appl. No. 12/872,140, 9 pages.
Non-Final Office Action dated Apr. 19, 2012 relating to U.S. Appl. No. 12/872,140, 12 pages.
Non-Final Office Action dated May 11, 2016 relating to U.S. Appl. No. 11/258,795, 15 pages.
Intl Prelim Rep on Patentability and Written Opinion for PCT/US10/25263 dated Aug. 30, 2011.
European Search Report dated Sep. 10, 2012 for EP08732724.3 (046).
Copending U.S. Appl. No. 11/932,907—RCE Response dated Sep. 15, 2011.
Copending U.S. Appl. No. 11/258,795 Non-Final Office Action dated Apr. 26, 2011.
Copending U.S. Appl. No. 11/689,670, RCE Response dated Sep. 19, 2011.
Copending U.S. Appl. No. 10/614,352, Final Office Action dated Jul. 12, 2010.

(56) References Cited

OTHER PUBLICATIONS

Copending U.S. Appl. No. 11/932,602 Final Response to Office action dated Jun. 11, 2011.
Copending U.S. Appl. No. 11/671,556 Response filed Aug. 23, 2010.
Copending U.S. Appl. No. 11/438,537 Supplemental Final Rejection dated Sep. 25, 2009.
IPR—International Publication WO/2008/116203, published Sep. 22, 2009 for PCT/US08/57948.

\* cited by examiner

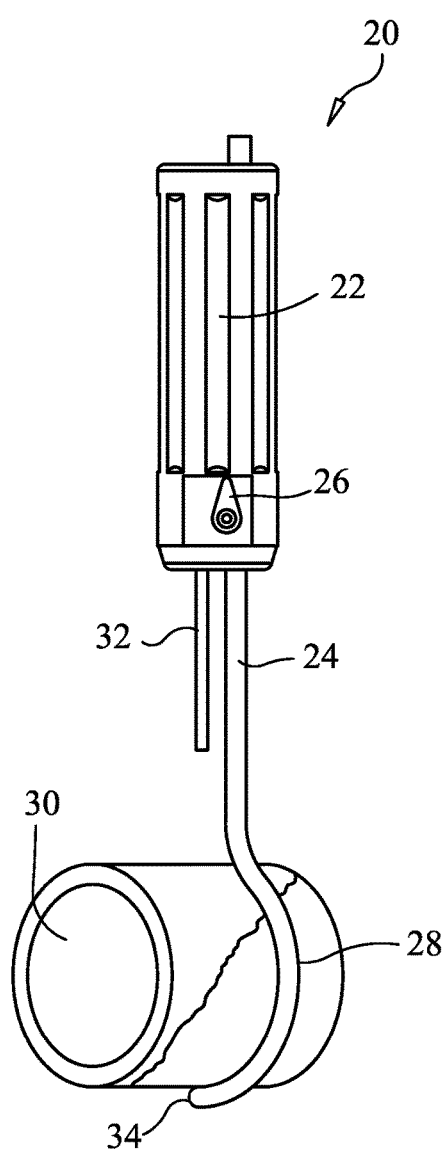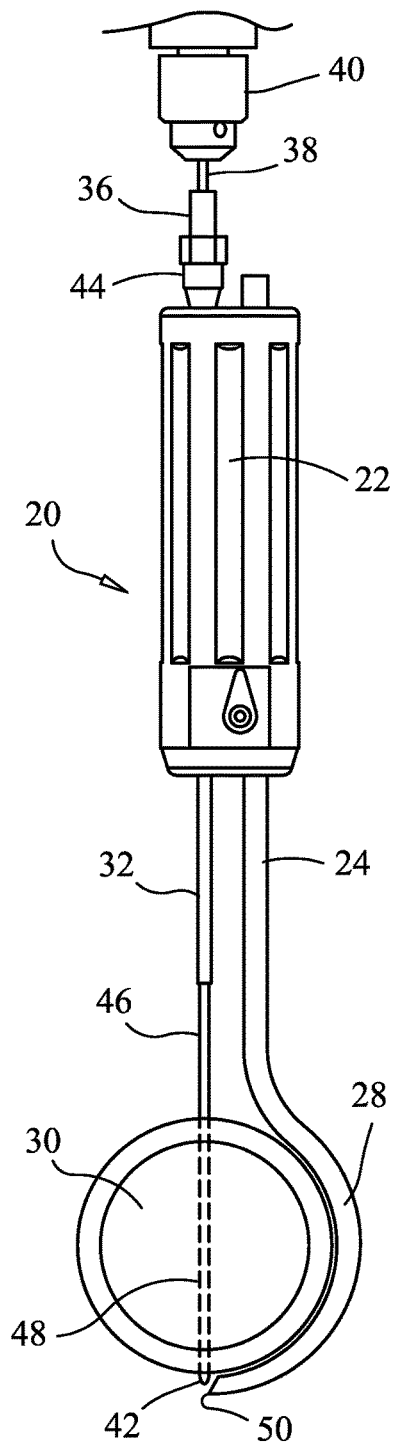
FIG. 1
FIG. 2

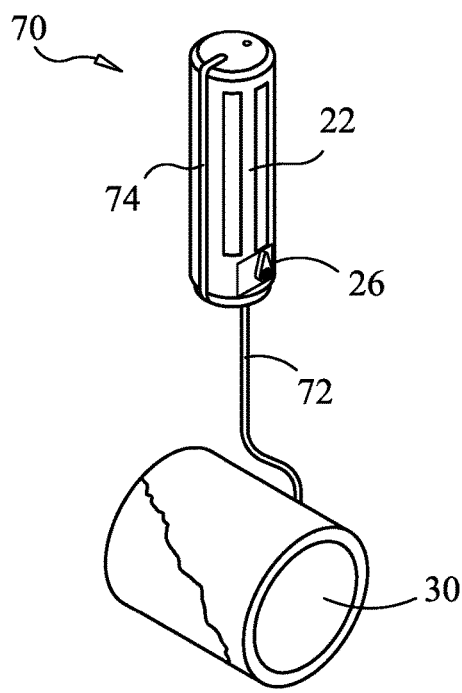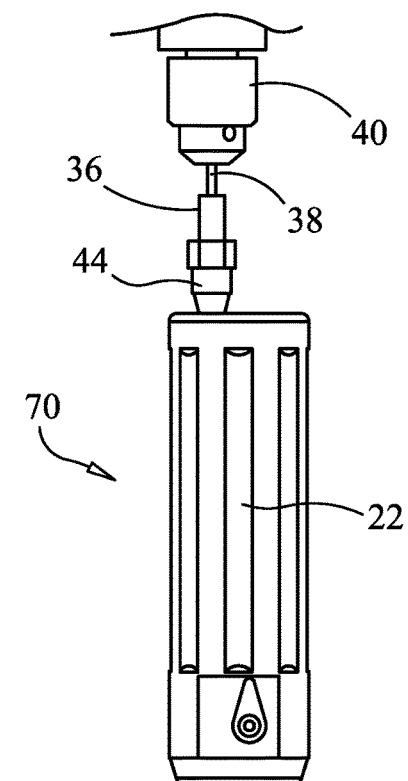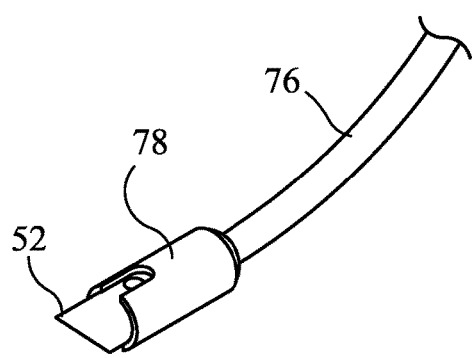
FIG. 10
FIG. 12
FIG. 11

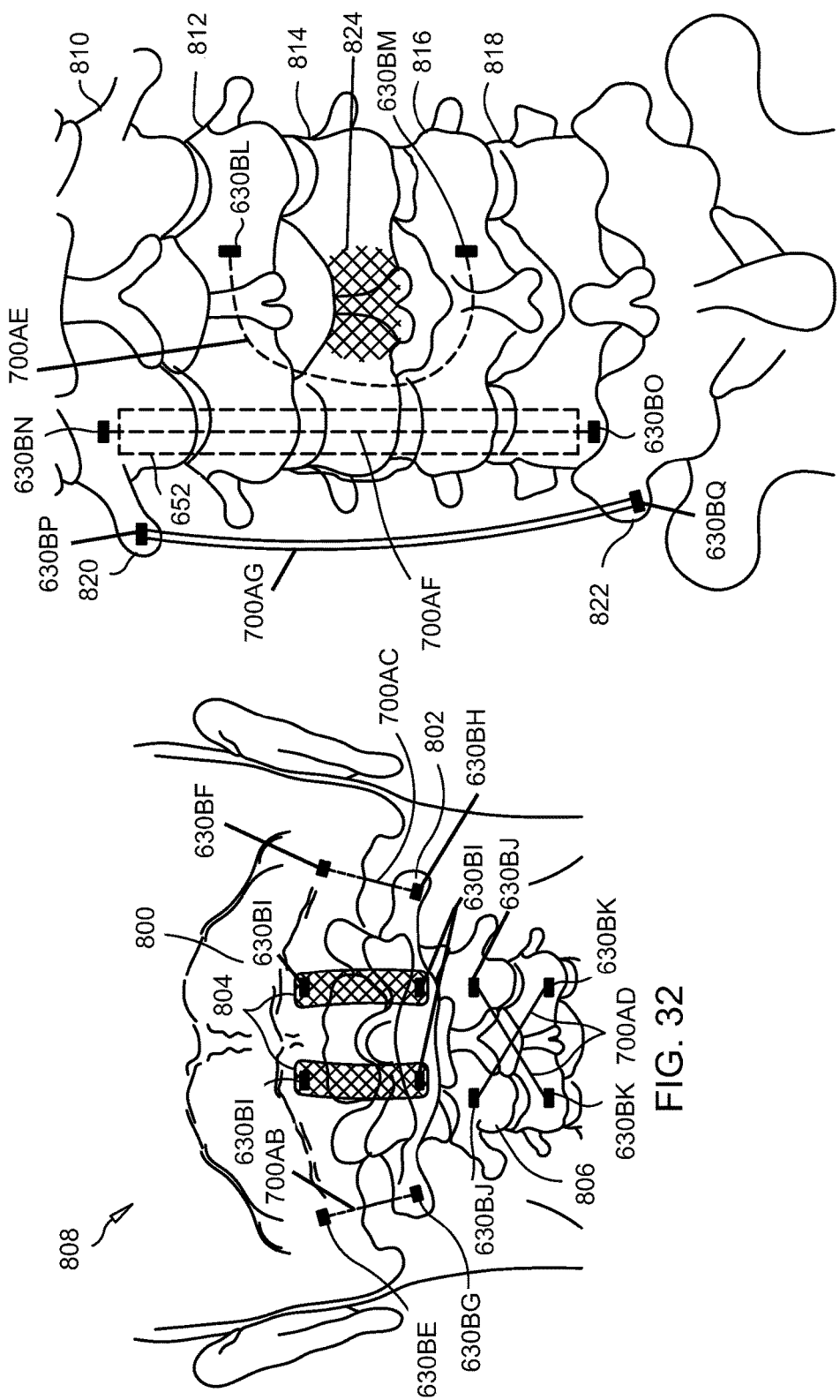

TISSUE FIXATION SYSTEM AND METHOD

CROSS REFERENCE TO RELATED APPLICATIONS

This application is continuation of application Ser. No. 12/576,992, filed Oct. 9, 2009, which is a continuation-in-part of prior application Ser. No. 11/258,795, filed Oct. 26, 2005, which claims the benefit of U.S. Provisional Application No. 60/622,095, filed Oct. 26, 2004; is a continuation-in-part of prior application Ser. No. 11/358,311, filed Feb. 21, 2006, which claims the benefit of U.S. Provisional Application No. 60/655,140, filed Feb. 22, 2005; and is a continuation of prior application Ser. No. 11/202,294, filed Oct. 5, 2005; all of which are incorporated by reference.

BACKGROUND

The present disclosure is directed to surgical repair, stabilization, and/or fixation of tissue and/or implants. More specifically, the present disclosure pertains to guiding, positioning, repairing, reconstructing, augmenting, stabilizing, and/or fixing surgical devices, implants, tissues, within the body.

In the medical arts, physicians use various methods and devices to attach soft tissue to other soft tissue, soft tissue to hard tissue, and hard tissue to other hard tissue. These same or similar techniques and devices are also used to position or fix an implant within the body. Such implants may include bone plates, fasteners, stents, filters, drug eluting implants, tissue alignment members, organ transplants, tissue scaffolding, tissue grafts, intervertebral disc replacement components, nucleus pulposus replacement component, and other joint replacements components, prostheses, robotic components, nanotechnology devices, sensors, emitters, radiofrequency emitting diodes, computer chips, RFID (radiofrequency identification) tags, adhesives, and sealants.

Applying pressure or compression to tissue and/or an implant helps during the healing process. Incised or torn soft tissue, for example, may be approximated with bandages, sutures, or staples. Proper and more rapid healing of broken or fractured bones likewise may be facilitated by applying constant pressure to the bone. For instance, physicians may insert pins, screws, or bolts in the area of the fracture in order to apply compression and stabilization to the fracture.

However, inserting screws through or around fractures can be complex and time-consuming. For example, the process of inserting a screw typically involves multiple steps conducted from multiple incisions or openings that provide access to the treated bone or tissue, including the steps of drilling holes, measuring the relevant distances to determine the appropriate screw selection, tapping the hole to establish threads, and screwing the screw into the hole.

In addition to the length and complexity of the process, bone screws also may lose their grip and strip out of the bone. Also, currently available lag screws typically provide only one side of cortex fixation and are generally not suited for percutaneus surgery. Moreover, when placing the screws in the bone, the physician may not accurately set the screw into the distal hole or may miss the distal hole completely, thereby resulting in the screw stripping the threads or breaking the bone.

Many devices and instruments have been disclosed to fasten soft and hard tissue for enhanced healing or tissue reconstruction. Examples of such devices include bone plates, bone wraps, external bone supports, and the like.

For example, U.S. Pat. No. 4,257,411 to Cho discloses a surgical drill guide tool adapted to be temporarily mounted about a distal portion of the femur for drilling a bony tunnel through a portion of the femur. The surgical tool allows for very precise location of the drill exit within the intercondylar notch, which is often critical in proper reconstruction of the anterior cruciate ligament of the knee. The surgical tool drill guide is characterized by having a first and second upright, with first and second drill sheaths located at their respective distal ends wherein transverse mounting means are provided to allow the surgeon to position the first and second drill sheaths tightly against opposite surfaces of the femur to provide a continuing and exact alignment for the drilling of the bony tunnel. The drill sheath at the distal end of the second upright is configured to fit inside the intercondylar notch, and allow exact placement of the exit of a bony tunnel which is drilled extra-articularly through the skin, and through the lateral femoral condyle.

U.S. Pat. No. 4,922,897 to Sapega et al. discloses a method and apparatus for the permanent surgical reconstruction of the anterior cruciate ligament in the human knee, which will stabilize the tibia and femur relative to each other and restore a full range of motion to the knee, by precisely locating the ends and angular relationship of a replacement ligament within the knee joint, at bone attachment sites such that the degree of shortening and lengthening experienced by the replacement ligament over the range of joint motion is either as close to zero (isometric) as possible, or closely matches that of the natural uninjured ligament (physometric), whichever the surgeon feels is most desirable.

U.S. Pat. No. 5,573,538 to Laboureau discloses ancillary instruments for the reconstruction of a posterior cruciate knee ligament by drilling one or two tibial canals using a surgical operation performed from the front. The instrument set includes a system for protecting the posterior surface of the upper tibia end and an aiming device for guiding at least one drill. The protection system includes at least one bent tube removably coupled by an extension portion to a locking handle for securing the tube through the intercondylar fossa of the femur on the posterior surface of the upper end of the tibia, so that the distal end of the bent tube serves as the stop to the drill guided by the aiming device and emerging from the tibial bone canal, and the bent tube can form, together with a rectilinear wire feed-through tube disposed in the place of the drill, a continuous canal for guiding a metallic loop used to draw the prosthetic posterior cruciate knee ligament from the anterior surface of the tibia to the femur insertion point.

U.S. Patent Publication No. 2003/0216742 to Wetzler et al. discloses a surgical drill guide generally including a handle connected to an arm with an end that contacts bone. The handle has a plurality of non-parallel channels therein for receiving a sleeve at different angles. Once properly positioned, the sleeve can be used to guide a K-wire into the bone, which can then be used as a guide for drilling a tunnel. The various angles allow the surgeon to achieve a range of tunnel lengths. In some embodiments, the guide has a locking mechanism for locking the sleeve in the channels.

Accordingly, a need exists for a method and device which can provide guided positioning and flexible or rigid fixation of tissue and/or an implant within the body while accessing the procedure site from a small skin portal.

During a surgical procedure, tissue is either intentionally or accidentally displaced, torn, or fractured to create a pathway to a desired operation site. In doing so, this tissue is damaged to a point where it may not function properly. After the intended surgical procedure or implantation is performed at the operation site, the skin incision is approximated. Currently, however, the other tissue like the muscles, ligaments, tendons, cartilage, bones, etc. which were damaged to create the pathway are not necessarily repaired or reconstructed. For example, following spinal surgery, a frequent complication is late instability where there is shearing antero-posteriorly or superior inferiorly due to excess motion because the ligaments have been damaged during surgical exposure. This complication may lead to degenerative disc disease and lower back pain.

Various methods and devices have been disclosed for repairing tissue. For example, U.S. Pat. No. 6,425,919 issued to Lambrecht discloses a disc herniation constraining device for implantation into the disc. The constraining device includes a fastener, a barrier, and a support member connecting the fastener and barrier. The barrier closes a defect in the annulus of the disc, while the fastener supports the position of the barrier. The barrier is placed between the annulus and the nucleus of the disc. The barrier may include a sealant and an enlarger.

In another example, U.S. Pat. No. 6,592,625 issued to Cauthen discloses a collapsible patch which is inserted through a surgical incision or rupture of the annulus. The patch is positioned within the subannular space. The patch expands to bridge the incision or rupture thereby occluding the aperture from the interior of the disc and preventing migration of nucleus pulposus.

U.S. Pat. No. 6,679,889 issued to West, Jr. et al discloses a method and apparatus of repairing the anterior cruciate ligament. The device enables the surgeon to independently apply a desired tensile load onto individual strands of a multiple-stranded soft tissue graft. The device is equipped with structure for fastening or otherwise attaching the device to a patient's limb during the conditioning and pre-tensioning procedure.

Additionally, U.S. Pat. No. 6,699,286 issued to Sklar discloses methods and apparatus of making repairs with graft ligaments. The method for graft ligament reconstruction includes harvesting a graft ligament consisting entirely of soft tissue. The graft ligament is compacted through compression so as to significantly reduce the cross-sectional area and increase the density of the collagen material of the graft ligament. The compressed graft ligament is deployed within the human body.

Various methods and devices have been disclosed for inserting an implant within the body. For example, U.S. Pat. No. 5,108,438 issued to Stone discloses a mesh skirt to anchor a prosthetic intervertebral disc. The implant includes a dry, porous, volume matrix of biocompatible and bioabsorbable fibers which may be interspersed with glyscosaminoglycan molecules. The matrix is adapted to have an outer surface contour substantially the same as that of a natural intervertebral disc. A mesh member extends from the lateral surface of the implant. After implantation, the mesh member may be sutured to adjacent tissue to anchor the disc in place. The mesh member may function in this capacity until sufficient tissue ingrowth occurs to provide that function.

In another example, U.S. Pat. No. 6,733,531 issued to Trieu discloses a spinal implant which is anchored using a device having an elongated anchoring body, such as an anchoring rod, and at least one securing member attached to the anchoring rod. The anchoring body or rod is configured to anchor, hold, or otherwise retain a spinal implant. The securing members are spaced apart along the length of the anchoring rod and may define a region for disposing an implant therebetween. The anchoring rod has a first end and a second end, wherein the first end is securable to an adjacent vertebra.

Once tissue has been repaired or an implant has been inserted within the body, the repaired region and surrounding tissue may be stabilized to enhance healing. U.S. Pat. No. 6,652,585 issued to Lange discloses a spine stabilization system including a flexible member attachable to a portion of the spinal column. The member includes components that are oriented and function similar to the natural fiber orientation of the anterior longitudinal ligament and annulus tissue. The use of components resist loading applied by extension and rotation of the spine, while the flexibility of the member does not subject it to the compressive loading of the spinal column segment to which it is attached.

In addition, U.S. Pat. No. 6,293,949 issued to Justis et al. discloses a device for stabilizing the spinal column. The device includes a longitudinal member sized to span a distance between at least two vertebral bodies and being at least partially formed of a shape-memory material exhibiting pseudoelastic characteristics at about human body temperature. The longitudinal member is reformed from an initial configuration to a different configuration in response to the imposition of stress caused by relative displacement between the vertebral bodies, and recovers toward the initial configuration when the stress is removed to thereby provide flexible stabilization to the spinal column.

There exists a need for devices and methods for repairing, reconstructing, augmenting, and securing tissue or an implant during surgery and "on the way out" after surgery has been performed at an intended operation site. Upon completion of the intended surgery, tissue may be compressed to other tissue or an implant to improve healing. Hard tissue, for example, may require rigid fixation while soft tissue to require flexible fixation. The repair, reconstruction, and augmentation of tissue and the securing of implants "on the way out" of the body after performing a surgical procedure creates a stabilized and enhanced healing environment.

It is well-known in the medical arts that applying pressure to tissue helps during the healing process. Incised or torn soft tissue, for example, may be approximated with bandages, sutures, or staples. Proper and more rapid healing of broken or fractured bones likewise may be facilitated by applying constant pressure to the bone. For instance, physicians may insert pins, screws, or bolts in the area of the fracture in order to apply pressure to the fracture.

However, inserting screws through or around fractures can be complex and time-consuming. For example, the process of inserting a screw typically involves multiple steps conducted from multiple incisions or openings that provide access to the treated bone or tissue, including the steps of drilling holes, measuring the relevant distances to determine the appropriate screw selection, tapping the hole to establish threads, and screwing the screw into the hole.

In addition to the length and complexity of the process, bone screws also may lose their grip and strip out of the bone. In addition, currently available lag screws also typically provide only one side of cortex fixation and are generally not suited for percutaneous surgery. Moreover, when placing the screws in the bone, the physician may not accurately set the screw into the distal hole or may miss the distal hole completely, thereby resulting in the screw stripping the threads or breaking the bone.

Many devices and instruments have been disclosed to fasten soft and hard tissue for enhanced healing or tissue reconstruction. Examples of such devices include bone plates, bone wraps, external bone supports, and the like.

For example, U.S. Pat. No. 5,921,986, the contents of which are incorporated herein by reference, discloses a bone suture and associated methods for implantation and fracture fixation. The '986 Patent describes fasteners and anchors used in conjunction with an elongate fixation element, such as a suture. In some cases, it may be advantageous to use more rigid fixation elements.

Accordingly, a need exists for a tissue fixation instrument which can provide flexible or rigid fixation of tissue while accessing the tissue from a small skin portal.

SUMMARY

The present disclosure includes instruments and methods for guiding and positioning various implants within the body. The instrument may provide for the placement of a biocompatible implant within tissue and/or may provide for dynamic and rigid fixation of tissue. An implant guidance and positioning device includes a body member connected with a hook. The hook may have a lumen extending therethrough. The device also includes a guide channel disposed in the body member. The longitudinal axis of the guide channel may be generally aligned with or slightly offset from a distal end of the hook. The device may further include a pushrod for positioning a fastener and suture in the lumen of the hook. Furthermore, the device may include an elongated claw dimensioned for insertion through the guide channel. The claw may include means for grabbing the suture.

In another embodiment, the positioning device includes a body member, an elongated member connected with the body member, a socket member connected to the distal end of the elongated member, and a guide slot disposed in the body member. The longitudinal axis of the guide slot is generally aligned with or slightly offset with the socket member. The socket member may be dimensioned and configured for holding a fastener. The device may also include a fastening member dimensioned for insertion in the guide slot. The fastening member may include means for attaching the fastening member to the fastener, such as threads, ribs, magnets, adhesives, or expandable material.

In a related aspect of the present invention, the distal portion of the hook or elongated member is curved to be positionable at least partially on the distal or backside of the bone or tissue, while the proximal portion of the hook or elongated member may be generally parallel with the guide channel or slot. The hook or elongated member may be removably connected with the body member with means for holding and releasing the hook or elongated member.

The positioning device may further include a drill system having a drill bit dimensioned for insertion through the guide channel or slot. The drill system may create a linear or non-linear passage in tissue. The drill system may be a cannulated drill system. The positioning device may also include means for clamping the device to tissue. Such means may include a threaded tube adjustably attached to the body member, a tube and a finger grip attached to the body member, or one or more pins placed between the positioning device and tissue. Furthermore, the device may include a tensioning mechanism for tensioning the suture or fastening member.

The present disclosure includes the repair, reconstruction, augmentation, and securing of tissue or implants during a surgical procedure and "on the way out" after the surgical procedure has been performed. Hard and soft tissue at and around the operation site and tissue between the operation site and the skin incision may be compressed and/or rebuilt so that tissue-function may be at least partially restored and the operation region may be stabilized for enhanced healing. This could be ligament repair, tendon repair, muscle repair, bone repair, cartilage repair, and repair of any other tissue type. Ligaments may be fastened to ligaments; ligaments to bones; bones to bones; ligaments to muscles; muscles to muscles; tissue grafts to bone; tissue grafts to ligaments; grafts to grafts; and any other combination of tissue and implants. It is further contemplated that the methods and devices of the present invention may be utilized with minimally invasive techniques.

In accordance with one aspect of the present invention, a method for stabilizing a body joint is provided. A fastener is positioned in contact with first body tissue on one side of the joint. Another fastener is positioned in contact with second body tissue on the other side of the joint. A suture is placed between the fasteners and tensioned. The tensioned suture is secured to the fasteners to restrict normal movement of the joint. The fasteners may be positioned in contact with the outer surface of the body tissues or inside of the body tissues. The suture may be positioned adjacent to the joint, through the joint, or in combination.

The body tissues may be bones, muscles, ligaments, tendons, nerves, skin, organs, cartilage, fascia, and blood vessels. The bones and ligaments may be bones and ligaments of the knee, ankle, elbow, wrist, feet, hand, hip, shoulder, jaw, and spine. Specifically, bones of the knee may include the femur, tibia, and patella. Ligaments of the knee may include the medial collateral ligament, lateral collateral ligament, posterior oblique ligament, arcuate ligament, oblique popliteal ligament, anterior cruciate ligament, and posterior cruciate ligament. Bones of the spine may include transverse process, pedicle, facet, spinous process, posterior arch, odontoid process, posterior tubercle, lateral articular process, uncinate process, anterior tubercle, carotid tubercle, odontoid process, lamina, and vertebral body. Ligaments of the spine may include the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine. Such bones of the spine and ligaments of the spine (as well as all other body tissues associated with the spine) may be referred to as spinal anatomical structures.

A tubular member may be positioned between the fasteners, and the suture may be placed within the tubular member such that a portion of the tubular member contacts the first body part and another portion of the tubular member contacts the second body part thereby maintaining the body parts in alignment with each other.

In accordance with another aspect of the present invention, there is provided a method for approximating an incision in tissue. A suture is positioned in portions of tissue located on opposite sides of the incision. The proximal and distal ends of the suture extend from the tissue and are adjacent the incision. A fastener is placed transverse to the incision with the ends of the suture disposed within at least one channel of the fastener. The suture is tensioned and secured to the fastener to thereby approximate the incision. The tissue may be bone, muscle, ligament, tendon, skin, organ, cartilage, and blood vessels.

Additionally, two fasteners may be positioned generally parallel to an incision with the first fastener placed on one side of the incision and the second fastener placed on the opposite side of the incision. A suture may be positioned in portions of tissue located on opposite sides of the incision with the middle section of the suture slidably disposed within at least one channel of the first fastener and the end portions of the suture disposed within at least one channel of the second fastener. The suture may be tensioned and secured to the fasteners to thereby approximate the incision.

In accordance with another aspect of the present invention, a fastener is provided. The fastener includes an elongated member and at least one channel extending therethrough generally perpendicular to the longitudinal axis of the elongated member. A portion of the outer surface of the fastener may be concave, flat, and/or convex.

There is also provided a method of using a fastener. At least a portion of the surface of the fastener is placed in contact with tissue. The fastener may be placed in contact with an outer surface of the tissue and/or the inner portion of the tissue. A portion of the surface of the fastener may be flat, convex, or concave. A convex portion of the fastener may be placed in contact with a concave portion of the tissue. A flat portion of the fastener may be placed in contact with a flat portion of the tissue. A concave portion of the fastener may be placed in contact with a convex portion of the tissue. In these configurations, the shaped portions of the fasteners mate with the tissue.

In accordance with yet another aspect of the present invention, a fastener assembly is provided. The assembly includes a plurality of fastener members, each fastener member having at least one channel extending therethrough. A plurality of connecting members links the fastener members to each other. The fastener members may be linked together end to end, side to side, or end to side. When linked together, the fastener members may form a linear, circular, rectangular, J, L, or U configuration. The connecting members may be hinges, pins, ball and socket, interconnecting loops, hooks, flexible filaments and/or rigid members. There may be two or more connecting members which link adjacent fastener members. The channels of the fastener members may be generally transverse to the longitudinal axis of the fastener member. Each fastener member may include two or more channels, and the channels may be generally parallel to each other.

Furthermore, a fastener strip or assembly is provided. The fastener strip or assembly includes a plurality of fastener members disposed on a flexible strip. Each fastener member has at least one channel extending therethrough. The channel may be generally transverse to the longitudinal axis of the fastener member. The fastener members are positioned on the flexible strip to form a linear, circular, rectangular, J, L, and/or U configuration. The fastener members may be affixed to the upper surface of the flexible strip. The fastener members may be affixed to the upper surface of the flexible strip with adhesive. The flexible strip may also have adhesive on its lower or bottom surface for adhesion to tissue. Such adhesives may include cyanoacrylate adhesives, hydrogel adhesives, monomer and polymer adhesives, fibrin, polysaccharide, Indermil® or any other biocompatible adhesive. The flexible strip may be bioabsorbable, bioerodible, degradable, biodegradable, expandable, and/or hydrophilic.

There is also provided a method for using a fastener assembly. The fastener assembly is positioned against tissue. A suture or sutures are positioned within the tissue and through the suture assembly to secure the assembly to the tissue. In one embodiment, the assembly is placed over an incision in the tissue. The fastener members are positioned such that channel of the fastener members are located on each side of the incision. A suture or sutures are positioned within the portions of tissue on opposite sides of the incision and through the fastener assembly. The suture or sutures are tensioned and secured with the fastener members. The type and configuration of the fastener assembly is determined with respect to the shape or configuration of the tissue. The shape of the incision also determines the shape of the fastener assembly.

In accordance with a further aspect of the present invention, a total disc replacement implant is provided. The implant includes a superior or upper portion made of a rigid material. The upper surface of the superior portion is configured to adjoin to a cut portion of a superior or upper vertebra. The implant also includes an inferior or lower portion made of a rigid material. The lower surface of the inferior portion is configured to adjoin to a cut portion of an inferior or lower vertebra. The implant further includes a middle portion made of a flexible material. The middle portion is affixed to the lower surface of the superior portion and the upper surface of the inferior portion.

The superior and inferior portions of the implant may include polymeric, composite, metallic, ceramic, and expandable material. The portions may also include synthetic bone and body tissue like bone, collagen, cartilage, and ligaments. The portions may also be bioabsorbable, bioerodible, degradable, and biodegradable. The middle portion of the implant may include rubber, gel, foam, polymer, collagen, and body tissue. The total disc replacement implant may be made of a plurality of components; that is, the implant may be modular. The components may be connected with each other to form the implant. The components may mechanically interlock with one another. Each component may have a size approximately the same as the length of the incision through which the components are inserted.

In addition, there is provided a method for total disc replacement. An incision is made through tissue for access to the spine. The dimensions of the incision may be minimized to reduce trauma to surrounding tissue like muscle, ligaments, tendons, and cartilage. The vertebra located superior to the damaged disc being replaced is cut. The cut may be made on the lower or bottom portion of the superior vertebra. The cut may be planar or multiplanar. The superior vertebra may be cut without disturbing or at least minimally disturbing the adjacent ligaments, cartilage, and muscles. The cut may be angled to avoid damaging or loosening the spinal ligaments like the anterior and posterior longitudinal ligaments.

The vertebra located inferior to the disc being removed is cut in a similar manner, except the upper surface of the inferior vertebra is cut. Once cut, the cut portions of vertebrae and the intervertebral disc are removed through the incision. The cut vertebrae are further prepared for receiving an implant. The total disc replacement implant or modular implant is positioned between the cut superior and inferior vertebrae. A modular implant may be positioned one component at a time or already assembled. The implant is anchored to the surrounding tissue like the adjacent vertebral bodies. Any ligaments, muscles, cartilage, tendons, or other body tissue cut or damaged during the procedure is repaired prior to closing the incision. Finally, the incision is approximated.

In accordance with another aspect of the present invention, a tissue alignment sleeve is provided. The sleeve includes a tubular member having a wall. The interior surface of the wall is generally smooth. The exterior surface of the wall includes means for gripping and creating friction. The gripping means may include threads, a plurality of raised regions, and a plurality of circumferential elevated areas or rings. The wall may include a plurality of openings for tissue ingrowth and outgrowth. The wall may include one or more longitudinal slits such that the tubular member or sleeve may be bendable to increase and decrease the diameter of the sleeve.

There is further provided a method of using a tissue alignment sleeve. A channel is created in tissue. The sleeve is positioned within the tissue. The gripping or friction means of the sleeve holds the sleeve within the tissue. The tissue may include first and second portions. When positioned within the first and second portions of the tissue, the portions are aligned and maintained in position relative to each other. The first and second portions may be portions of bone on opposite sides of a fracture. The portions may be tissue of a body joint. The portions may be bones of a joint located on opposite sides of the joint, such that when the sleeve is positioned, movement of the joint is restricted.

A sleeve with at least one longitudinal slit may be positioned with the channel created in tissue. The diameter of the sleeve may be decreased by closing the gap in the longitudinal slit. In a decreased diameter, the sleeve may be inserted into the channel. Once positioned, the diameter of the sleeve may be increased thereby engaging the gripping means with the tissue. A suture or sutures may be placed through the lumen of the sleeve to secure tissue located at the ends of the sleeve. After the sleeve has gripped the adjacent tissue with the gripping means, therapeutic substances or graft material (autogenic, allogenic, xenogenic, or synthetic) may be packed into the tubular member.

In accordance with a further aspect of the present invention, a method for stabilizing an implant is provided. A first fastener is positioned in contact with tissue located adjacent the implant. A second fastener is positioned in contact with tissue located adjacent the implant generally opposite the first fastener. A suture is placed between the fasteners and in contact with the implant. The suture is tensioned, and the fasteners are secured to the tensioned suture such that the suture transmits force to the implant. The suture may be positioned in contact with the surface of the implant. The suture may also be positioned within the implant.

In addition, a method for stabilizing an implant within a body is provided. A first fastener is positioned in contact with the implant. A second fastener is positioned in contact with tissue located adjacent the implant. A suture is placed between the fasteners. The suture is tensioned, and the fasteners are secured to the tensioned suture to anchor the implant to the tissue. The first fastener may be positioned within the implant or on the surface of the implant. The suture may be placed against or within the implant.

In accordance with another aspect of the present invention, there is provided a method for anchoring an implant for directional expansion within the body. A first fastener is positioned in contact with the first side of an expandable implant. A second fastener is positioned in contact with tissue located adjacent a second side of the implant which is opposite the first side. A first suture is positioned between the fasteners and tensioned. The first suture is secured with the first and second fasteners. In this configuration, the first side of the expandable implant is restricted from expanding, but all other sides of the implant can expand.

For further restriction of expansion, a third fastener is positioned in contact with the second side of the implant. A fourth fastener is positioned in contact with tissue located adjacent the first side of the implant. A second suture is positioned between the third and fourth fasteners. The second suture is tensioned and secured with the fasteners. The second side of the implant is restricted from expanding.

To further restrict expansion of the implant, more fasteners and sutures may be positioned as previously described such that the implant is limited to expansion in one, two, or more directions.

The sutures may be positioned in contact with the expandable implant such that the sutures transmit force to the implant thereby anchoring the implant and further restricting expansion.

In accordance with a further aspect of the present invention, a device for anchoring an implant is provided. The device includes a pouch dimensioned and configured for receiving an implant. The pouch has an access port for inserting the implant. At least one anchoring point is connected with the pouch. The device may further include a flap attached to the pouch for closing the access port. The implant may be expandable, and when positioned in the pouch, the implant generally expands primarily in the direction of the access port. The pouch may include a plurality of access ports. An expandable implant placed in a pouch with a plurality of access ports expands primarily in the directions of the access ports.

In accordance with another aspect of the present invention, there is provided a method for repairing a ligament. A fastener is positioned in contact with the ligament adjacent the first side of a damaged region of the ligament. Another fastener is positioned in contact with the ligament adjacent a second side of the damaged region which is generally opposite the first side. A suture is positioned between the fasteners. The suture is tensioned and secured with the fasteners such that the ligament is tightened. The suture may be positioned through the ligament. The suture may also be positioned through tissue adjacent the damaged area. The tissue may be spine tissue such as one or more vertebrae and one or more intervertebral discs. The ligament may be a ligament of the spine such as the anterior or posterior longitudinal ligament, or any of the previously identified ligaments. The damaged region may be a loosened ligament area, a torn ligament area, or a missing ligament area.

Furthermore, a method for reconstructing a ligament is provided. A tissue graft is positioned adjacent a damaged region of the ligament. A first fastener is positioned in contact with the tissue graft on a first side of the damaged region. A second fastener is positioned in contact with the tissue graft on a second side of the damaged region which is generally opposite the first side. A suture is positioned between the fasteners with the suture passing through the tissue graft and ligament. The suture is tensioned and secured with the fasteners to hold the tissue graft against the ligament. The tissue graft may include ligamentous tissue or bone tissue. The ligament may be a ligament of the spine. The suture may be positioned within tissue located adjacent the ligament. The tissue may be spine tissue including one or more vertebrae and one or more intervertebral discs.

Moreover, there is provided another method for reconstructing a ligament. A tissue graft is positioned adjacent a damaged region of the ligament. A first fastener is positioned in contact with the tissue graft on a first side of the damaged region. A second fastener is positioned in contact with tissue adjacent the ligament. A suture is positioned between the fasteners with the suture passing through the tissue graft and ligament. The suture is tensioned and secured to the fasteners such that at least a portion of the tissue graft is held to the ligament. The tissue graft may include ligamentous tissue or bone tissue. The ligament may be a ligament of the spine like the anterior or posterior longitudinal ligament. The suture may be positioned within the tissue adjacent the ligament. The tissue may be spine tissue including one or more vertebrae and one or more intervertebral discs.

The present disclosure includes a tissue fixation system. The system comprises an elongate fastening member and a fastener moveable with respect to the elongate fastening member from a first orientation to a second orientation, the fastener having a body with a tissue contacting surface that includes a groove configured and dimensioned to receive a portion of the elongate member in the first orientation. The system can also include a second fastener or other means for maintaining tension in the elongate fastening member.

A biasing means can be provided to maintain the fastener in the first orientation. The biasing means can be an adhesive between the groove and the portion of the elongate fastening member received in the groove. The biasing means could also be a frangible connection between the groove and the portion of the elongate fastening member received in the groove.

The fastener body can have a free surface opposite the tissue contacting surface, with the free surface including a channel configured and dimensioned to receive a portion of the elongate member in the first orientation. The fastener body can also include a through bore extending from the tissue contacting surface through the free surface.

In one embodiment, the fastener body includes leading and trailing ends. The leading end can be tapered or otherwise shaped to facilitate insertion. The groove terminates at the through bore and extends toward one of the leading and trailing ends and the channel terminates at the through bore and extends toward the other of the leading and trailing ends. In an exemplary embodiment, the groove extends toward the leading end and the channel extends toward the trailing end.

The free surface of the fastener body can be provided with a well surrounding the through bore. The well can be configured and dimensioned to receive at least a portion of the stop. A distal end of the elongate fastening member can include a stop larger than the through bore.

The present invention also relates to a medical instrument or device for securing the fastener with respect to the elongate fastening member. The medical device tensions the elongate fastening member and crimps either the fastener or a bushing. Another aspect of the invention relates to methods of tissue fixation using the disclosed tissue fixation systems.

In an aspect, a method for stabilizing a spinal anatomical structure may include introducing, into a body, a curved segment of an elongate, fastener placement rod approximate to, adjacent to or on a spinal anatomical structure, the curved segment having a leading end; providing, at the leading end of the curved segment of the fastener placement rod, a fastener approximate to, adjacent to or on the spinal anatomical structure; and securing the fastener with respect to the spinal anatomical structure.

In a detailed embodiment, the fastener may be secured with respect to the spinal anatomical structure utilizing at least one flexible line. In a detailed embodiment, the at least one flexible line may extend from the fastener, through at least a portion of the spinal anatomical structure to a separate securing point within the body. In a detailed embodiment, a method may include securing the at least one flexible line at the separate securing point by a second fastener. In a detailed embodiment, the step of securing the at least one flexible line at the separate securing point by the second fastener may include crimping the second fastener to the flexible line. In a detailed embodiment, the crimping step may include introducing a crimping mechanism extending from an elongate rod of a crimping tool through an incision in the body and adjacent to the second fastener. In a detailed embodiment, the at least one flexible line may include a suture. In a detailed embodiment, the at least one flexible line may include a cable.

In a detailed embodiment, the flexible line may be provided attached to the fastener approximate to, adjacent to or on the spinal anatomical structure, and the method may include a step of passing the flexible line from the fastener and at least through the portion of the spinal anatomical structure to the separate securing point within the body. In a detailed embodiment, the passing step may be performed utilizing a gripper at a leading end of an elongate gripper rod which pulls the flexible line from the fastener and at least through the portion of the spinal anatomical structure to the separate securing point within the body. In a detailed embodiment, the elongate fastener placement rod and elongate gripper rod may extend from a hand-held guidance and positioning device. In a detailed embodiment, a method may include forming a hole through the portion of the spinal anatomical structure prior to the pulling step. In a detailed embodiment, the hole forming step may be performed by an elongate drill rod extending from the hand-held guidance and positioning device. In a detailed embodiment, the elongate gripper rod and elongate drill rod may be guided by a guide tube extending from the hand-held guidance and positioning device.

In a detailed embodiment, the elongate gripper rod may extend from the hand-held guidance and positioning device along an axis that runs adjacent to or through the leading end of the curved segment of the fastener placement rod.

In a detailed embodiment, a method may include forming a hole through the portion of the spinal anatomical structure prior to the passing step.

In a detailed embodiment, the spinal anatomical structure may be a first spinal anatomical structure; the flexible line may be provided attached to the fastener approximate to, adjacent to or on the spinal anatomical structure; and a method may include a step of passing the flexible line from the fastener and at least through the portion of the first spinal anatomical structure, through at least a portion of a second anatomical structure to the separate securing point within the body, thereby stabilizing at least the first and second spinal anatomical structures with respect to each other. In a detailed embodiment, the first spinal anatomical structure may include an intervertebral disc and the second spinal anatomical structure may include a vertebra. In a detailed embodiment, the first spinal anatomical structure may include a first vertebra and the second spinal anatomical structure may include a second vertebra. In a detailed embodiment, the first spinal anatomical structure may include a vertebra and the second spinal anatomical structure may include an intevertebral disc. In a detailed embodiment, the first spinal anatomical structure may include a first spinous process and the second spinal anatomical structure may include a second spinous process. In a detailed embodiment, the first spinal anatomical structure may include a first ligament segment and the second spinal anatomical structure may include a second ligament segment. In a detailed embodiment, the first and second ligament segments may be torn or severed segments of the same ligament. In a detailed embodiment, the first spinal anatomical structure may include a ligament and the second spinal anatomical structure may include a vertebra. In a detailed embodiment, the first spinal anatomical structure may include a ligament and the second spinal anatomical structure may include an intevertebral disc. In a detailed embodiment, the first spinal anatomical structure may include a vertebra and the second spinal anatomical structure is a ligament. In a detailed embodiment, the first spinal anatomical structure may include an intervertebral disc and the second spinal anatomical structure may include a ligament.

In a detailed embodiment, a method may include a step of passing the flexible line from the fastener and at least through the portion of the first spinal anatomical structure, through at least a portion of a second anatomical structure, and through at least a portion of a third anatomical structure to the separate securing point within the body, thereby stabilizing at least the first, second and third spinal anatomical structures with respect to each other. In a detailed embodiment, at least two of the first, second and third spinal anatomical structures may include spinous processes. In a detailed embodiment, at least two of the first, second and third spinal anatomical structures may include facets.

In a detailed embodiment, the drawing step may include passing the flexible line through an implant. In a detailed embodiment, the implant may include a graft. In a detailed embodiment, the implant may include a disc implant. In a detailed embodiment, the implant may include a scaffold.

In a detailed embodiment, the first spinal anatomical structure may include a spinous process and the second spinal anatomical structure may include at least one of a pedicle and bone of a facet joint. In a detailed embodiment, the first spinal anatomical structure may include at least one of a pedicle and bone of a facet joint and the second spinal anatomical structure may include a spinous process. In a detailed embodiment, the first spinal anatomical structure may include a first side of a cervical spine and the second anatomical structure may include a second side of the cervical spine. In a detailed embodiment, a method may include passing the flexible line through a tubular implant positioned between the first and second spinal anatomical structures. In a detailed embodiment, the first spinal anatomical structure may include a first facet and the second spinal anatomical structure may include a second facet.

In a detailed embodiment, a method may include a step of tensioning at least a portion of the flexible line extending between the fastener and the separate securing point. In a detailed embodiment, the spinal anatomical structure may include annulus fibrosus. In a detailed embodiment, the spinal anatomical structure may include nucleus pulposus. In a detailed embodiment, the flexible line may extend through an intervertebral disc and through an adjacent vertebra. In a detailed embodiment, the flexible line may extend through adjacent vertebrae and an intervertebral disc between the adjacent vertebrae. In a detailed embodiment, the flexible line may extend through two vertebrae and a disc positioned between but not adjacent to each of the two vertebrae. In a detailed embodiment, the flexible line may extend through an upper spinous process and through a lower spinous process. In a detailed embodiment, the flexible line may extend through a vertebra and to or though a disc implant. In a detailed embodiment, the flexible line may extend through the spinal anatomical structure to or through a graft.

In a detailed embodiment, the flexible line may extend through the spinal anatomical structure and through or to a disc implant or a vertebral implant. In a detailed embodiment, the spinal anatomical structure may include annulus fibrosus. In a detailed embodiment, the spinal anatomical structure may include a vertebra. In a detailed embodiment, the spinal anatomical structure may include a facet.

In a detailed embodiment, the flexible line may extend through two severed portions of a spinal ligament. In a detailed embodiment, the flexible line may extend through two portions of a spinal ligament. In a detailed embodiment, the flexible line further may extend through a vertebra adjacent to at least one of the two portions of the spinal ligament. In a detailed embodiment, the flexible line may further extend through an intervertebral disc.

In a detailed embodiment, the flexible line may extend to or through a stabilization rod or plate. In a detailed embodiment, the spinal anatomical structure may include a spinuous process.

In a detailed embodiment, the flexible line may extend through at least one portion of a spinal ligament and through or to a ligament graft.

In a detailed embodiment, at least a portion of the elongate fastener placement rod may be hollow. In a detailed embodiment, the portion of the elongate fastener placement rod that may be hollow may open onto the leading end of the curved segment of the fastener placement rod. In a detailed embodiment, the step of providing, at the leading end of the curved segment of the fastener placement rod, a fastener approximate to, adjacent to or on the spinal anatomical structure, may include a step of sending the fastener through the portion of the elongate faster placement rod that is hollow to the leading end of the curved segment. In a detailed embodiment, the sending step may further include sending a flexible line with the fastener through the portion of the elongate fastener placement rod that may be hollow to the leading end of the curved segment, wherein the fastener may be secured in place utilizing at least a portion of flexible line.

In a detailed embodiment, the step of providing, at the leading end of the curved segment of the fastener placement rod, a fastener approximate to, adjacent to or on the spinal anatomical structure, may be preceded by a step of engaging the fastener with the leading end of the curved segment of the fastener placement rod.

In a detailed embodiment, a method may include a step of engaging the fastener with the leading end of the curved segment of the fastener placement rod. In a detailed embodiment, the engaging step may include a step of disposing at least a portion of the fastener within the leading end of the curved segment of the fastener placement rod. In a detailed embodiment, a method may include a step of disengaging the fastener from the leading end of the curved segment of the fastener placement rod while the fastener is approximate to, adjacent to or on the spinal anatomical structure.

In a detailed embodiment, the introducing step may include introducing the curved segment of an elongate, fastener placement rod through an incision in the skin as part of a minimally invasive procedure.

In a detailed embodiment, the spinal anatomical structure may include at least one of bone, vertebral body, nucleus pulposus, muscle, tendon and cartilage.

In a detailed embodiment, the spinal anatomical structure may include at least one bone such as a transverse process, pedicle, facet, spinous process, posterior arch, odontoid process, posterior tubercle, lateral articular process, uncinate process, anterior tubercle, carotid tubercle, odontoid process, lamina and vertebral body.

In a detailed embodiment, the spinal anatomical structure may include at least one ligament taken such as an anterior longitudinal ligament, posterior longitudinal ligament, interspinous ligament, supraspinous ligament, ligamentum flavum, intertransverse ligament, facet capsulary ligament, ligamentum nuchae, ligament of the sacrum and ligament of the coccyx spine.

In an aspect, a method for stabilizing a spinal anatomical structure may include connecting a flexible line and a fastener; introducing, through an incision in the body, a curved segment of an elongate, fastener placement rod approximate to, adjacent to or on a spinal anatomical structure, the curved segment having a leading end; providing, at the leading end of the curved segment of the fastener placement rod, the fastener and attached flexible line at a fastener placement point that is approximate to, adjacent to or on the spinal anatomical structure, the providing step including passing the fastener and attached flexible line through the curved segment of the elongate fastener placement rod to the leading end; passing the connected flexible line from approximate the fastener placement point through at least a portion of the spinal anatomical structure to a securing point; tensioning the flexible line between the fastener placement point and the securing point; and securing the flexible line at the securing point.

In a detailed embodiment, the step of securing the flexible line at the securing point may include a step of tying the flexible line. In a detailed embodiment, the step of securing the flexible line at the securing point may include a step of fastening the flexible line at the securing point using another fastener. In a detailed embodiment, the step of fastening the flexible line at the securing point using another fastener may include crimping the other fastener to the flexible line. In a detailed embodiment, the flexible line may include a suture. In a detailed embodiment, the flexible line may include a cable.

In a detailed embodiment, the passing step may be performed utilizing a gripper at a leading end of an elongate gripper rod to pull the connected flexible line from approximate the fastener placement point through at least the portion of the spinal anatomical structure to the securing point. In a detailed embodiment, the elongate fastener placement rod and the elongate gripper rod may extend from a hand-held guidance and positioning device. In a detailed embodiment, a method may include forming a hole through the portion of the spinal anatomical structure prior to the pulling step. In a detailed embodiment, the hole forming step may be performed by an elongate drill rod extending from the hand-held guidance and positioning device. In a detailed embodiment, the elongate gripper rod and the elongate drill rod may be guided by a guide tube extending from the hand-held guidance and positioning device.

In a detailed embodiment, the spinal anatomical structure may include annulus fibrosus. In a detailed embodiment, the flexible line may extend through an intervertebral disc and through an adjacent vertebra. In a detailed embodiment, the flexible line may extend through adjacent vertebrae and an intervertebral disc between the adjacent vertebra. In a detailed embodiment, the flexible line may extend through two vertebrae and a disc positioned between but not adjacent to each of the two vertebrae. In a detailed embodiment, the flexible line may extend through an upper spinous process and through a lower spinous process. In a detailed embodiment, the flexible line may extend through a vertebra and to or though a disc implant. In a detailed embodiment, the flexible line may extend through the spinal anatomical structure to or through a graft.

In a detailed embodiment, the flexible line may extend through the spinal anatomical structure and through or to a disc implant or a vertebral implant. In a detailed embodiment, the spinal anatomical structure may include annulus fibrosus. In a detailed embodiment, the spinal anatomical structure may include a vertebra. In a detailed embodiment, the spinal anatomical structure may include a facet.

In a detailed embodiment, the flexible line may extend through two severed portions of a spinal ligament.

In a detailed embodiment, the flexible line may extend through two portions of a spinal ligament. In a detailed embodiment, the flexible line may further extend through a vertebra adjacent to at least one of the two portions of the spinal ligament. In a detailed embodiment, the flexible line may further extend through an intervertebral disc.

In a detailed embodiment, the flexible line may extend to or through a stabilization rod or plate. In a detailed embodiment, the spinal anatomical structure may include a spinuous process.

In a detailed embodiment, the flexible line may extend through at least one portion of a spinal ligament and through or to a ligament graft.

In a detailed embodiment, the spinal anatomical structure may include a first spinal anatomical structure; and a method may include a step of passing the flexible line from approximate the fastener and at least through the portion of the first spinal anatomical structure, through at least a portion of a second anatomical structure to the securing point, thereby stabilizing at least the first and second spinal anatomical structures with respect to each other. In a detailed embodiment, the first spinal anatomical structure may include an intervertebral disc and the second spinal anatomical structure may include a vertebra. In a detailed embodiment, the first spinal anatomical structure may include a first vertebra and the second spinal anatomical structure may include a second vertebra. In a detailed embodiment, the first spinal anatomical structure may include a vertebra and the second spinal anatomical structure may include an intevertebral disc. In a detailed embodiment, the first spinal anatomical structure may include a first spinous process and the second spinal anatomical structure may include a second spinous process.

In a detailed embodiment, the first spinal anatomical structure may include a first ligament segment and the second spinal anatomical structure may include a second ligament segment. In a detailed embodiment, the first and second ligament segments may include torn or severed segments of the same ligament.

In a detailed embodiment, the first spinal anatomical structure may include a ligament and the second spinal anatomical structure may include a vertebra. In a detailed embodiment, the first spinal anatomical structure may include a ligament and the second spinal anatomical structure may include an intevertebral disc. In a detailed embodiment, the first spinal anatomical structure may include a vertebra and the second spinal anatomical structure may include a ligament. In a detailed embodiment, the first spinal anatomical structure may include an intervertebral disc and the second spinal anatomical structure may include a ligament.

In a detailed embodiment, the method may include a step of passing the flexible line from the fastener and at least through the portion of the first spinal anatomical structure, through at least a portion of a second anatomical structure, and through at least a portion of a third anatomical structure to the separate securing point within the body, thereby stabilizing at least the first, second and third spinal anatomical structures with respect to each other. In a detailed embodiment, at least two of the first, second and third spinal anatomical structures may include spinous processes. In a detailed embodiment, at least two of the first, second and third spinal anatomical structures may include facets.

In a detailed embodiment, the passing step may further include passing the flexible line through an implant. In a detailed embodiment, the implant may include a graft. In a detailed embodiment, the implant may include a disc implant. In a detailed embodiment, the implant may include a scaffold.

In a detailed embodiment, the first spinal anatomical structure may include a spinous process and the second spinal anatomical structure may include at least one of a pedicle and bone of a facet joint. In a detailed embodiment, the first spinal anatomical structure may include at least one of a pedicle and bone of a facet joint and the second spinal anatomical structure may include a spinous process. In a detailed embodiment, the first spinal anatomical structure may include a first side of a cervical spine and the second anatomical structure may include a second side of the cervical spine. In a detailed embodiment, the method may further include passing the flexible line through a tubular implant positioned between the first and second spinal anatomical structures. In a detailed embodiment, the first spinal anatomical structure may include a first facet and the second spinal anatomical structure may include a second facet.

In an aspect, a method for stabilizing a spinal anatomical structure may include a step for introducing a fastener approximate to, adjacent to or on a spinal anatomical structure using a curved end of an introducer means; a step for passing a flexible line attached to the fastener through at least a portion of the spinal anatomical structure to a securing point; and a step for securing the flexible line at the securing point.

In a detailed embodiment, a method may include a step for tensioning the flexible line between the fastener and the securing point.

BRIEF DESCRIPTION OF THE DRAWINGS

The detailed description refers to the following figures in which:

FIG. 1 shows an exemplary embodiment of the guidance and positioning device of the present invention;

FIG. 2 illustrates a cannulated drill system inserted in the device;

FIG. 10 illustrates another embodiment of the implant guidance and positioning device;

FIG. 11 shows a cannulated drill system disposed in a guide slot of the device;

FIG. 12 illustrates a fastener disposed in a socket on the distal end of a hookshaped member of the device;

FIG. 32 illustrates stabilization of the cervical spine and head; and

FIG. 33 shows decompression and stabilization of the spinal column.

DETAILED DESCRIPTION OF THE INVENTION

Figure 3:
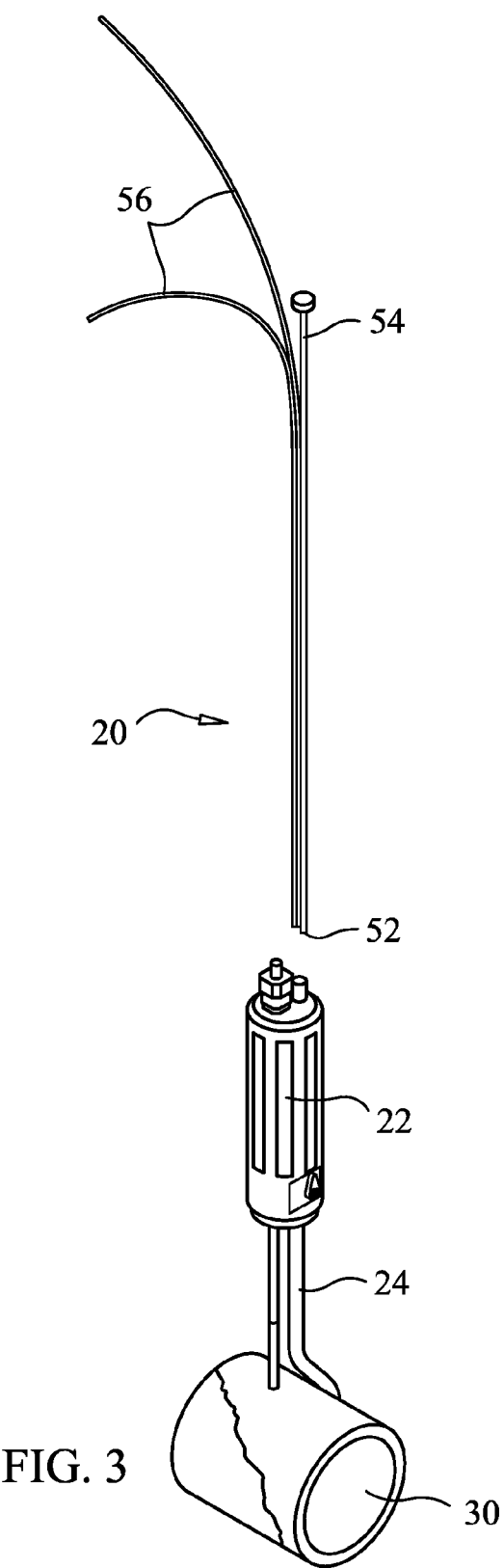
FIG. 3 shows a pushrod configured for inserting a fastener and suture into a hook of the positioning device.

The present disclosure includes instruments and methods for guiding and positioning tissue and/or an implant within the body. The instrument may provide for the placement of a biocompatible implant within tissue or may provide for dynamic and rigid fixation of tissue. The device can access and treat a fractured, incised or torn tissue, or the like, from one access area (i.e., from only one opening to the tissue to be fastened) instead of requiring two or more openings. That is, the device is a linear system that can be used with a single, small incision or portal in the skin or other soft tissue to gain access to the tissue, for example a fractured bone.

The guidance and positioning device may be an all-in-one system for creating a passage in tissue, positioning fasteners or other implants, and tensioning an elongated fastening member, like a suture, thread, wire, or pin (generally, a "flexible line"). In some embodiments, the device may allow for the implantation of multiple sutures and fasteners in tissue with little or no repositioning of the device. For example, the device may have two or more of the elements described below connected to a single grip or handle. Likewise, the incision or opening providing access to the treated bone or tissue may extend at least partially in a direction along the length of the treated area so that the processes described below may be repeatedly performed on other, nearby portions of the bone or tissue in a similar manner.

Tissue Repair

Referring now to the drawing figures in which like reference designators refer to like elements, there is shown in FIG. 1 an exemplary embodiment of the guidance and positioning device 20. The device includes a generally cylindrical handle 22 and a hook 24 with a proximal end connected to the handle 22. In one embodiment, the hook has a tubular construction (e.g., may be hollow). An interior passageway may extend from the proximal end to the distal end. The hook 24 (which may be referred to as a fastener placement rod) may be curved as illustrated in the Figures, may be angular (e.g., may have an open-sided geometric shape), or may have any other desired shape so that its distal end is disposed approximately around the bone or tissue to be treated or fastened.

The proximal portion of the hook 24 may be positioned generally parallel with the longitudinal axis of the handle 22. A plurality of interchangeable hooks 24 may be releasably and interchangeably connected to the handle. In this manner, hooks of different sizes, shapes, or other features may be selected and used as desired by a physician. Thus, the device 20 may have a lever, clip, set-screw, button, spring, match, or latch 26 that allows selective securing and releasing of hooks 24 to or from the handle 22. The lever 26 allows different sized hooks 24 to be placed in the handle 22. For example, the hook may include different sized lumens extending therethrough, may be different lengths, and/or may have different radii of curvature. The curved or angled portion 28 of the hook 24 may be configured for positioning around a fractured bone 30 (as seen in FIG. 1), multiple pieces of similar tissue, multiple pieces of different tissue, or a single tissue element. Examples of such tissue includes, not is not limited to, bone, muscle, cartilage, ligament, tendon, skin, etc. Also, the tissue may be stomach tissue, and the positioning device may be used during bariatric surgery, like gastric stapling. It is further contemplated that measurements such as the depth, angle, length, and/or compression of the hook may be determined. The handle may include guides or indicia for measuring and displaying these measurements. Alternatively, the positioning device may include sensors for taking these measurements. For example, the handle of the device may include sensors and/or radiofrequency transmitters for determining and sending measurements to a computer and/or display.

A guide channel 32 (which may be referred to as a guide tube) extends through the handle 22. Preferably, the guide channel 32 extends generally parallel with the longitudinal axis of the handle 22. The longitudinal axis of the guide channel 32 is generally aligned with or is slightly offset from the distal end 34 of the hook 24. For instance, the shortest distance between the longitudinal axis of the guide channel and the distal end of the hook may be about 2 cm or less. In other embodiments, the shortest distance may be about 1 cm or less, or even about 0.25 cm or less.

Preferably, the guide channel 32 and hook 24 are configured so that the device can be used with a single, small incision in the skin or other soft tissue to gain access to the fractured bone or other tissue requiring fixation. For example, the portions of the guide channel 32 and hook 34 that are near the opening or incision may be spaced apart from each other by about 5 cm or less, and preferably are spaced about 2 cm or less from each other near the incision or opening. In one embodiment, the guide channel and hook are generally parallel and relatively close to each other for a substantial portion of the distance between the handle and the incision or opening.

In use, the device 20 is positioned with the curved portion 28 (also referred to as a curved segment) of the hook 24 placed next to and around the tissue to be fastened. The hook may be positioned subcutaneously, percutaneously, and/or minimally invasively. The tissue may be a fractured bone, a tissue fragment having tendon and bone or ligament and bone, or a tissue with avulsion type fragments. In FIG. 2, a curved portion 28 of the hook 24 is placed around a fractured bone 30 (fracture not shown) or tissue. A drill system 36 is positioned in the guide channel 32. The drill system 36 includes a headpiece 38 configured for attachment to a drill 40. A drill bit 42 (also referred to as a drill rod) is positioned at the distal end of the drill system 36. A drill stop 44 is located distal from the headpiece 38 and prevents the drill bit 42 from penetrating too far beyond the tissue to be drilled. The drill system 36 may be a cannulated drill system. A cannula or sleeve 46 may encircle the drill bit 42 or at least the shaft portion of the drill bit 42. As the drill bit 42 creates a passage 48 through the bone 30, the sleeve 46 is positioned in the passage 48 to link the bone passage 48 and the guide channel 32. The drill system 36 is used to create a passage 48 in the bone 30 from the proximal side of the bone 30 to the distal side of the bone 30, then the drill 40 and drill bit 42 are removed from the sleeve 46 and guide channel 32. The distal opening of the bone passage 48 is generally near the distal aperture 50 (which may be located at or near the leading end) of the hook 24.

It is contemplated that the drill system may be used to create a non-linear passage in tissue. The non-linear passage may be formed to go around implants such as an intramedullary rod or prosthesis. The non-linear passage may also allow a physician to avoid critical body parts or tissues such as vessels or organs. Alternatively, a no drill system may be employed to create a passage in the tissue. Rather, as described in more detail below, the guide channel may be used to guide and position a self-introducing elongate member like a guide wire, k-wire, claw, grabber, etc. The self-introducing member may be forced through the soft or hard tissue instead of pre-drilling a passage.

Next, as seen in FIG. 3, a fastener 52 is positioned at the distal end of a flexible pushrod 54. The fastener 52 may be connected with the pushrod 54 or may be loosely fitted with the distal end of the pushrod 54. A suture 56 is looped through or connected with the fastener 52 such that one, two, or more sections, legs, strands, or portions of the suture 56 extend from the fastener 52. Examples of fasteners may be found in U.S. Pat. Nos. 5,163,960 and 5,593,425 entitled "Surgical Devices Assembled Using Heat Bondable Materials" which disclose fasteners assembled from a plurality of discrete components, one of which includes a heat bondable material for bonding the components together. The heat bondable material is preferably a polymeric or composite material suitable for surgical applications and implantation in the human body. The heat bondable material may be a biodegradable material. A laser, hot air gun, welding gun, soldering gun, or Bovie tip may be used as a heat source for bonding the fastener. U.S. Pat. No. 6,368,343 entitled "Method of Using Ultrasonic Vibration to Secure Body Tissue" further discloses using ultrasonic vibration energy to bond the heat bondable material of the components of the fastener.

U.S. Pat. No. 5,403,348 entitled "Suture Anchor" discloses an anchor for securing a suture in the body. The anchor includes a tubular wall having a central axis. The tubular wall has a proximal end and a distal end each free of axially inwardly extending slots. The tubular wall also has an inner surface extending for the entire length of the tube and defining in the anchor a central opening extending between the proximal end and the distal end. The anchor has a width less than its length. A suture may extend through the anchor within the central opening. First and second end portions of the suture extend out of opposite ends of the anchor and are sufficiently long to project out of the body when the suture is secured in the body by the anchor. The anchor has an anchoring orientation in the body achieved by manipulation of the distal end of the anchor by pulling on the second end portion of the suture. Furthermore, the anchor has a removal orientation in the body achieved by manipulation of the proximal end of the anchor by pulling on the first end portion of the suture.

U.S. Pat. No. 5,464,426 entitled "Method of Closing Discontinuity in Tissue" discloses a suture anchor having a generally cylindrical configuration with a lumen extending therethrough. In use, a suture is inserted through openings in a plurality of anchors. Pulling on the suture presses the anchors against the body tissue and presses the body tissue together. The anchors may be pushed through the body tissue with a pusher member or by pushing the anchors against each other.

U.S. Pat. No. 5,549,630 entitled "Method and Apparatus for Anchoring a Suture" discloses a tubular anchor having a polygonal cross-sectional configuration with flat outer side surfaces areas connected by a plurality of outer corner portions. A passage through the anchor may be formed by flat inner side surfaces interconnected by inner corner portions. A suture is inserted through the passage. A concentrated force may be applied against a limited area on a trailing end of the anchor to rotate the anchor to move an outer corner portion of the anchor into engagement with body tissue. The suture may engage an inner corner portion of the anchor. The suture may be inserted through a plurality of anchors and the anchors moved through a tubular member into the body tissue under the influence of force transmitted from a trailing anchor to a leading anchor. When the leading anchor is moved into the body tissue, it is rotated under the influence of force applied against a trailing end of the leading anchor. If desired, two anchors may be interconnected. A groove may advantageously be provided along the leading end and side of an anchor to receive the suture.

U.S. Pat. No. 5,713,921 entitled "Suture Anchor" discloses a suture anchor formed from body tissue. The body tissue is shaped to a desired configuration for the anchor and defines a passage through the anchor. A suture is inserted into the passage in the body tissue of the anchor. The anchor is then positioned in a patient's body with a suture extending into the passage in the anchor. The anchor may be formed of osseous body tissue, hard compact bone, dense connective body tissue, or other body tissue. The body tissue may be dried so that it absorbs fluid and expands upon being inserted into a patient's body.

U.S. Pat. No. 5,718,717 also entitled "Suture Anchor" discloses an anchor formed of a material which absorbs body liquid when exposed to body liquid. The anchor may be at least partially formed of a material having a strong affinity for body liquids. This enables the anchor to absorb body liquid and expand upon being inserted into a patient's body. At least one embodiment of the suture anchor has portions formed of a relatively hard material which does not absorb body liquids and is pressed against body tissue by the material which absorbs body liquid to mechanically interlock the suture anchor and the body tissue. The anchor may be at least partially formed of a cellular material. The cells expand to absorb body liquid. At least one embodiment of the anchor has a pointed leading end portion to form an opening in an imperforate surface on body tissue. The configuration of the anchor may be changed by tensioning the suture while the anchor is disposed in body tissue.

U.S. Pat. No. 5,782,862 entitled "Suture Anchor Inserter Assembly and Method" discloses a suture anchor inserter assembly including a manually engageable handle and a shaft which extends axially outward from the handle. The shaft includes an inner member which is fixedly connected with the handle and an outer member which is retractable into the handle. An anchor is received in a chamber formed at the outer end of the shaft.

U.S. Pat. No. 5,814,072 entitled "Method and Apparatus for Use in Anchoring a Suture" discloses a suture anchor inserter including a manually engageable handle and a shaft which extends from the handle through a passage in the anchor. During insertion of the anchor into body tissue, an end portion of the shaft pierces the body tissue in advance of the anchor. At the same time, a pusher surface on the shaft applies force against a trailing end portion of the anchor to push the anchor into the body tissue. When the orientation of the anchor is to be changed, rotational force is applied to the anchor by tensioning the suture and pressing the end portion of the shaft against an inner surface of the passage in the anchor.

U.S. Pat. No. 5,814,073 entitled "Method and Apparatus for Positioning a Suture Anchor" discloses an inserter assembly operable between a closed condition blocking movement of a suture anchor through the inserter assembly and an open condition in which the inserter assembly is ineffective to block movement of the anchor.

U.S. Pat. No. 5,845,645 entitled "Method of Anchoring a Suture" discloses a process of fastening a suture to an anchor. The suture is inserted through passages which are spaced apart along and extend transversely to a longitudinal central axis of an anchor. When the anchor is moved into body tissue, a first portion of the suture extends from the first passage in the anchor through an opening in the body tissue to a location disposed to one side of the body tissue. A second portion of the suture extends from the second passage in the anchor through the opening in the body tissue. The suture is tensioned to apply force to the anchor. The force applied to the anchor by the suture initiates tipping of the anchor and movement of an end surface on the anchor across a leading end surface on an inserter member.

U.S. Pat. No. 5,921,986 entitled "Bone Suture" discloses an anchor connected with a suture moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor.

U.S. Pat. No. 5,948,002 entitled "Apparatus and Method for Use in Positioning a Suture Anchor" discloses an apparatus which includes a tubular outer member and an inner or pusher member. During assembly of the apparatus, a suture is positioned in a slot in the outer member. During use of the apparatus, the slot facilitates visualization of the position of the suture anchor relative to body tissue. In addition, the slot facilitates separation of the apparatus from the suture after the suture anchor has been positioned in the body tissue. A suture anchor retainer may be provided at one end of the tubular outer member to grip the suture anchor and hold the suture anchor in place during assembly. The tubular outer member may be utilized to guide a drill during formation of an opening in body tissue and may be subsequently utilized to guide movement of a suture anchor into the opening in the body tissue.

U.S. Pat. Nos. 6,010,525; 6,159,234; and U.S. Pat. No. 6,475,230 entitled "Method and Apparatus for Securing a Suture" disclose improved method to secure a suture relative to body tissue. A suture retainer is moved along first and second sections of a suture toward the body tissue. When a predetermined minimum force is being transmitted between the suture retainer and the body tissue, the first and second sections of the suture are gripped with the suture retainer by plastically deforming material of the suture retainer. The material of the suture retainer cold flows under the influence of force applied against the surface areas on the suture retainer. One or more bends are formed in each of the sections of the suture to increase the holding action between the suture retainer and the sections of the suture. The bends may be formed by wrapping a turn of the suture around a portion of the suture retainer. During movement of the suture retainer toward the body tissue, the bends are moved along the first and second sections of the suture.

U.S. Pat. No. 6,045,551 entitled "Bone Suture" discloses an anchor connected with a suture moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor. The passage may extend across a fracture in the bone. The passage may have either a nonlinear or linear configuration. A tubular member may be positioned in the passage with the tubular member extending into portions of the passage on opposite sides of the fracture. Opposite end portions of the tubular member may be disposed in a compact outer layer of the bone. If desired, a member other than a suture may be used as a force transmitting member between the two anchors. The tubular member may be formed of bone.

U.S. Pat. No. 6,447,516 entitled "Method of Securing Tissue" discloses a retainer member formed of bone which secures tissue against movement relative to a portion of a bone in a patient's body. The retainer member is utilized to form an opening in a compact outer layer of a portion of the bone in the patient's body. The retainer member formed of bone is advantageously enclosed in a tubular member or sleeve to prevent breaking of the retainer member during the forming of the opening in the bone. The extent of movement of the retainer member into the bone in the patient's body is determined as the retainer member is moved into the bone. A suture may be connected with the retainer member and used to connect tissue with the bone.

U.S. Pat. No. 6,592,609 entitled "Method and Apparatus for Securing Tissue" discloses an anchor having a pointed end portion may be utilized to form an opening in a bone in a patient's body. The anchor is moved into the opening formed in the bone in the patient's body with a suture connected to the anchor. The suture may then be utilized to retain body tissue in a desired position relative to the bone. The body tissue may be either hard or soft body tissue. If desired the anchor may be utilized in conjunction with layers of soft body tissue. When a suture is used it may be secured by connecting a retainer with the suture. Alternatively, sections of the suture may be interconnected. It is believed that it may be preferred to secure the suture in place after at least a predetermined tension has been established in the suture and/or a predetermined force has been transmitted to the body tissue. The suture may be secured in place by exposing a retainer to ultrasonic vibratory energy or by applying the ultrasonic vibratory energy directly to sections of the suture.

U.S. Pat. No. 6,635,073 entitled "Method of Securing Body Tissue" discloses a process to secure a first body tissue with a second body tissue. A first anchor is moved along a first path through the first body tissue into the second body tissue. A second anchor is moved along a second path through the first body tissue into the second body tissue. A suture extending between the anchors may be tightened by moving the second anchor along a path which extends transverse to the path of the first anchor. The suture which extends between the anchors may have free ends which are connected with a suture retainer. The free ends of the suture may be interconnected either before or after the anchors are moved along the first and second paths. Alternatively, the suture may be a continuous loop which extends between the two anchors. A guide assembly may be provided to guide movement of the anchors along the two paths. The paths along which the anchors move may intersect so that the anchors may be interconnected at the intersection between the two paths.

U.S. Pat. No. 6,719,765 entitled "Magnetic Suturing System and Method" discloses an instrument and method for passing a medical implement through tissue with magnetic forces. The implement can be an implant, either permanent or temporary, and is provided with a magnetic component. A magnetic field is established and the magnetic component and/or magnetic field is manipulated to drive the implant through tissue. Alternatively, the instrument itself is the implement and includes at least one magnetic element so that a magnetic field established by an external magnetic generator drives the instrument through tissue. In another embodiment, the instrument includes two magnetic elements that are moveable with respect to one another and interaction between the magnetic elements drives the instrument through the tissue. Examples of applications of the present invention include a suture passer and a tissue anchor.

Other fastener types and fastening methods are disclosed in U.S. Patent Application Publication No. 2003/0181800, entitled "Methods of Securing Body Tissue," which discloses an improved method of securing body tissue performed with a robotic mechanism. The robotic mechanism may be utilized to tension a suture with a predetermined force and urge a suture retainer toward body tissue with a predetermined force. Ultrasonic vibratory energy may be transmitted to the suture retainer to effect a gripping of the suture by the suture retainer. The body tissue may be secured with a staple. Legs of the staple may be bonded together to secure the staple. The legs of the staple may be bonded together by transmitting ultrasonic vibratory energy to the legs of the staple. A tissue positioning assembly may be used to hold the body tissue in a desired position. Images of the body tissue being secured may be obtained using various known devices including one or more endoscopes, a fluoroscope, a magnetic resonance imaging device, and/or other known imaging devices.

U.S. Pat. No. 7,094,251, entitled "Apparatus and Method for Securing a Suture," discloses a suture retainer having an upper or cover section and a lower or base section which cooperate to define passages through which portions of a suture extend. Projections on the cover section of the retainer extend into recesses on the base section of the retainer. A center projection on the base section extends between the two projections on the cover section. The projections cooperate with surfaces on body sections of the cover and base section of the retainer to position and grip portions of the suture. The retainer may be moved along the portions of the suture while the retainer is gripped by an applicator assembly. The applicator assembly is operable to apply energy to the retainer to bond end portions of the projections on the cover section to bottoms of recesses in the base section of the retainer.

U.S. Patent Application Publication Nos. 2004/0230223 and 2004/0220616 and U.S. Pat. No. 7,329,263, entitled "Method and Device for Securing Body Tissue," disclose sutures and suture retainers positioned relative to body tissue. Energy, such as ultrasonic vibratory energy, is utilized to heat the suture retainer and effect a bonding of portions of the suture retainer to each other and/or to the suture. Portions of the body tissue may be pressed into linear apposition with each other and held in place by cooperation between the suture and the suture retainer. The suture retainer may include one or more portions between which the suture extends. The suture retainer may include sections which have surface areas which are bonded together. If desired, the suture may be wrapped around one of the sections of the suture retainer. The suture retainer may be formed with a recess in which the suture is received. If desired, the suture retainer may be omitted and the sections of the suture bonded to each other.

The characteristics and features of the fasteners and fastening methods just described may be combined and integrated with the devices and methods of the present invention. The above cited patents and patent applications are incorporated herein by reference.

Furthermore, the fasteners may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, Morse taper single piece, multi-component, solid, hollow, polygon-shaped, pointed, locking and unlocking, self-introducing, knotless, and combinations thereof. Also, the fasteners may include metallic material, polymeric material, ceramic material, composite material, body tissue, synthetic tissue, hydrophilic material, expandable material, compressible material, heat bondable material, biocompatible adhesive, and combinations thereof. Examples of body tissue include bone, collagen, cartilage, ligaments, or tissue graft material like xenograft, allograft, autograft, and synthetic graft material. The fasteners may also be made from a porous matrix or mesh of biocompatible and bioresorbable fibers acting as a scaffold to regenerate tissue.

The fasteners may also be made of or have a coating made of an expandable material. The material could be compressed then allowed to expand. Alternatively, the material could be hydrophilic and expand when it comes in contact with liquid. Examples of such expandable materials are PEEK, ePTFE, and desiccated body tissue. It is contemplated that the fasteners and implants of the present invention may include any combination of materials and agents disclosed herein. For example, a fastener may include combinations of hydrophilic material, synthetic body tissue, collagen, synthetic collagen, heat bonded material, biocompatible adhesive, and cells, such as stem cells.

Moreover, the fasteners described herein and incorporated by reference may include therapeutic substances to promote healing. These substances could include antibiotics, hydroxypatite, anti-inflammatory agents, steroids, antibiotics, analgesic agents, chemotherapeutic agents, bone morphogenetic protein (BMP), tissue inductive factors, demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener or implant. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

In addition to including the materials and agents described elsewhere herein, a fastener may take the configuration of an integrated fastener and arm member. The flexible arm may be incorporated into the fastener and extend therefrom. The arm may be connected with an end portion of the fastener or with any portion between the end portions, like the midpoint. The fastener and flexible arm may include the same or different materials and/or therapeutic agents. In use with the positioning device of the present invention, the fastener may be positioned at the distal end of the hook with the flexible arm extending from the fastener either within the lumen of the hook or exterior to the hook. Once the fastener is properly placed within the body, the flexible arm may be positioned through or around tissue and/or an implant and tensioned to compress and stabilize the tissue and/or implant. Another fastener may be connected with the flexible arm to maintain tension and position of the arm.

The sutures of the present invention may be made of metallic material, non-metallic material, composite material, ceramic material, polymeric material, copolymeric material, or combinations thereof. The sutures may be degradable, biodegradable, bioabsorbable, or nonbiodegradable. Examples of suture materials are polyethylene, polyester, cat gut, silk, nylon, polypropylene, linen, cotton, PLA, PGA, caprolactam, and copolymers of glycolic and lactic acid. Preferably, the sutures are flexible or bendable. They may be threadlike, monofilament, multifilament, braided, or interlaced. The sutures may have a coating of therapeutic substances or drugs. For example, the sutures may include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Figure 4:
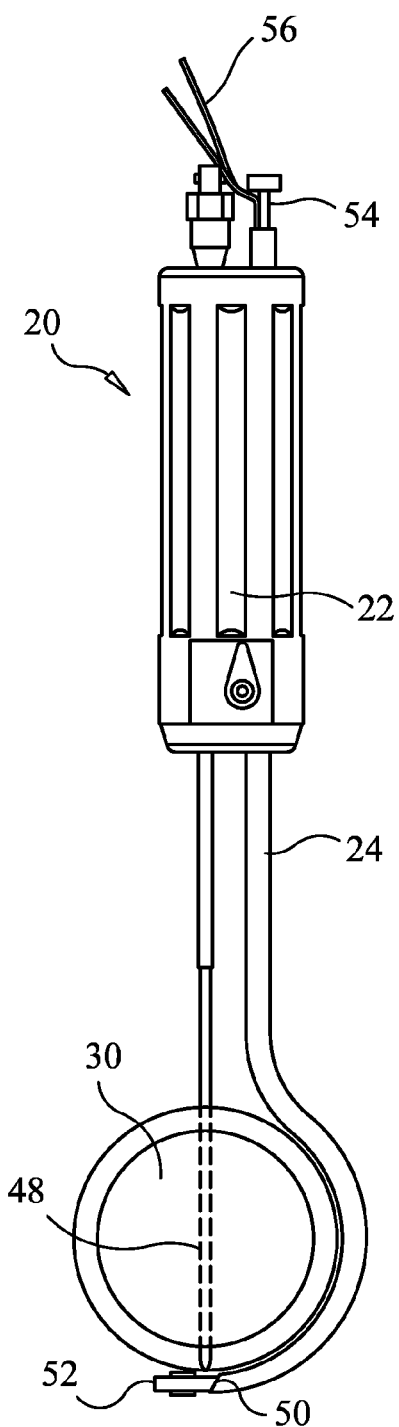
FIG. 4 illustrates a fastener and suture positioned in the hook.

With the fastener 52 and suture 56 on the distal end of the flexible pushrod 54, the pushrod 54 is moved distally through the lumen of the hook 24 until the fastener 52 is positioned generally next to the distal opening of the bone passage 48, as seen in FIG. 4. The pushrod 54 may be advanced to push the fastener 52 beyond the distal aperture 50 of the hook 24 or may be advanced to position the fastener 52 partially in and partially out of the hook 24. In the latter configuration, the fastener 52 may be easily withdrawn, if necessary, from the hook 24 by moving the pushrod 54 proximally.

Alternatively, the fastener 52 and suture assembly may be assembled in the lumen prior to inserting the device in a patient. For example, a suture may be threaded into the lumen from the distal end of the hook 24, or may be inserted through the proximal end as described above before inserting the hook into the patient's body. This allows visual confirmation of that the fastener is in a desired position before introducing it into the patient's body. The hollow interior of the hook 24 may be sized to allow sutures to be placed therethrough, but sufficiently small to preclude the fastener 52 from entering it. The distal end may have a bracket or assembly that holds the fastener 52 in a desired position. The bracket or assembly may grip the fastener in place, such as by an interference fit or with friction. In one embodiment, application of tensioning forces to the suture helps hold the fastener 52 in a desired position relative to the distal end of the hook 24.

Figure 5:
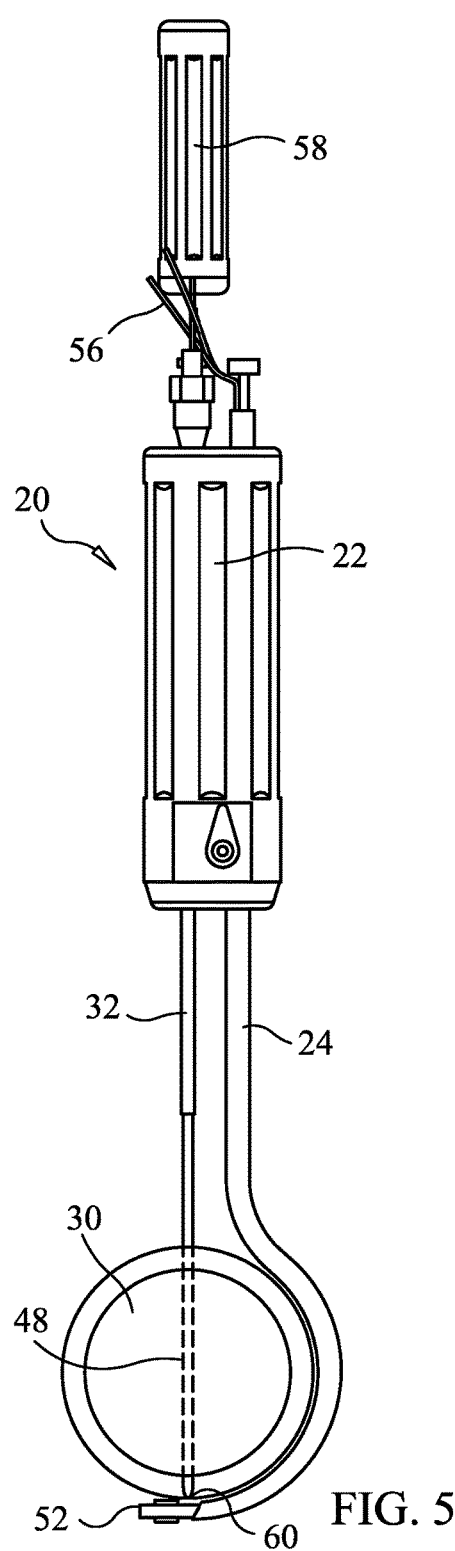
FIG. 5 shows a suture claw positioned in the guide channel of the device.

As illustrated in FIG. 5, a suture claw or grabber 58 (which may be referred to as a gripper rod) is positioned in the guide channel 32 and through the bone passage 48. A hook, claw, or clip 60 (which may be referred to as a gripper) is attached to the distal end of the suture claw 58. When the suture claw 58 is inserted distally into the guide channel 32, the hook or clip 60 exits or at least partially exits the distal opening of the bone passage 48. Since the fastener 52 is positioned near the distal opening of the bone passage 48, the hook or clip 60 of the suture claw 58 can grab or capture the suture 56 extending from the fastener 52. The suture 56 may be grabbed by rotating the suture claw 58 and allowing the suture 56 to wrap around the hook 60 at the distal end of the suture claw 58. Alternatively, the suture 56 may be grabbed with a clip 60, like an alligator clip, which may be activated from the proximal end of the suture claw 58. In another embodiment, a spiral member, like a corkscrew, may be disposed on the distal end of the suture claw. The suture claw may be twisted to thereby allow the spiral member to grab the suture. It should be understood that the suture claw should grab all the suture legs or portions attached to the fastener. For example, in FIG. 5, there are two suture legs extending from the fastener. Both legs should be captured by the suture claw either simultaneously or sequentially.

It is also contemplated that the fastener or suture may be pulled or placed in position using magnetic or electromagnetic force. For example, once a passage is drilled through tissue or an implant, a magnet may be used to pull a suture through the passage. Alternatively, when using a fastener with a flexible arm, the arm may be pulled through the passage. In these embodiments, the suture or flexible arm may include a material which is attracted to a magnet.

As previously described, a passage may not need to be pre-drilled into the tissue or bone. In this instance, the suture claw may include a distal tip configured for penetrating into and through the tissue. Using a self-introducing suture claw eliminates the need to bore a passage through the tissue before pulling the suture through the tissue.

Figure 6:
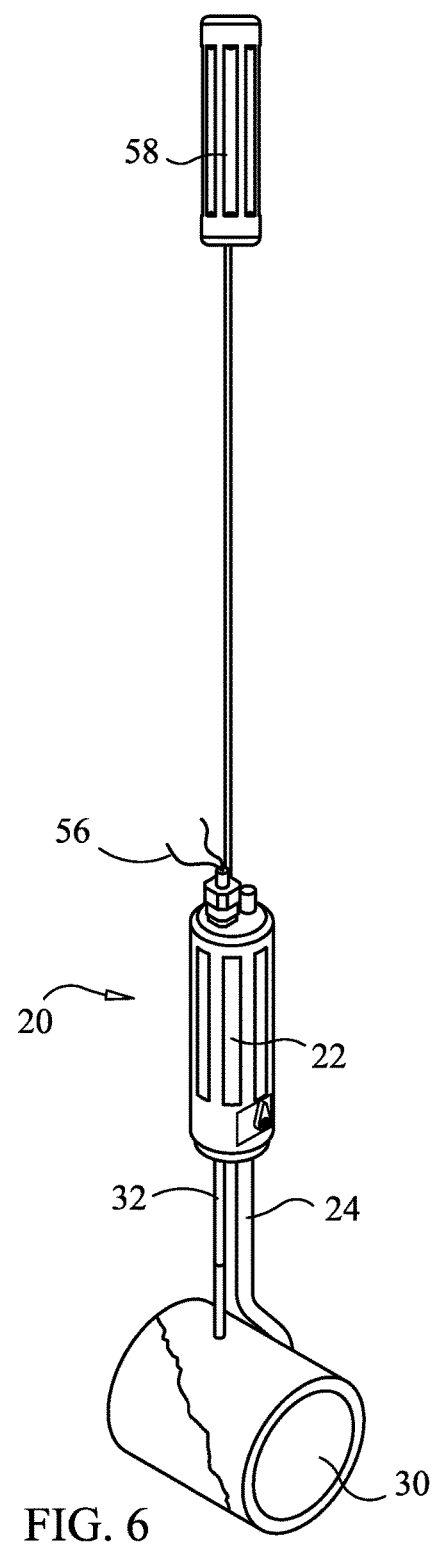
FIG. 6 illustrates the suture claw withdrawn from the guide channel with the suture disposed in the guide channel.
Figure 7:
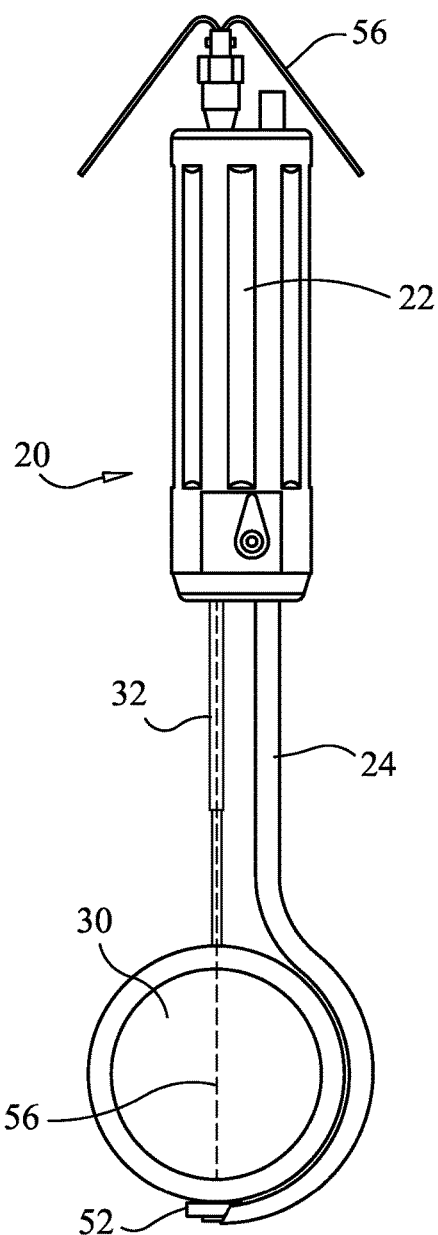
FIG. 7 shows the suture connected with the fastener on the distal side of the bone and the suture extending from the drill system.

In FIG. 6, the suture claw 58 is shown retracted from the guide channel 32. As the suture claw 58 is retracted, it pulls the suture and/or suture portions 56 from the lumen of the hook 24 and into the guide channel 32. As seen in FIG. 7, the proximal ends of the suture portions 56 may extend beyond the proximal end of the guide channel 32 when the suture claw is fully retracted.

Figure 8:
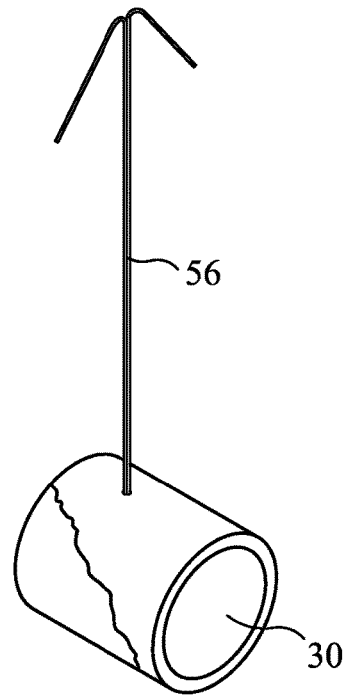
FIG. 8 illustrates a fractured bone with the suture extending therethrough.
Figure 9:
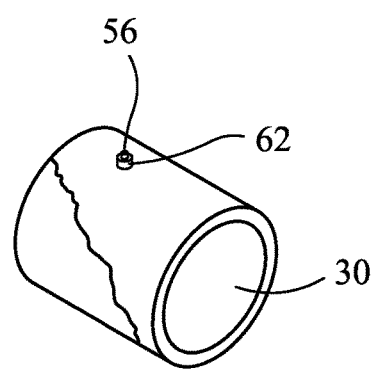
FIG. 9 shows a fastener positioned on the proximal side of the bone and secured to the suture.

As illustrated in FIG. 8, the hook, handle, and drill sleeve of the drill system are removed from the bone 30. The fastener 52 (not shown) is located on the distal side of the bone 30. The suture 56 extends from the fastener 52 through the bone passage and out the proximal opening of the bone or tissue passage. In FIG. 9, another fastener 62 is placed around or otherwise connected with the suture and/or suture portions 56. The suture 56 is tensioned, and the fastener 62 is secured to the suture 56 to thereby approximate the fracture and stabilize the bone 30. The tension of the suture pulls on the fasteners 52 and 62 generally towards each other, thereby applying pressure to the fractured bone or tissue.

Another exemplary embodiment of the guidance and positioning device 70 is illustrated in FIG. 10. The device 70 is shown positioned around a fractured bone 30. It should be understood that the device may be used to fasten any tissue type or combination of tissues as described herein. The device 70 includes a generally cylindrical handle 22 and a hookshaped elongated member 72 attached to the handle 22. In this embodiment, the hook-shaped elongated member 72 does not necessarily include a lumen extending therethrough. The proximal portion of the hook-shaped member 72 may be positioned generally parallel with the longitudinal axis of the handle 22. The device 70 may include a lever, clip, set-screw, button, spring, or latch 26 for securing and releasing the hook-shaped elongated member 72. The lever 26 allows different sized hooks to be placed in the handle 22. For example, the hooks may be of different lengths, have different radii of curvature, or have different types or sizes of bone engagement portions 28.

A guide slot 74 extends through the handle 22 generally parallel with the longitudinal axis of the handle 22. The longitudinal axis of the guide slot 74 is generally aligned with the distal end of the hook-shaped member 72. The guide slot 74 and hook-shaped member 72 are generally parallel and relatively close to each other at and just distal to the handle 22. In this configuration, a single, small, percutaneous incision may be made in skin or other soft tissue to gain access to the fractured bone or other tissue requiring fixation.

In use, the device 70 is positioned with the hook-shaped portion 76 of the hook-shaped elongated member 72 placed next to and around the tissue to be fastened. In FIG. 11, the hook-shape portion 76 is placed around a fractured bone 30 (fracture not shown). A drill system 36 is positioned in the guide slot. The drill system 36 includes a headpiece 38 configured for attachment to a drill 40. A drill bit 42 is positioned at the distal end of the drill system 36. A drill stop 44 is located distal from the headpiece 38 and prevents the drill bit 42 from penetrating too far beyond the tissue to be drilled. The drill system 36 may be a cannulated drill system. The drill system 36 is used to create a passage 48 in the bone 30 from the proximal side of the bone 30 to the distal side of the bone 30. The distal opening of the bone passage 48 is generally near a socket 78 at the distal end of the hook-shaped portion 76 of the elongated member 72.

As previously noted, a drill system may not be needed to form a passage in the tissue. An elongated member with a distal tip configured for penetrating through tissue may be placed in the guide slot and used for passage through tissue. The elongate member may be a guide wire, k-wire, needle, or like device.

FIG. 12 illustrates the socket 78 at the distal end of the hook-shaped portion 76 of the elongated member. The socket 78 is dimensioned and configured for holding and/or carrying a fastener 52. The socket 78 may be a hollow cylinder or any other configuration capable of accepting a fastener 52. As seen in FIG. 11, the socket 78 is positioned at the distal end of the hook-shaped member 72 such that the fastener 52 is generally aligned with the distal opening of bone passage 48. The fastener may include characteristics, materials, therapeutic substances, coatings, or any other features as described herein. It is contemplated that the socket may hold the fastener magnetically, frictionally, with an interlocking mechanism such as a snap, with adhesive, etc.

Figure 13:
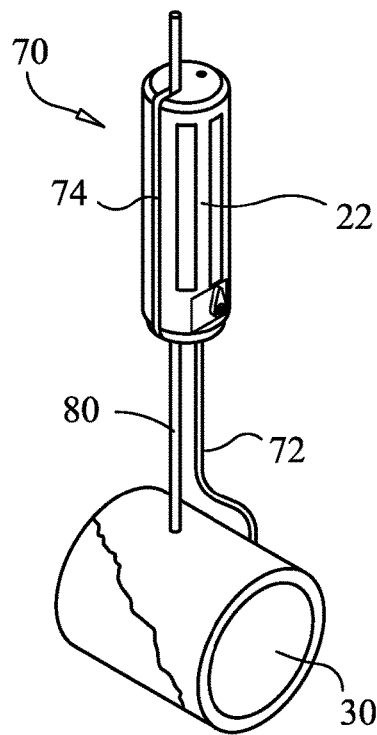
FIG. 13 shows a fastening member positioned in the guide slot of the device.
Figure 14:
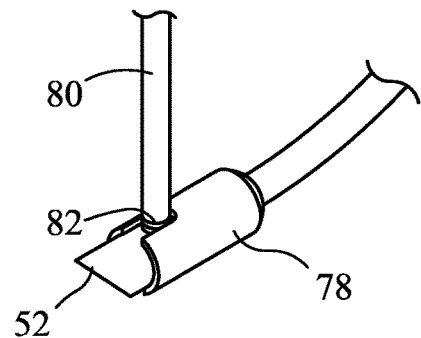
FIG. 14 illustrates a threaded distal portion of the fastening member disposed in a threaded hole of the fastener.

Next, as shown is FIG. 13, the drill system is removed from the guide slot 74. A fastening member 80 is placed in the guide slot 74 and through the passage in the bone 30. The fastening member 80 is moved distally through the passage and inserted into the fastener disposed in the socket at the distal end of the hook-shaped member 72. The fastening member may be made of metal, polymer, ceramic, composite, body tissue, or combinations thereof. The fastening member may also include features, therapeutic agents, and coatings similar to the fastener and suture described herein. FIG. 14 illustrates one exemplary embodiment of the connection between the fastening member 80 and the fastener 52. The distal end of the fastening member includes a threaded portion 82, and the fastener 52 includes a threaded hole. The fastening member 80 is screwed into the fastener 52. Other examples of connecting the fastening member and fastener include ball and socket, hook and loop, mechanical expansion, material expansion, dovetail, orientation change, heat bondable material, biocompatible adhesive, and other similar connection means.

In the embodiment wherein a drill system is not used create a passage in the tissue, the fastening member 80 may include a sharp or pointed distal tip to allow the member to be moved through the tissue, free of a passage. Using a self-introducing fastening member may eliminate the need to pre-drill the passage in the tissue.

Figure 15:
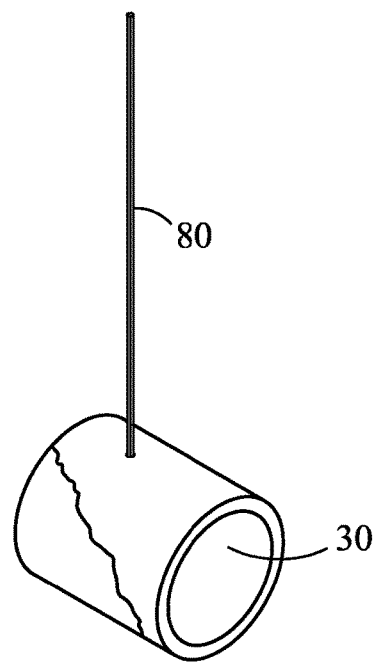
FIG. 15 shows a fractured bone with the fastening member extending therethrough.
Figures 16, 17:
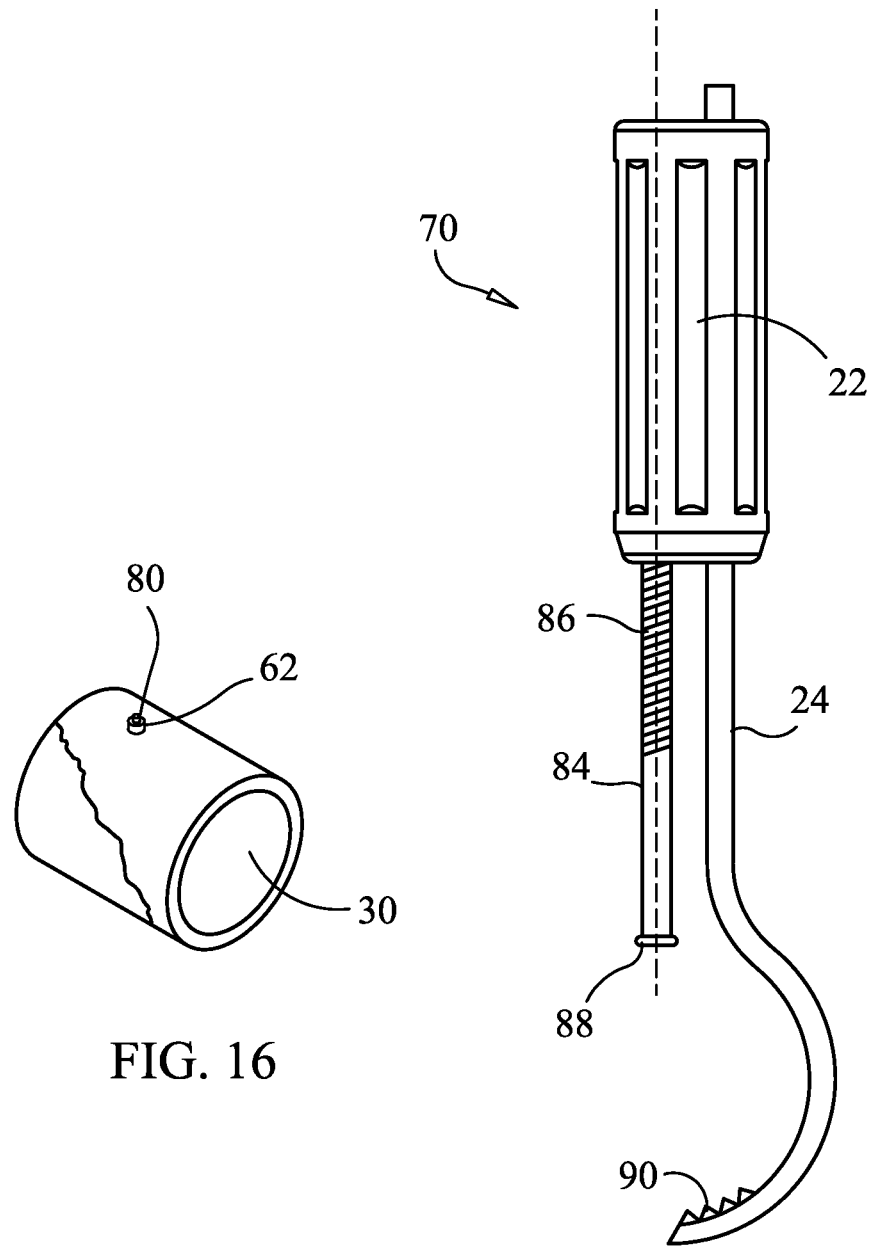
FIG. 16 illustrates a fastener positioned on the proximal side of the bone and secured to the fastening member.
FIG. 17 shows one embodiment of a clamping mechanism of the device.

As illustrated in FIG. 15, the guidance and positioning device is removed from the bone 30. The fastener 52 (not shown) is located on the distal side of the bone 30. The fastening member 80 extends through the bone passage and out the proximal opening of the bone passage. In FIG. 16, another fastener 62 is placed around the fastening member 80. The fastening member 80 is tensioned, and the fastener 62 is secured to the fastener member 80 to thereby approximate the fracture and stabilize the bone 30. Once again, the tension of the fastening member pulls the fasteners toward each other, which in turn causes pressure to be applied to the treated bone or tissue.

It is further contemplated that the guidance and positioning device 20, 70 may be used without a distal fastener. In this embodiment, the device 20,70 is used to position a suture on the backside or distal portion of the tissue. The suture claw, grabber, or elongate member may be placed in the guide channel or guide slot and moved distally toward the suture located at the distal end of the hook. Using the suture claw, one or two sections of the suture may be pulled through the tissue to the proximal side of the tissue. The suture or sutures may be pulled through a pre-drilled passage created by a drill system or may be pulled through a passage created by a self-introducing suture claw. Once a portion of the suture is positioned on the proximal side of the tissue (e.g., a securing point), it may be tensioned and secured with a fastener. Alternatively, the proximally extending suture section may be fastened with another section of the suture extending from the distal end of the hook and around the tissue. In this embodiment a suture loop is formed with tissue caught or positioned in the middle of the loop. The two sections of the suture may be secured with a knot or a fastener.

Figure 18:
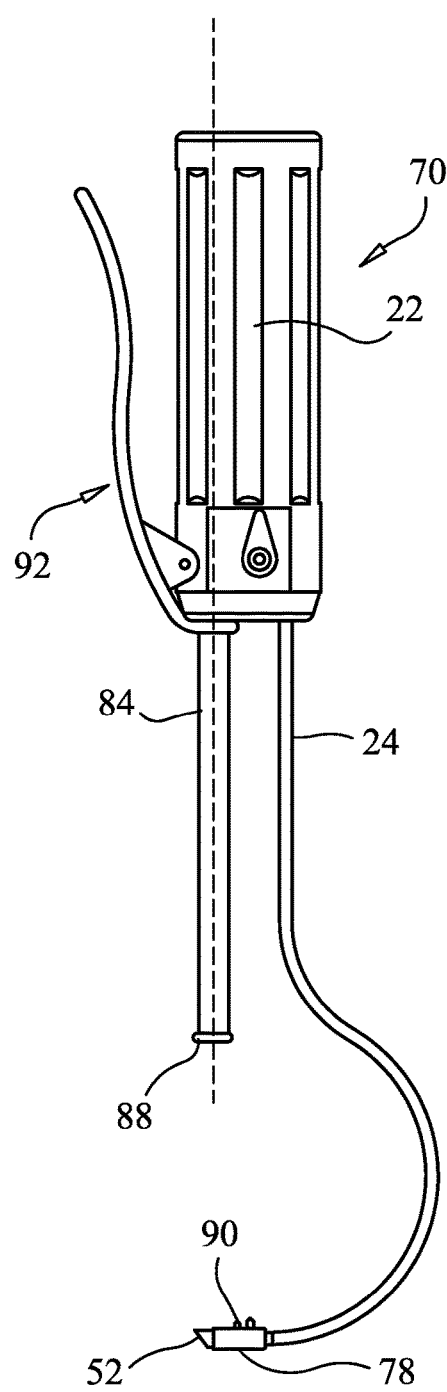
FIG. 18 illustrates another embodiment of the clamping mechanism of the device.

FIGS. 17 and 18 illustrate exemplary embodiments of clamping mechanisms for the guidance and positioning device. FIG. 17 shows a tubular clamp member 84 connected with the handle 22 of the device 20,70. The clamp member 84 includes a lumen extending therethrough for allowing passage of the drill system, suture claw, and suture as previously described. The proximal portion of the clamp member 84 includes threads 86, a ratchet, or the like for advancing the clamp member 84 into and out of the handle 22. The distal end of the clamp member 84 may include a tissue pad 88 for contacting tissue.

The tissue pad 88 may be integrally formed on the distal end of the clamp member. For example, during fabrication of the clamp member, its cross-section may initially be relatively the same size along its length, including at the distal end. Subsequently, the distal end may be deformed or flattened to have a larger cross section.

Alternatively, the tissue pad 88 also may be connected to the clamp member in a manner that allows it to rotate and/or swivel. As the clamp member 84 is moved toward the bone or tissue, some areas of the tissue pad 88 may begin to make contact even though the clamp member 84 may require additional rotation or advancement in order to obtain a desired amount of contact. If the tissue pad 88 is able to rotate or swivel, it can adjust to the contours of the bone or tissue while also reducing potential abrasion.

The contact surface of the tissue pad 88 may be substantially flat, as shown in FIG. 17, but it also may be curved or have a different shape that may correspond generally to the curvature or shape of the bone or tissue that it may contact. The contact surface also may be deformable so that it can more easily conform to an uneven surface of bone or tissue. The deformable surface of the tissue pad may be formed from a layer of elastomeric material (e.g., rubber or urethane), foam material, or any other elastomeric material suitable for use in a surgical procedure.

In use, the device 20 is positioned about a bone, or other tissue. The clamp member 84 is moved or rotated distally so that the tissue pad 88 contacts the proximal side of the bone. Further advancement of the clamp member 84 causes the tissue pad 88 to apply pressure on the bone or tissue.

Teeth or other friction means 90 may be disposed on the distal portion of the hook 24 to make contact with the distal side of the bone so that when the clamp member 84 extended, the device 20 is clamped or held in position relative to the bone. The contacting surface of the hook also may be modified or configured in the manner described above for the tissue pad.

FIG. 18 shows another embodiment of a clamping mechanism. The tubular clamp member 84 is slideably disposed or connected with the handle 22 of the device 20,70. The clamp member 84 may also include a lumen extending therethrough. A squeeze/finger grip 92 is connected with the handle 22 for advancing and retracting the clamp member 84 relative to the handle 22. When the squeeze grip 92 is moved toward the handle 22, the clamp member 84 may be moved or ratcheted distally thereby pressing the tissue pad 88 against the bone or other tissue. In this configuration, the clamp member functions like a come-along with detents and/or teeth. The squeeze grip 92 may be moved away from the handle 22 to move the clamp member 84 proximally, or a release button or spring or clip may be activated to permit the clamp member 84 to move proximally. Teeth or other friction means 90 may be disposed on the proximal side of the socket 78. With the clamp member 84 extended, the device 70 is held to the bone or other tissue between the tissue pad 88 and teeth 90 or socket 78.

Other embodiments of the clamping mechanism are further contemplated. For example, the guidance and positioning device 20,70 may include one or more inflatable members, such balloons. An inflatable balloon may be positioned along the hook at a location where the hook passes near the proximal surface of the tissue. That is, the balloon may be located at the proximal end of the curved portion of the hook. In a deflated configuration, the device may be properly positioned by the physician. The balloon may then be inflated to press against the proximal side of the tissue causing the distal end of the hook to press against the distal side of the tissue and thereby hold or lock the device in place. The balloon may be inflated with air, gas, or liquid. Inflation may be made manually with a hand pump, electrically with an electric pump or battery-operated pump, or pneumatically with a pressure cartridge. The balloon may also help guide the distal end of the hook into the proper position. Multiple balloons may be inflated and/or deflated together or separately to guide the hook. Also, the balloon(s) may be used to create space in tissue.

In another example, the device 20,70 may include a balloon at the distal end of the hook. Operation of the balloon may be similar to as previously described; however, in the current embodiment, the balloon may inflate to press against the distal side of the tissue causing the proximal portion of the hook (which may include a tissue pad or gripping teeth) to press against the proximal side of the tissue to thereby hold the device in position. Furthermore, two or more balloons may be used to position and hold the device relative to the tissue. The plurality of balloons may be located along the hook or guide channel and inflated together or individually to properly align and hold the device in place. In addition to holding the device relative to the tissue, the balloon or balloons may compress the tissue, tissue elements, and/or implant. With the tissue and/or implant compressed, a fastener or other implant may be positioned within the body.

Figure 19:
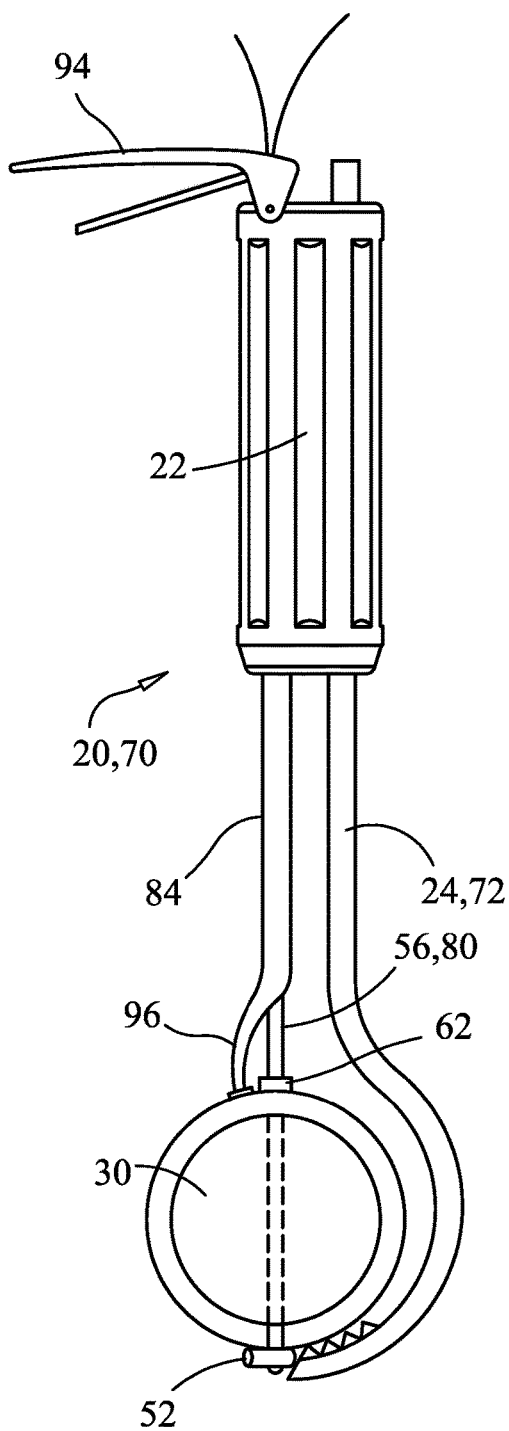
FIG. 19 shows an embodiment of a tensioning mechanism of the device.

As illustrated in FIG. 19, the device 20,70 may include a tensioning mechanism 94 to tension the suture 56 or fastening member 80. The tensioning mechanism 94 may be attached to the handle 22, tubular member 24, elongated member 72, or other component of the device 20,70. After the suture 56 or fastening member 80 is inserted through the passage in tissue, like a fractured bone 30, the tensioning mechanism 94 may pull and tension the suture 56 or fastening member 80 while a proximal fastener 62 is positioned to maintain the tension in the suture 56 or fastening member 80. The tensioning mechanism 94 may be, but is not limited to, two elements which pinch the suture 56 or fastening member 80 to pull it proximally or a spool which rotates to pull the suture 56 or fastening member 80. A tension gauge, strain gauge, read-out display, tension limiter, and/or an audio or visual tension indicator may be used to apply the proper tension to the suture or fastening member. Also, measurement of the tension may be accomplished with a spring, a radiofrequency emitting device, and/or a sensor such as an electrical sensor, flexible sensor, compressive sensor, piezoelectric sensor. Other examples of tension applicators are disclosed in U.S. Pat. No. 6,010,525 entitled "Method and Apparatus for Securing a Suture"; U.S. Pat. No. 6,447,516 entitled "Method of Securing Tissue"; and U.S. Pat. No. 6,635,073 entitled "Method of Securing Body Tissue." The above mentioned patents are hereby incorporated by reference.

As further shown in FIG. 19, the distal portion 96 of the tubular clamp member 84 may be offset or curved thereby exposing the suture 56 or fastening member 80 between the fractured bone 30 and clamp member 84. The tubular clamp member 84 may include a lumen extending therethrough with the lumen having an aperture at or near the proximal end of the offset portion 96 or the distal end of the straight section of the clamp member 84. The offset distal portion 96 allows a fastener 62 to be placed around the suture 56 or fastening member 80 adjacent to the proximal side of the bone 30. When the suture 56 or fastening member 80 is tensioned with the tensioning mechanism 94, the fastener 62 may be applied to maintain the tension in the suture 56 or fastening member 80.

Figure 43:
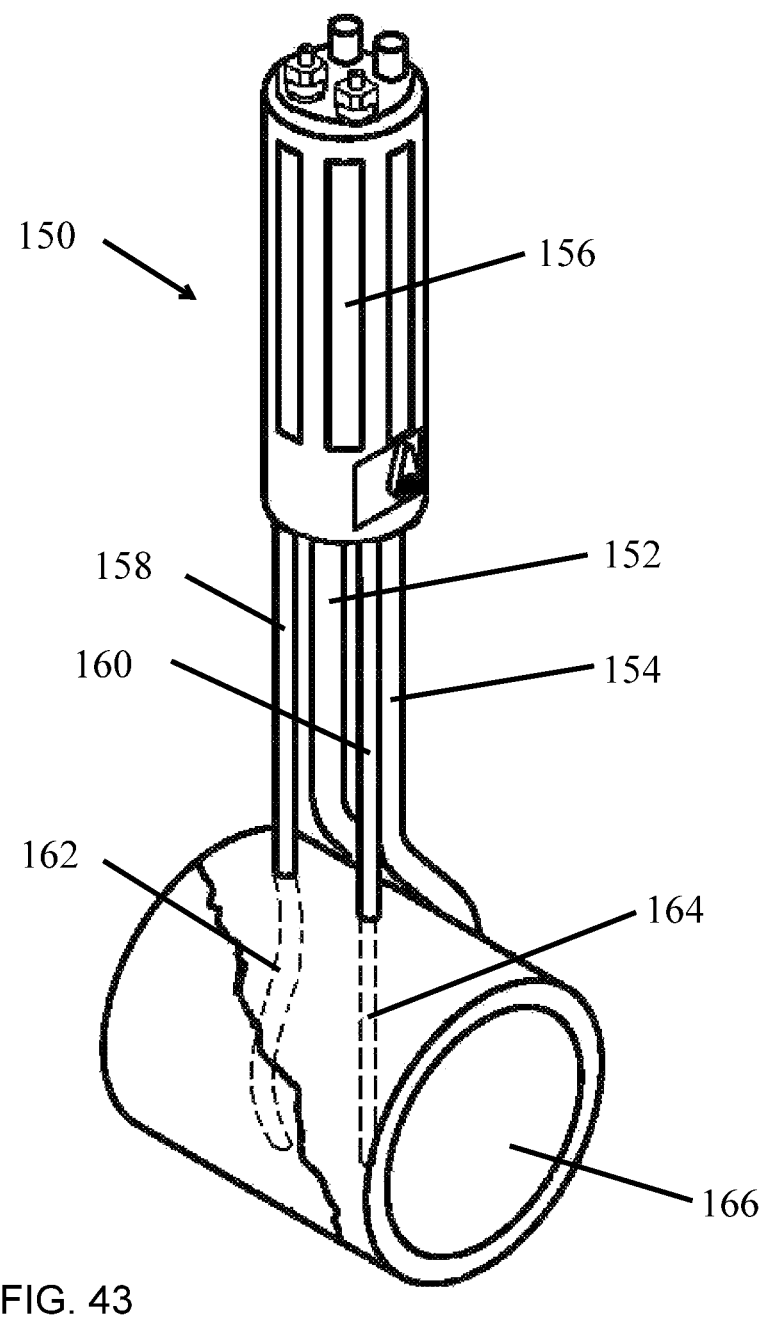
FIG. 43 shows another embodiment of the guidance and positioning device having multiple hooks and guide channels.

It is contemplated that the guidance and positioning device of the present invention may include more than one hook or elongated member for positioning multiple fasteners at the distal side of tissue. For example, as illustrated in FIG. 43, the device 150 may include two hooks or elongated members 152 and 154 attached to the handle 156 and positioned generally parallel to each other. The handle 156 may then include two guide channels, slots, or pins 158 and 160, each being aligned with one of the distal ends of the hook shaped tubular or elongated members. In this configuration, two passages 162 and 164 may be drilled in tissue, like a fractured bone 166, and two sutures or fastening members may be positioned through the passages, tensioned, and secured. One passage 162 may be non-linear while the other passage 164 may be linear. Having multiple hooks and guide channels or slots allows a physician to implant multiple fasteners thereby producing compression on the implant or tissue, enhancing the healing environment, and allowing for tissue ingrowth. The device with multiple hooks or pins may also be used to position other implants disclosed herein, such as adhesives, tissue scaffolds, medicaments, etc.

It is also contemplated that the device of the present invention may be disposable or may be sterilized after use and reused. The device may be partly disposable and partly reusable. For example, the handle may be reusable and the hook and/or guide channel may be disposable. Alternatively, the handle may be disposable. The device, its components, fasteners, drill bits, sutures, and other apparatus disclosed herein may be package in a kit. The kit may be set-up of a specific procedure, such as repair of a fractured bone, securing of an implant, approximating body tissue, etc.

Positioning Implants

The present invention not only provides an instrument and method for dynamic and rigid fastening of tissue, but it also provides for the guidance and positioning of an implant within the body. For example, the present invention may be utilized with tissue scaffolds as described in U.S. Pat. No. 7,299,805, entitled "Scaffold and Method for Implanting Cells," by Peter M. Bonutti. Viable cells may be positioned on a support structure then implanted within a body. One or more blood vessels may be connected with the support structure to provide a flow of blood through the support structure. The devices and methods of the present invention may be used to guide and position the support structure within the body and fasten the scaffold to tissue or another implant by way of a sling support and/or strut. The above mentioned application is hereby incorporated by reference.

Furthermore, the present invention may be used in combination with a medical system for the administration of a pharmaceutical agent in vivo to a patient. The medical system may include an implant positionable in a body of a patient. A pharmaceutical agent may be disposed on the medical implant and at least partially coated with a reactive coating. The reactive coating acts to control the release of the pharmaceutical agent. An energy unit may be provided for transmitting an energy signal to the reactive coating, wherein the reactive coating reacts to the energy signal to control the release rate of the pharmaceutical agent. Additionally, the energy unit may also heat up the treatment site, locally increasing vascularity at the treatment site and allowing thermal necrosis of tissue. The localized increasing in temperature increases the permeability of the local tissue, allowing for an increased and more efficient adsorption of the pharmaceutical agent into the treatment site. Additionally, in response to localized increase in temperature, which can be perceived as physical damage or an infection to the local area, the local cells may release beneficial proteins, enzymes, hormones, etc.

In another embodiment, a pharmaceutical agent, drug, or medicament may be delivered within the body using the positioning device described herein. The hook and/or guide channel of the positioning device may conduct the passage of a medicament to a specific location within the body. The drug may be transported through the lumen of the hook or guide channel or, alternatively, may be placed on the exterior of the hook or guide channel. When the positioning device has been properly aligned, the medicament may be released in a constant stream or in a pulsatile manner Examples of medicaments that may be used with the present invention include those disclosed throughout this application and, additionally, but not limited to, an anti-inflammatory agent, non-proliferative agent, anti-coagulant, anti-platelet agent, Tyrosine Kinase inhibitor, anti-infective agent, anti-tumor agent, anti-leukemic agent, and combinations thereof. One or more medicaments may be placed in one or more reservoirs which are in fluid communication with the positioning device. The reservoir may be physically separate from the device with tubing interconnecting the device and reservoir. Alternatively, the reservoir may be integrated into or attached to the positioning device. Release of the medicament may be achieved through manual operation such as with a plunger, air pressure, or valve or through electrical operation such as with a pump or valve. The medicament may be released from the positioning device or remotely away from the device as with a radiofrequency or signal emitting device.

It is contemplated that an adhesive may be delivered within the body in the way a medicament is delivered as described above. The adhesive could a polysaccharide based adhesive, fibrin adhesive, mollusc based adhesive, cyanoacrylate based adhesive, polymeric based adhesive, or other biocompatible adhesive. The adhesive could be thermally activated or pH activated. The adhesive could be a single part adhesive or a two part adhesive requiring both parts to activate the adhesive. The adhesive may also be hydrophilic or include hydrophilic material. The hydrophilic adhesive/material may expand upon imbibing liquid, such as body fluid. In use, the adhesive may be delivered within the body to bond tissue together such as soft tissue to soft tissue, soft tissue to hard tissue, or hard tissue to hard tissue. For example, portions of a fractured bone may be adhered, a muscle may be bonded to other muscle or to a tendon, and a ligament may be adhered to another ligament, to muscle, and/or to bone. The adhesive may also be used to bond an implant with body tissue or to another implant. For example, a bone or joint replacement component may be adhered to another replacement component or to other bone, tissue scaffolding with cells may be bonded to other tissue or other scaffolding, and fasteners may be adhered to tissue or sutures.

In another embodiment, an energy sink, such as a pH sink, may be incorporated into a medical implant or be positioned separate from the medical implant. The pH sink is configured to absorb energy from the energy unit, releasing a chemical to either increase or decreasing the local pH. The change in local pH can either increase or decrease the degradation rate of a degradable polymer coating, which in turn can control the release rate of a pharmaceutical agent. The pH sink can be formed from calcium carbonate. Additionally, the localized change in pH created by the pH sink has beneficial effects, which include (but are not limited to): aiding in the alleviation of localized pain, fighting of local infections, and increasing vascular flow and permeability of vessels at the treatment site to control delivery of pharmaceutical agent.

For example, a localized increasing in pH increases the permeability of the local tissue, allowing for an increased and more efficient adsorption of the pharmaceutical agent into the treatment site. The energy sink may also be used to induce the release of beneficial enzymes, proteins, hormones, etc. from the cells in the treatment site. A localized increase in acidity and/or temperature can be perceived as a physical damage or an infection to the local area. In response, to the local cells may release beneficial proteins, enzymes, hormones, etc. The positioning device and method of the present invention may be used to guide and position a drug-eluting implant, a heat sink, or pH sink within the body.

The present invention may also be used with various procedures for repairing, reconstructing, and stabilizing tissue and implants within the body. Examples of such tissue include bone, muscle, ligament, tendon, skin, organ, cartilage, and blood vessels. Examples of implants include an organ, partial organ grafts, tissue graft material (autogenic, allogenic, xenogenic, or synthetic), a malleable implant like a sponge, mesh, bag/sac/pouch, collagen, or gelatin, or a rigid implant made of metal, polymer, composite, or ceramic. Other implants include breast implants, biodegradable plates, metallic fasteners, rods, plates, screws, screw strips, spacers, cages, compliant bearing implants for one or more compartments of the knee, nucleus pulposus implant, stents, meniscal implants, tissue grafts, tissue scaffolds, biodegradable collagen scaffolds, polymeric or other biocompatible scaffolds, abdominal hernia meshes, cochlear implants, tracheal implants, small intestine submucosal grafts, TISSUEM END scaffolds, prostheses, nanotechnology devices, sensors, emitters, radiofrequency emitting diodes, computer chips, RFID (radiofrequency identification) tags, adhesives, and sealants.

Example devices and methods may provide for the repair, reconstruction, augmentation, and securing of tissue and/or implants during a surgical procedure and "on the way out" after the surgical procedure has been performed but before the skin incision has been closed. Tissue at and around the operation site and tissue between the operation site and skin incision is rebuilt so that tissue-function may be at least partially restored and the operation region may be stabilized for enhanced healing.

The devices used to repair, reconstruct, augment, and/or secure tissue or implants may be any biocompatible fastener described herein or found in the prior art. Examples of fasteners, implants, and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; and Ser. No. 10/797,685. The above-cited patents and patent applications are hereby incorporated by reference.

The fasteners may be, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the fasteners may include, but are not limited to, metallic material, polymeric material, ceramic material, composite material, body tissue, synthetic tissue, hydrophilic material, expandable material, compressible material, heat bondable material, and combinations thereof.

The fasteners of the present invention may be linear fixation fasteners. Such fasteners secure tissue or an implant with access to only one side of the tissue or implant. Generally, the fastener is advanced through the tissue or implant, usually through a pre-made passage or without a passage when the fastener is self-introducing. Once placed through the tissue or implant, a distal portion of the fastener expands, biases outward, or changes configuration such that the distal portion prevents the fastener from being pulled back out of the tissue or implant. The proximal portion of the fastener is secured thereby anchoring the tissue or implant. Examples of linear fixation fasteners are further disclosed in the incorporated references.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured during and "on the way out" following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

Exemplary Fasteners

The following Examples 1 through 8 which illustrate uses of the present invention are for illustrative purposes and are not limiting examples. As mentioned above, any fastener disclosed herein or incorporated by reference may be used with the exemplary methods. To simplify the disclosure of the present invention, a limited number of fastener types will be used to illustrate the exemplary methods. For example, the fasteners disclosed in U.S. Pat. No. 5,921,986 will be used to represent any disclosed or known fastener.

As described in the above-mentioned patent, the fasteners may be placed against tissue, and a suture may be looped through the tissue with the ends of the suture positioned within the fasteners. The suture is tensioned, and the ends of the suture are secured using a knot or any other suitable means for maintaining the tension of the suture between the fasteners. The tensioning of the suture, or similar cable, pin, thread, etc., may be controlled and monitored with sensor technology, like a magnetic sensor, which may unload the pressure if necessary. Other known tensioning apparatus may also be utilized. For example, the tensioning system may be spring loaded, pneumatic, electrical, pisoelectric, and magnetic. The tensioning system may be connected with an introducer or cannula or may be part of a fastener or implant. The tensioning system may include a read-out display outside the body. The read-out display may receive tension data through radiofrequency energy, infrared energy, or other suitable energy source.

Additionally, two or more fasteners may be utilized to secure body tissue and/or an implant. When two fasteners are used, one fastener is placed against or within one tissue area and the second fastener is placed against or within another tissue area. The suture is looped through one fastener while the ends of the suture are positioned within the second fastener. The suture is tensioned and the ends fastened with a knot or fastened using a device or method disclosed herein or incorporated by reference. In this configuration, the suture includes two generally parallel legs or portions located between the fasteners. Furthermore, when two fasteners are used, a single suture may be employed leaving only one leg between the fasteners. In this configuration, each end of the suture is positioned in different fasteners. The suture may be tensioned and the ends secured. It is further contemplated that the fasteners and sutures may be inserted through a passage in the tissue or implant. For example, a passage may be drilled through tissue or implant for insertion of the fastener or suture. With the fastener in place, these passages may be packed or filled with tricalcium phosphate (TCP), calcium phosphate, a thermal polymer, polymethyl methacrylate (PMMA) with hydroxyaptite (HA), polylactic acid (PLA) with HA, and other suitable materials. These materials may harden within the passage and would provide additional stabilization of the tissue or implant.

Figure 20A:
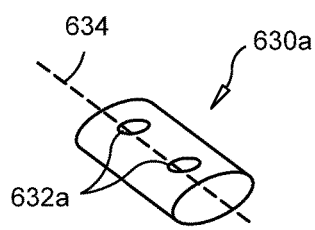
FIG. 20A illustrates one embodiment of a fastener.
Figure 20B:
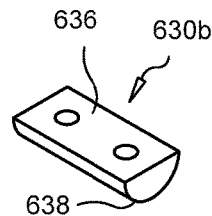
FIG. 20B illustrates one embodiment of a fastener.
Figure 20C:
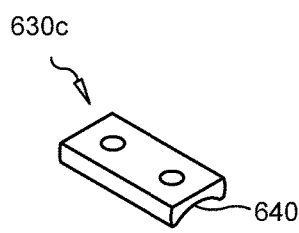
FIG. 20C illustrates one embodiment of a fastener.
Figure 20D:
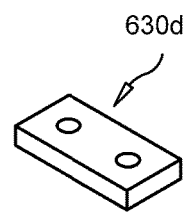
FIG. 20D illustrates one embodiment of a fastener.

FIGS. 20A-20F illustrate exemplary fasteners 630 with at least one channel 632. In an exemplary embodiment, FIG. 20A shows a generally cylindrical shaped fastener 630a. Two channels or slots 632a for receiving a suture or other similar filament extend through the fastener 630a and are generally perpendicular to the longitudinal axis 634 of the fastener 630a. FIG. 20B shows a generally half cylindrical shaped fastener 630b. The fastener 630b includes a generally flat surface 636 on one side and an arched surface 638 on the other side. The flat surface 636 may be placed against the tissue or implant to provide increased contact area. FIG. 20C shows a cylindrical shaped fastener 630c with a hemispheric or concave surface 640 on one side. This surface 640 may be placed against an implant or tissue, like a bone, which has a convex surface, so that the concave surface 640 of the fastener 630c and the convex surface of the tissue/implant are in contact. FIG. 20D shows a generally rectangular fastener 630d. The fastener 630d may have a thickness which minimizes protrusion of the fastener 630d from the outer surface of the tissue or implant which it is positioned against.

Although the exemplary fasteners have been described as generally longitudinal members, it is also contemplated that the fasteners can take the form of a square, oval, sphere, button, or any other suitable configuration.

Figure 20E:
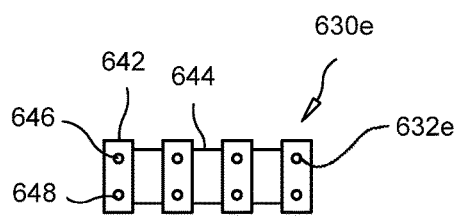
FIG. 20E illustrates one embodiment of a fastener assembly.

FIG. 20E shows a fastener assembly 630e having a plurality of fastener members 642 positioned generally parallel to each other with connecting members 644 between them. The fastener members 642 may take the form of any shape described herein or incorporated by reference. The connecting members 644 attach the fastener members 642 to each other. The connecting members 644 may be hingedly or pivotally connected with the fastener members 642 to allow the fastener assembly 630e to flex or bend. Alternatively, the connecting members 644 may be made of a flexible material such as a suture, wire, cable, or thread, which could flex or bend. In an exemplary embodiment, the channels 632e of the fastener members 642 are positioned such that a row of channels 646 are aligned over one portion of tissue located on one side of an incision while another row of channels 648 are aligned over the other portion of the tissue located on the opposite side of the incision. Multiple sutures may be used with the fastener assembly for securing tissue or an implant.

Figure 20F:
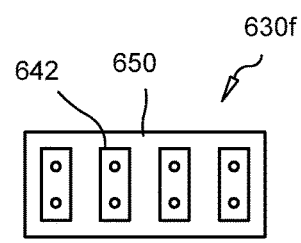
FIG. 20F illustrates one embodiment of a fastener assembly.

Alternatively, the fastener members 630e may be connected with one another with a flexible strip 650. As seen in FIG. 20F, four fastener members 642 are affixed to the flexible strip 650 and are generally parallel to each other and spaced apart from each other. The strip 650 may be handled and placed against tissue or an implant thereby positioning all the fastener members 642 at about the same time. In this regard, the flexible strip 650 can be made of or include graft material such as collagen, demineralized bone, etc. The flexible strip 650 may be expandable, hydrophilic, bioabsorbable, bioerodible, degradable, biodegradable, or combinations thereof. It may include a therapeutic substance such as antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, germicides, and combinations thereof.

The flexible strip 650 may also include an adhesive on one side to adhere the fastener members 642 to the strip 650 and may further include adhesive of the other side to adhere the strip 650 to tissue or implant. Such adhesives may include cyanoacrylate adhesives, hydrogel adhesives, monomer and polymer adhesives, fibrin, polysaccharide, Indermil® or any other biocompatible adhesive.

Figure 20G:
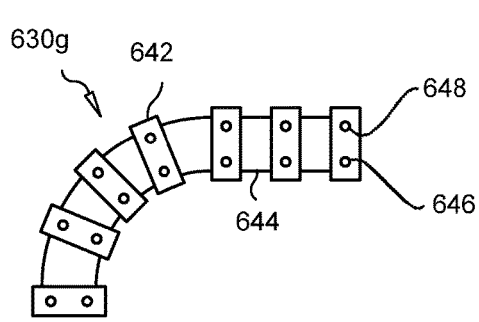
FIG. 20G illustrates one embodiment of a fastener assembly.
Figure 20H:
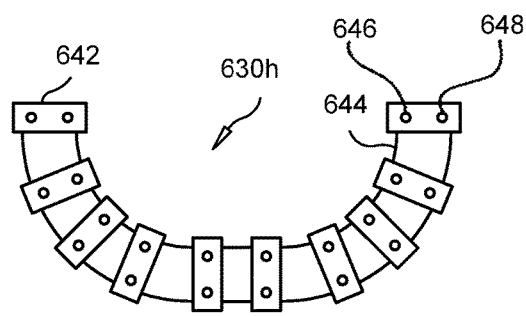
FIG. 20H illustrates one embodiment of a fastener assembly.

FIG. 20G shows another fastener assembly 630g of the present invention. This fastener assembly 630g is generally L-shaped or J-shaped. Like the fastener assemblies of FIGS. 20E and 20F, the fastener members 642 of FIG. 20G may be attached to one another with connecting members 644 or with a flexible strip 650. FIG. 20H shows a U-shaped fastener assembly 630h for closing a U-shaped incision in tissue, like those frequently made in the annulus. The rows of channels 646 and 648 of the fastener members 642 are arranged as described herein, with one line of channels 646 on one side of the incision and the other line of channels 648 of the other side of the incision.

The type and shape of the incision determine the size and configuration of the fastener assembly used. For example, a U-shaped incision could be closed with a U-shaped fastener assembly 630h, and an L-shaped incision could be closed with an L-shaped fastener assembly 630g. The suture or sutures used with the fastener assemblies may be tensioned and secured with a knot, or alternatively may be secured with devices and methods described herein and those incorporated by reference.

The exemplary fasteners may be utilized with one or more sutures, filaments, cables, or other similar implant. Generally, one suture may be used for the fasteners of FIGS. 20A-20D when only one fastener is employed. When two or more fasteners of FIGS. 20A-20D are used, multiple sutures may be employed. Similarly, the fasteners of FIGS. 20E-20H may use multiple sutures. The ends of sutures may be placed through the channels of the fastener members, and the sutures tensioned. Alternatively, a single suture could be used. That is, the single suture may be threaded in and out of the channels of the fastener members to secure tissue or an implant.

The exemplary fasteners and fastener assemblies of the present invention may be formed of any natural or artificial material. For example, they may be formed from material which is polymeric, metallic, composite, ceramic, or combinations thereof. Furthermore, the fasteners and assemblies may be made of body tissue including bone, collagen, cartilage, ligaments, or tissue graft material like xenograft, allograft, and autograft. They may be bioabsorbable, bioerodible, degradable, biodegradable, mechanically expandable, hydrophilic, and combinations thereof. The fasteners and assemblies may be made from a porous matrix or mesh of biocompatible and bioresorbable fibers acting as a scaffold to regenerate tissue.

The fasteners and assemblies may also be made of or have a coating made of an expandable material. The material could be compressed then allowed to expand once sutured to tissue or an implant. Alternatively, the fastener and assembly material could be hydrophilic and expand when it comes in contact with liquid. Examples of such expandable materials are desiccated body tissue, foam, and expandable polymers.

Furthermore, the fasteners, fastener assemblies, and implants described herein and incorporated by reference may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener or implant. Alternatively, the therapeutic substances may be impregnated or coated on the fastener or implant. Time-released therapeutic substances and drugs may also be incorporated into or coated on the surface of the fastener or implant. The therapeutic substances may also be placed in a bioabsorbable, degradable, or biodegradable polymer layer or layers.

The sutures of the present invention may be made of metallic material, non-metallic material, composite material, ceramic material, polymeric material, copolymeric material, or combinations thereof. The sutures may be degradable, biodegradable, bioabsorbable, or non-biodegradable. Examples of suture materials are polyethylene, polyester, cat gut, silk, nylon, polypropylene, linen, cotton, and copolymers of glycolic and lactic acid. In an exemplary embodiment, the sutures are flexible or bendable. They may be threadlike, monofilament, multifilament, braided, or interlaced. The sutures may have a coating of therapeutic substances or drugs. For example, the sutures may include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Figure 21A:
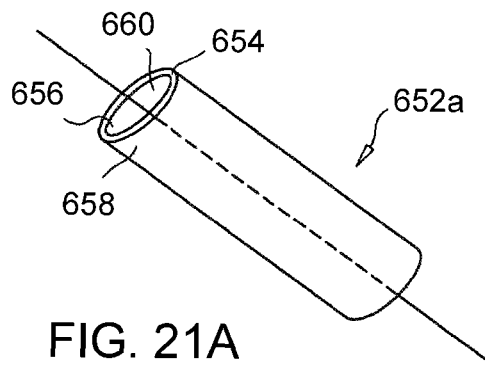
FIG. 21A illustrates one embodiment of a tissue alignment sleeve.
Figure 21B:
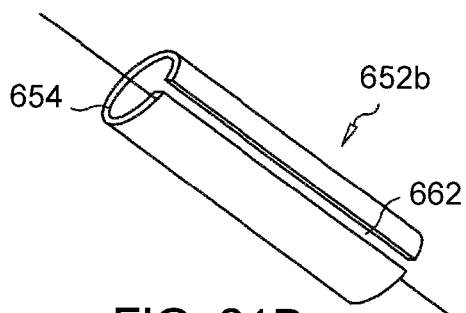
FIG. 21B illustrates one embodiment of a tissue alignment sleeve.
Figure 21C:
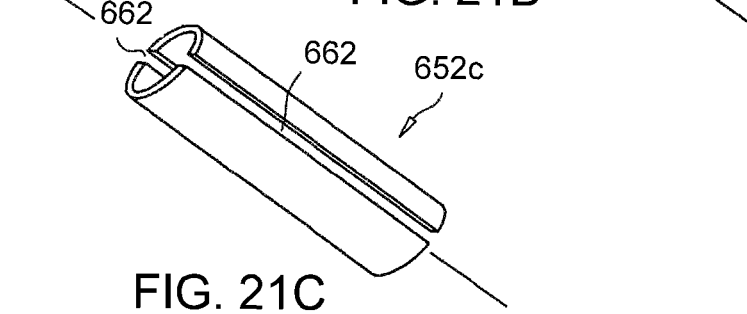
FIG. 21C illustrates one embodiment of a tissue alignment sleeve.

FIGS. 21A-21C illustrate exemplary embodiments of another fastener 652. The fastener or tubular member or sleeve 652a in FIG. 21A is generally tubular shaped having a wall 654 with an inner surface 656 and an outer surface 658. The inner surface 656 defines a lumen 660 which is dimensioned and configured for receiving a suture, cable, K-wire, or similar device. In another embodiment, FIG. 21B shows a sleeve 652b with a slit 662 through the tubular wall 654. The slit 662 allows the sleeve 652b to be decreased in diameter for implantation and increased in diameter after implantation for proper alignment of the implantation site. In a further embodiment, the sleeve 652c of FIG. 21C includes two slits 662 in the tubular wall 654 thereby forming two semi-tubular members. The semi-tubular members may be placed separately at the implantation site then aligned to form a complete tubular member. In another embodiment, the tubular member is a solid member.

The tubular member may be flexible to enable the tubular member to be inserted into a nonlinear passage through the bone. The tubular member may be formed of metallic material, composite material, ceramic material, polymeric material, or combinations thereof. The tubular member may be made from a degradable, biodegradable, bioerodible, or bioabsorbable material, such as a polymer, composite, or ceramic. The tubular member may also include a therapeutic substance to form a composite tubular member, or the therapeutic substance may be coated onto the tubular member. Furthermore, therapeutic substances or graft material (autogenic, allogenic, xenogenic, or synthetic) may be packed into the tubular member.

Figure 21D:
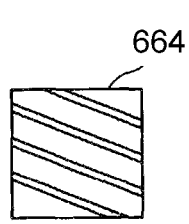
FIG. 21D illustrates one embodiment of a tissue alignment sleeve.
Figure 21E:
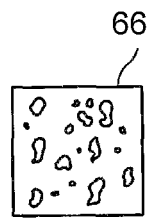
FIG. 21E illustrates one embodiment of an outer surface of a tissue alignment sleeve.
Figure 21F:
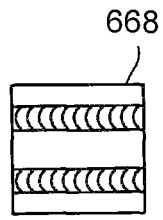
FIG. 21F illustrates one embodiment of an outer surface of a tissue alignment sleeve.
Figure 21G:
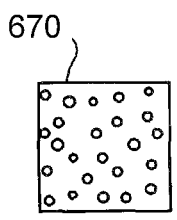
FIG. 21G illustrates one embodiment of an outer surface of a tissue alignment sleeve.

Additionally, the outer surface 658 of the tubular member 652 may include a friction or gripping means. FIG. 21D shows a portion of the outer surface 658 of the tubular member with threads 664. In FIG. 21E, the outer surface 658 includes raised pebbles, or bumps 666. FIG. 21F illustrates raised ridges or hills 668 around the outer surface 658. In addition to a friction means on the outer surface of the tubular member, the wall of the sleeve may include openings 670 for tissue ingrowth, as shown in FIG. 21G. It is contemplated that any of the fasteners, fastener assemblies, and implants disclosed herein and incorporated by reference may also include a friction or gripping means as described above.

It is further contemplated that tissue and implants may be secured with biologic adhesive, or fasteners disclosed herein and incorporated by reference may be used with the biologic adhesive. Such adhesives may include cyanoacrylate adhesives, hydrogel adhesives, monomer and polymer adhesives, fibrin, polysaccharide, Indermil® or any other biocompatible adhesive. For example, tissue scaffolds and tissue welding fasteners disclosed herein or incorporated by reference may be used with adhesive and an energy source, like ultrasound, RF, laser, electromagnet, ultraviolet, infrared, electro-shockwave, or other suitable energy source, to activate or deactivate the adhesive.

Example 1—Intervertebral Disc Repair

As previously described, the present invention provides devices and methods for fastening body tissue and/or an implant. One example is the fastening or repair of ligamentous tissue. Ligamentous tissue is found, among other locations, within intervertebral discs of the spinal column. The spinal column is formed from a number of vertebrae which are separated from each other by intervertebral discs. The intervertebral discs stabilize and distribute force between the many vertebrae. As used herein, "spinal joint" or joint of the spine includes this intervertebral space.

Generally, intervertebral discs are made of a soft, central nucleus pulposus surrounded by a tough, woven annulus fibrosus. Herniation of a disc is a result of a weakening in the annulus. Symptomatic herniations occur when weakness in the annulus allows the nucleus pulposus to bulge or leak posteriorly toward the spinal cord and major nerve roots. One treatment of a herniated, displaced, or ruptured intervertebral disc is a discectomy. This procedure involves removal of disc materials impinging on the nerve roots or spinal cord posterior to the disc. Depending on the surgeon's preference, a varying amount of nucleus pulposus is removed from within the disc space either through the herniation site or through an incision in the annulus. In addition to a discectomy, other surgical procedures where the present invention may be used include a vertebroplasty and kyphoplasty.

Figures 22, 23:
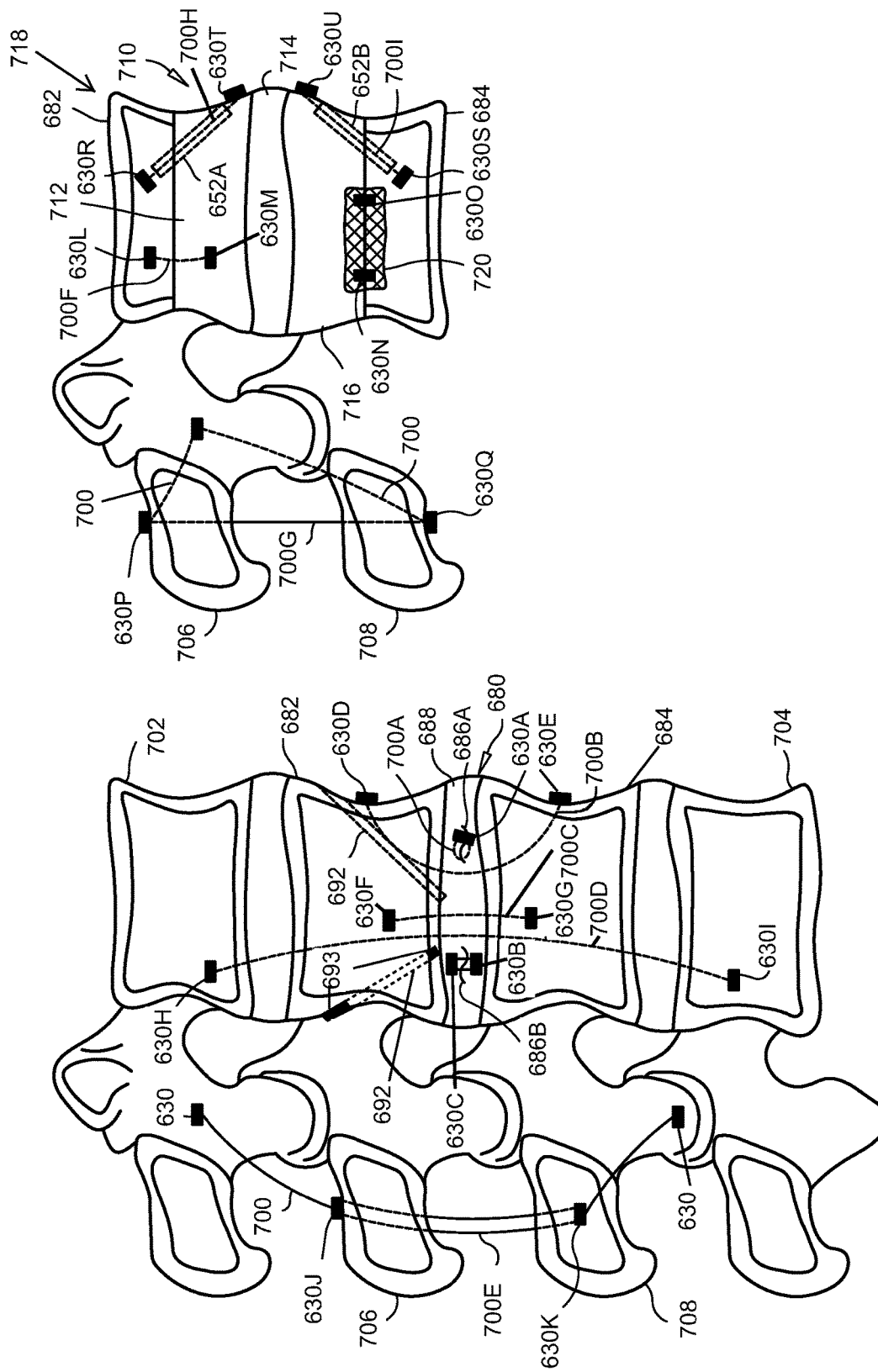
FIG. 22 illustrates the repair of the annulus of an intervertebral disc as well as stabilization of the spinal joint.
FIG. 23 illustrates a total intervertebral disc replacement implant.

FIG. 22 illustrates an exemplary embodiment of repairing an intervertebral disc 680. The disc 680 is located between a superior vertebra 682 and an inferior vertebra 684. During a discectomy, an incision 686A is made through the annulus fibrosus 688 for the removal of all or a portion of the nucleus pulposus 690. After the appropriate amount of the nucleus 690 has been removed, the incision 686A is approximated. In one embodiment showing the closing of the incision 686A, a fastener 630A is positioned generally transverse to the incision 686A. The fastener 630A is positioned on the outer surface of the annulus 688 with one channel 632 on one side on the incision 686A and the other channel 632 on the other side of the incision 686A. A suture 700A is positioned through the portions of annulus 688 located on opposite sides of the incision 686A in a generally U-shaped, looped, or curved configuration. The ends of the suture 700A are placed within the channels 632 of the fastener 630A and tensioned to draw together the two portions of the annulus 688 on opposite sides of the incision 686A. The suture 700A is secured to the fastener 630A with a knot or other means disclosed herein or incorporated by reference. Depending on the length of the incision, a plurality of fasteners and sutures may be used to fully close the incision.

One or more additional incisions 686B in the annulus 688 may be necessary for increased access to the nucleus 690. These other incisions will also need to be approximated. As seen in FIG. 22, one fastener 630B is placed on one side of the incision 686B generally parallel to the incision 686B. A second fastener 630C is positioned on the other side of the incision 686B. Closure of the incision 686B is accomplished by placing a suture or sutures through the annulus 688 so that the annulus portions on opposite sides of the incision 686B are drawn together when the suture is tensioned. The ends of the suture are secured by the fasteners 630B, 630C. Depending on the length of the incision, more than two fasteners may be utilized to approximate the incision. The closure of the incision enhances the natural healing and reconstruction of the annulus wall.

While the incisions of FIG. 22 are generally linear, other incision configurations may be made for increased accessibility through the annulus. For example, the incision may be circular, L-shaped, U-shaped, C-shaped, J-shaped, etc. Different configurations and types of fasteners illustrated in FIG. 20 may be used to close these non-linear incisions. Furthermore, these incisions may be made anywhere along the annulus (posterior, anterior, or sides) or between the annulus and vertebral body.

It is further contemplated that access to the nucleus pulposus may be obtained through a vertebral body. A channel(s) or passage(s) 692 may extend from the outer side surface of the vertebral body to the adjacent nucleus. The channel may be formed with a bone drill bit and/or a tissue harvesting device as described in U.S. Pat. No. 5,269,785 entitled Apparatus and Method for Tissue Removal, which is hereby incorporated by reference. The nucleus pulposus material may be fully or partially removed through the channel 692. Means for removing the material may include suction, scrapper, scooper, syringe, or other similar device. When no new material is required to be implanted in the region where the nucleus pulposus material was removed, the physician may close the channel 692 with graft material such as autograft material, allograft material, and/or other implantable materials disclosed herein. Alternatively, a plug/seal 693 made of metal, polymer, composite, or ceramic may be inserted into the channel 692 at either end of the channel or at both ends of the channel. The plug 693 may be removable for gaining access to the nucleus pulposus during a subsequent surgery. In this method, the annulus fibrosus is not incised, punctured, or weakened thereby reducing the healing time of the disc.

Depending on the severity of herniation or damage to the disc, nucleus pulposus replacement material or a nucleus pulposus prosthesis may be positioned between a superior vertebra and inferior vertebra. One or more incisions may be made through the annulus for access to the nucleus. The nucleus pulposus may be removed, and the replacement material or prosthesis may be inserted. Alternatively, the nucleus pulposus also remain in place with the replacement material or prosthesis positioned next to or along with the existing nucleus pulposus. Furthermore, the nucleus pulposus can be removed, conditioned or treated, and then re-implanted either alone or with a replacement material. In this regard, the temporarily removed nucleus pulposus can serve as a scaffold seeded with cells or treated with a growth factor or any other of the therapeutic agents disclosed herein. The fasteners and sutures of the present invention may be used to approximate the annulus incisions. Any number of fasteners may be used to fully close the incision.

The nucleus pulposus replacement material or prosthesis may also be positioned between the superior and inferior vertebrae through a vertebral body. As mentioned previously, a passage or channel may be made through the vertebral body extending from the outer surface to the adjacent nucleus pulposus. All, some, or none of the existing nucleus pulposus may be removed prior to insertion of the replacement material or prosthesis. In an exemplary embodiment, the replacement material is injected through the incision or channel in the vertebra and into the nucleus pulposus area. This material may be flowable for injection then once injected may become less flowable to form a gel-like material or, alternatively, may become generally solid to form a rubber-like material. Additionally, the nucleus pulposus replacement material may be flowable or injected into a balloon or bladder which may be positioned between adjacent vertebral bodies.

In another embodiment, the replacement material or prosthesis may be rubber-like or gel-like pellets having a configuration which allows them to be passed through the incision or channel. The replacement material or prosthesis may be expandable so that, once inserted, it can fill the implant area. The materials or prosthesis may include an adhesive and/or therapeutic substances, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Surgery of the intervertebral disc may leave the spine with increased motion or shear which can cause further disc failure, facet hypertrophy, or arthritis of the facet joints. To stabilize the repaired intervertebral disc "on the way out," the devices and methods of the present invention may be utilized. Flexible fixation of tissue at and near the operation site may allow compression of tissue and limited motion of the repaired intervertebral disc allowing ligaments, the annulus fibrosis, interspinous ligaments, and other soft tissue to properly heal. Stabilizing one vertebral body to another vertebral body under compression would still allow for some range of motion of the joint yet prevent disc degeneration.

The vertebral bodies may be stabilized anteriorly and/or posteriorly or with a hybrid approach such as an anterior-lateral or posterior-lateral approach. For example, on the anterior side of the spine, two fasteners 630D, 630E are positioned to secure the ends of a suture 700B placed through the intervertebral disc 680 and through adjacent vertebrae 682 and 684 in a curved or looped configuration. Two other fasteners 630F, 630G are positioned against or within the vertebrae 682 and 684 to hold the ends of a suture or sutures 700C placed through the disc 680 and through the adjacent vertebrae 682 and 684 in a generally straight configuration. Two more fasteners 630H, 630I are positioned against or within two vertebrae 702 and 704 located a distance from the repaired disc 680. A suture or sutures 700D are placed between these vertebrae 702 and 704 and tensioned. These fasteners and sutures provide stability and an enhanced healing environment for the intervertebral disc.

Finally, FIG. 22 illustrates another exemplary embodiment for stabilizing tissue around a repaired tissue region. One fastener 630J is positioned against or within an upper spinous process 706 adjacent the repaired disc 680, while another fastener 630K is positioned against or within a lower spinous process 708 also adjacent the repaired disc 680. A suture or sutures 700E are placed between the fasteners 630J, 630K and tensioned. This configuration and placement of fasteners and sutures limits or prevents the movement of the repaired disc.

Example 2—Intervertebral Disc Replacement

A damaged intervertebral disc may require replacement instead of just minor repair. The disc may be replaced with a prosthetic disc which may include a biocompatible material such as metal, polymer, composite, ceramic, or combinations thereof. FIG. 23 illustrates a total intervertebral disc replacement using the devices and methods of the present invention. While a disc replacement is shown and described below, it is contemplated that any skeletal region, like a joint, may be fitted with an implant, and the implant fastened and stabilized with the sutures, fasteners, and methods disclosed herein and incorporated by reference. For example, a knee replacement component may be affixed to the femur, tibia, or patella in accordance with the following described methods.

A disc replacement component may be positioned between the lower surface of a superior vertebra and the upper surface of an inferior vertebra. In this configuration, the disc replacement component takes the place of the original intervertebral disc and provides the proper spacing between the vertebrae. Such a disc component may be anchored to the surfaces of the superior and inferior vertebrae with the fasteners and sutures described herein and incorporated by reference.

Alternatively, and as shown in FIG. 23, the disc replacement implant 710 may be larger in height than the normal height of an intervertebral disc. The implant 710 may include upper 712, middle 714, and lower 716 sections. The upper and lower sections 712 and 716 are made of a biocompatible material which allows integration of the bone tissue of the vertebral bodies. This material may be polymeric, composite, metallic, ceramic or combinations thereof. Furthermore, the material may be body tissue including bone, collagen, cartilage, ligaments, or tissue graft material. The material may be bioabsorbable, bioerodiable, degradable, and/or biodegradable.

The upper and lower sections 712 and 716 of the disc replacement component 710 may include therapeutic substances, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides. Finally, the upper and lower sections 712 and 716 may include an expandable material. This material could be compressed then allowed to expand once implanted. Alternatively, the material could be hydrophilic and expand when it comes in contact with liquid. Examples of such expandable materials are desiccated body tissue, foam, and expandable polymers.

The middle section 714 of the disc implant 710 includes a flexible or resilient material. The middle section 714 functions as the original intervertebral disc. Materials which may be used in the middle section 714 include rubber, gel, foam, polymer, collagen, body tissue, or other suitable material. The middle section 714 may also include an expandable material. Furthermore, therapeutic substances such as antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides may be included in the middle section 114 of the disc replacement implant 710.

The disc implant 710 is positioned as follows. The superior vertebra 718 may be cut to receive the upper section 712 of the disc implant 710, while the inferior vertebra 720 may be cut to receive the lower section 716 of the implant 710. The cuts may be made from any side of the vertebral body. However, it is preferred that cutting the vertebrae 718 and 720 results in minimal disruption of the surrounding tendons, muscles, nerves, and ligaments, like the anterior and posterior longitudinal ligaments. The cuts may be planar and generally perpendicular to the longitudinal axis of the spine. The cuts may also be multi-planar such that the pedicles and facet joints are not affected or weakened.

The upper, middle, and lower sections 712, 714, and 716 of the implant 710 combine to form a height which when the implant 710 is positioned between the cut portions of the superior and inferior vertebrae 718 and 720, is generally the same height of the normal intervertebral disc and adjacent vertebral bodies. This technique is analogous to a total knee replacement procedure. The femur, tibia, and patella are cut and prepared for implant components. Once affixed, the knee replacement components return the knee joint to its normal height, configuration, and function. The spinal implant 710 of the present invention is similar; it returns the spinal column to its normal height and function.

To secure the disc implant 710 to the cut superior and inferior vertebrae 682 and 684, the sutures, fasteners, and methods of the present invention may be used. As seen in FIG. 23, a fastener 630L is positioned within or against the superior vertebra 682, while a second fastener 630M is placed within or against the upper section 712 of the disc implant 710. A suture 700F positioned between the fasteners 630L, 630M is tensioned thereby anchoring the implant 710 to the superior vertebra 682. In addition, a graft 720, like a tissue graft, is positioned over the lower section 716 of the implant 710 and the inferior vertebra 684. Two fasteners 630N, 6300 with sutures hold the graft 720 in place thereby anchoring the implant 710 to the inferior vertebra 684. To help stabilize the region around the disc implant 710, a first fastener 630P is positioned within or against a spinous process 706, while a second fastener 630Q is placed within or against a different spinous process 708. A suture 700G extends between the fasteners 630P, 630Q and is tensioned to limit movement of the spinous processes 706 and 708 and their relative vertebral bodies.

The disc implant 710 is further anchored to the superior and inferior vertebrae 682 and 684 with fasteners, sutures, and tubular members. Two fasteners 630R, 630S are positioned within or against the vertebrae 682 and 684. Two other fasteners 630T, 630U are placed within or against the disc implant. Sutures 700H, 700I are positioned within tubular members or sleeves 652A, 652B that extend between the fasteners. The tubular members 652A, 652B may have a thin cylindrical wall which engages the bone of the vertebrae 682 and 684 and material of the implant 710. By inserting the tubular members 652A, 652B in such an orientation, the superior and inferior vertebrae 682 and 684 and disc implant 710 are maintained in alignment.

It is also contemplated that the tubular member or sleeve may be placed within ligaments, tendons, muscles, bones, or combinations thereof. For example, the tubular member may be positioned in bones, including transverse process, pedicles, facets, spinous process, posterior arch, odontoid process, posterior tubercle, lateral articular process, uncinate process, anterior tubercle, carotid tubercle, and vertebral body. The tubular member may also be positioned in ligaments, including the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine.

Following intervertebral disc replacement, the spine and surrounding tissue may be become weakened. To stabilize these regions "on the way out," the devices and methods of the present invention may be utilized. Flexible fixation of tissue at and near the operation site may allow compression of tissue and limited motion of the prosthetic intervertebral disc allowing ligaments, the annulus fibrosis, interspinous ligaments, and other hard or soft tissue to properly heal. Stabilizing one vertebral body to another vertebral body under compression would allow for some range of motion of the joint and prevent disc degeneration and reduce the incidence of postoperative pain.

Example 3—Implant Anchoring

The devices and methods of the present invention may be further used to stabilize an implant positioned within the body. In addition to the type of implants mentioned elsewhere herein, the implant may be an organ, partial organ grafts, tissue graft material (autogenic, allogenic, xenogenic, or synthetic), a malleable implant like a sponge, mesh, bag/sac/pouch, collagen, or gelatin, or a rigid implant made of metal, polymer, composite, or ceramic. Other implants include breast implants, biodegradable plates, metallic fasteners, rods, plates, screws, spacers, cages, compliant bearing implants for one or more compartments of the knee, nucleus pulposus implant, stents, meniscal implants, tissue grafts, tissue scaffolds, biodegradable collagen scaffolds, and polymeric or other biocompatible scaffolds.

Also, fasteners and sutures may be utilized to position bone replacement implants including joint replacement components such as for the knee and hip, drug delivery implants, pain pumps, spinal implants, dental implants, tissue implants, tissue patches such as porcine, bovine, or patches disclosed in U.S. Pat. No. 6,592,625 to Cauthen, and other implants. The previously mentioned patent is hereby incorporated by reference. The implants, fasteners, and sutures may also include cells bonded to their surface. The cells may be bonded with a biocompatible adhesive, such as those describe herein, and/or may be bonded electromagnetically or with vanderwalls forces. While implant anchoring is described below in reference to intervertebral disc implants, it should be understood that the methods described herein may be used for anchoring any implant with the body.

Figure 24:
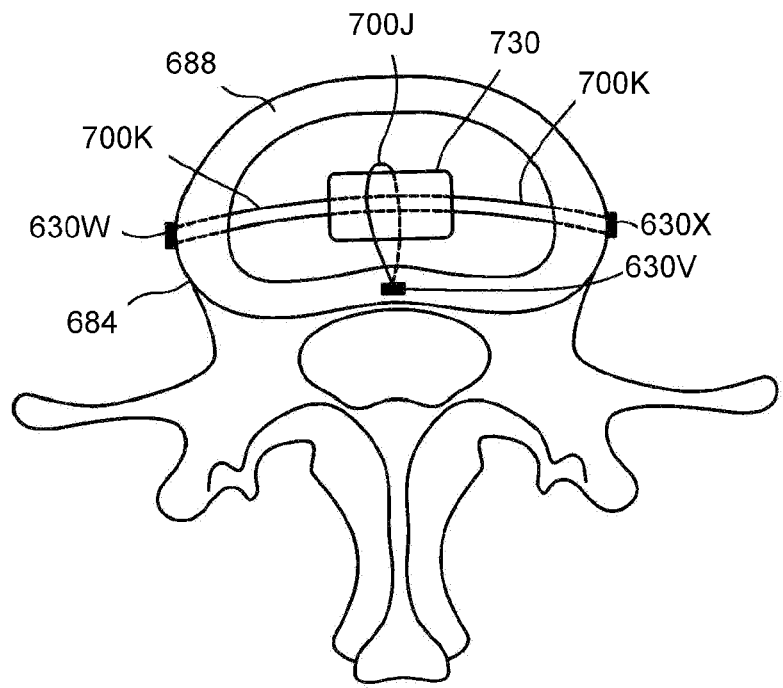
FIG. 24 illustrates an embodiment for the anchoring of an implant.

In FIG. 24, a prosthetic disc implant 730 is positioned between two vertebrae (only one shown) 684. The annulus fibrosis 688 encircles the implant 730. A fastener 630V is placed within the posterior portion of the annulus 688. A suture 700J loops around and/or through the implant 730, and the suture 700J is secured with the fastener 630V. Tensioning the suture 700J in this configuration stabilizes the implant 730 by preventing movement of the implant 730 in a posterior-anterior direction. Two other fasteners 630W, 630X are positioned against the annulus 688 generally on the sides of the annulus. A suture 700K connects these two fasteners 630W, 630X and holds the implant 730 preventing movement in a side-to-side or lateral direction. It is contemplated that the sutures and fasteners used to anchor an implant may extend through or around the implant.

Figure 25:
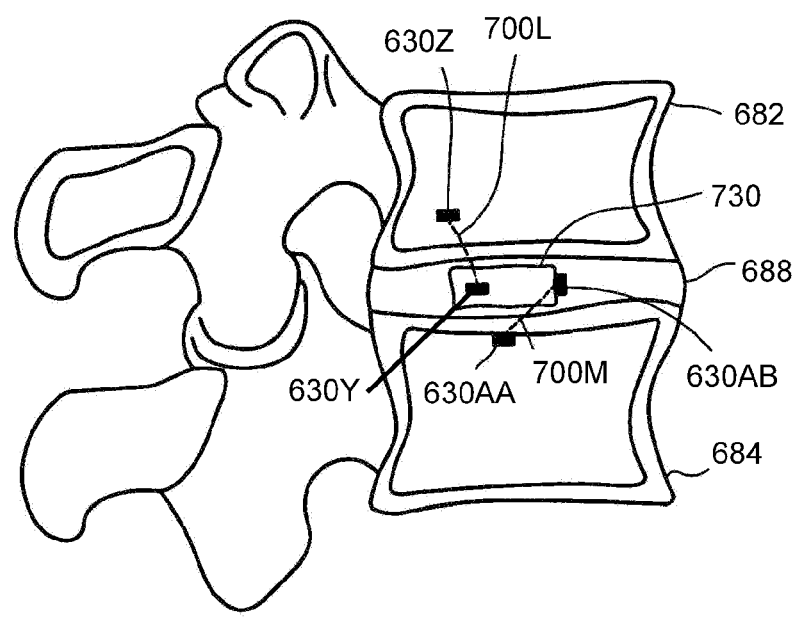
FIG. 25 shows a further embodiment for the anchoring of an implant.

FIG. 25 illustrates a disc implant 730 stabilized between a superior vertebra 682 and inferior vertebra 684. A fastener 630Y is positioned within the implant 730 while another fastener 630Z is placed within or against the superior vertebra 682. A suture 700L is tensioned between the fasteners 630 to hold the implant 730 to the lower surface of the superior vertebra 682. For added stability, a fastener 630AA is placed within or against the inferior vertebra 684 while another fastener 630AB is positioned against the implant 730. A suture 700M passes through the implant 730 and the fasteners 630AA, 630AB, and the ends of the suture 700M are secured. Any of the methods and devices described herein or incorporated by reference may be used to fasten the ends of the suture.

As previously mentioned, the implant may be any object surgically placed within the body. The implant may be made from various biocompatible materials. Also, the implant may be expandable within the body. A hydrophilic implant may swell or expand by absorbing liquid. A resilient implant may be compressed prior to implantation, then expand once positioned within the body. It is contemplated that an expandable implant may be stabilized using any method and device disclosed herein. In addition, the expandable implant may be held with fasteners and sutures such that expansion of the implant may be directed in a preferred direction or directions. Moreover, electromagnetic pulsed energy may be used to thermally lock a suture to the implant within the body.

Figure 26:
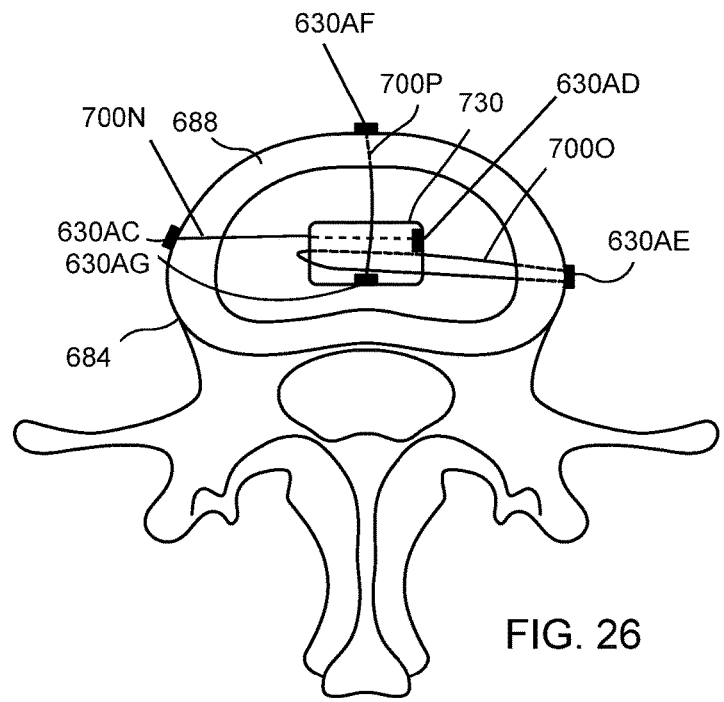
FIG. 26 illustrates anchorage of an expandable implant for directional expansion.

In FIG. 26, an implant 730 is stabilized to a vertebra 684 with multiple sutures and fasteners in a way to allow the implant to expand anteriorly. A first fastener 630AC is positioned against the left side of the annulus 688, while a second fastener 630AD is placed within or against the right side of the implant 730. A suture 700N extends between the first and second fasteners 630AC, 630AD. When tensioned, the suture 700N prevents the implant 730 from expanding to the right while holding the top of the implant 730 as well. A third fastener 630AF is positioned against the right side of the annulus 688. A suture 700O is looped around and/or through the implant 730 and secured with the third fastener 630AE to thereby prevent the implant 730 from expanding to the left. A fifth fastener 630AF is positioned against the anterior side of the annulus 688, while a sixth fastener 630AG is place within or against the posterior side of the implant 730. A suture 700P positioned between the fifth and sixth fasteners 630AF, 630AG keeps the implant 730 from expanding in the posterior direction. Given this configuration of sutures and fasteners, the implant 730 is limited to expansion in only the anterior direction. It is contemplated that other configurations of sutures and fasteners may be used to limit the expansion of the implant to one or more directions. That is, the implant may be allowed to expand to the left, right, posterior, anterior, up, down, diagonally, or any combination thereof.

Figure 27A:
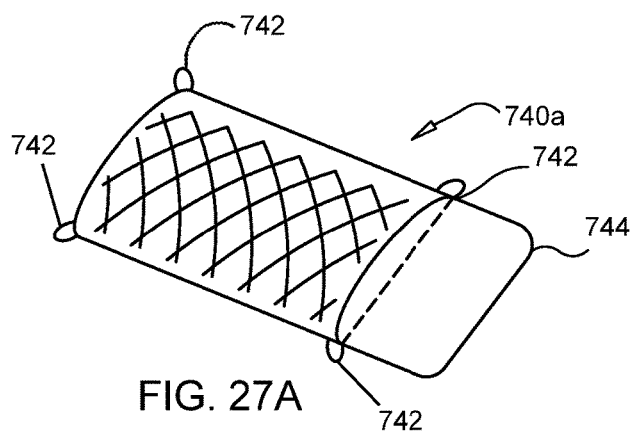
FIG. 27A illustrates one embodiment of an implant pouch.

The present invention also provides an enclosure 740 for stabilizing and anchoring an implant and furthermore to direct expansion of the implant in zero, one, or more desired directions. FIG. 27A illustrates an enclosure (or pouch, bag, sac, etc) 740a for an implant. The implant may be expandable or non-expandable. The pouch 740 may include one or more anchoring points 742. The anchoring points 742 may be placed on any of the corners, edges, or other surfaces so that when anchored the pouch 740 is properly secured at the desired location and orientation. A flap or lid 744 allows access into the pouch 740 for positioning of the implant. The flap 744 may be closed and sealed so the entire implant is enclosed. A pouch that completely encloses an expandable implant would allow the implant to expand omni-directionally until restricted by the pouch. The lip or flap may be resealable such that the material may be added to or removed from the pouch inside the body.

The pouch may be made from any natural or artificial material. For example, it may be formed from material which is polymeric, composite, metallic, ceramic, or combinations thereof. Furthermore, the pouch may be made of or include body tissue including bone, collagen, cartilage, muscle, tendon, ligaments, or other tissue graft material. The material of the pouch may be solid, porous, bioabsorbable, bioerodible, degradable, and/or biodegradable. The pouch may be made from a porous matrix or mesh of biocompatible and/or bioabsorbable fibers or filaments acting as a scaffold to regenerate tissue. The fibers or filaments may be interlaced, braided, or knitted to form the pouch.

The pouch may include or may be filled with therapeutic substances or drugs, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides. The pouch may further include or be filled with a gelatin which may contain a therapeutic agent. The gelatin inside the pouch may slowly osmotically leak out into the surrounding tissue.

The pouch may also include an adhesive to bond the pouch to the implant, to bond the pouch to the implantation site, and/or bond the flap to the pouch. Such adhesives may include cyanoacrylate adhesives, hydrogel adhesives, monomer and polymer adhesives, fibrin, polysaccharide, Indermil® or any other biocompatible adhesive. A pouch filled with one or more therapeutic agents may form a drug cocktail implant. The therapeutic agents selected to be inserted within the pouch may be specifically tailored to the needs of the patient. The pouch may be filled outside or within the patient. Once placed within the body, the therapeutic agent may slowly dissolve and exit the pouch through an osmotic member to reach the surrounding tissue.

Figure 27B:
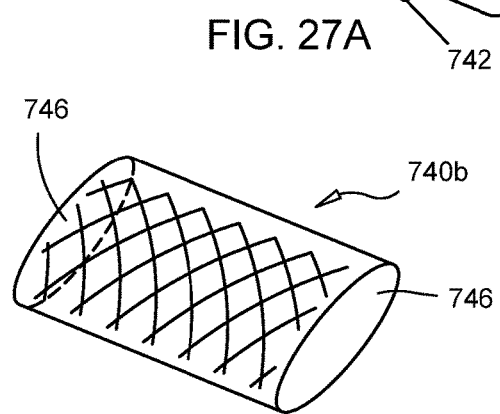
FIG. 27B illustrates one embodiment of an implant pouch.
Figure 27C:
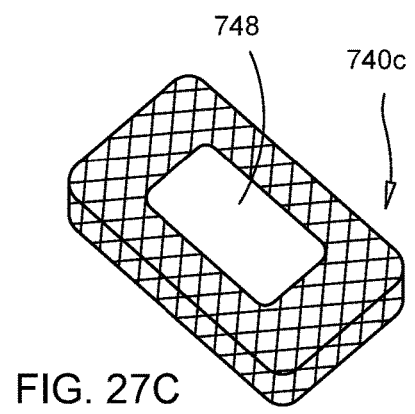
FIG. 27C illustrates one embodiment of an implant pouch.

In another exemplary embodiment, FIG. 27B shows a pouch 740*b* with a bi-directional expansion ports 746 on the left and right sides. When an expandable implant is placed in the pouch 740 and secured at the implantation site, the implant is restricted in expansion in all directions except to the left and right. It is contemplated that the pouch 740 may be designed with one or more expansion ports 746 facing in any direction. In FIG. 27C, the pouch 740*c* includes a unidirectional expansion port 748. The pouch 740 allows the expandable implant to expand upward. A pouch with an upward or downward pointing expansion port may be particularly useful for prosthetic disc replacement. Once placed in the pouch and positioned between two vertebrae, an expandable implant may expand to increase the space between the vertebrae.

Example 4—Ligament Repair

Instability of joints between bones has long been the cause of disability and functional limitation in patients. Joints of the musculoskeletal system have varying degrees of intrinsic stability based on joint geometry and ligament and soft tissue investment. Ligaments are soft tissue condensations in or around the joint that reinforce and hold the joint together while also controlling and restricting various movements of the joints. When a joint becomes unstable, either through disease or traumatic injury, its soft tissue or bony structures allow for excessive motion of the joint surfaces relative to each other and in directions not normally permitted by the ligaments.

Common problems associated with excessive joint motion are malalignment problems, subluxation of the joint, and possibly joint dislocation. Typically, the more motion a joint normally demonstrates, the more inherently loose is the soft tissue surrounding the joint. A loose ligament or group of ligaments ultimately causes skeletal disorders. However, over tensioning ligaments restricts motion of the joint and can also cause musculoskeletal problems.

The present invention also provides methods of tensioning a ligament (or tendon) or group of ligaments (or tendons) during a surgical procedure and "on the way out" after the surgical procedure to prevent joint instability and reduce pain. These methods can be applied to any ligament in the body, including the ligaments of the knee (like the anterior cruciate ligament and iliotibial band), shoulder, elbow, wrist, hip, ankle, hands, and feet. For illustrative purposes, the methods of the present invention are described with reference to the spine.

When an intervertebral disc becomes herniated and loses nucleus pulposus tissue, the distance between the adjacent vertebrae is reduced from the compression of the annulus and remaining nucleus pulposus. As a result, the spine ligaments may become relaxed. These ligaments may include, but are not limited to, the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine.

Figure 28:
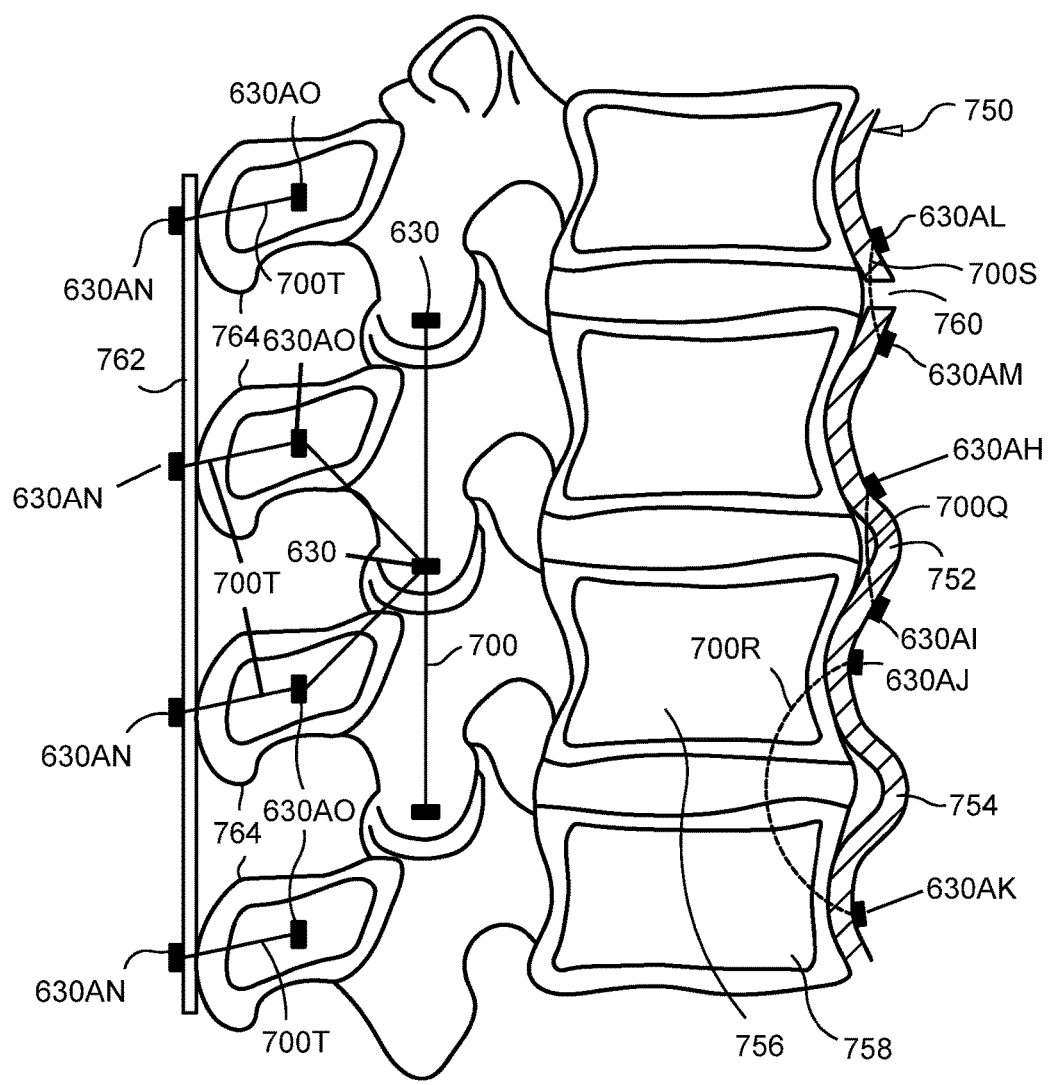
FIG. 28 illustrates ligament repair and stabilization.

FIG. 28 shows an anterior longitudinal ligament 750 which has become weakened. The fasteners and sutures of the present invention may be used to tighten the anterior longitudinal ligament 750 and decrease anteroposterior translation of the adjacent intervertebral discs. It should be understood that the methods described with respect to the anterior longitudinal ligament may also be applied to tightening other ligaments of the body.

A fastener 630AH is positioned against the ligament 750 adjacent the upper end of a loosened region 752 of the ligament 750. Another fastener 630AI is positioned against the ligament 750 adjacent the lower end of the loosened region 752. A suture 700Q is positioned through the ligament 750 and through the fasteners 630AH, 630AI. The suture 700Q is tensioned thereby tightening the loosened region 752 of the ligament 750.

In another embodiment, a fastener 630AJ is positioned against the ligament 750 above a stretched region 754. Another fastener 630AK is placed against the ligament 750 below the stretched region 754. A suture 700R is placed through the ligament 750, adjacent vertebrae 756 and 758, and intervertebral disc 680 in a curved or looped configuration. The suture 700R is tensioned to tighten the stretched region 754.

In a further embodiment represented in FIG. 28, one fastener 630AL is positioned against the ligament 750 above a missing or torn ligament region 760. Another fastener 630AM is positioned against the ligament 750 below the missing region 760. The suture 700S is positioned through the superior and inferior ends of the ligament 750 at the missing or torn region 760. The suture 700S is tensioned between the fasteners 630AL, 630AM causing the ends of the ligament 750 to be drawn together.

To stabilize the spine while a loosened or torn ligament heals, a stabilization implant, such as a rod or plate 762, may be positioned adjacent spinous processes 764. The fasteners and sutures of the present invention may be used to secure the rod or plate 762 to the spine. A plurality of fasteners 630AN is positioned against the rod or plate 762 proximate to each spinous process 764. A second plurality of fasteners 630AO is placed within or against the spinous processes 764. Sutures 700T extend between the fasteners 630AN, 630AO and are tensioned. Once anchored, the rod or plate 762 limits movement of the spinous processes 764 relative to each other thereby limiting movement of the anterior longitudinal ligament 750.

It is contemplated that the fasteners of the present invention be placed within or adjacent any bone of the body. When used in the knee, for example, the fasteners may be placed adjacent the femur, tibia, or patella. Within the spine, an fastener may be positioned adjacent a posterior arch, a spinous process, a lateral or medial articular process, a pedicle, odontoid process, uncinate process, a posterior tubercle, carotid tubercle, or a vertebral body.

Example 5—Ligament Reconstruction

The present invention may also be used in ligament or tendon reconstruction. Ligaments are frequently damaged, detached, torn, or ruptured as the result of injury or surgery. A damaged ligament can impede proper motion of a joint and cause pain. Therefore, during or "on the way out" from a surgical procedure, a ligament may be reconstructed using a fastener, a tissue graft, and/or a tissue scaffold with or without cells.

The devices and methods of the present invention may be used with a tissue or artificial graft to tension and stabilize the damaged ligament. Any ligament of the body may be repaired using the present invention, including the ligaments of the spine, shoulder, elbow, hip, knee, ankle, feet, and hands. The present invention is described in reference to ligaments of the spine including the anterior and posterior longitudinal ligaments, interspinous ligaments, supraspinous ligaments, superior costotransverse ligaments, ligamentum flavum, facet capsulary ligament, intertransverse ligament, ligamentum nuchae, and ligaments of the sacrum and coccyx spine.

Figure 29:
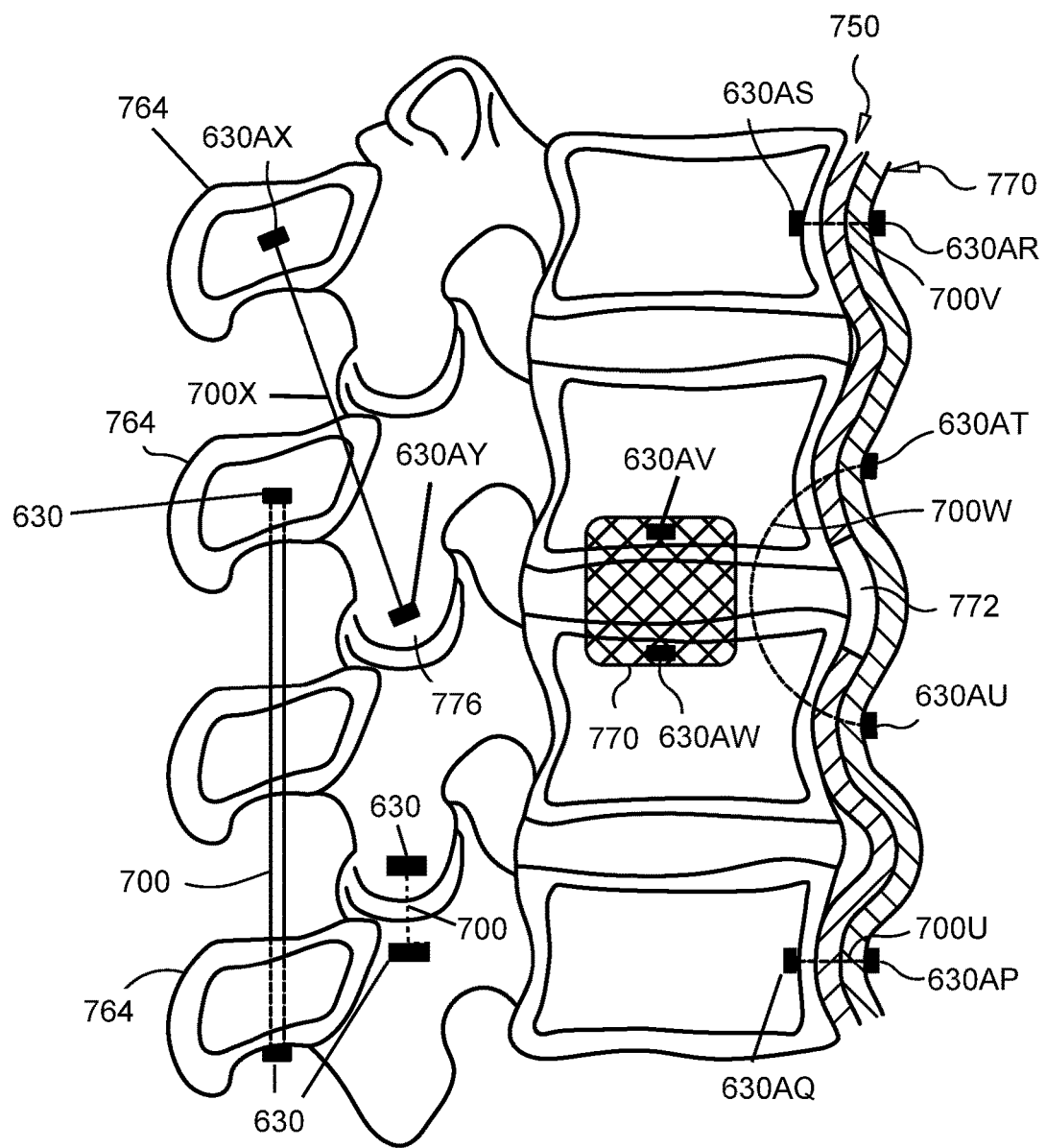
FIG. 29 shows ligament reconstruction and stabilization.

In an exemplary embodiment, FIG. 29 shows a damaged anterior longitudinal ligament 750. A ligament graft 770 is positioned adjacent the damaged region 772. A first fastener 630AP is placed against the inferior end of the ligament graft 770, while a second fastener 630AQ is positioned within or against a vertebral body 774. A suture 700U extends through the graft 770, ligament 750, and vertebra 774. The suture 700U is tensioned, and the ends of the suture 700U are secured. Similarly, two fasteners 630AR, 630AS and a suture 700V are positioned at the superior end of the ligament graft. To further anchor the ligament graft 770 to the anterior longitudinal ligament 750, one fastener 630AT is positioned against the graft 770 on one side of the damaged region 772, and another fastener 630AU is placed against the graft 770 on the other side of the damaged region 772. A suture 700W is placed through the graft 770, ligament 750, adjacent vertebrae 682 and 684, and intervertebral disc 680 in a generally curved, looped, or C configuration. The suture 700W is tensioned, and the ends of the suture 700W secured. It is also contemplated that the curved or looped suture may be placed through multiple intervertebral discs and vertebrae.

In another embodiment, FIG. 29 shows a graft 770 positioned between two adjacent vertebrae 682 and 684. The ligament or bone graft 770 is positioned adjacent the damaged region 772 of the anterior longitudinal ligament 750. The graft 770 may be attached using any of the devices and methods described herein and incorporated by reference. In an exemplary embodiment, two fasteners 630AV, 630AW are placed at the superior and inferior ends of the graft 770. Two other fasteners (not shown) are positioned within or against each vertebra 682 and 684. Sutures are positioned between the fasteners and tensioned.

To stabilize the longitudinal ligament 750 while the damaged region 772 heals, sutures and fasteners may be placed on the posterior side of the spine for stabilization. One fastener 630AX is placed within or against a spinous process 764, while another fastener 630AY is positioned within or against a pedicle or bone of the facet joint 776. A suture 700X extends between the fasteners 630AX, 630AY thereby limiting movement of the spine. FIG. 29 shows an additional stabilization device between an upper and lower spinous process. In this configuration, the suture and fasteners provide additional restriction to the movement of the spine.

The ligament or bone graft may be obtained from a variety of sources and/or made from various materials. In an exemplary embodiment, the ligament graft is made of collagen. The graft could also include autograft, allograft, or xenograft material. The graft may be a tendon graft, bone-tendon-bone graft, or a meniscus graft. Other material which may be used in the formation of the graft is polymer, carbon fiber, PEEK, PTFE, a biodegradable material, elastic or flexible material, Gore-Tex®, or woven fiber. The ligament graft may include therapeutic substances. These include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Use of grafts or patches to repair, reconstruct, and augment tissue, like a ligament, may include patches such as TissueMend® patches, Restore® patches, or similar products.

Example 6—Ligament Augmentation

In addition to ligament repair and reconstruction, the devices and methods of the present invention may be used for ligament or tendon augmentation. Ligament augmentation reinforces or supplements natural ligaments. A ligament may be augmented or reinforced after it has been repaired or reconstructed. Also, a non-repaired ligament may be augmented prophylactically. In this case, the augmentation may be used to increase the load-bearing capacity of the ligament or tendon. Additionally, or alternatively, the augmentation may be used to prevent a potential injury to a ligament or tendon. For example, an athlete may undergo minimally invasive surgery to reinforce a ligament or tendon so as to prevent the ligament or tendon from being injured later in the athlete's career. Many talented athletes' careers are cut short because of any injury to a body joint, like the knee, shoulder, ankle, spine, wrist, or hip. If an athlete desired to prevent or at least reduce the chance of sustaining a career ending injury, he/she could have surgery to augment or "fail-safe" a joint and its ligaments and tendons even if there are no other risk factors other than the occupation. Of course, other risk factors, such as genetic predisposition, could be considered, if desired.

The devices and techniques described herein relate to augmenting any ligament or tendon of the body including ligaments of the knee, shoulder, spine, hand, foot, hip, and elbow. For illustrative purposes only, ligament augmentation is described with reference to the anterior cruciate ligament (ACL) of the knee. It should be understood that the description of augmentation to the knee is not limiting to other ligaments and tendons.

Figure 30:
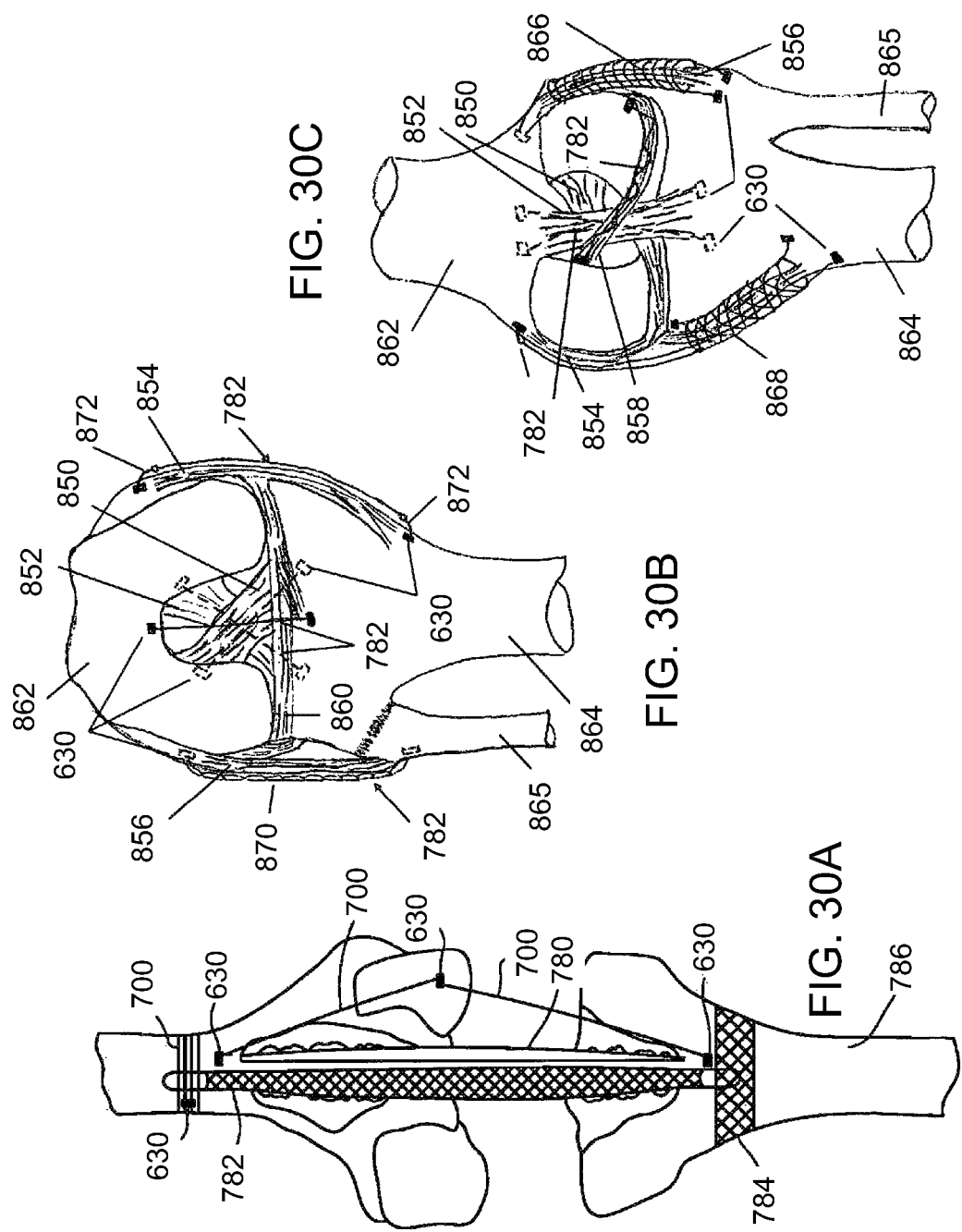
FIG. 30A illustrates one embodiment of ligament augmentation/reinforcement.
FIG. 30B illustrates one embodiment of ligament augmentation/reinforcement.
FIG. 30C illustrates one embodiment of ligament augmentation/reinforcement.

In an exemplary embodiment, fasteners and a suture (or similar device like a cable, band, flexible moment arm, pin, rod, or K-wire) may be used to augment a ligament. Referring to FIGS. 30A, 30B, and 30C, a fastener 630 may be positioned near one end of the ligament 780, while another fastener 630 may be placed near the opposite end of the ligament 780. The suture or cable 700 may be placed between the fasteners 630 and may be generally parallel with the ligament 780. The suture 700 may be tensioned, and the ends of the suture 700 secured with the fasteners 630. It is contemplated that multiple fasteners and multiple sutures may be utilized to augment the ligament. For example, a suture 700 may be placed at an angle to the ligament 780 with the ends of the suture 700 secured with fasteners 630. Having multiple sutures at different angles relative to each other and/or the ligament may provide multiple-direction augmentation.

In a further exemplary embodiment, a tissue graft or scaffold (reinforcement means) 782 may be used to augment the ligament or tendon 780. The graft or scaffold 782 may be configured and include materials as described herein. The graft or scaffold 782 may be positioned generally parallel to the ligament 180 requiring augmentation. The ends of the graft 782 may be anchored to bone, ligament, or other tissue using the devices and methods of the present invention. For example, one fastener may be positioned in or against the graft while another fastener may be placed in or against adjacent tissue. A suture may be tensioned between the fasteners, and the ends of the suture secured with the fasteners. Also, a fastener 630 may be positioned against the graft or adjacent tissue, and a suture 700 may be wrapped around the adjacent tissue and graft one or multiple times to form a band or latching. The suture 700 may be tensioned and secured with the fastener 630. It is contemplated that multiple grafts and/or scaffolds may be used to augment the ligament or tendon. For example, grafts or scaffolds may be at different angles to the ligament to provide augmentation in multiple directions.

Furthermore, it is contemplated that the graft or scaffold 782 used to augment the ligament or tendon may be secured to tissue using a band-like device 784. The band 784 may be wrapped around the graft or scaffold 782 and adjacent tissue, like a bone 786. The band 784 may be a biocompatible elastic band, a tissue graft, a polymeric or metallic tie (like a wire tie), or other suitable banding apparatus.

The suture and/or graft (reinforcement means) 782 used to augment the ligament or tendon may be placed parallel or diagonal to the ligament or tendon. Also, the suture and/or graft may be helically or spirally wrapped around the ligament or tendon. The ligament or tendon may be helically or spirally wrapped around the suture or graft. The reinforcement means may be positioned within or interwoven, braided, or weaved into the ligament or tendon.

As previously described, an athlete may desire to undergo elective surgery to "fail safe" a joint and/or ligaments. A football player, for example, who is at high risk for a knee injury may choose to augment or reinforce the anterior cruciate ligament 850, posterior cruciate ligament 852, tibial collateral ligament 854, fibular collateral ligament 856, posterior meniscofemoral ligament 858, and/or transverse ligament 860. The suture, cable, and/or graft used to reinforce the ligament may be tensioned and positioned such that the natural ligament is exclusively used during normal athletic activities. However, when the joint (knee) is extended or dislocated beyond its normal range of motion, the reinforcement means (suture, cable, graft, flexible rod, etc.) engages to stop the extension or dislocation thereby preventing injury to the joint. The engagement of the reinforcement means may provide a sudden stopping action when the joint or ligament is about to reach or has reached an abnormal position. Alternatively or additionally, the engagement of the reinforcement means may provide a gradual stopped action (e.g. stretching/elastic) as the joint/ligament approaches its maximum normal range.

The reinforcement means 782 may be implanted between bones, ligaments, and/or tendons. When the ACL is to be augmented or reinforced, the reinforcement means may extend between the femur 862, tibia 864, and/or fibula 865, may extend from the superior end of the ligament to the tibia and/or fibula, may extend from the inferior end of the ligament to the femur, and/or may extend between the superior and inferior ends of the ligament itself. The reinforcement means may be positioned parallel or at an angle to the ligament. The means may be a tubular sheath 866 that encapsulates the ligament, like a sheath on a wire or a braided sheath 868 on a fuel or hydraulic line. The sheath (reinforcement means) would function as previously described, i.e. provide gradual and/or sudden stopping action to the joint/ligament.

It is contemplated that augmentation or reinforcement of ligaments and tendons of a joint for athletes or other patients be performed using minimally invasive techniques. In the case of an athlete undergoing reinforcement or "fail safe" surgery, the surgeon must produce a minimum amount of dislocation and resection of soft tissue in order to minimize recovery time. Furthermore, physicians could take into consideration the natural growing rate of the athlete/patient. As the athlete grows and/or gains size and weight from physical workouts, the length, strength, and size of joints/ligaments/tendons may change. To account for this, the reinforcement means may be modifiable using a small portal in soft tissue to access the means in the joint. Once accessed, an extension 870 may be added to the reinforcement means. Alternatively, the reinforcement means may include three portions. The two end portions 872 may be fastened in tissue while the middle portion 874 resides between the end portions. The middle portion 874 may be disconnected from the end portions 872 and replaced with a different middle portion 874 having a different length, strength, and/or size. In this configuration, the end portions are not removed from the tissue therefore there is no healing time required for the end portions to secure to tissue.

Example 7—Laminectomy

A laminectomy is a surgical procedure which is designed to relieve pressure on the spinal cord or nerve root that is being caused by a slipped or herniated disk in the lumbar spine. A laminectomy removes a portion of bone over the nerve root or disc material from under the nerve root to give the nerve root more space and a better healing environment. Also, a laminectomy is effective to decrease pain and improve function for a patient with lumbar spinal stenosis. Spinal stenosis is caused by degenerative changes that result in enlargement of the facet joints. The enlarged joints place pressure on the nerves. During a laminectomy, there is much muscle stripping and ligament tearing. The back muscles or erector spinae are dissected off the lamina on both sides and at multiple levels. The facet joints, directly over the nerve roots, are cut to give the nerve roots space. Usually, once the nerve roots are provided with more room, the operation is completed by closing the skin incision. The methods and devices of the present invention may be used to repair, reconstruct, augment, and stabilize tissue or an implant "on the way out" of the pathway created in the soft tissue to access the nerve roots. Muscle may be reattached to muscle; ligaments may be repaired or reconstructed; tissue grafts may be implanted; bones may be stabilized; and implants may be inserted.

Figure 31:
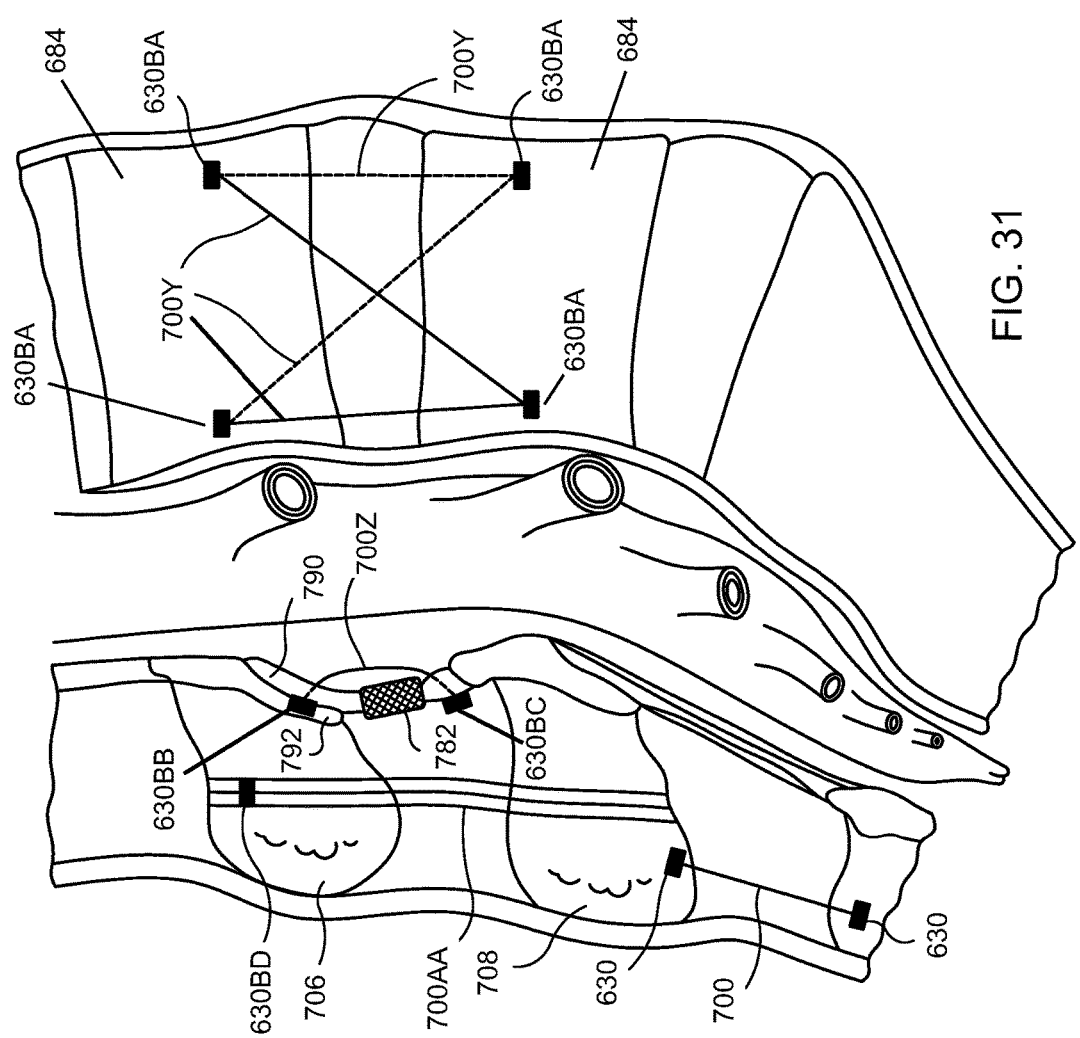
FIG. 31 shows a laminectomy site.

Referring to FIG. 31, a laminectomy site is illustrated. A portion of the ligamentum flavum 790 is dissected and removed between two spinous processes 706 and 708. The distal end of the lamina 792 is removed from the superior spinous process 706. The laminectomy site and surrounding tissue is repaired, reconstructed, or augmented to compress and stabilize the tissue for enhanced healing. Fasteners 630BA and sutures or cables 700Y are placed in the adjacent vertebral bodies 682 and 684 to provide flexible fixation of the spinal joint and limit the range of motion of the spine. A fastener 630BB is positioned on the posterior side of the ligamentum flavum 790 above the laminectomy site. Another fastener 630BC is positioned on the posterior side of ligamentum flavum 790 below the operation site. A suture 700Z is placed between the fasteners 630BB, 630BC. The suture 700Z is tensioned and secured with the fasteners 630BB, 630BC to provide flexible fixation of the ligamentum flavum 790.

Another fixation device is placed between the inferior and superior spinous processes. A fastener 630BD may be positioned against one of the spinous processes 764, and a suture 700AA may be wrapped between two spinous processes 706, 708. The suture 700AA may be tensioned, and the ends of the suture 700SS may be secured with the fastener 630BD. This configuration provides further flexible stabilization of the spinal column near the laminectomy site. Finally, a ligament graft or scaffold 782 may be positioned along the ligamentum flavum 790 over the laminectomy site. The graft 782 may reconnect and stabilize the ligamentum flavum 790. It should be understood that additional fasteners may be used to compress and stabilize surrounding tissue.

Example 8—Joint Stabilization

Following surgery within the body, especially surgery of a joint, the soft tissue around and near the joint may become weakened, and the range of motion of the joint usually increases thereby allowing excessive tissue laxity. Also, instability of a joint may be caused by structural changes within the joint as a result of trauma, degeneration, aging, disease, surgery, or a combinations thereof. An unstable joint may be fused to form a permanent or rigid internal fixation of all or part of the joint. Alternatively, joints may be stabilized with the devices and methods of the present invention, without fusion. In an exemplary embodiment, tissue may be repaired, reconstructed, augmented, and stabilized during and "on the way out" of a surgical procedure such as those surgical procedures described herein. Compressing and stabilizing the tissue around a joint enhances tissue healing. Using flexible fixation, the tissue may be secured but still allow for some range of motion of the joint. Where flexible fixation is not desired, the devices and methods of the present invention may be used for rigid fixation, such as for bones.

As a further example, fasteners and sutures could be used to stabilize the knee joint. The sutures could be positioned between at least two of the femur, tibia, patella, and adjacent ligaments to stabilize the knee without significantly restricting the knee's normal range of motion. Moreover, the devices and methods may be used to stabilize any joint of the body, including the spine, shoulder, elbow, wrist, hip, knee, ankle, and joints of the hands and feet. Additionally, the present invention may be used with a temporal mandibular joint, SI joint, facet joint, temporomandibular joint, and sacroiliac joint.

For illustrative purposes, the present invention is described in greater detail with respect to the spine. FIG. 32 shows a posterior view of the head and cervical spine with three vertebrae: C1 (Atlas), C2 (Axis), and C3. The cervical spine and head are stabilized using diagonally positioned sutures. Fasteners 630BE, 630BF are positioned within or against the left and right side of the occipital bone 800 of the head. Two other fasteners 630BG, 630BH are placed within or against the left and right sides of the posterior arch of the C1 vertebra 802. A suture 700AB extends between the left fasteners 630BE, 630BG, while another suture 700AC extends between the right fasteners 630BF, 630BH. When tensioned, the sutures 700AB, 700AC limit movement of the head relative to the cervical spine.

FIG. 32 also shows tissue graft 804, such as a ligament and/or bone graft, positioned between a vertebra 806 and the head 808. The grafts 804 may be attached using any of the devices and methods described herein and incorporated by reference. In an exemplary embodiment, fasteners 630BI are placed at the superior and inferior ends of the graft. Other fasteners (not shown) are positioned within or adjacent the bone. Sutures extend between the fasteners and are tensioned.

Further stabilization of the cervical spine may be obtained by placing sutures and fasteners lower in the cervical spine. In an exemplary embodiment, a crisscross pattern of sutures is placed between two adjacent vertebrae. The upper fasteners 630BJ may be placed within or against the superior vertebra 682, while the lower fasteners 630BK may be positioned within or against the inferior vertebra 684. Sutures 700AD extend between the fasteners, and when tensioned, the sutures 700AD stabilize the vertebrae 682 and 684 from movement between one another.

In another embodiment as shown in FIG. 33, a vertebra 814 has been decompressed using fasteners and a suture. A first fastener 630BL is placed within or adjacent an upper vertebra 812, and a second fastener 630BM is positioned within or adjacent a lower vertebra 816. A suture 700AE is positioned through the left side of the vertebrae 812, 814, and 816 in a curved, looped, or C configuration. The suture 700AE is tensioned, and the ends of the suture 700AE secured. By tensioning the suture 700AE, the right side of the middle vertebra 814 becomes decompressed.

In another exemplary embodiment, multiple vertebrae may be decompressed by positioning fasteners 630BN, 630BO on two vertebrae 810 and 818 which are separated by two or more vertebrae. A tubular member or sleeve 652 is positioned between the fasteners 630BN, 630BO and through the vertebrae in between. A suture 700AF is placed within the sleeve 652, tensioned, and secured with the fasteners 630BN, 630BO. Moreover, the fasteners 630BN, 630BO may be placed on any part/portion of the vertebrae 810 and 818, as described previously, so when the suture is tensioned, one or more vertebrae are decompressed, forming a decompressed region 824.

As further seen in FIG. 33, the spine has been stabilized using the pedicles of the spine. A fastener 630BP is placed within or adjacent a pedicle 820. A second fastener 630BQ is placed within or adjacent another pedicle 822. A suture 700AG extends between the fasteners 630BP, 630BQ either through the pedicles or outside the pedicles. The suture 700AG is tensioned and the ends of the suture secured.

While FIG. 33 illustrated a suture positioned between two pedicles, it is contemplated that the suture may be affixed to any portion/part of the vertebrae. For example, a suture may be tensioned between any one or more of the following: transverse process, pedicles, facets, spinous process, posterior arch, odontoid process, posterior tubercle, lateral articular process, uncinate process, anterior tubercle, carotid tubercle, and vertebral body.

The suture, or similar device like a cable, band, flexible moment arm, pin, rod, or K-wire, is made of a material having sufficient strength and fatigue characteristics. The suture may be biodegradable and/or flexible. It may include metallic material, ceramic material, polymeric material, composite material, or combinations thereof. In one embodiment, the suture is formed of fiber material like carbon or polyamide fibers. Sutures may also be formed from Mersilene®, polypropylene braided or collagen strips, allograft or xenograft strips, braided mesh, a polymer, PTFE, or Gore-Tex®. The suture may be made of or include an elastic, flexible material which stabilizes the skeletal and ligamentous system but allows some movement of the joints. Also, the suture may be barbed or could be a threaded wiring device.

The disclosed methods for spine stabilization described thus far included positioning fasteners against bone or an implant. However, the present invention also contemplates stabilizing a joint of the body by affixing a suture between ligaments, tendons, bones, cartilage, tissue grafts or combinations thereof. For example, a suture may be positioned between a vertebra and a longitudinal ligament, between a spinous process and the supraspinous ligament, or between a facet and a facet capsulary ligament. Any combination of attachment points is contemplated to stabilize the joint.

Furthermore, any of the methods described herein could utilize a plurality of sutures and more than two fasteners. The use of multiple sutures can vary the tension or resistance between the fasteners securing the suture, thereby providing various levels of stability. The use of multiple fasteners, preferably spaced apart and positioned adjacent the region of the joint to be stabilized, could provide various angles of stabilization.

It is further contemplated that by using multiple sutures and fasteners at different locations of the spine, ligaments and bones of the spine may be selectively tightened or stabilized to provide a customized environment for spine healing. For example, the sutures may be tightened sequentially between the fasteners, or the entire construct could be tightened down together.

Related Techniques

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled, Apparatus and Method for Use in Positioning a Suture Anchor, discloses devices for controlling the placement depth of a fastener. Also, U.S. Patent Application Publication No. 2003/0181800 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. Pat. Nos. 6,702,821, 6,770,078, and 7,104,996. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

Moreover, the devices and methods of the present invention may by used to approximate a skin incision where there may be undue tension on the skin. Fasteners may be placed on opposite sides of the incision, and a suture or cable may be placed between the fasteners. When the suture is tensioned, the skin may be pulled together and held until the skin tissue relaxes. Then, the fasteners may be unlocked, and the suture may be tensioned again to further approximate the skin incision. The locking and unlocking of the fasteners along with the tensioning of the suture may be repeated until the incision is fully closed.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

In addition, intramedullary fracture fixation and comminuted fracture fixation may be achieved with the devices and methods of the present invention. For example, a plate or rod may be positioned within or against the fractured bone. A fastener may be driven across the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled, Surgical Devices Assembled Using Heat Bondable Materials. For example, the fasteners of the present invention may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the fasteners and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the fasteners and methods described and incorporated herein may be used to approximate the damaged portion of the vessel.

The guidance and positioning device of the present invention may be used to stabilize or fasten various implants and tissues. For example, the spine may be repaired or stabilized with fasteners, sutures, and cables to provide flexible or rigid reinforcement of the joints of the spine. Also, the nucleus pulposus of an intervertebral disc may be repaired or replaced using the guidance and positioning device of the present invention. For example, a prosthetic disc nucleus is positioned between two vertebral bodies and may be secured to surrounding tissue with fasteners and sutures. Additionally, the annulus may be repaired following a nucleus pulposus repair or replacement. The positioning device of the present invention may be used to position a fastener and suture on the internal side of the annulus. The suture may be pulled proximally through the annulus, tensioned, and secured with another fastener. Finally, the tissue alignment sleeves disclosed in the provisional application may be guided and positioned with the instrument and methods of the present invention. The above mentioned provisional application is incorporated herein by reference.

It is contemplated that the present invention may be utilized with the tracheal tube positioning apparatus of U.S. Pat. No. 6,820,614, entitled "Tracheal Intubation," by Peter M. Bonutti. That patent discloses positioning apparatus located relative to a patient's trachea by engaging the patient's trachea. Indicia on relatively movable sections of the positioning apparatus provide an indication of the distance between the patient's mouth and the patient's larynx. A flexible guide rod is moved through a distance corresponding to the distance between the patient's mouth and larynx, as determined by the positioning apparatus. A magnet is utilized to attract a leading end portion of the guide rod. A plurality of emitters may be disposed in an array around the patient's trachea. Outputs from the emitters are detected by a detector connected with the tracheal tube. The above mentioned patent is hereby incorporated by reference.

Drill/Sleeve Combination

In another embodiment of the present invention, a drill bit and sleeve combination 100 is provided. In the following description, the drill bit and sleeve combination or system 100 is explained with reference to the fixation of two bones, like two portions of a fractured bone. It should be understood that the present embodiment may be utilized for fastening or securing tissue to tissue, an implant to tissue, or an implant to an implant.

Figure 34:
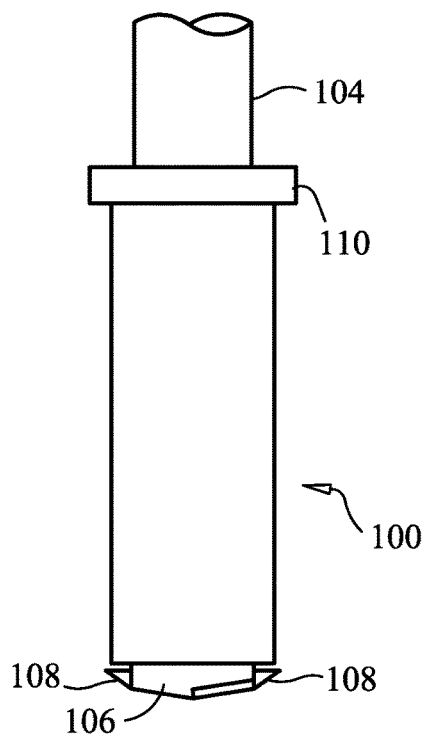
FIG. 34 illustrates a drill/sleeve combination in accordance with the present invention.

In FIG. 34 the system 100 includes a tubular member or sleeve 102 for aligning two portions of bone located on opposite sides of a fracture. A drill bit 104 extends through the longitudinal lumen of the sleeve 102. The distal portion 106 of the drill bit 104 has one or more pivoting blades 108. The system 100 may also include a pusher means 110 for inserting the sleeve 102 into the bone passage created by the drill bit 104. The pusher means 110 may be connected to the sleeve, bit, or the drill. Preferably, a portion of the pusher means 110 does not rotate with the bit or drill so that the sleeve 102 is not rotated as the pusher means 110 contacts the sleeve 102 during the drilling operation. Examples of the pusher means 110 include a washer-shaped member or donut-shaped member positioned over the bit or a U-shaped fork positionable around the shaft of the bit. The lower side of the pusher means 110 may be configured for contact with the proximal end of the sleeve, while the upper side of the pusher means 110 may be configured of applying a distal force with a hand, hammer, or press.

Figure 35:
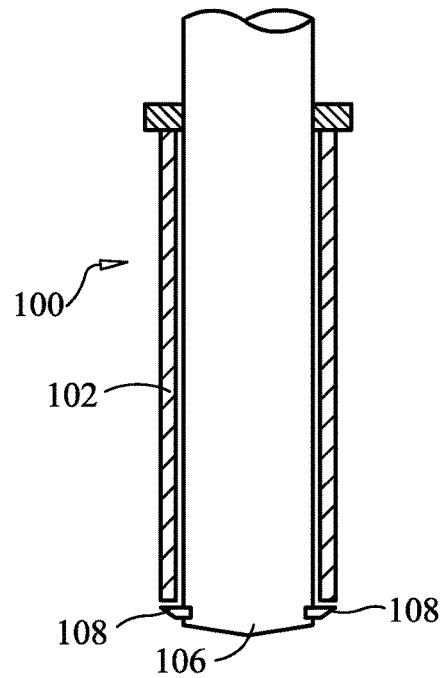
FIG. 35 is a cross sectional view of FIG. 34.

As seen in FIG. 35, the blades 108, when extended from the bit 104, increase the drilling diameter of the bit 104. The bone passage created by the drill bit 104 and the extended blades 108 has a diameter generally equal to the outside diameter of the sleeve 102. The blades 108, when retracted, pivot into or against the distal portion 106 of the bit 104. The diameter of the drill bit 104 with the blades 108 retracted is slightly less than the inside diameter of the sleeve 102.

The pivoting blades 108 of the system 100 may be connected with the distal portion 106 of the bit 104 in a variety of ways, but preferably, the blades 108 are pivotally attached to the bit 104. In one exemplary embodiment as seen in FIGS. 34 and 21, the blades 108 extend and retract along radial axes of the bit 104. The blades 108 may pivot downwardly or distally into an extended configuration and may pivot upwardly or proximally into a retracted configuration. In the retracted state, the blades 108 may be positioned within a groove or notch within the distal portion 106 of the bit 104. Furthermore, the blades 108 may be spring loaded to normally reside in the retracted configuration. When the drill bit 104 is rotated with a drill, the centrifugal force generated by the drill may cause the blades 108 to pivot into the extended configuration. Once in the extended position, the blades 108 may be locked into position to allow drilling or cutting of the bone.

In another exemplary embodiment, the blades 108 may be manually pivoted distally and proximally. A pin or shaft may extend along the center of the drill bit 104 with the distal end of the pin in contact with the blades 108. As the pin moved longitudinally, the blades 108 may extend and retract. The proximal portion of the pin may include a lever or other means for moving or advancing the pin along the center axis of the bit 104.

It is further contemplated that the blades 108 may be extended and retracted radially in and out of the distal portion of the bit 104 along a linear path instead of being pivoted as previously described. In this embodiment, the blades 108 may extend with centrifugal force and retract with a spring-like mechanism or may be manually extended and retracted with a pin or shaft along the central axis of the bit 104. Furthermore, other embodiments of the blades are contemplated. For example, the blades may be generally arch-shaped to conform to the outside circumference of the bit. The distal ends of the blades may be pivotally attached to the bit allowing the blades to extended radially outward for maximum cutting diameter or retract against the outer surface of the bit to minimize the bit diameter.

Figure 36:
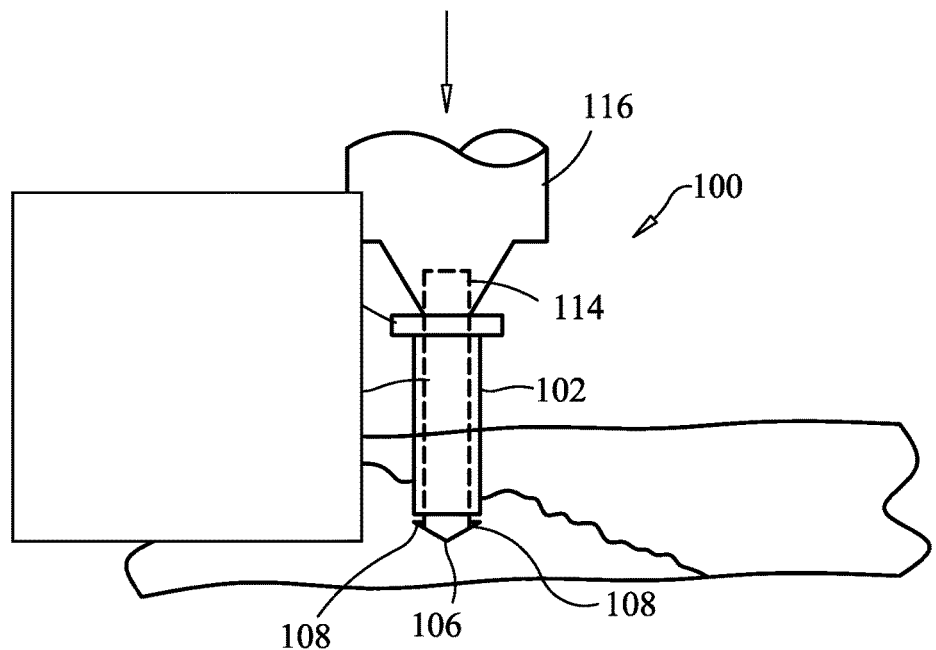
FIG. 36 shows the drill/sleeve combination in use to repair a fractured bone.
Figure 37:
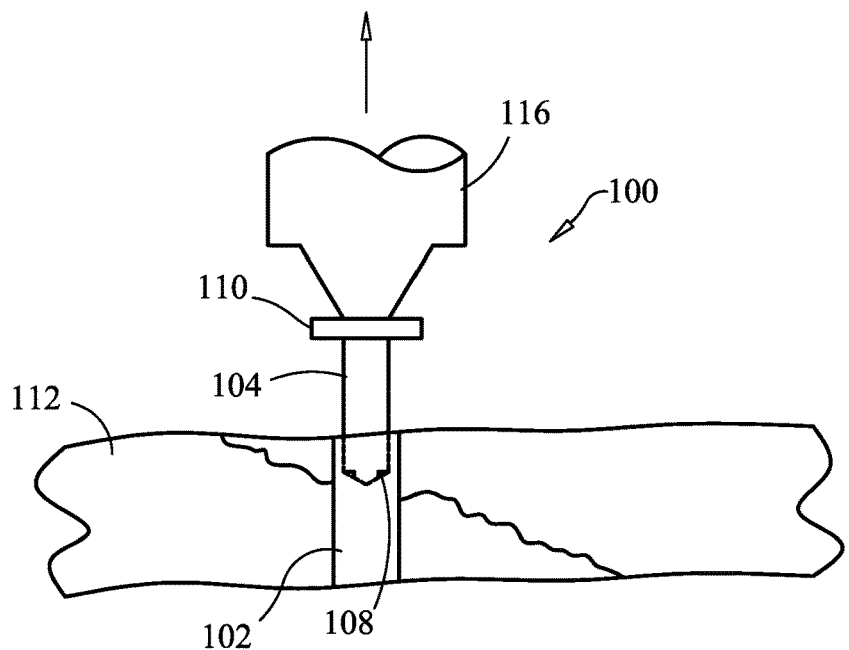
FIG. 37 illustrates the sleeve positioned across the fracture of the bone.

FIGS. 36 and 37 illustrate the drill bit and sleeve system 100 in use to repair a fractured bone 112. The drill bit 104 is inserted into the lumen of the sleeve 102. The distal portion 106 of the bit 104 and the pivoting blades 108 extend beyond the distal end of the sleeve 102. Preferably, the amount of bit 104 extending from distal end of the sleeve 102 is minimized to prevent damage to soft tissue of the distal side of the bone 112. The proximal portion of the bit or shank 114 extends from the proximal end of the sleeve 102 and is connected to a drill 116. The pivoting blades 108, located beyond the distal end of the sleeve 102, are in the extended configuration. The bit 104 is rotated and advanced distally through the fractured bone 112. As the bit 104 advances and creates a passage in the bone 112, the sleeve 104 is moved distally into the passage with the pusher means 110. The sleeve 102 is tight or snug within the passage since the diameter of the passage is generally equal to the outside diameter of the sleeve 102. When the sleeve 102 is in its proper position securing the bone portions 118 and 120 of the fractured bone 112, and the drill bit 104 may be removed from the lumen of the sleeve 102. The bit 104 may be pulled from the lumen of the sleeve 102 because the blades 108 may be positioned in the retracted configuration giving the drill bit 104 a diameter generally smaller than the diameter of the lumen of the sleeve 102. With the sleeve 102 in place, the bone is compressed, and the fracture is stabilized.

Figure 38:
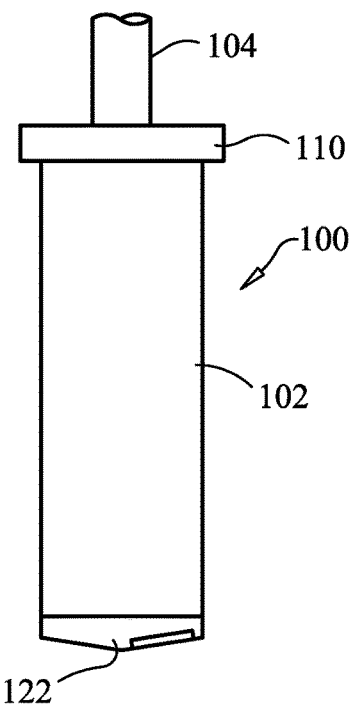
FIG. 38 shows another exemplary embodiment of the drill/sleeve combination.
Figure 39:
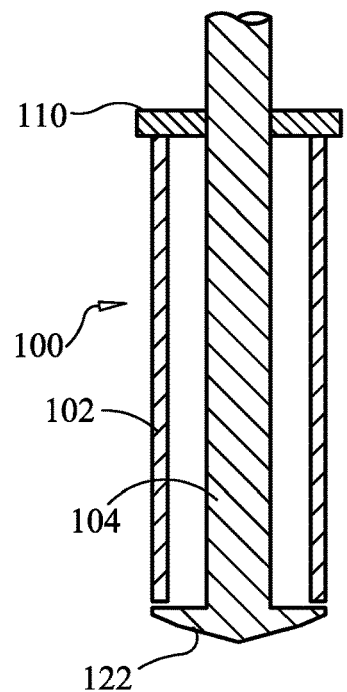
FIG. 39 is a cross sectional view of FIG. 38.

In another embodiment of the present invention, the drill bit and sleeve combination or system 100 is dimensioned and configured for transformation into a fastener. As shown in FIGS. 38 and 39, the system 100 includes the tubular member or sleeve 102, the pusher means 110, and a drill bit 104 with an expanding distal portion 122. The drill bit 104 extends through the lumen of the sleeve 102 with the distal portion 122 of the bit 104 extending beyond the distal end of the sleeve 102. The cutting diameter of the distal portion 122 of the bit 104 is generally equal to the outside diameter of the sleeve 102. In this embodiment, the distal portion 122 of the bit 104 does not include pivoting cutting blades. However, the distal portion 122 does include means for expansion to a diameter greater than the cutting diameter.

Figure 40:
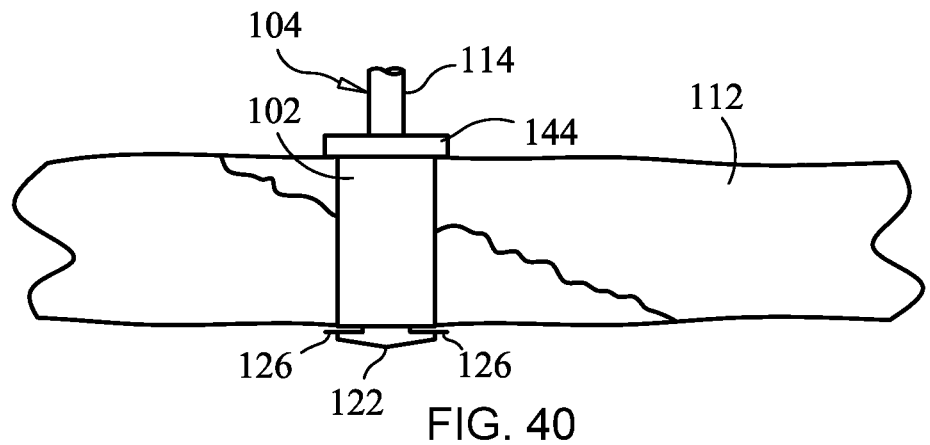
FIG. 40 illustrates the drill/sleeve combination functioning as a fastener.
Figure 41:
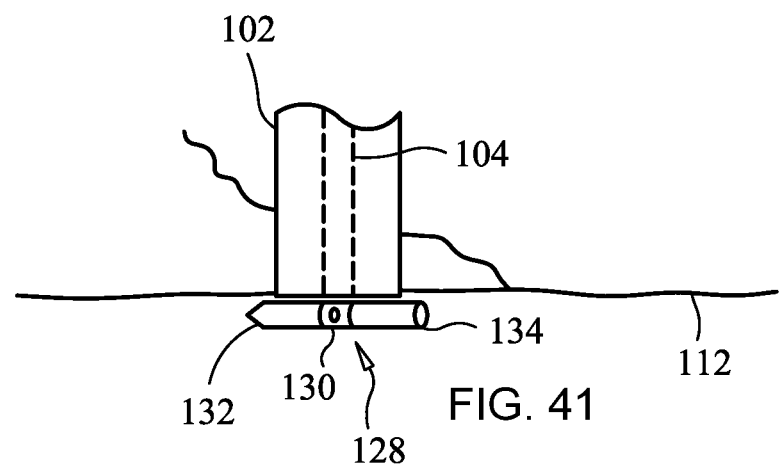
FIG. 41 shows an exemplary distal portion of the fastener.
Figure 42:
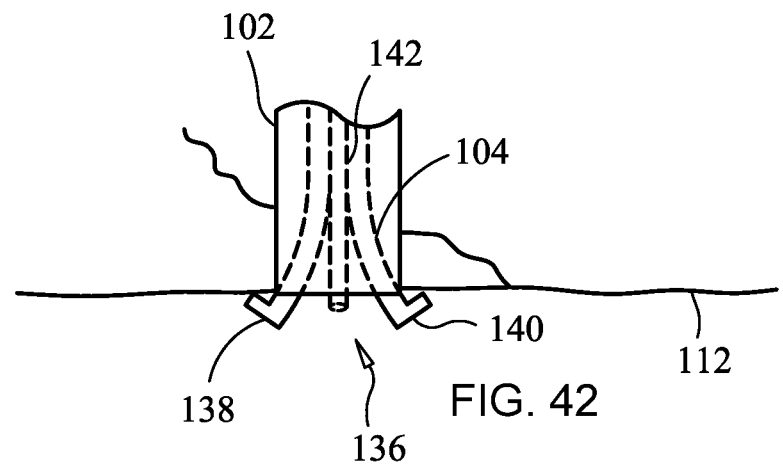
FIG. 42 illustrates another exemplary distal portion of the fastener.

Some examples of expansion means are shown in FIGS. 40-42. In FIG. 40 the expansion means includes one or more mechanically extending barbs 126 from the distal portion 122 of the bit 104. When extended or expanded, the barbs 126 increase the overall diameter of the drill bit 104. The barbs 126 may extend to the outside diameter of the sleeve 102, but preferably the barbs 126 extend beyond the outside edge of the sleeve 102. Most preferably, the barbs 126 extend over or into the distal side of the fractured bone 112. In the expanded configuration, the drill bit 104 is prevented from being pulled proximally out of the sleeve 102.

In FIG. 41, the expansion means includes a distal portion 128 of the drill bit 104 which pivots. In a first orientation during a drilling procedure, the distal portion 128 of the bit 104 is generally in-line with rest of the drill bit 104. After drilling, the distal portion 128 of the bit 104 is rotated about a pivot point into a second orientation. In the second orientation, the distal portion 128 is generally perpendicular to the rest of the drill bit 104. As a result, the end sections 132 and 134 of the pivoted distal portion 128 of the bit 104 extend beyond the outer diameter of the sleeve 102. Preferably, the end sections 132 and 134 extend over or into the distal side of the fractured bone 112 to prevent the bit 104 from being pulled from the sleeve 102.

In FIG. 42, the expansion means includes a distal portion 136 of the bit 104 which has two or more longitudinal sections 138 and 140 that are biased radially outward. The longitudinal sections 138 and 140 may be normally biased outward but held together by the lumen of the sleeve 102 when drilling through the bone 112. Alternatively, the longitudinal sections 138 and 140 may be normally in a non-biased configuration. After the passage is drilled in the bone 112, a plunger 142 within the drill bit 104 may be moved distally biasing the longitudinal sections 138 and 140 radially outward. With the longitudinal sections 138 and 140 biased, the distal portion 136 of the bit 104 may extend over or into the distal side of the fractured bone 112 to secure the bit 104 within the sleeve 102 and bone passage.

The drill bit and sleeve system 100 which transforms into a fastener may be utilized to secure various tissue and implants. Generally, in use, the drill bit 104 is inserted into the lumen of the sleeve 102 with the distal portion of the bit 104 extending beyond the distal end of the sleeve 102. The proximal portion of the bit or shank 114 extends from the proximal end of the sleeve 102 and connects to a drill. The bit 104 is rotated and advanced distally through the fractured bone 112. As the bit 104 advances and creates a passage in the bone 112, the sleeve 102 is moved distally into the passage with the pusher means 110. When the sleeve 102 is in its proper position connecting the two portions 118 and 120 of a fractured bone 112, the shank 114 of the drill bit 104 is removed from the drill. The distal portion of the bit 104, which extends just beyond the distal surface of the bone 112, is expanded with the expansion means.

Once expanded, the drill bit 104 is prevented from being pulled out of the bone passage. A retainer 144 may then be placed around the shank 114 of the bit 104 and moved distally to engage the proximal side of the bone 112. The retainer 144 is secured to the shank 114. With the distal portion of the bit expanded and the retainer connected to the shank, the drill bit (and the sleeve) is transformed into a fastener which holds the fractured bone in compression. It is also contemplated that the drill bit may be used without the sleeve so that the drill bit alone becomes a fastener.

The tubular member or sleeve of the present invention is generally tubular shaped having a wall with an inner surface and an outer surface. The inner surface defines a lumen which is dimensioned and configured for receiving a drill bit, suture, cable, K-wire, or similar device. The sleeve may include a slit through the tubular wall. The slit allows the sleeve to be decreased in diameter for implantation and increased in diameter after implantation for proper alignment of the implantation site. In a further embodiment, the sleeve may include two slits in the tubular wall thereby forming two semi-tubular members. The semi-tubular members may be placed separately at the implantation site then aligned to form a complete tubular member. In another embodiment, the tubular member is a solid member.

The tubular member or sleeve may be flexible to enable the tubular member to be inserted into a linear or nonlinear passage through the bone. The tubular member may be formed of metallic material, composite material, ceramic material, polymeric material, or combinations thereof. The sleeve may be made from a degradable, biodegradable, bioerodible, or bioabsorbable material, such as a polymer, composite, or ceramic. The tubular member may also include a therapeutic substance to form a composite tubular member, or the therapeutic substance may be coated onto the tubular member. Furthermore, therapeutic substances or graft material (autogenic, allogenic, xenogenic, or synthetic) may be packed into the sleeve.

Additionally, the outer surface of the tubular member may include a friction or gripping means. A portion of the outer surface of the tubular member may include threads, raised pebbles, bumps, raised ridges, or hills. In addition to a friction means on the outer surface of the tubular member, the wall of the sleeve may include openings for tissue ingrowth. The tubular member of the present invention is further described in U.S. Provisional Patent No. 60/622,095 entitled "Devices and Methods for Stabilizing Tissue and Implants," which is hereby incorporated by reference.

Guidance and Navigation

The guidance and positioning device of the present invention may be placed within the body of a patient with precise navigation. For example, one or more guide wires or k-wires may be utilized—one to hold the device in position and a second wire to drill or pass through tissue toward the distal end of the hook of the device. One of the guide wires or an additional wire can be used to pull a suture or fastener through the tissue. Alternatively, the positioning device may be positioned through an expanding retractor with percutaneous guidance.

Other navigation techniques for precise placement of the positioning device of the present invention include endoscopic guidance, magnetic resonance imaging, CT scan, ultrasound, fluoroscopy, X-ray, computer assisted navigation, magnetic guidance, electromagnetic guidance, radiofrequency guidance, optical guidance, and laser guidance. For example, the hook and/or guide channel of the positioning device may include a magnet, a radiofrequency emitter, or a thermal emitter/sensor. U.S. Pat. No. 7,104,996 entitled "Method of Performing Surgery" discloses computer assisted navigation. In using computer assisted navigation with the present invention, emitters, receivers, and/or reflectors may be attached to the positioning device and/or tissue. The computer navigation system may utilize multiple separate registers which have optical feedback to a central unit. The computer navigation system may utilize electromagnetic or photo-optical feedback. U.S. Pat. No. 5,329,924 entitled "Sequential Imaging Apparatus"; U.S. Pat. No. 5,349,956 entitled "Apparatus and Method for Use in Medical Imaging"; and U.S. Pat. No. 5,542,423 entitled "Indexing Assembly for Joint Imaging" disclose further devices and methods for use in medical imaging. Also, the present invention may be performed using robotics, such as haptic arms or similar apparatus. The above mentioned patents are hereby incorporated by reference.

It is contemplated that the device and method of the present invention be applied using minimally invasive incisions and techniques to preserve muscles, tendons, ligaments, bones, nerves, and blood vessels. A small incision(s) may be made adjacent the target area to be repaired, and a tube, delivery catheter, sheath, cannula, or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening. The above mentioned patent is hereby incorporated by reference.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

The present invention may also be utilized with minimally invasive surgery techniques disclosed in U.S. Pat. Nos. 6,702,821, 6,770,078, and 7,104,996. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

Furthermore, it is contemplated that the present invention may be used with bariatric surgery, gastric stapling, colorectal surgery, plastic surgery, gastroesophageal reflex disease (GERD) surgery, ligament reconstruction surgery (such as the anterior cruciate ligament, ACL), or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the device and method of the present invention.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant secured within the body using the present invention may include tissue harvested, configured, and implanted as described in the patents. The above mentioned patents are hereby incorporated by reference.

Additionally, it is contemplated that the device and method of the present invention may be used with heat bondable materials as disclosed in U.S. Pat. No. 5,593,425 entitled "Surgical Devices Assembled Using Heat Bondable Materials." For example, fasteners may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above mentioned patent is hereby incorporated by reference.

Moreover, the device and method of the present invention may be used for the repair and reconstruction of a tubular pathway like a blood vessel, intestine, urinary tract, esophagus, or similar tubular body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the positioning device of the present invention may be used then to approximate the damaged portion of the vessel.

Radiofrequency Identification

The devices, fasteners, and other apparatus disclosed herein may include RFID (radiofrequency identification) tags. Moreover, any surgical device, described herein or not, such as surgical instruments, implants, trays, sponges, screws, bolts, plates, knives, scalpels, etc. may include RFID emitting chips. RFID provides for inventory control before, during, and after surgery. Objects with RFID chips/tags which are located under sterile drapes or within sterile containers may be easily located without having to break the sterile environment. Also, surgical devices and instruments stored in cabinets or placed in an operating room may be scanned with an RFID receiver to help technicians and nurses quickly identify location, type, and quantity. RFID chips/tags placed on surgical objects may save significant time and money during surgery and inventory. Furthermore, matching RFID chips/tags may be placed on an instrument/device and on the tray which holds the device. Using the RF scanner/transmitter, the correct placement of the device can be determined. It is further contemplated that the kits previously described may include RFID chips/tags placed on the container and the components therein.

Surgical Tools

In another exemplary embodiment, the guidance and positioning device of the present invention may be used with pneumatic operated surgical instruments. For example, a gas-powered drill may be couple with the channel guide and/or handle of the positioning device. A surgeon may operate the drill by activating a switch to start the fluid of gas which rotates an air motor thereby rotating a drill bit. The drill may be connected to a compressed gas source with tubing. However, preferably, the drill includes a connecting port for attaching a gas cartridge or canister. Such a drill would be free from electrical and battery power and free from encumbering wires and hoses. The gas cartridge may be sized to fit within the drill body or attached externally on the drill body. The cartridge may be refillable or disposable. In addition to the drill being gas-powered, the clamping mechanism of the positioning device may be gas-powered. By activating the flow of gas, the clamp may be moved to engage and compress tissue and/or an implant, holding the tissue and/or implant in place until fasteners may be inserted. It is further contemplated that other surgical tools, such as saws, shavers, reamers, grinders, etc., may include gas cartridges as previously described. These gas-powered tools may also include a microprocessor for control and feedback.

The present disclosure includes a tissue fixation system for dynamic and rigid fixation of tissue. The system can be utilized for the fixation and stabilization of body tissue, including soft tissue to soft tissue, soft tissue to bone, and bone to bone. The surgical system can additionally be used to affix implants and grafts to body tissue. The system can access and treat fractured, incised or torn tissue, or the like, from one access area (i.e., from only one opening to the tissue to be fastened) instead of requiring two or more openings. That is, the system is a linear fixation system that can be used with a single, small incision or portal in the skin or other soft tissue to gain access to the fractured bone. The fixation system may be an all-in-one system, packaged as a system kit, for creating a passage in tissue, positioning fasteners, and tensioning an elongate fastening member (e.g., a flexible line), like a suture, thread, cable, wire, rod, or pin. The individual components of the system can either be reusable or single use components.

Figure 44:
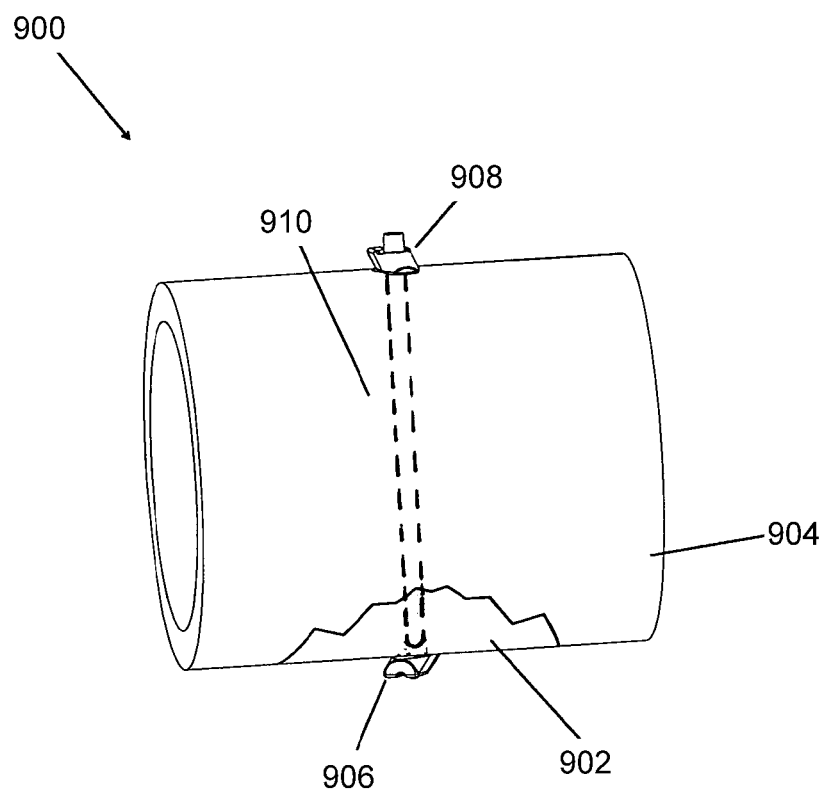
FIG. 44 shows a schematic illustration of a tissue fixation system according to the present invention utilized for fracture fixation.
Figure 45:
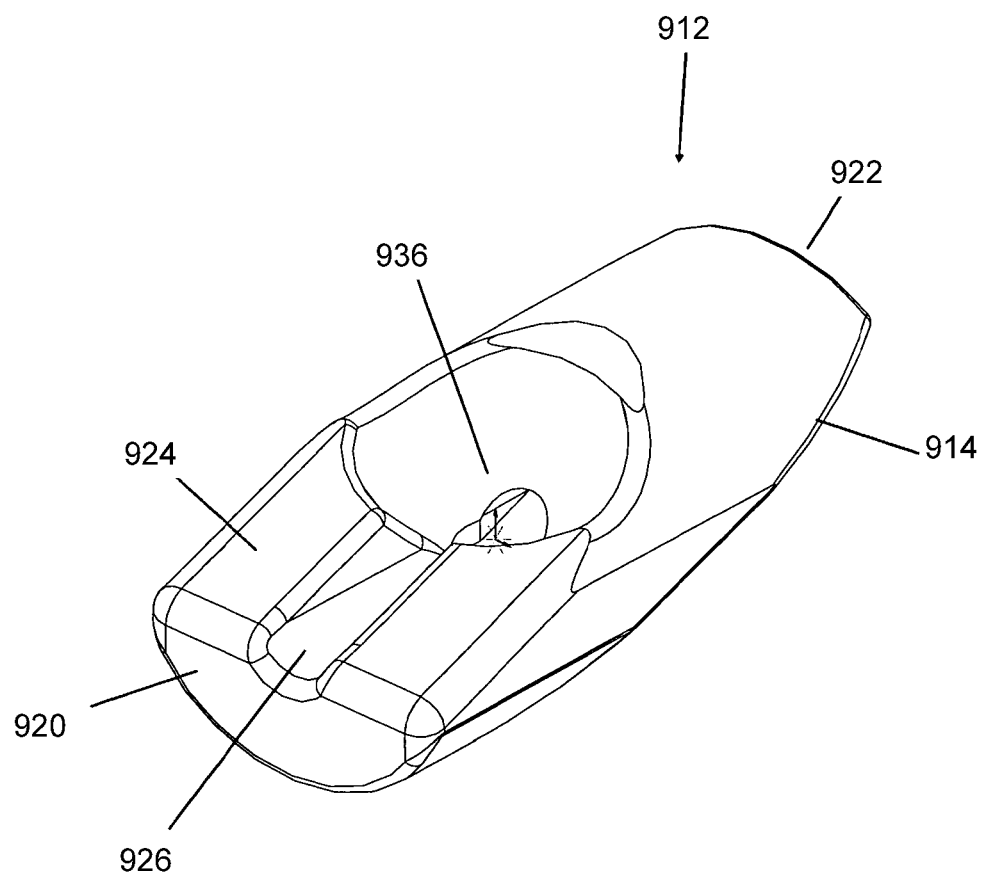
FIG. 45 shows a perspective view of a fastener according to the present invention.
Figure 46:
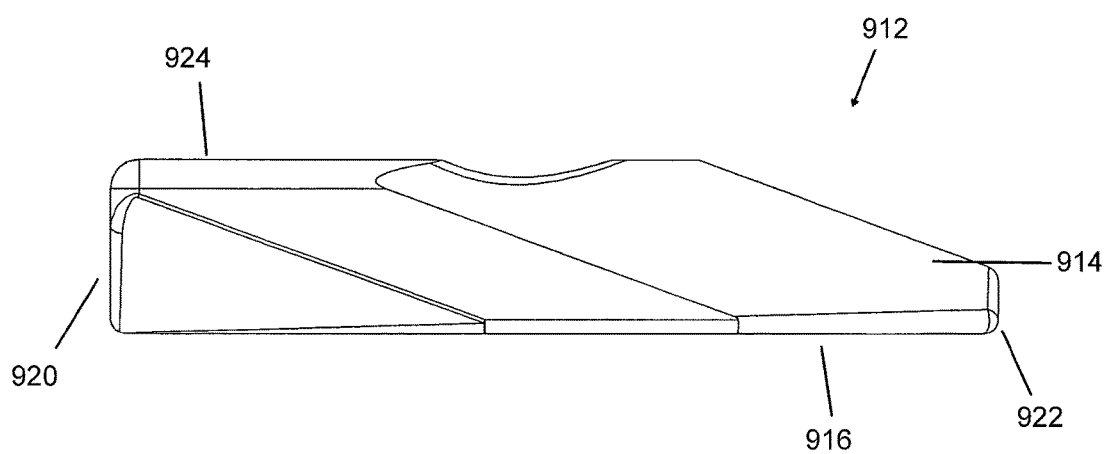
FIG. 46 shows a side view of the fastener of FIG. 45.
Figure 47:
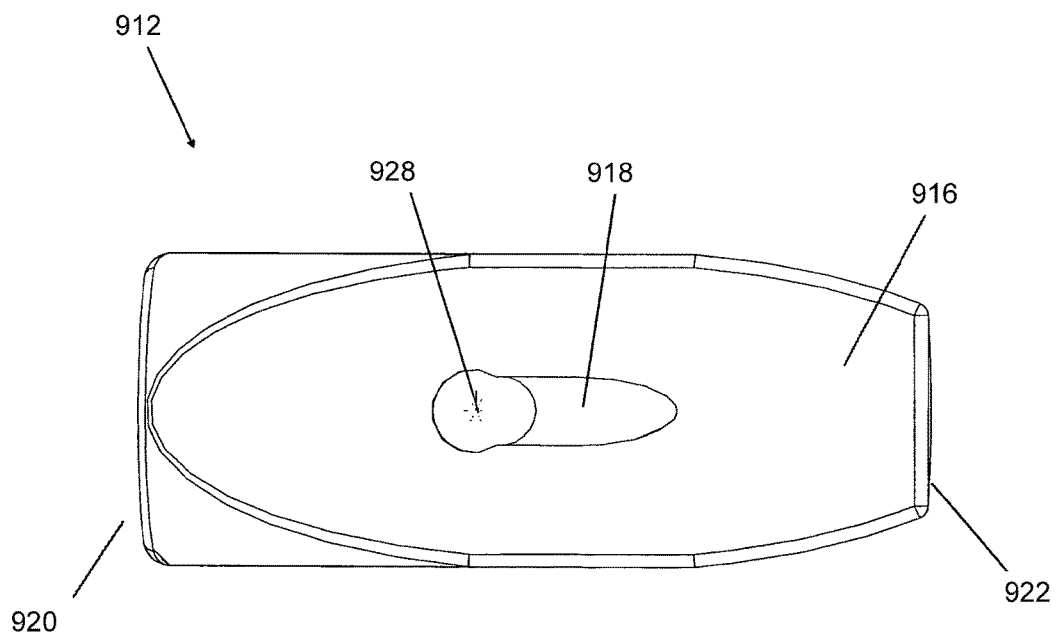
FIG. 47 shows a bottom view of the fastener of FIG. 45.

Referring now to the drawing figures in which like reference designators refer to like elements, FIG. 44 shows an exemplary embodiment of a tissue fixation system 900 according to the present invention. A fractured portion 902 of a bone 904 is approximated by system 900. Use of system 900 is not limited to any particular type of fracture. Furthermore, use of system 900 is not limited to fracture fixation. In other words, system 900 can be utilized for other tissue fixation applications (such as soft tissue) or similar clinical indications. Examples of such tissue includes, are not limited to, muscle, cartilage, ligament, tendon, skin, etc. Also, the tissue may be stomach tissue, and the system may be used during bariatric surgery, like stomach stapling. Additionally, the system 900 can be used for the fixation of implants to tissue.

In this regard, the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

Although the invention is described primarily on a macroscopic level, it is also envisioned that the present invention can be used for microscopic applications. For example, in the repair of nerve tissue, individual cells or fibers may need to be repaired. Similarly, muscle repair may require tightening of individual muscle fibers.

System 900 includes a distal fastener 906 contacting fracture portion 902, a proximal fastener 908 contacting bone 904, and an elongate fastening member 910 extending through the fracture and coupling distal and proximal fasteners 906, 908. Tension is maintained in elongate fastening member 910 to press fasteners 906, 908 against opposite sides of bone 904 with a desired force. This force presses fracture portion 902 against bone 904 firmly together to promote healing of the fracture. If desired, buttons or other force distributing members could be provided between fasteners 906, 908 and the bone. Although FIG. 44 shows distal and proximal fasteners 906, 908 as having the same construction, they could have differing construction. However, for convenience and practical purposes, it may be beneficial if distal and proximal fasteners 906 and 908 have substantially the same construction.

Figure 48:
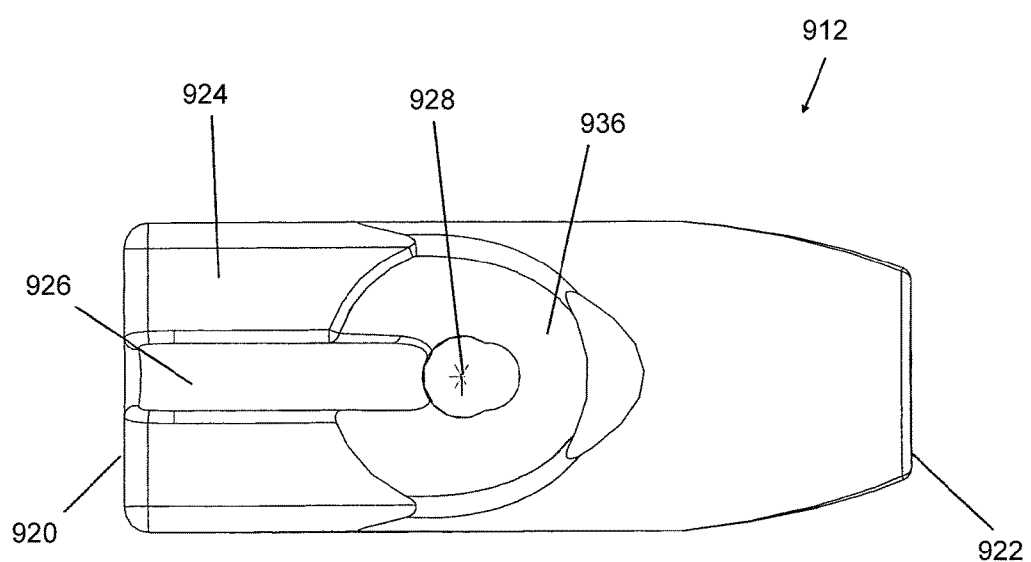
FIG. 48 shows a top view of the fastener of FIG. 45.
Figure 49:
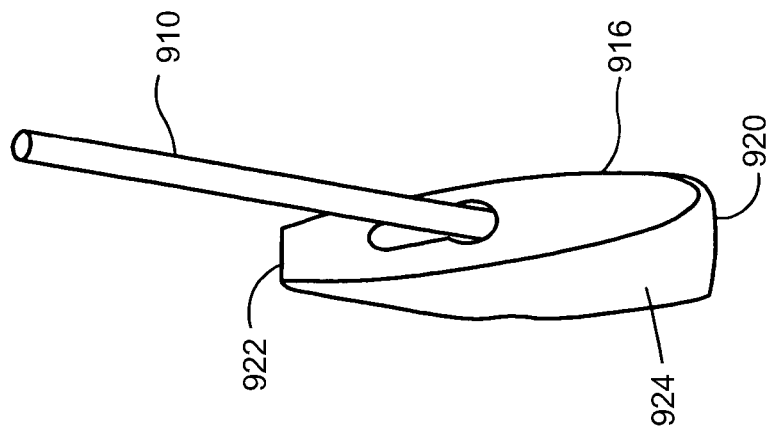
FIG. 49 shows a fastener and elongate fastening member with the fastener in a first orientation with respect to the elongate fastening member.

FIGS. 45-48 show an exemplary embodiment of a fastener 912 that can be used as part of system 900, i.e. as either or both of distal and proximal fasteners 906, 908. Fastener 912 has a body 914 that is configured and dimensioned to facilitate implantation through minimally invasive procedures, e.g. through a cannula or sleeve. In particular, body 914 includes a tissue contacting surface 916 that is provided with groove 1018 that receives a portion of elongate fastening member 910 when fastener 912 is in a first orientation with respect to elongate fastening member 910. This is seen in FIG. 49. The accommodation of elongate fastening member 910 within groove 918 helps to minimize the profile of the assembly of fastener 912 and elongate fastening member 910. The reduced profile can be more readily passed through a cannula or sleeve. If desired, an adhesive can be provided within groove 918 to bias fastener 912 in the first orientation. Alternatively, a frangible connection can be provided between groove 918 and the portion of elongate fastening member 910. This frangible connection keeps fastener 912 in the first orientation with respect to elongate fastening member 910 until it is broken.

Figure 51:
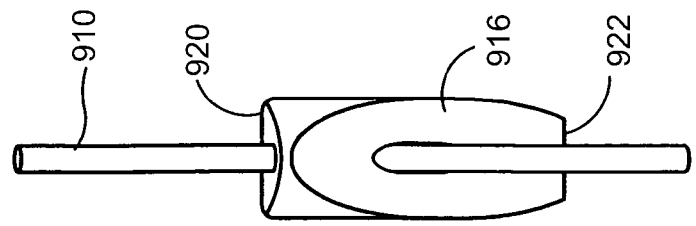
FIG. 51 shows a back view of the fastener and elongate fastening member of FIG. 50.
Figure 50:
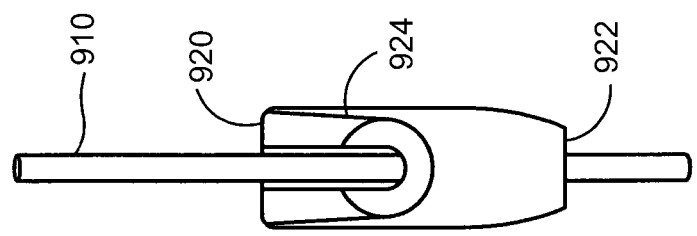
FIG. 50 shows a front view of a fastener in the first orientation with respect to the elongate fastening member with the fastener rotated 180° compared to FIG. 49.

Fastener 912 is provided with first and second ends 920, 922. As shown in FIG. 49, first end 920 is the leading end and second end 922 is the trailing end. In this position, when fastener 912 is pivoted to a second orientation, like distal fastener 906 of FIG. 44, tissue contacting surface 916 is in contact with the tissue. As shown in FIGS. 50 and 51, second end 922 is the leading end and first end 920 is the trailing end. In this position, when fastener 912 is pivoted to the second orientation, like proximal fastener 908 of FIG. 44, tissue contacting surface 916 is in contact with the tissue.

Fastener body 914 has a free surface 924 opposite tissue contacting surface 916. Free surface 924 is provided with a channel 926 that receives a portion of elongate fastening member 910 when fastener 912 is in a first orientation with respect to elongate fastening member 910. As shown in FIGS. 50 and 51, fastener 912 is being slid along elongate fastening member 910. In particular, a through bore 928 extends from tissue contacting surface 916 through free surface 924. Through bore 928 is larger in diameter than elongate fastening member 910 so that fastener 912 freely slides along elongate fastening member 910. A portion of elongate fastening member 910 fits within channel 926 on free surface 924 and a portion of elongate fastening member 910 fits within groove 918 on tissue contacting surface 916.

Fastener body 914 is shown with first end 920 having a substantially flat profile and second end 922 having a tapered profile. In general, any suitable external configuration can be used for fastener 912. Examples of fasteners may be found in U.S. Pat. Nos. 5,163,960; 5,403,348; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,159,234; 6,368,343; 6,447,516; 6,475,230; 6,592,609; 6,635,073; 6,719,765; 7,094,251; and 7,329,263. Other fastener types are disclosed in U.S. Patent Application Publication Nos. 2003/0181800, 2004/0230223, and 2004/0220616. The above cited patents and patent applications are hereby incorporated by reference.

Fastener 912 can be made of any biocompatible material suitable for a given application. For example, the fasteners may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, multi-component, solid, hollow, polygon-shaped, pointed, self-introducing, and combinations thereof. Also, the fasteners may include metallic material, polymeric material, ceramic material, composite material, body tissue, synthetic tissue, hydrophilic material, expandable material, compressible material, heat bondable material, and combinations thereof. Examples of body tissue include bone, collagen, cartilage, ligaments, or tissue graft material like xenograft, allograft, and autograft. The fasteners may also be made from a porous matrix or mesh of biocompatible and bioresorbable fibers acting as a scaffold to regenerate tissue.

The fasteners may further be made of or have a coating made of an expandable material. The material could be compressed then allowed to expand. Alternatively, the material could be hydrophilic and expand when it comes in contact with liquid. Examples of such expandable materials are ePTFE and desiccated body tissue.

Moreover, the fasteners described herein and incorporated by reference may include therapeutic substances to promote healing. These substances could include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

Figures 52A, 52B:
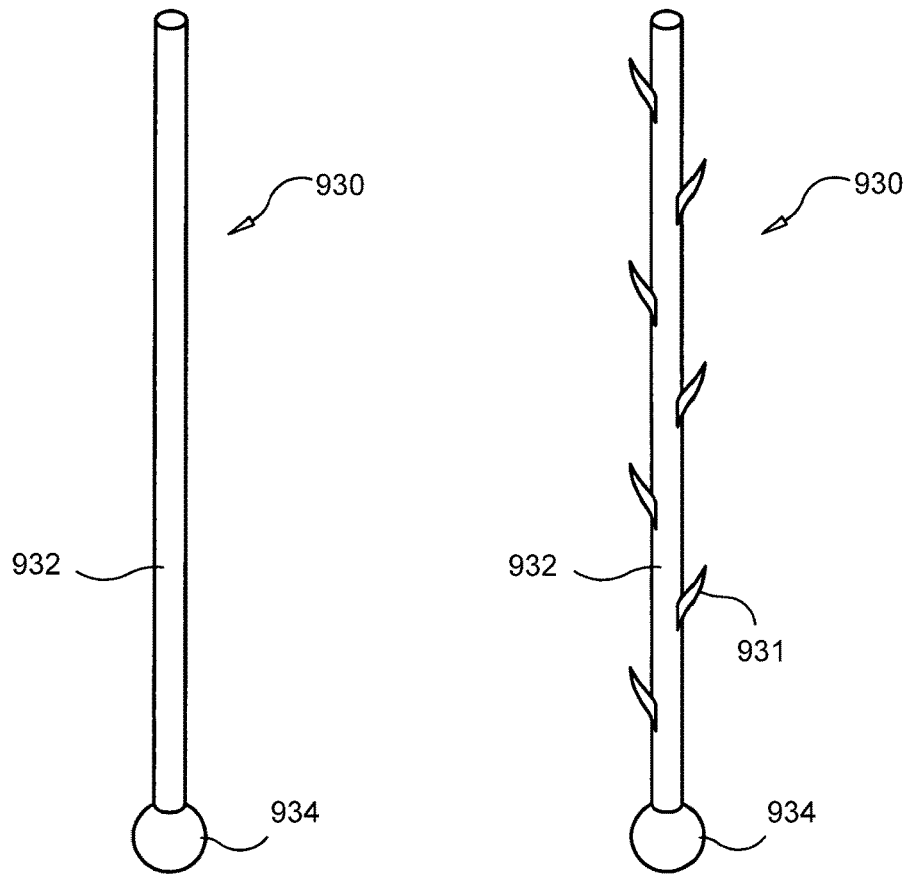
FIG. 52A shows an elongate fastening member according to the present invention.
FIG. 52B shows an elongate fastening member including expandable members.

FIG. 52A shows an exemplary embodiment of an elongate fastening member 930. Elongate fastening member 930 includes a body 932 and has a stop 934 at a distal end. Body 932 can be selected for a given application. For example, if a rigid elongate fastening member 930 is needed, body 932 can be a rod or a tube. If a more flexible elongate fastening member 930 is needed, body 932 can be a suture. In general, a wire analogous to those used for cerclage of bone fractures is believed to provide a suitable combination of strength and flexibility. Although body 932 is shown as a single strand wire, the invention can be used with any type of surgical cable, such as a multi-strand cable.

Figure 53:
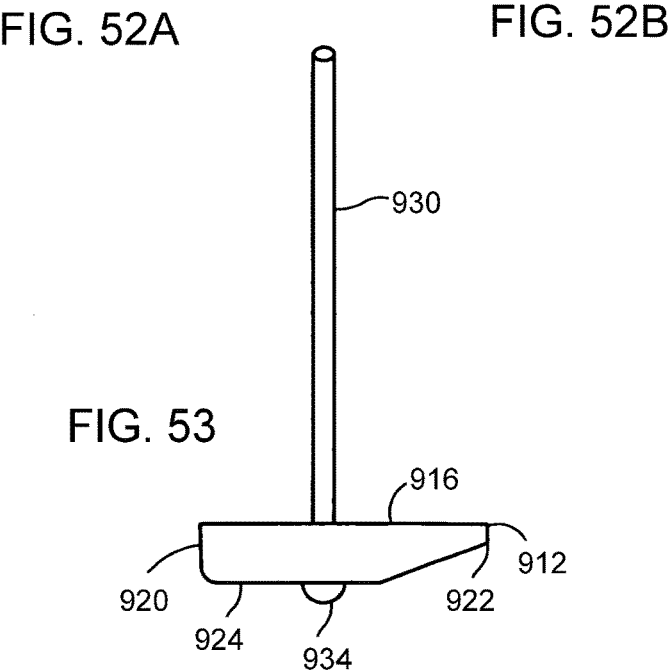
FIG. 53 shows a fastener in a second orientation with respect to an elongate fastening member.

Stop 934 can be made integral with body 932 or separate and then attached. Stop 934 is larger in diameter than through bore 928 in body 914 of fastener 912. Thus, once stop 934 reaches through bore 928, fastener 912 cannot be slid any further along elongate fastening member 930. As shown in FIG. 48, free surface 924 of fastener 912 is provided with a well 936 surrounding through bore 928. Well 936 is configured and dimensioned to receive at least a portion of stop 934. As shown in FIG. 53, this helps reduce the profile of the assembly when fastener 912 is in a second orientation with respect to elongate fastening member 930.

Referring to FIG. 52B, in another embodiment, the elongated fastener member 930 includes expandable members 931, positioned along the body 932. Upon insertion into the tissue, the expandable members 931 expand to engage the surrounding tissue. For examples, the expandable members 931 can be barbs. The barbs 931 engage the surrounding tissue, maintaining the elongated fastener member's 930 position within the tissue.

The elongate fastening members of the present invention may be made of metallic material, non-metallic material, composite material, ceramic material, polymeric material, co polymeric material, or combinations thereof. The members may be degradable, biodegradable, bioabsorbable, or nonbiodegradable. Examples of suture materials that can be used for the elongate fastening members are polyethylene, polyester, cat gut, silk, nylon, polypropylene, linen, cotton, and copolymers of glycolic and lactic acid. Preferably, the members are flexible or bendable. They may be threadlike, monofilament, multifilament, braided, or interlaced. The members may have a coating of therapeutic substances or drugs. For example, the members may include antibiotics, hydroxyapatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Figure 54:
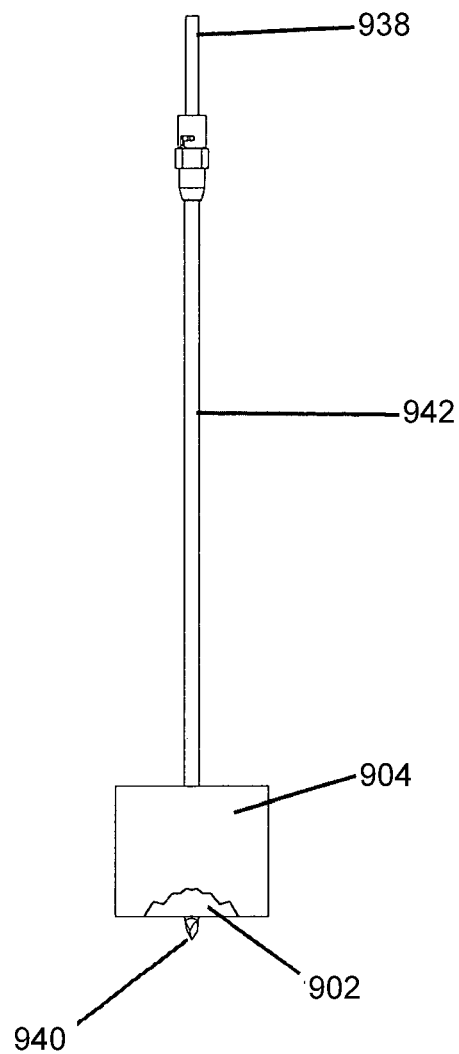
FIG. 54 shows a cannulated drill system used to create a passage through the tissue to be fixed.

The use of the tissue fixation system according to the present invention will now be described using fracture fixation as an example. If necessary, the fracture is reduced bringing fracture portion 902 into contact with bone 904 (FIG. 54). The reduction can be achieved using any number of techniques.

Figure 55:
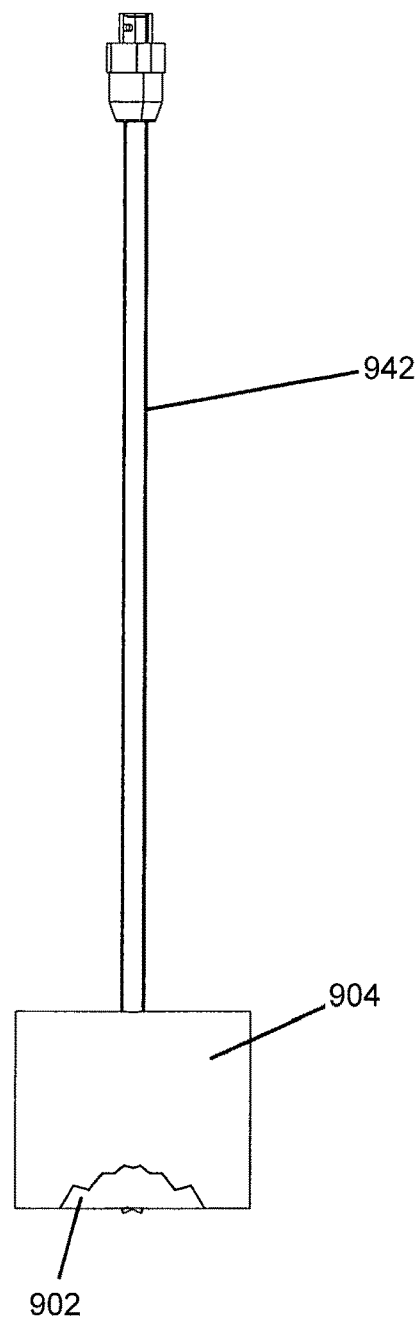
FIG. 55 shows a sleeve having a lumen through which the fixation system can be passed.

As also shown in FIG. 54, a drill system 938 is used to drill across the fracture, thereby creating a passage completely through bone 904. Drill system 938 includes a drill bit 940 with a headpiece configured for attachment to a drill. A drill stop can be placed on the headpiece and prevents drill bit 940 from penetrating too far beyond the tissue to be drilled. Drill system 938 may be a cannulated drill system that fits over a k-wire or other similar guide wire. A cannula or sleeve 942 may encircle drill bit 940 or at least the shaft portion of drill bit 940. As drill bit 940 creates a passage through bone 904, sleeve 942 is positioned in the passage. Drill system 938 is used to create a passage in bone 904 from the proximal side of bone 904 to the distal side of bone 904, then the drill and drill bit 940 are removed from sleeve 942 (FIG. 55).

Figure 56:
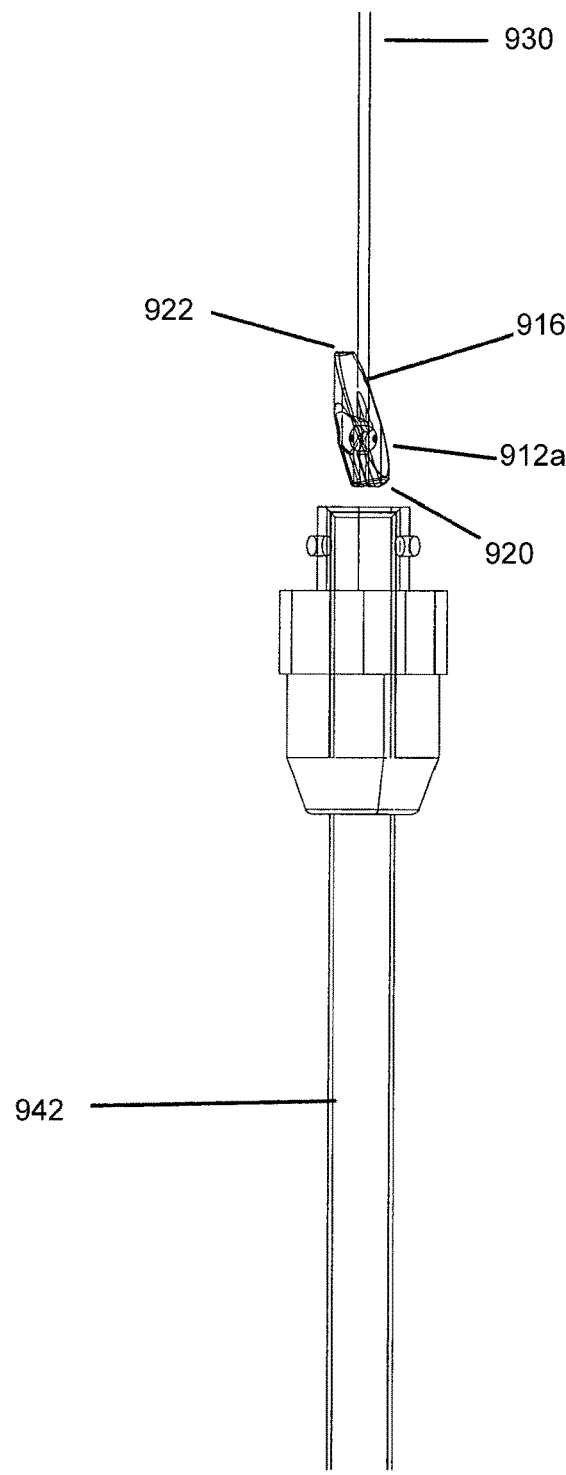
FIG. 56 shows a distal fastener being inserted into the sleeve.
Figure 57:
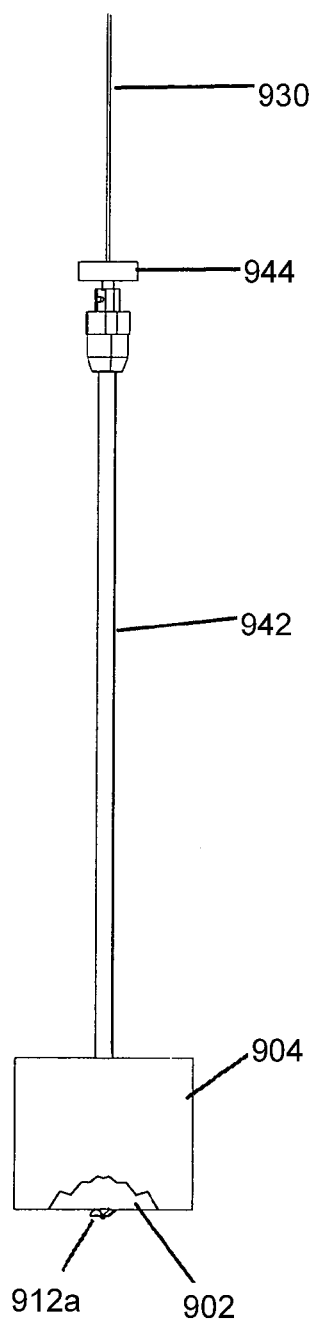
FIG. 57 shows a pushrod used to move the distal fastener through the sleeve.
Figure 58:
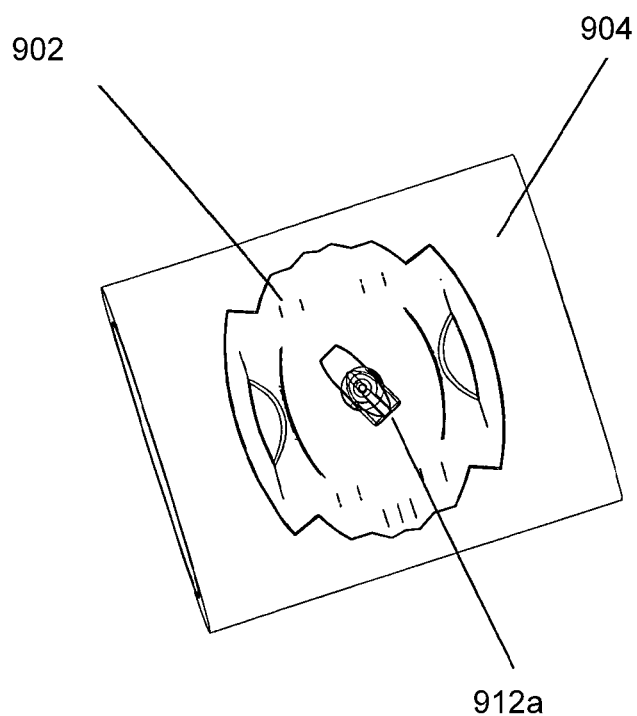
FIG. 58 shows the distal fastener in the second orientation.

As shown in FIG. 56, a distal fastener 912a is inserted into sleeve 942. Distal fastener 912a is inserted in the first orientation with respect to elongate fastening member 930 with first end 920 as the leading end. In this configuration, tissue contacting surface 916 will be in contact with fracture portion 902 when distal fastener 912a is pivoted into the second orientation. This is best seen in FIGS. 57 and 58, in which a pushrod 944 is used to advance distal fastener 912a and elongate fastening member 930 through sleeve 942. Pushrod 944 also facilitates the pivoting of distal fastener 912a from the first orientation to the second orientation. This pivoting is not possible until distal fastener 912a has exited through sleeve 942. Also, since the length of distal fastener 912a is larger than the passage created in bone 904, pulling back on elongate fastening member 930 helps to ensure distal fastener 912a is in the second orientation and flush against fracture portion 902.

Figure 59:
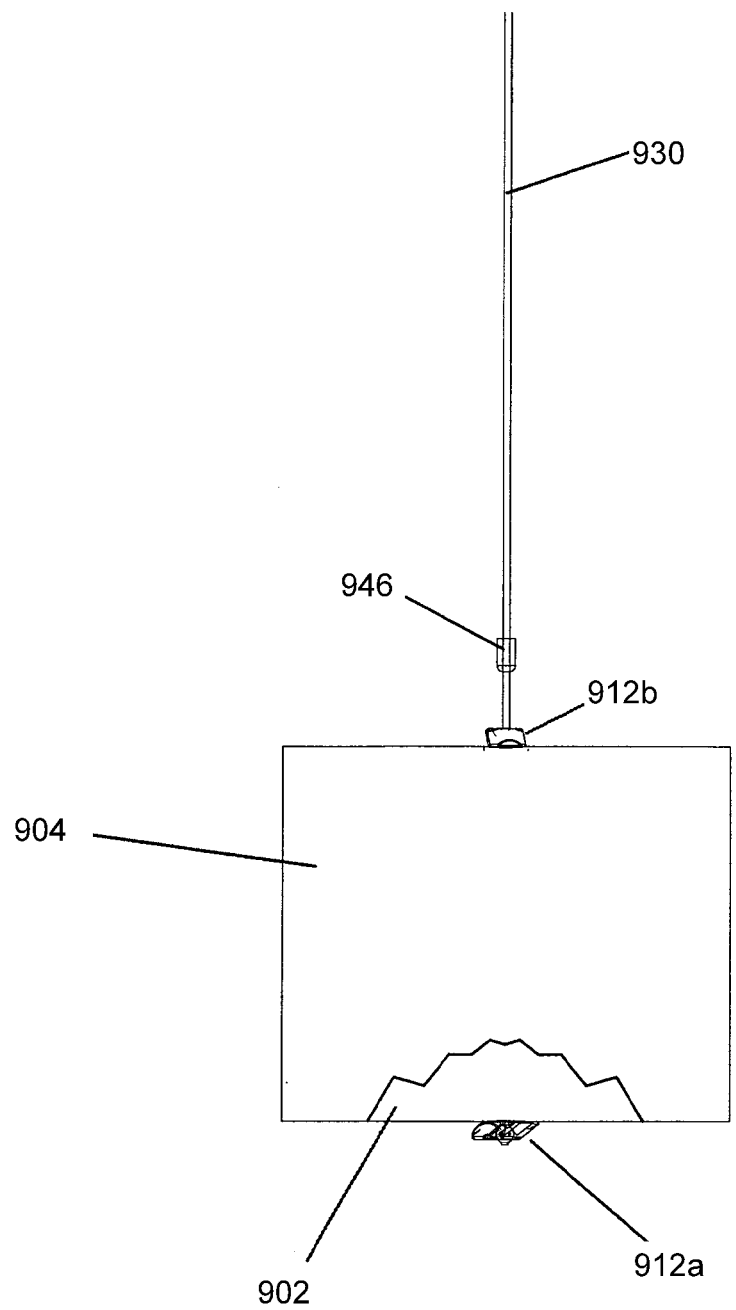
FIG. 59 shows a proximal fastener being used to maintain the tension in the elongate fastening member.

As illustrated in FIG. 59, sleeve 942 is removed from bone 904. Fastener 912a is located on the distal side of bone 904. Elongate fastening member 930 extends from fastener 912a through the bone passage and out the proximal opening of the bone or tissue passage. Any suitable means can be used to keep distal fastener 912a against fracture portion 902 with tension, where the tension can be measure and controlled in accordance with use. For example, elongate fastening member 930 can be deformed at the proximal end of the passage such that the deformed section rests against bone 904. The deformation would depend on the nature of elongate fastening member 930. If elongate fastening member 930 is a relatively flexible element, such as a suture, cable, or wire, then simply tying a knot in fastening member 930 could be sufficient to maintain the tension. If elongate fastening member 930 does not allow a knot, such as would be the case with a rod or tube, then mechanical deformation of elongate fastening member 930 to create an enlarged head could be sufficient to maintain the tension. U.S. Pat. No. 7,361,178, the contents of which are incorporated herein by reference, discloses mechanisms to mechanically deform an extension member and could be used to deform elongate fastening member 930.

Alternatively, the elongated fastening member 930 can be deformed by an energy, such as thermal energy, to deform elongate fastening member 930 to create an enlarged head sufficient to maintain the tension.

In an exemplary embodiment, a proximal fastener 912*b* is used to secure distal fastener 912*a* and elongate fastening member 930. In this embodiment, proximal fastener 912*b* is identical to distal fastener 912*a*. If not already pre-loaded, proximal fastener 912*b* is loaded onto elongate fastening member 930. Proximal fastener 912*b* is loaded as shown in FIGS. 50 and 51, i.e. with second end 922 as the leading end so that after proximal fastener 912*b* is slid down against bone 904 and pivoted into the second orientation, tissue contacting surface 916 is in contact with bone 904.

Elongate fastening member 930 is tensioned, and proximal fastener 912*b* is secured to elongate fastening member 930 to thereby approximate the fracture and stabilize bone 904. The tension of elongate fastening member 930 pulls on distal and proximal fasteners 912*a*, 912*b* generally toward each other, thereby applying pressure to the fractured bone or tissue. In this regard, a bushing 946 can be used to secure proximal fastener 912*b* with the desired tension. Single or multiple elongated members 930 can be used to secure the fractured bone or tissue.

Although a number of mechanisms can be used to secure bushing 946, an instrument or medical device particularly useful for this will now be described.

In this regard, the present invention also provides a medical device for securing a fastener against relative movement with respect to a cable. As previously disclosed, a cable and pair of oppositely spaced fasteners can be used to secure a bone facture. The cable is passed through the bone and fracture; a first fastener secures the cable on a first side (fracture side) of the bone; and a second fastener is positioned about the cable on a second side of the bone, opposite the first fastener. A bushing is positioned onto the cable to secure the second fastener against the second side of the bone. A force is applied to the bushing, compressing the second fastener against the second side of the bone and providing a tension to the cable. The tension in the cable can be measured and controlled, for example, with the used of a sensor and spring element. The spring can apply the force to tension the cable, and the sensor can be used to measure the resulting tension. Alternatively, the sensor can measure the compression of the tissue to determine the tension. The bushing is crimped about the cable, securing the second fastener against the second side of the bone, such that a tension is provided through the cable between the first and second fasteners.

Figure 60:
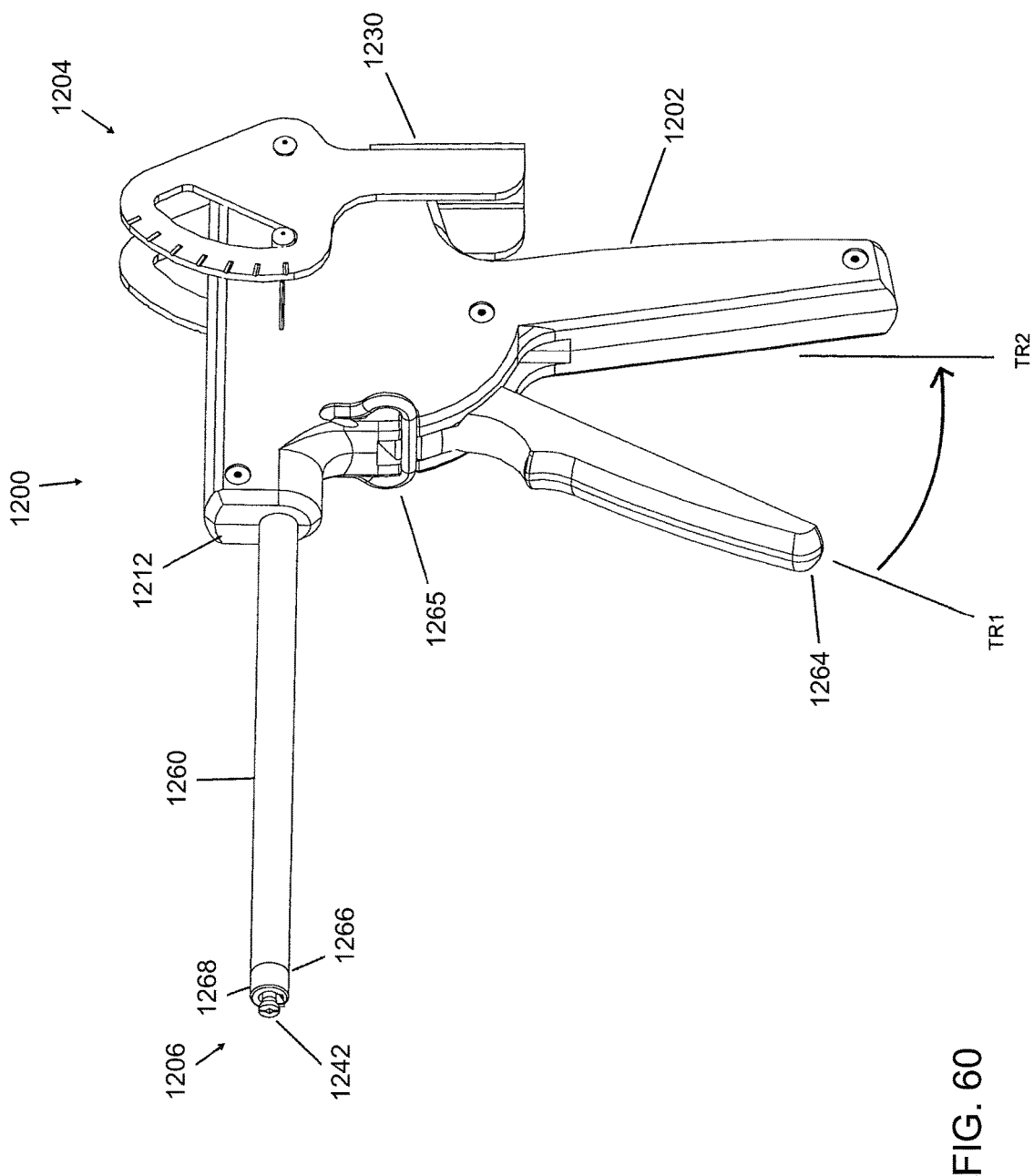
FIG. 60 depicts a front isometric view of the medical device of the present invention.

Referring to FIG. 60, a medical device 1200 is provided for securing the bushing to the cable. The medical device 1200 includes a handle portion 1202 having a tensioning mechanism 1204, tensioning the cable and applying a force to the bushing, and a crimping mechanism 1206 for securing the bushing to the cable.

Figure 61:
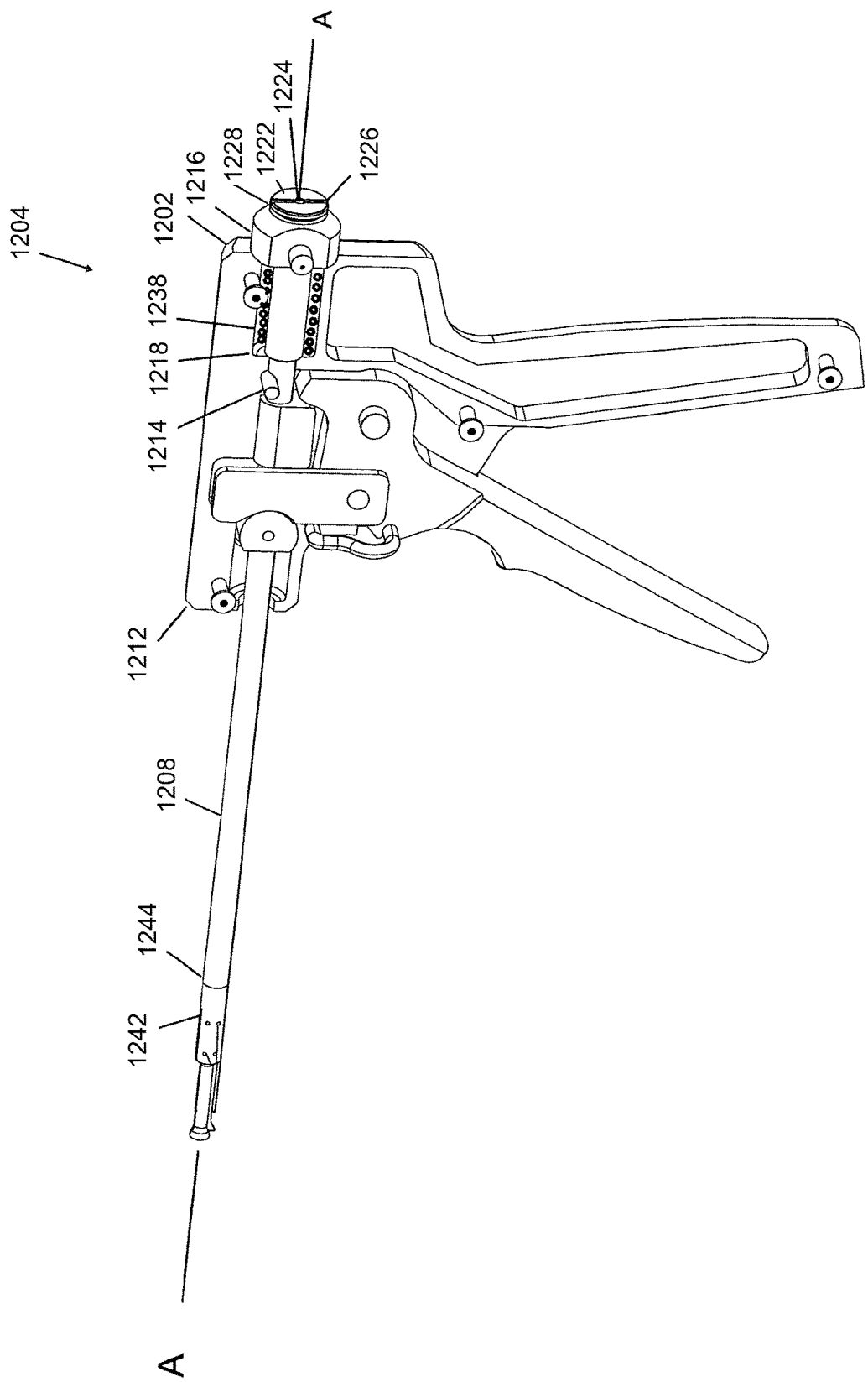
FIG. 61 depicts a rear partial isometric view showing the tensioning mechanism of the medical device of FIG. 60.
Figure 62:
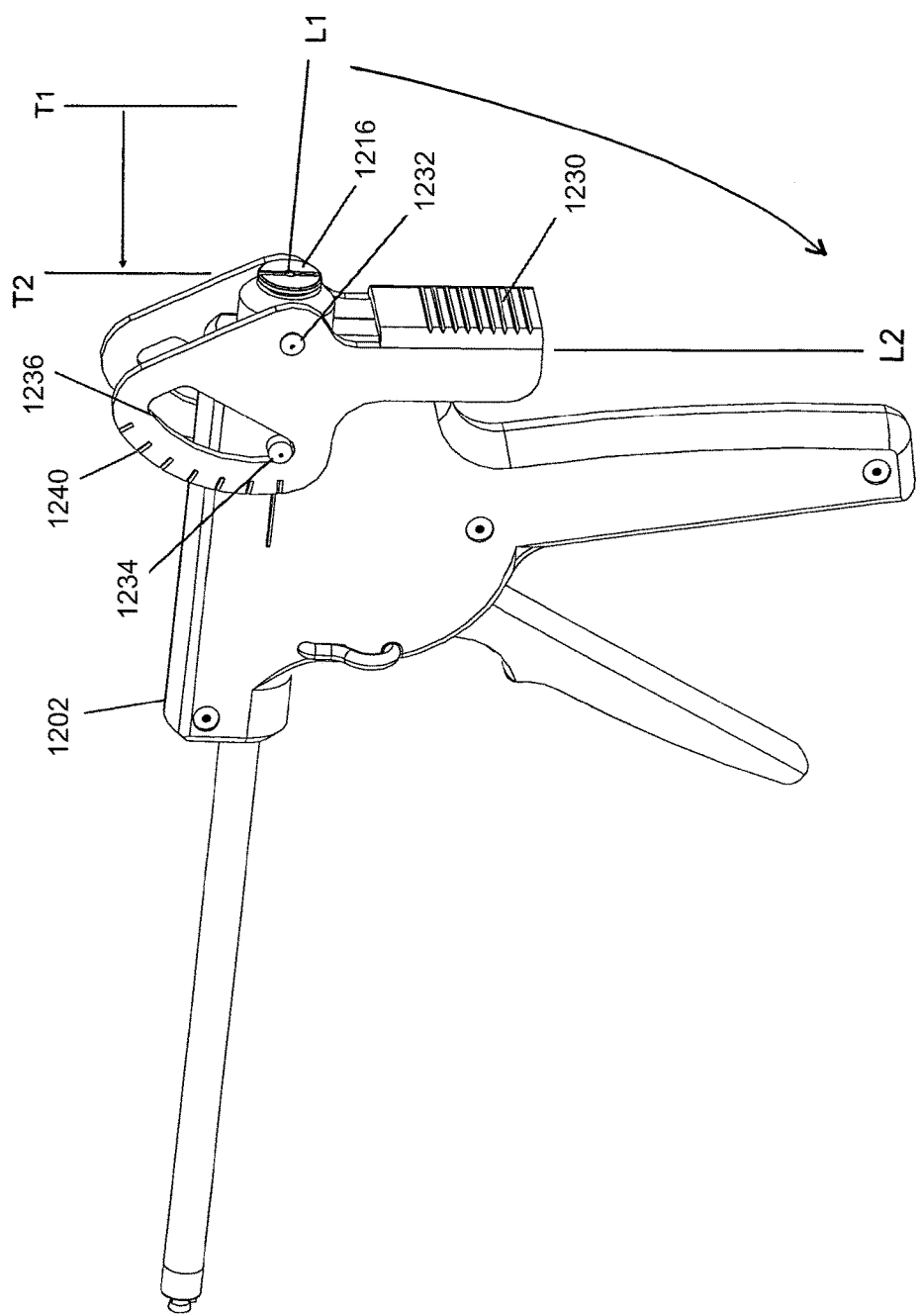
FIG. 62 depicts a rear isometric view showing the tensioning mechanism of the medical device of FIG. 60.

Referring also to FIGS. 61 and 62, the tensioning mechanism 1204 includes a collett holder 1208 defining a longitudinal passage along a central longitudinal axis A. The collett holder 1208 is affixedly positioned through a top portion 1212 of the handle portion 1202 with collett holder pin 1214. A cable tensioner 1216 is slidably positioned on a first end 1218 of the collett holder 1208. The cable tensioner 1216 defines a cable passage longitudinally aligned with the longitudinal passage of the collett holder 1208. An end portion 1222 of the cable tensioner 1216 includes a cable aperture 1224 for threading the cable there through. A radial groove 1226 and circumferential groove 1228 are provided on the end portion 1222 of the cable tensioner 1216, such that the cable can be wrapped about the circumferential groove 1228 of the cable tensioner 1216, thereby preventing relative movement between the cable and the cable tensioner 1216.

A cable tension lever 1230 is pivotally connected to the cable tensioner 1216 with a lever pin 1232. The cable tension lever 1230 is adjustably positioned on the handle portion 1202 with body pins 1234, wherein a body pin 1234 is mirrorly positioned on opposite sides of the handle portion 1202. The body pins 1234 are engaged in the cable tension lever 1230 arcuate lever slots 1236, such that cable tension lever 1230 and cable tensioner 1216 are movably connected to the handle portion 1202.

In use, as the cable tension lever 1230 is pivoted about the cable tensioner 1216 from a first lever position L1 to a second lever position L2, the body pins 1234 traverse the arcuate lever slots 1236, resulting in a translation of the cable tensioner 1216 along the first end 1218 of the collett holder 1208 from a first tensioner position T1 to a second tensioner position T2. A tension bias member 1238 is interposed between the cable tensioner 1216 and the handle portion 1202, biasing the cable tensioner 1216 into the first tensioner position T1. The cable tension lever 1230 includes tension indicating markings 1240 along each of the arcuate lever slots 1236. The tension markings 1240 indicate the tension to be applied to the cable.

Figure 77:
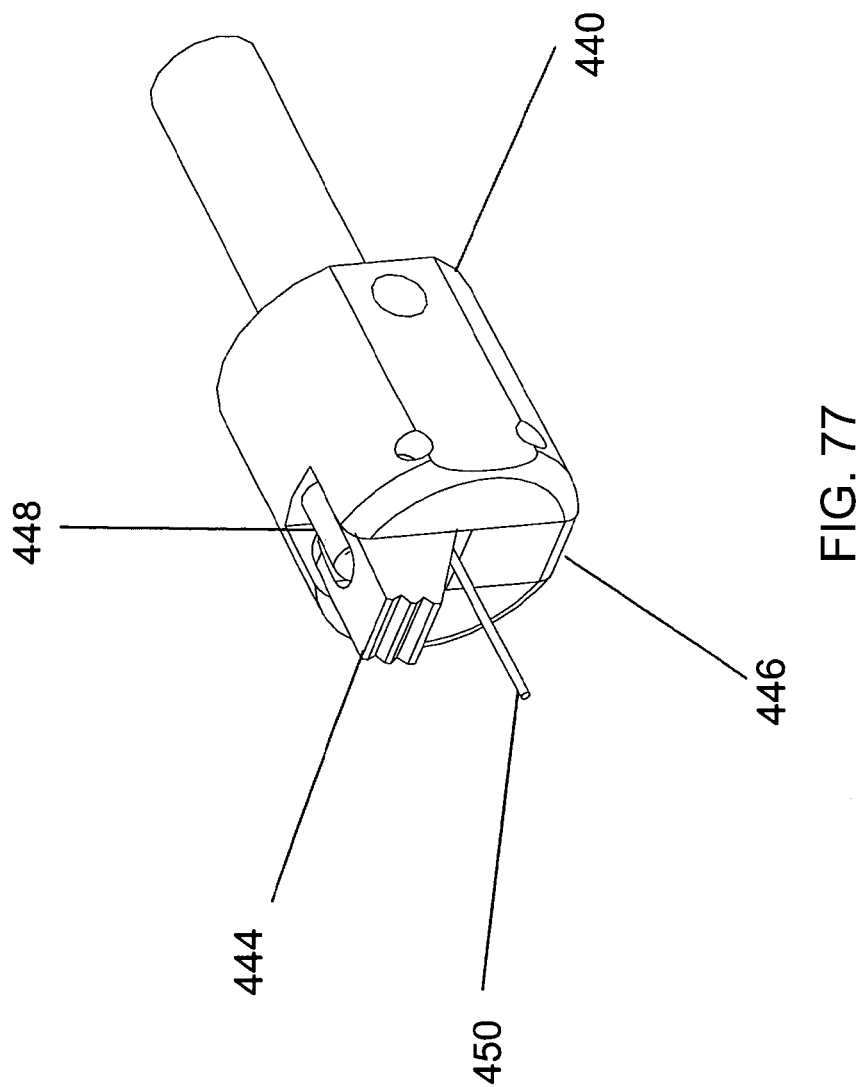
FIG. 77 depicts an alternative cable tensioner for the medical device of FIG. 60.
Figure 78:
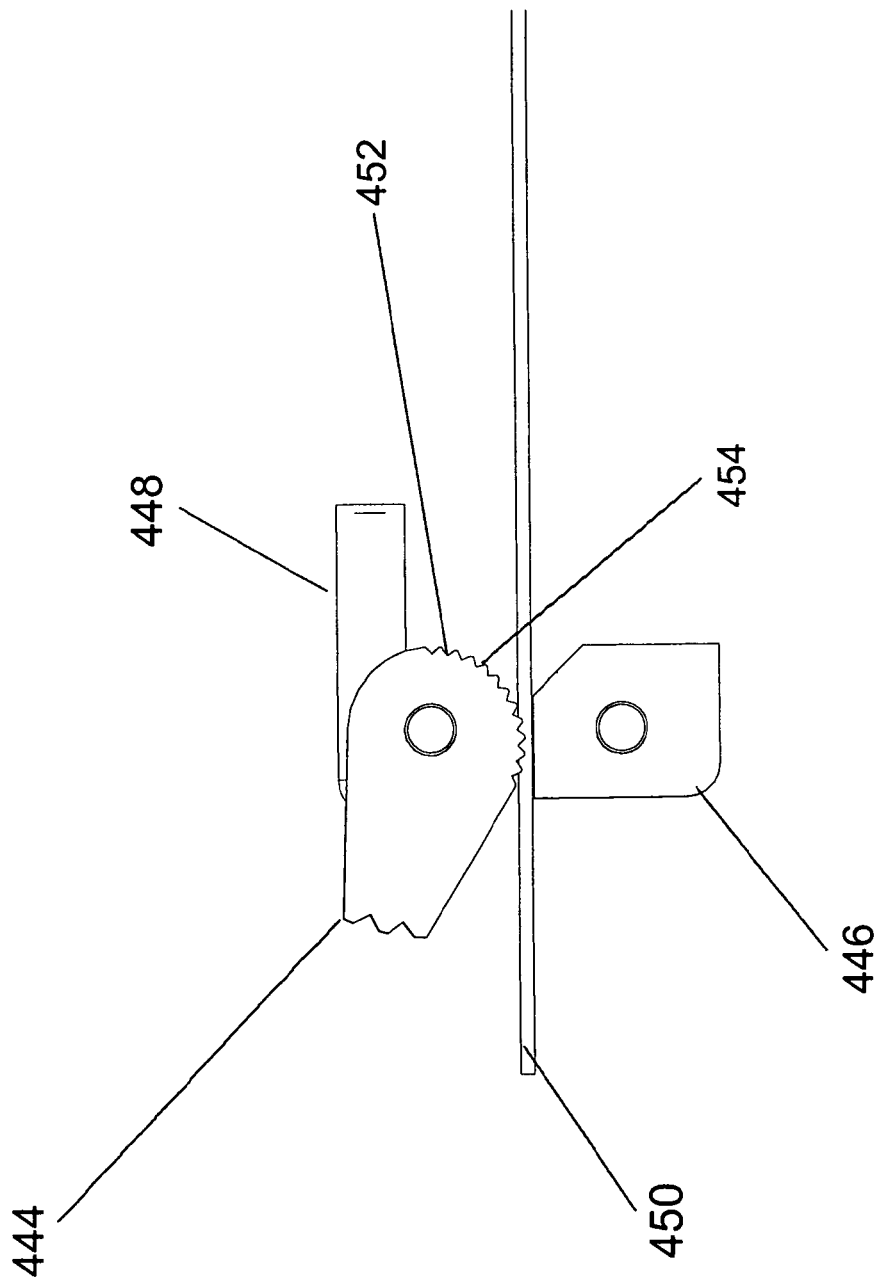
FIG. 78 depicts a sectional view of the cable tensioner of FIG. 77.

Referring also to FIG. 77 an alternative cable tensioner 440 is provided. Cable tensioner 440 is slidably positioned on a first end 1218 of the collett holder 1208. The cable tensioner 440 defines a cable passage longitudinally aligned with the longitudinal passage of the collett holder 1208. An end portion 442 of the cable tensioner 440 includes a cleat 444 and a cleat stop 446. The cleat 444 is pivotally mounted to the cable tensioner 440, including a bias member 448 biasing the cleat 444 into a closed position. A cable 450 is threadable between the cleat 446 and the cleat stop 448, where in the closed position the cleat 446 imparts a force onto the cable 450, securing the cable 450 in the cable tensioner 440.

The bias member 448 biases the cleat 444 such that in the closed position the cable can be further drawn through the cable tensioner 440, for example, to position the fastener proximal to the tissue while removing any initial slack from the cable 450. However, the cleat 444 prevents the cable 450 from being drawn back through the cable tensioner 440. For example, the cleat 444 can include an arcuate contact surface 452 such that the force imparted on the cable 450 in the closed position increases as the tension on the cable 450 increases, preventing the cable 450 from being drawn back through the cable tensioner 440. The cleat arcuate surface 452 can further include a plurality of teeth 454, which can be utilized to grip cable 450.

Figure 63:
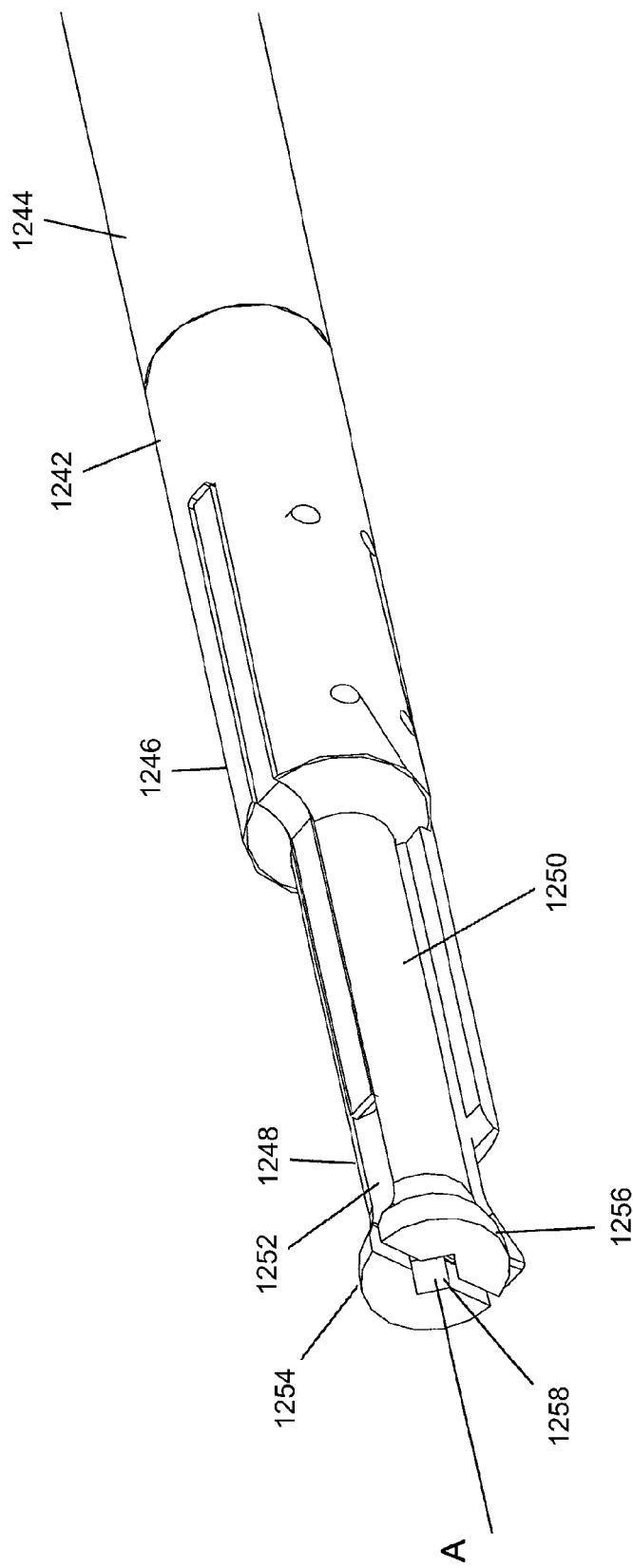
FIG. 63 depicts an isometric view of the crimping mechanism collett of the medical device of FIG. 60.

Referring to FIGS. 61 and 63, a collett 1242 is affixed to a second end portion 1244 of the collett holder 1208, opposite the cable tensioner 1216. The collett 1242 defines a collett passage longitudinally aligned with the longitudinal passage of the collett holder 1208 along the central longitudinal axis A. An end portion of the collett 1242 is bisected, forming first and second collett arms 1248 and 1250. A gap portion 1252 is provided between the first and second collett arms 1248 and 1250. Each of the first and second collett arms 1248 and 1250 includes force application end portions 1254 and 1256. The force application end portions 1254 and 1256 combine to form a bushing aperture 1258 configured to received the bushing therein. The collett 1242 is made of a semi-rigid material, such that the first and second collett arms 1248 and 1250 can be moved from an open to a closed position, closing the gap 1252 between the force application end portions 1254 and 1256.

In use, the tensioning mechanism 1204 is used to tension the cable. The cable can include a single or multiple filaments. The cable is inserted through the medical device 1200 along the central longitudinal axis A, through the collett 1242, collett holder 208, and the cable tensioner 1216, positioning the bushing in the bushing aperture 1258 and extending the cable through the cable aperture 1224. To tension the cable, the cable tension lever 1230 is actuated from the first lever position L1 to the second lever position L2, sliding the cable tensioner 1216 along the collett holder 1208 from the first tensioner position T1, into the handle portion 1202 against the tension bias member 1238, to the second tensioner position T2. The cable is positioned through the radial groove 1226 and wrapped about the circumferential groove 1228 on the end portion 1222 of the cable tensioner 1216, securing the cable to the cable tensioner 1216. The cable tension lever 1230 is released, such that tension bias member 1238 biases the cable tensioner 1216 from the second tensioner position T2 towards the first tensioner position T1. The movement of the cable tensioner 1216 towards the first tensioner position T1 applies a tension to the cable, forcing the bushing into the second fastener. The applied tension can be selected by actuating the cable tension lever 1230 to the desired tension marking 1240.

Figure 64:
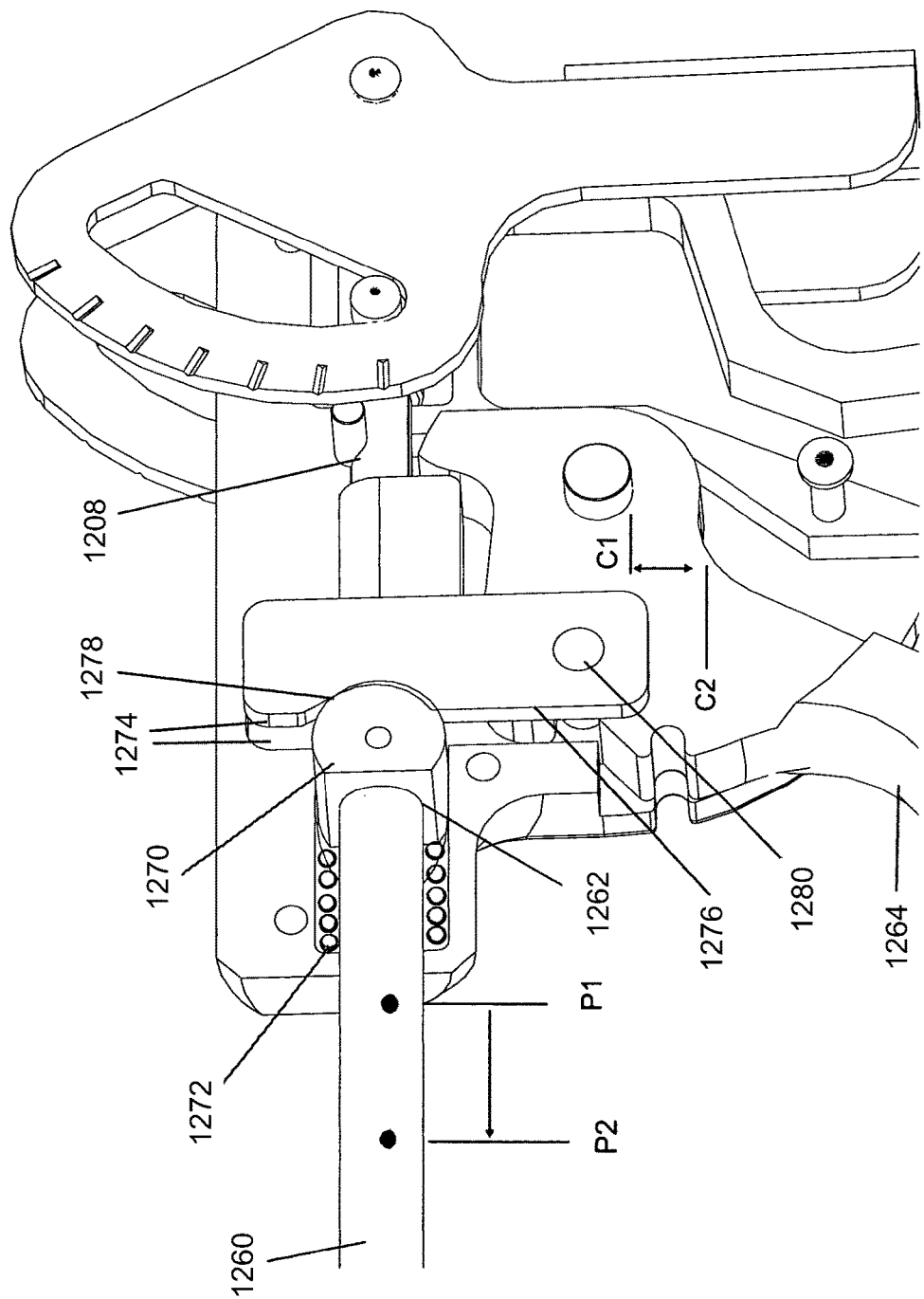
FIG. 64 depicts a partial isometric view showing the handle portion of the crimping mechanism of the medical device of FIG. 60.

Referring again to FIGS. 60 and 64, the crimping mechanism 1206 includes an outer tube 1260 slidingly positioned over the collett holder 1208. The outer tube 1260 includes a first end 1262 operably connected to a trigger 1264 and a second end 1266 connected to a collett closer 1268. The trigger 1264 is pivotally mounted in the handle portion 1202, such that the trigger 1264 can be actuated from a first trigger position TR1 to a second trigger position TR2. A locking mechanism 1265 prevents the trigger 1264 from being actuated. The locking mechanism 1265 is rotated to disengage the trigger 1264, allowing actuation of the trigger 1264.

The operable connection between the first end of the outer tube 1262 and the trigger 1264 includes an outer tube ferrule 1270 slidably positioned about the collett holder 1208 and affixed to the first end of the outer tube 1262. A tube bias member 1272 is interposed between the handle portion 1202 and the outer tube ferrule 1270, such that the tube bias member 1272 biases the outer tube ferrule 1270 and the outer tube 1260 into a first tube position P1. A pair of crimp cams 1274 are pivotally connected to the handle portion 1202 on opposite sides of the trigger 1264. The crimp cams 1274 each include first edges 1276 having an arcuate section 1278 for engaging the outer tube ferrule 1270, where the crimp cams 1274 are translatable with respect to the handle portion 1202 from a first cam position C1 to a second cam position C2.

An actuation of the trigger 1264 from a first trigger position TR1 to a second trigger position TR2 translated the crimp cams 1274 with respect to the handle portion from a first cam position C1 to a second cam position C2 position. The arcuate sections 1278 of the crimp cams 1274 engage the outer tube ferrule 1270, translating the outer tube ferrule 1270 and the outer tube 1260 along the collett holder 1208 from the first tube position P1 to a second tube position P2. As the trigger 1264 is released, the tube bias member 1272 biases the outer tube ferrule 1270 and the outer tube 1260 from the second tube position P2 to the first tube position P1. Simultaneously, the crimp cams 1274 and the trigger 1264 are moved to the first cam position C1 and the first trigger position TR1.

Figure 65:
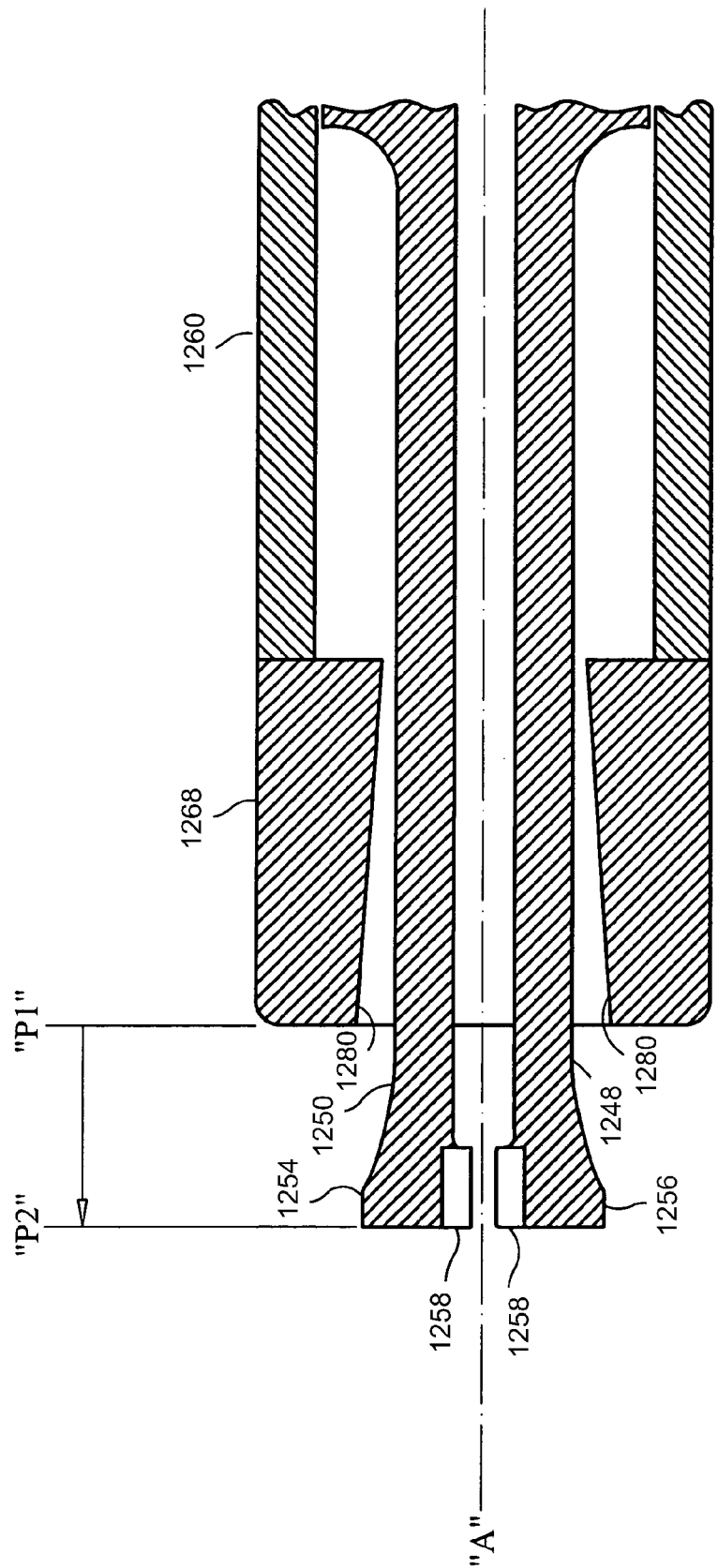
FIG. 65 depicts a top sectional view of the crimping mechanism collett closer of the medical device of FIG. 60.

Referring to FIGS. 60 and 65, the collett closer 1268 is positioned on the outer tube 1260 proximal to the force application end portions 1254 and 1256 of the first and second collett arms 1248 and 1250. As the outer tube 1260 is moved from the first tube position P1 to the second tube position P2, the collett closer 1268 is moved over the force application end portions 1254 and 1256. The collett closer 1268 includes inner tapered surfaces 1280, such that the inner tapered surfaces 1280 apply compressive forces to the force application end portions 1254 and 1256 as the collett closer 1268 is moved over the force application end portions 1254 and 1256, closing the gap 1252 there between.

In use, the trigger 1264 is actuated from the first trigger position TR1 to the second trigger position TR2. The actuation of the trigger 1264 slides the outer tube 1260 along the collett holder 1208 from the first tube position P1 to the second tube position P2, moving collett closer 1268 about the force application end portions 1254 and 1256 of the first and second collett arms 1248 and 1250. The inner tapered surfaces 1280 of the collett closer 1268 apply compressive forces to the first and second force application end portions 1254 and 1256, closing the gap 1252 there between. The trigger 1264 is released, allowing the tube bias member 1272 to bias the outer tube 1260 from the second tube position P2 to the first tube position P1, moving the collett closer 1268 from the force application end portions 1254 and 1256.

Figure 66:
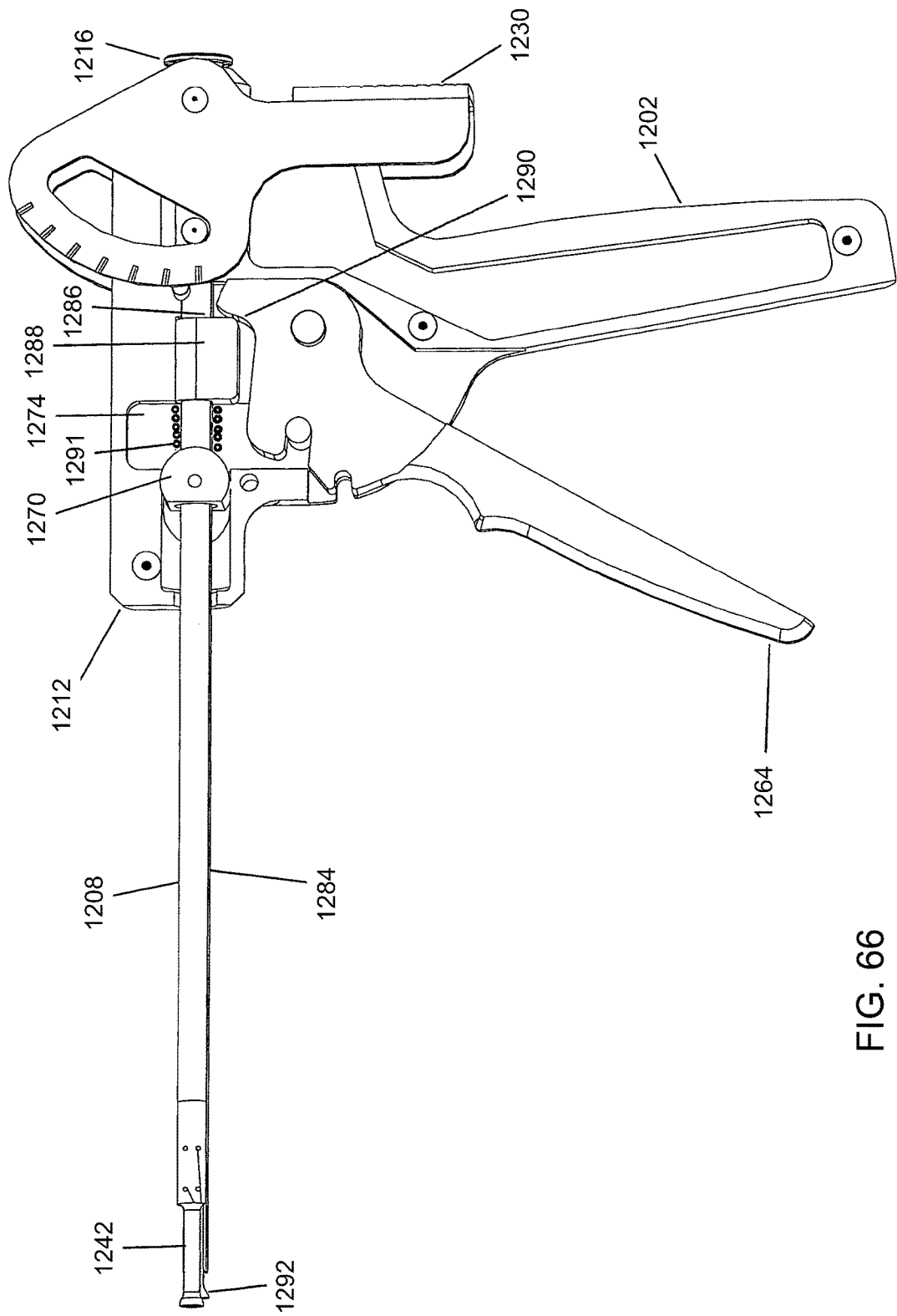
FIG. 66 depicts a partial isometric view showing the cutting mechanism of the medical device of FIG. 60.
Figure 67:
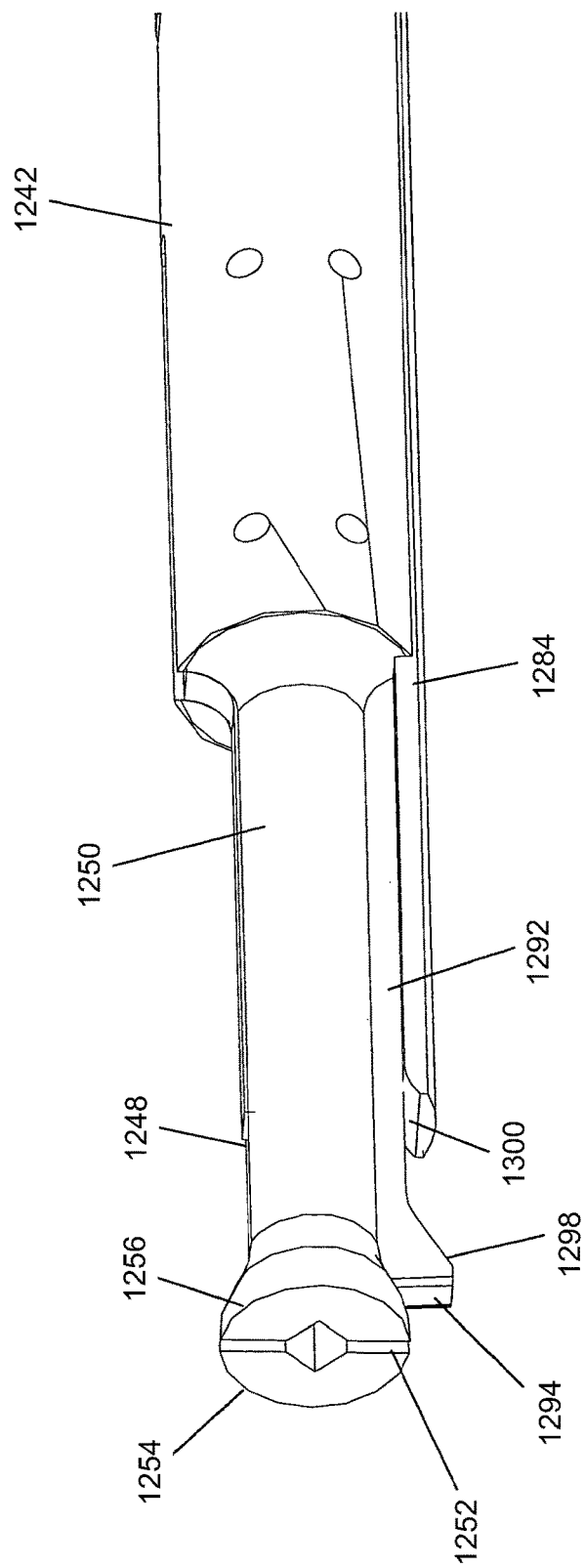
FIG. 67 depicts a partial isometric view showing the collett portion of the cutting mechanism of FIG. 66.
Figure 68:
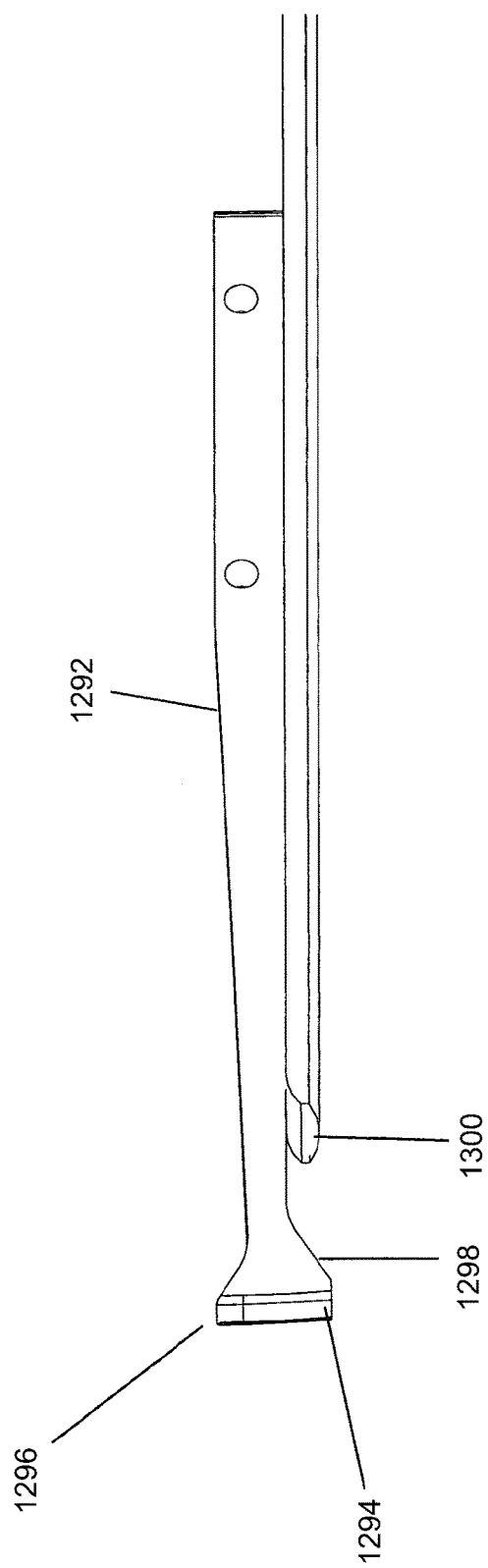
FIG. 68 depicts an isometric view showing the cutting arm of the cutting mechanism of FIG. 67.

Referring to FIGS. 66-68, the crimping mechanism 1206 can further include a cutting mechanism. The cutting mechanism includes a cut off cam 1284 slidingly positioned along a bottom portion of the collett holder 1208. The cut off cam 1284 includes a first end portion 1286 positioned through the outer tube ferrule 1270. A cut off cam ring 1288 is slidably positioned about the collett holder 1208, engaging the first end portion 1286 of the cut off cam 1284. The cut off cam ring 1288 is positioned proximal to the trigger 1264, such that as the trigger 1264 is actuated from the first trigger 1264 position TR1 to the second trigger 1264 position TR2, a top portion 1290 of the trigger 1264 engages the cut off cam ring 1288, sliding the cut off cam ring 1288 and cut off cam 1284 along the collett holder 1208. A cut off bias member 1291 is interposed between the outer tube ferrule 1270 and the cut off cam ring 1288.

A cut off arm 1292 is connected to the collett 1242, at least partially positioned in the gap 1252 between the first and second collett arms 1248 and 1250. The cut off arm 1292 includes a cutting head portion 1294 positioned proximal to the first and second force application end portions 1254 and 1256, at least partially positioned in the gap 1252, interposed between the first and second collett arms 1248 and 1250. The cutting head portion 1294 includes a cutting edge 1296, for cutting the cable, and a lower angular surface 1298 for engagement by a second end portion 1300 of the cut off cam 1284.

In use, the trigger 1264 is actuation from the first trigger position TR1 to the second trigger position TR2. The actuation of the trigger 1264 results in the top portion 1290 of the trigger 1264 engaging the cut off cam ring 1288, sliding the cut off cam ring 1288 and cut off cam 1284 along the collett holder 1208. The second end portion 1300 of the cut off cam 1284 engages the angular surface 1298 of the cutting head 1294, forcing the cutting edge 1296 into the cable, cutting the cable. The trigger 1264 is released, allowing the cut off bias member 1291 to bias the cut off cam 1284 from the cutting head 1294.

Figure 69:
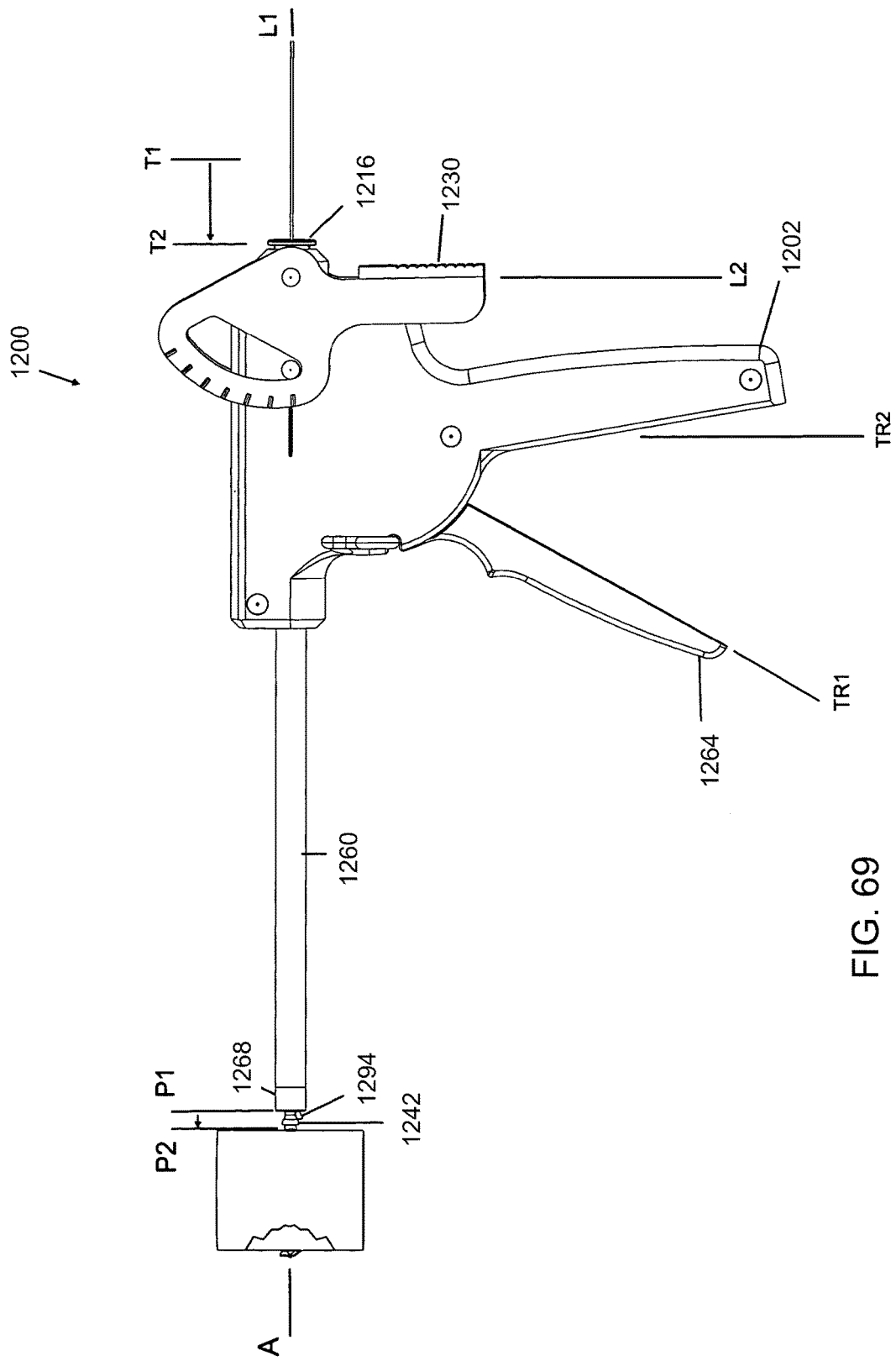
FIG. 69 depicts the medical device of FIG. 60 in use to secure a bone fracture.

Referring to FIG. 69, in a method of use, the cable is passed through the bone and fracture, where a first fastener secures the cable on a first side (fracture side) of the bone and a second fastener is positioned about the cable on a second side of the bone, opposite the first fastener. A bushing is positioned onto the cable to secure the second fastener against the second side of the bone.

The cable is inserted through the medical device 1200 along the central longitudinal axis "A", through the collett 1242, collett holder 1208, and the cable tensioner 1216, positioning the bushing in the bushing aperture 1258 and extending the cable through the cable aperture 1224. To tension the cable, the cable tension lever 1230 is actuated from the first lever position L1 to the second lever position L2, sliding the cable tensioner 1216 along the collett holder 1208 from the first tensioner position T1, into the handle portion 1202 against the tension bias member 1238, to the second tensioner position T2. The cable is positioned through the radial groove 1226 and wrapped about the circumferential groove 1228 on the end portion 1222 of the cable tensioner 1216, securing the cable to the cable tensioner 1216. The cable tension lever 1230 is released, such that tension bias member 1238 biases the cable tensioner 1216 from the second tensioner position T2 towards the first tensioner position T1. The movement of the cable tensioner 1216 towards the first tensioner position T1 applies a tension to the cable, pressing the bushing against the second fastener. The applied tension can be selected by actuating the cable tension lever 1230 to the desired tension marking 1240.

The trigger 1264 is actuated from the first trigger position TR1 to the second trigger position TR2. The actuation of the trigger 1264 slides the outer tube 1260 along the collett holder 1208 from the first tube position P1 to the second tube position P2, moving collett closer 1268 about the force application end portions 1254 and 1256 of the first and second collett arms 1248 and 1250. The inner tapered surfaces 1280 of the collett closer 1268 apply compressive forces to the first and second force application end portions 1254 and 1256, compressing the first and second force application end portions 1254 and 1256 about the bushing positioned in the bushing aperture 1258. The compressive forces crimp the bushing about the cable, securing the bushing to the cable.

Simultaneously, the actuation of the trigger 1264 results in the top portion 1290 of the trigger 1264 engaging the cut off cam ring 1288, sliding the cut off cam ring 1288 and cut off cam 1284 along the collett holder 1208. The second end portion 1300 of the cut off cam 1284 engages the angular surface 1298 of the cutting head 1294, forcing the cutting edge 1296 into the cable, cutting the cable.

In another embodiment a medical device 1320 of the present invention secures a fastener against relative movement with respect to a suture, with the fastener itself being deformed. Medical device 1320 is substantially similar to medical device 1200 and like reference number shall be used to indicate like items.

Figure 70:
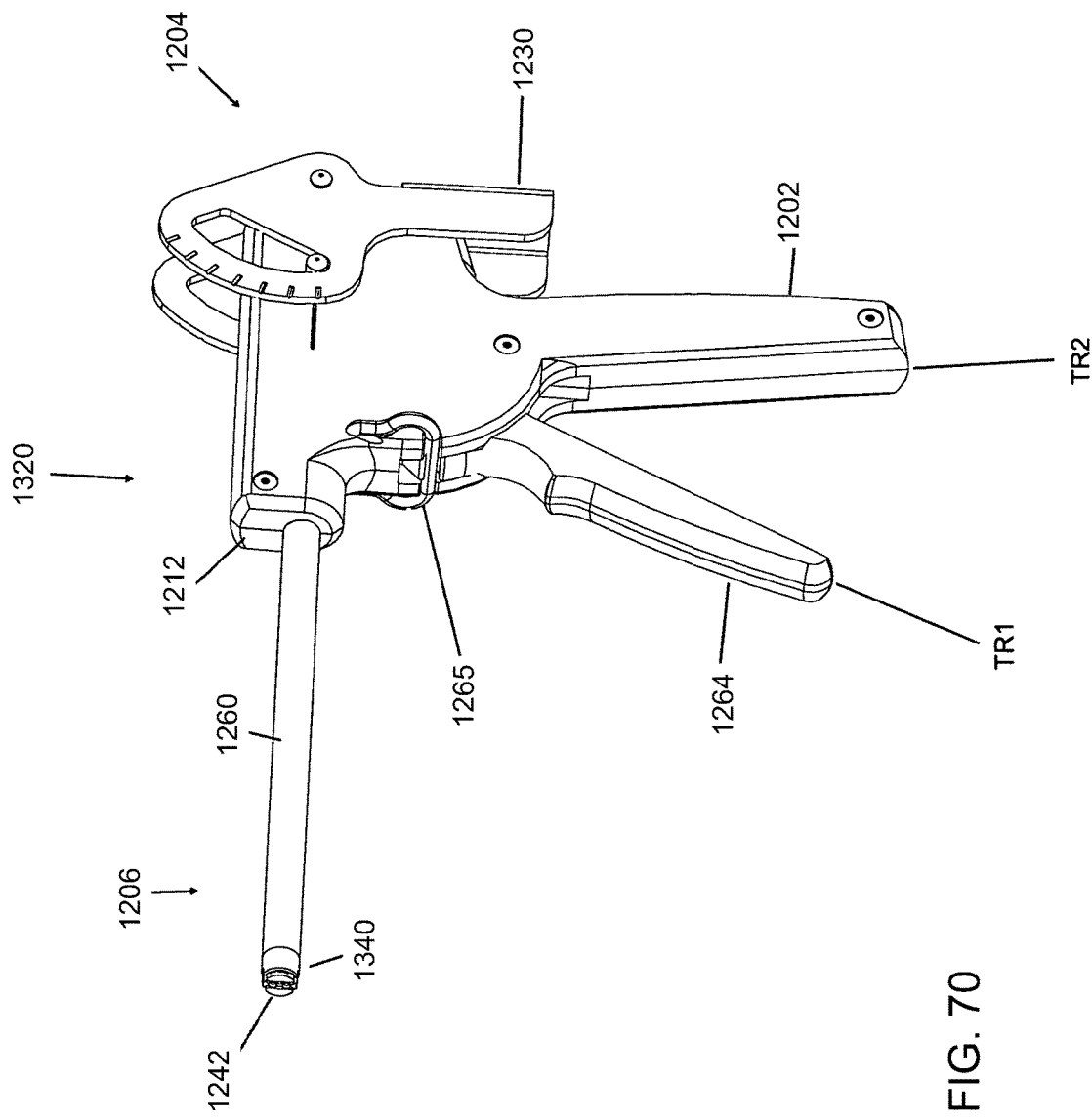
FIG. 70 depicts a front isometric view of an alternative medical device of the present invention.
Figure 71:
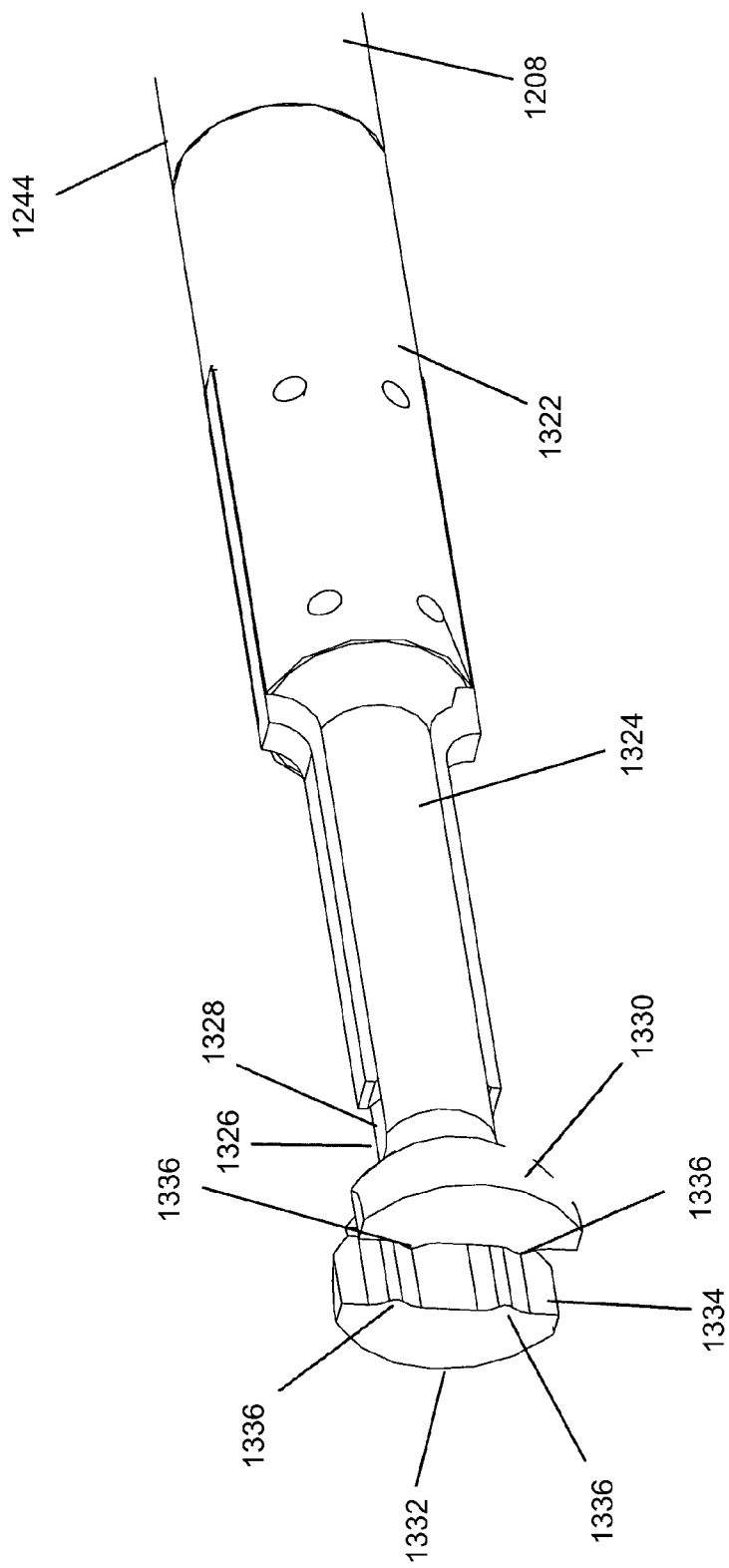
FIG. 71 depicts an isometric view of the crimping mechanism collett of the medical device of FIG. 70.

Referring to FIGS. 70 and 71, medical device 1320 includes collett 1322. As with collett 1242, previously disclosed and illustrated, collett 1322 is affixed to the second end portion 1244 of the collett holder 1208, opposite the cable tensioner 1216. The collett 1322 defines a collett passage longitudinally aligned with the longitudinal passage of the collett holder 1208, along the central longitudinal axis A. An end portion of the collett 1322 is bisected, forming first and second collett arms 1324 and 1326. A gap portion 1328 is provided between the first and second collett arm 1324 and 1326. Each of the first and second collett arms 1324 and 1326 includes force application end portions 1330 and 1332. The force application end portions 1330 and 1332 combine to form a fastener aperture 1334 configured to receive the fastener therein. The force application end portions 1330 and 1332 each include opposing compressive members 1336 for compressing the fastener about the suture.

Figure 72:
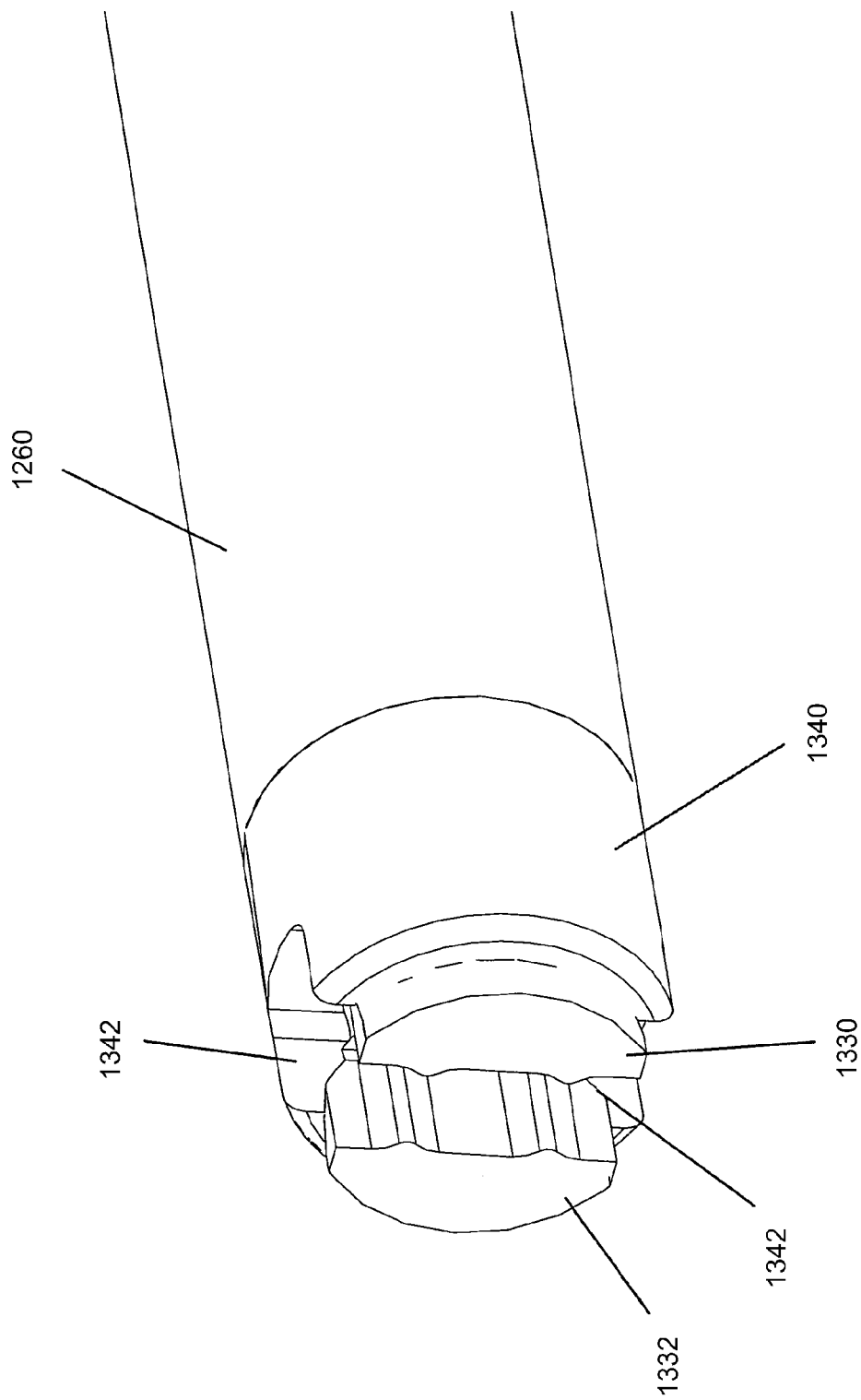
FIG. 72 depicts an isometric view of the crimping mechanism collett closer of the medical device of FIG. 70.

Referring to FIGS. 70 and 72, medical device 1320 includes collett closer 1340. The collett closer 1340 is positioned on the outer tube 1260 proximal to the force application end portions 1330 and 1332 of the first and second collett arms 1324 and 1326. The collett closer 1340 includes slotted sections 1342 configured for receiving end portions of the fastener therein. As the outer tube 1260 is moved from the first tube position P1 to the second tube position P2, the collett closer is moved over the force application end portions 1330 and 1332. Similar to collett closer 1268, the collett closer 1340 includes inner tapered surfaces 1280 (See FIG. 65), such that the inner tapered surfaces 1280 apply compressive forces to the force application end portions 1330 and 1332 as the collett closer 1340 is moved over the force application end portions 1330 and 1332, closing the gap 1328 there between.

Figure 73:
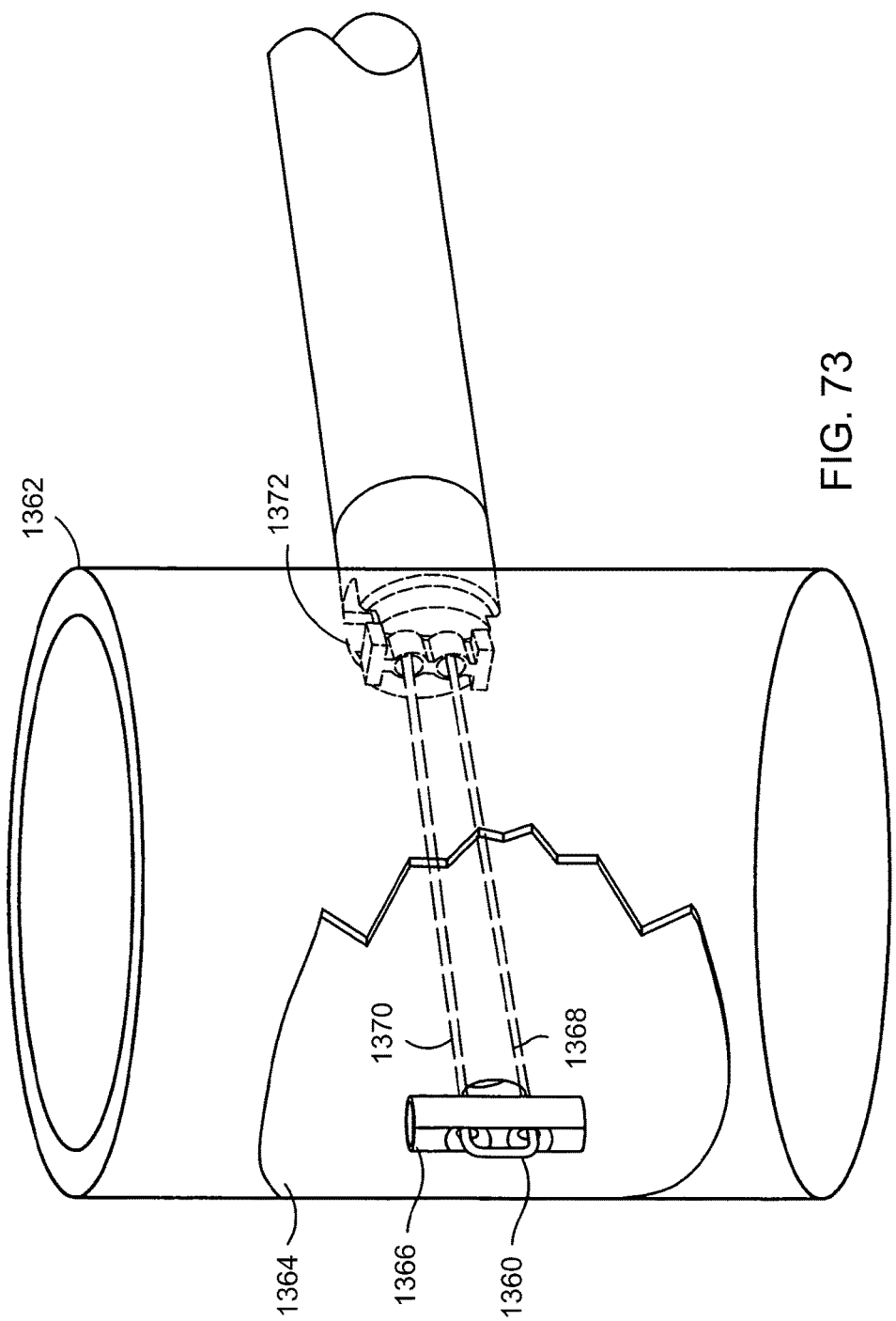
FIG. 73 depicts a sectional view of the medical device of FIG. 70 in use to secure a bone fracture.
Figure 74:
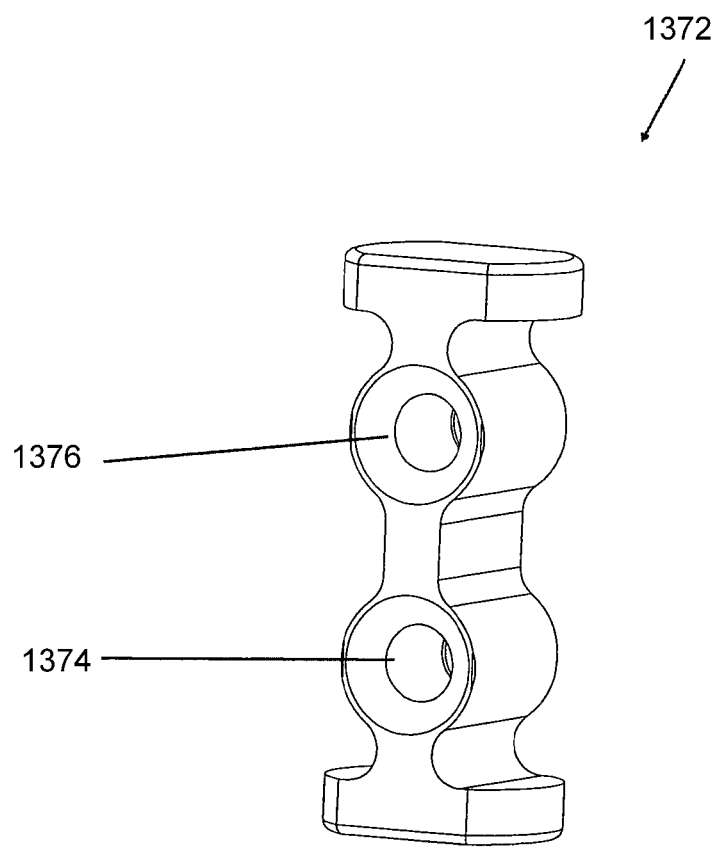
FIG. 74 depicts an exemplary fastener for use with the medical device of FIG. 70.

Referring to FIGS. 73 and 74, in a method of use suture 1360 is inserted through the bone 1362 and fracture 1364, where the suture 1360 is threaded through a fastener 1366 on a first side (fracture side) of the bone 1362. The suture 1360 is reinserted through the fracture 1364 and bone 1362, such that first and second ends 1368 and 1370 of the suture 1360 extend from the bone 1362. The first and second ends of the suture 1368 and 1370 are threaded through a fastener 1372, where the first end of the suture 1368 is threaded through a first aperture 1374 in the fastener 1372 and the second end of the suture 1370 is threaded through a second aperture 1376 in the fastener 1372.

Referring also to FIG. 69, the ends of the suture 1368 and 1370 are inserted through the medical device 1320 along the central longitudinal axis A, through the collett 1322, collett holder 1208, and the cable tensioner 1216, positioning the fastener 1372 in the fastener aperture 1334 and extending the ends of the suture 1368 and 1370 through the cable aperture 1224. To tension the suture 1360, the cable tension lever 1230 is actuated from the first lever position L1 to the second lever position L2, sliding the cable tensioner 1216 along the collett holder 1208 from the first tensioner position T1, into the handle portion 1202 against the tension bias member 1238, to the second tensioner position T2. The suture ends 1368 and 1370 are positioned through the radial groove 1226 and wrapped about the circumferential groove 1228 on the end portion 1222 of the cable tensioner 1216, securing the suture 1360 to the cable tensioner 1216. The cable tension lever 1230 is released, such that tension bias member 1238 biases the cable tensioner 1216 from the second tensioner position T2 towards the first tensioner position T1. The movement of the cable tensioner 1216 towards the first tensioner position T1 applies tension to the suture 1360, compressing the fastener 1372 against the bone 1362. The applied tension can be selected by actuating the cable tension lever 1230 to the desired tension marking 1240.

The trigger 1264 is actuation from the first trigger position TR1 to the second trigger position TR2. The actuation of the trigger 1264 slides the outer tube 1260 along the collett holder 1208 from the first tube position P1 to the second tube position P2, moving collett closer 1340 about the force application end portions 1330 and 1332 of the first and second collett arms 1324 and 1326. The inner tapered surfaces 1280 of the collett closer 1340 apply compressive forces to the first and second force application end portions 1330 and 1332, compressing compressive members 1336 of the first and second force application end portions 1330 and 1332 into the first and second fastener apertures 1374 and 1376. The compressive forces crimp the first and second fastener apertures 1374 and 1376 about the suture ends 1368 and 1370, securing the fastener 1372 to the suture ends 1368 and 1370.

Simultaneously, the actuation of the trigger 1264 results in the top portion 1290 of the trigger 1264 engaging the cut off cam ring 1288, sliding the cut off cam ring 1288 and cut off cam 1284 along the collett holder 1208. The second end portion 1200 of the cut off cam 1283 engages the angular surface 1298 of the cutting head 1294, forcing the cutting edge 1296 into the suture ends 1268 and 1270, cutting the suture ends 1368 and 1370.

Figure 75:
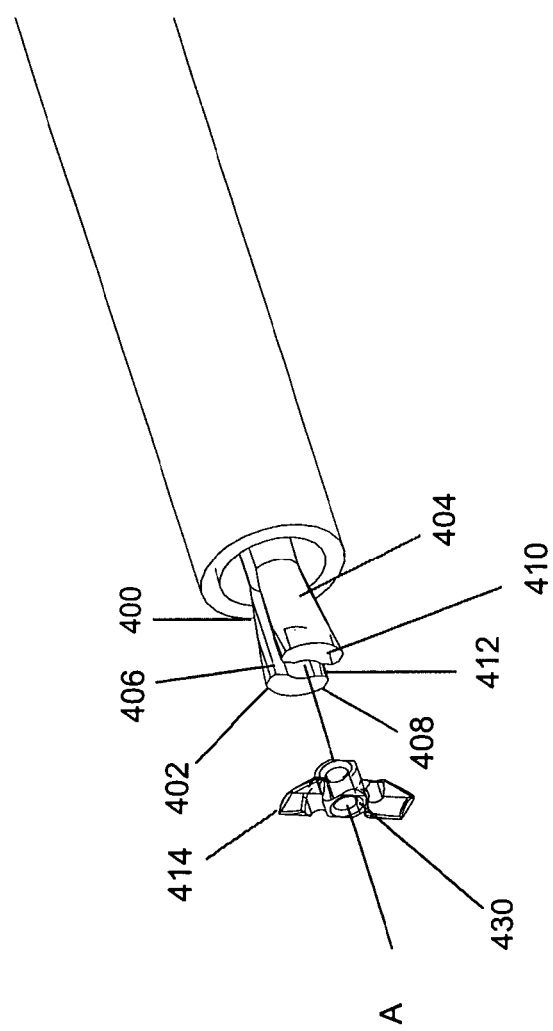
FIG. 75 depicts an alternative sectional view of the medical device of FIG. 70 in use to secure a bone fracture.
Figure 76:
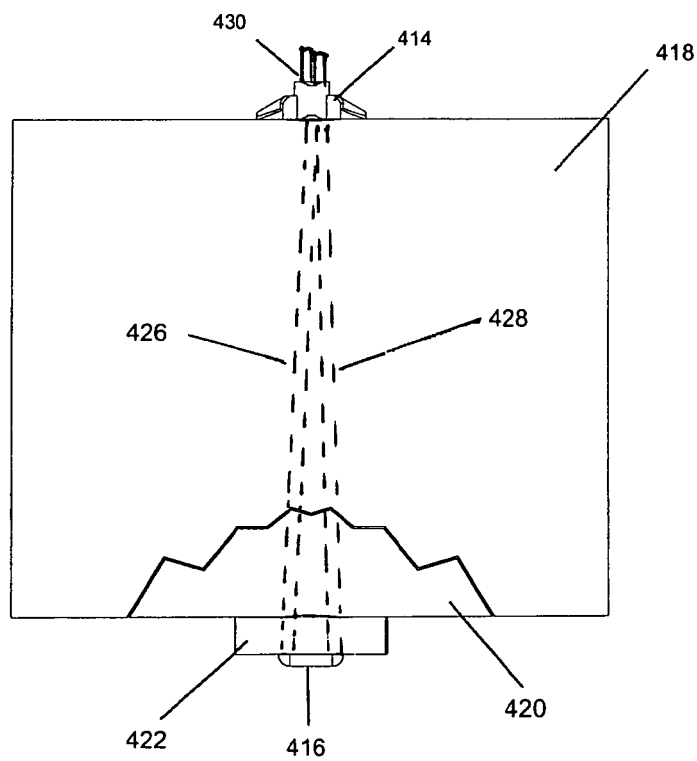
FIG. 76 depicts an alternative fastener for use with the medical device of FIG. 75.

Referring to FIG. 75, similar to FIGS. 61 and 63, a collett 400 is affixed to a second end portion 1244 of the collett holder 1208, opposite the cable tensioner 1216. The collett 400 defines a collett passage longitudinally aligned with the longitudinal passage of the collett holder 1208 along the central longitudinal axis A. An end portion of the collett 400 is bisected, forming first and second collett arms 402 and 404. A gap portion 406 is provided between the first and second collett arms 402 and 404. Each of the first and second collett arms 402 and 404 includes force application end portions 408 and 410. The force application end portions 408 and 410 combine to form a bushing aperture 412 configured to received the bushing therein 414. The collett 400 is made of a semi-rigid material, such that the first and second collett arms 402 and 404 can be moved from an open to a closed position, closing the gap 406 between the force application end portions 408 and 410.

Referring also to FIG. 75, in a method of use, suture 416 is inserted through the bone 418 and fracture 420, where the suture 416 is threaded through a fastener 422 on a first side (fracture side) of the bone 424. The suture 416 is reinserted through the fracture 420 and bone 418, such that first and second ends 426 and 428 of the suture 416 extend from the bone 418. The first and second ends of the suture 426 and 428 are threaded through a fastener 414, where the first and second ends 426 and 428 of the suture 416 is threaded through an aperture 430 in the fastener 414.

Referring also to FIGS. 69 and 72, the ends of the suture 426 and 428 are inserted through the medical device 1320 along the central longitudinal axis A, through the collett 400, collett holder 1208, and the cable tensioner 1216, positioning the fastener 414 in the fastener aperture 412 and extending the ends of the suture 426 and 428 through the cable aperture 1224. To tension the suture 416, the cable tension lever 1230 is actuated from the first lever position L1 to the second lever position L2, sliding the cable tensioner 1216 along the collett holder 1208 from the first tensioner position T1, into the handle portion 1202 against the tension bias member 1238, to the second tensioner position T2. The suture ends 426 and 428 are positioned through the radial groove 1226 and wrapped about the circumferential groove 1228 on the end portion 1222 of the cable tensioner 1216, securing the suture 1360 to the cable tensioner 1216. The cable tension lever 1230 is released, such that tension bias member 1238 biases the cable tensioner 1216 from the second tensioner position T2 towards the first tensioner position T1. The movement of the cable tensioner 1216 towards the first tensioner position T1 applies tension to the suture 416, compressing the fastener 414 against the bone 418. The applied tension can be selected by actuating the cable tension lever 1230 to the desired tension marking 1240.

The trigger 1264 is actuated from the first trigger position TR1 to the second trigger position TR2. The actuation of the trigger 1264 slides the outer tube 1260 along the collett holder 1208 from the first tube position P1 to the second tube position P2, moving collett closer 1340 about the force application end portions 408 and 410 of the first and second collett arms 402 and 404. The inner tapered surfaces 1280 of the collett closer 1340 apply compressive forces to the first and second force application end portions 408 and 410. The compressive forces crimp the aperture 430 about the suture ends 426 and 428, securing the fastener 414 to the suture ends 426 and 428.

Figure 79:
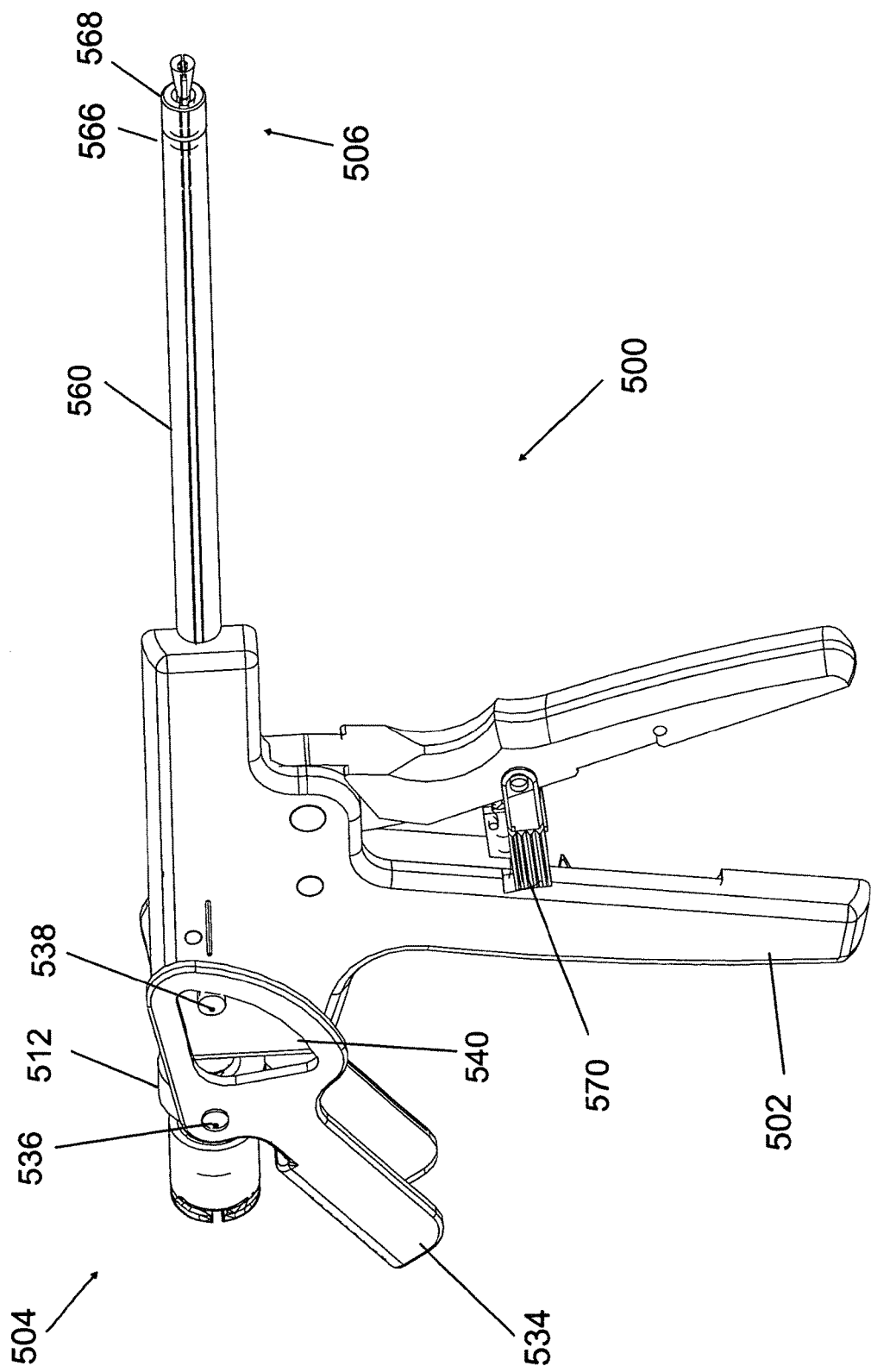
FIG. 79 depicts a front isometric view of the medical device of the present invention.

Referring to FIG. 79, a medical device 500 is provided for securing the bushing to the cable. The medical device 500 includes a handle portion 502 having a tensioning mechanism 504, tensioning the cable and applying a force to the bushing, and a crimping mechanism 506 for securing the bushing to the cable.

Figure 80:
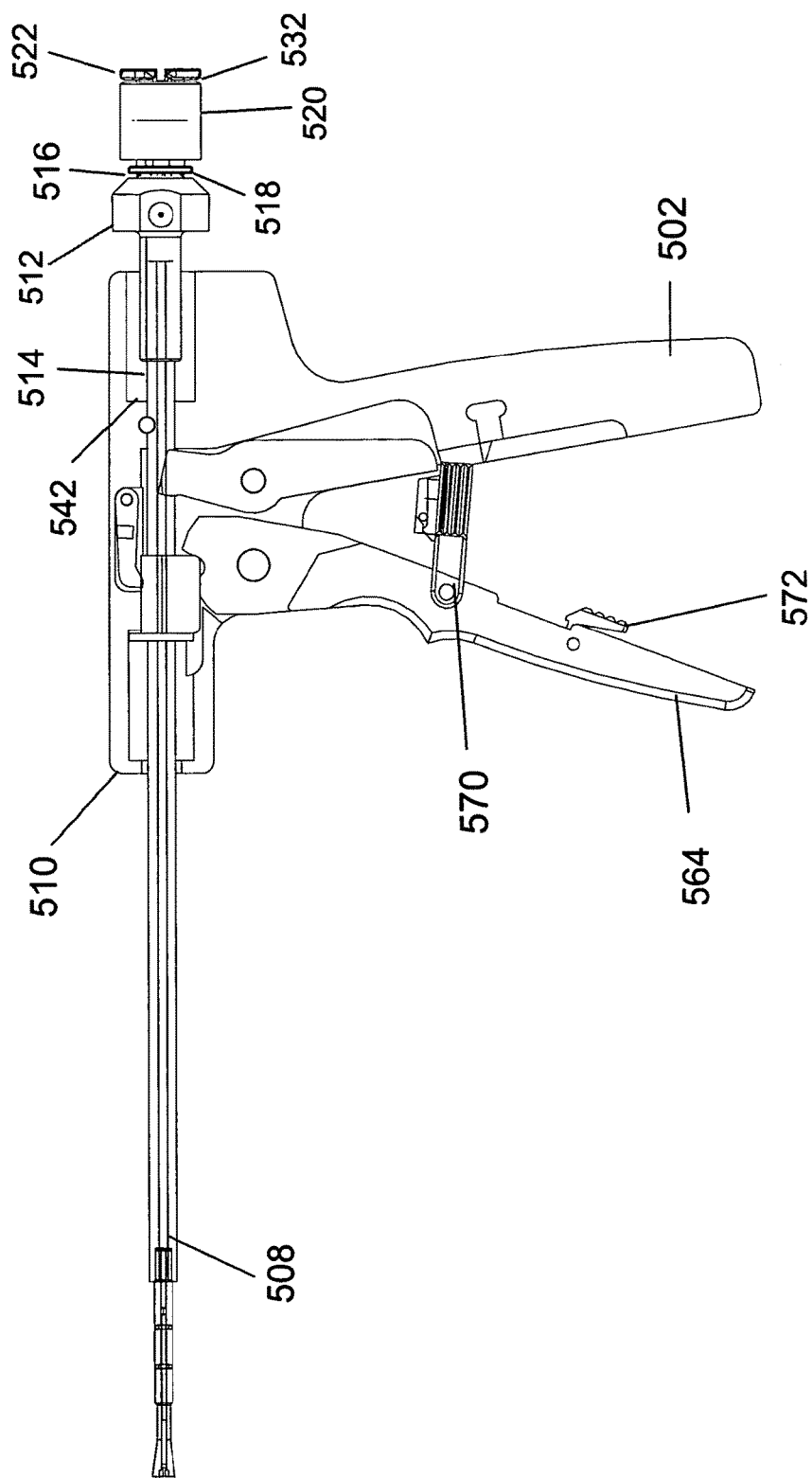
FIG. 80 depicts a side sectional view showing the tensioning mechanism of the medical device of FIG. 79.
Figure 81:
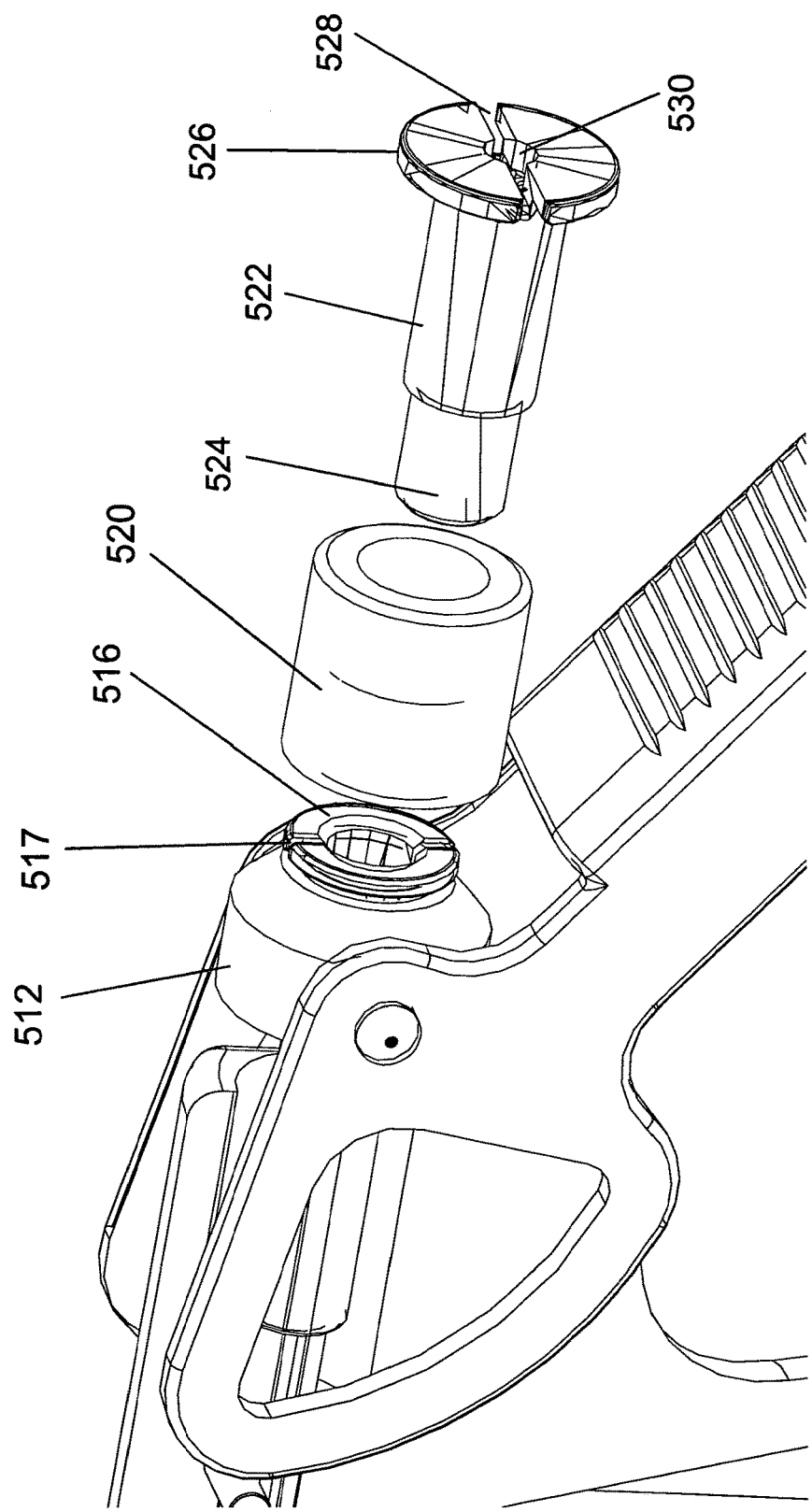
FIG. 81 depicts a rear exploded view showing the tensioning mechanism of the medical device of FIG. 79.

Referring also to FIGS. 80 and 81, the tensioning mechanism 504 includes a collett holder 508 defining a longitudinal passage along a central longitudinal axis A. The collett holder 508 is affixedly positioned through a top portion 510 of the handle portion 502. A cable tensioner 512 is slidably positioned on a first end 514 of the collett holder 508. The cable tensioner 512 defines a cable passage longitudinally aligned with the longitudinal passage of the collett holder 508. An end portion 516 of the cable tensioner 512 includes a cable aperture for threading the cable there through. A radial groove and circumferential groove 518 are provided on the end portion 516 of the cable tensioner 512, such that the cable can be wrapped about the circumferential groove 518 of the cable tensioner 512, thereby preventing relative movement between the cable and the cable tensioner 512.

In an exemplary embodiment, the cable tensioner 512 can include a retention bushing 520 and a tension insert 522. The tension insert 522 defines a cable passage longitudinally aligned with the longitudinal passage of the cable tensioner 512. The retention bushing 520 is positioned about a portion of the tension insert 522, where an end portion 524 is threaded into the end portion 516 of the cable tensioner 512. An opposite end portion 526 of the tension insert 522 includes a cable aperture 528 for threading the cable there through. A radial groove 530 is provided on the end portion 526 of the cable tensioner 512 and the retention bushing 520 and the tension insert 522 combine to form a circumferential groove 532, such that the cable can be wrapped about the circumferential groove 532, thereby preventing relative movement between the cable and the cable tensioner 512.

A cable tension lever 534 is pivotally connected to the cable tensioner 512 with a lever pin 536. The cable tension lever 534 is adjustably positioned on the handle portion 502 with body pins 538, wherein a body pin 538 is mirrorly positioned on opposite sides of the handle portion 502. The body pins 538 are engaged in the cable tension lever 536 arcuate lever slots 540, such that cable tension lever 534 and cable tensioner 512 are movably connected to the handle portion 502.

In use, as the cable tension lever 534 is pivoted about the cable tensioner 512 from a first lever position L1 to a second lever position L2, the body pins 538 traverse the arcuate lever slots 540, resulting in a translation of the cable tensioner 512 along the first end 514 of the collett holder 508 from a first tensioner position T1 to a second tensioner position T2. A tension bias member 542 is interposed between the cable tensioner 512 and the handle portion 502, biasing the cable tensioner 512 into the first tensioner position T1.

Figure 82:
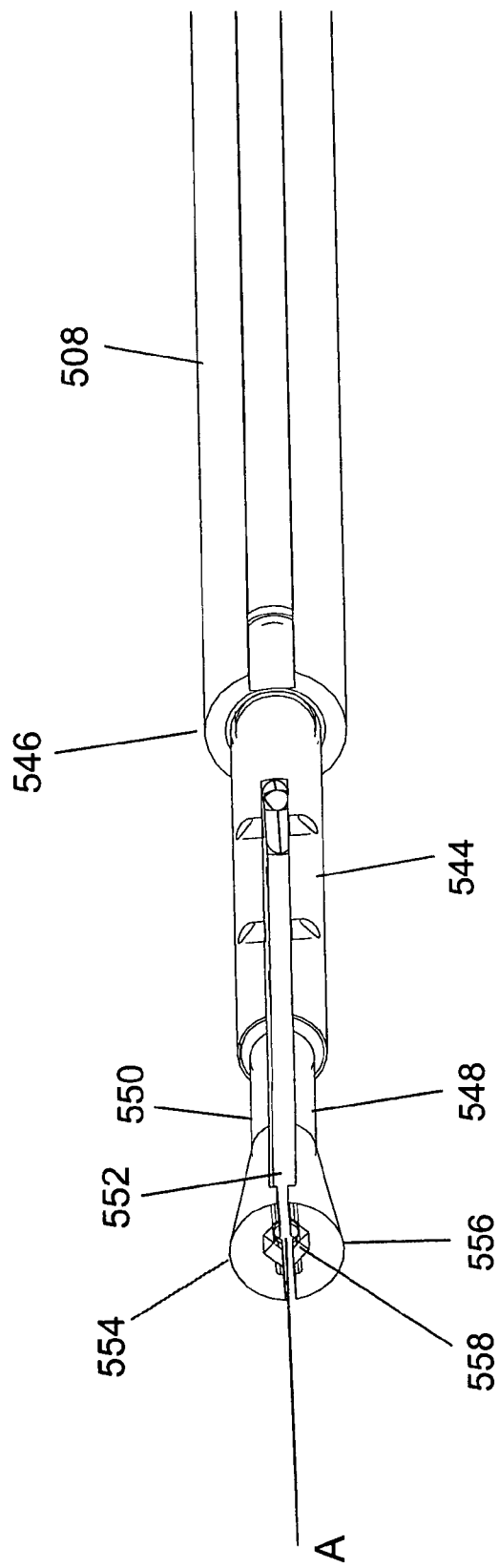
FIG. 82 depicts an isometric view of the crimping mechanism collett of the medical device of FIG. 79.

Referring to FIGS. 80 and 82, a collett 544 is affixed to a second end portion 546 of the collett holder 508, opposite the cable tensioner 512. The collett 544 defines a collett passage longitudinally aligned with the longitudinal passage of the collett holder 508 along the central longitudinal axis A. An end portion of the collett 544 is bisected, forming first and second collett arms 548 and 550. A gap portion 552 is provided between the first and second collett arms 548 and 550. Each of the first and second collett arms 548 and 550 includes force application end portions 554 and 556. The force application end portions 554 and 556 combine to form a bushing aperture 558 configured to received the bushing therein. The collett 544 is made of a semi-rigid material, such that the first and second collett arms 548 and 550 can be moved from an open to a closed position, closing the gap 552 between the force application end portions 554 and 556.

In use, the tensioning mechanism 504 is used to tension the cable. The cable can include single or multiple filaments. The cable is inserted through the medical device 500 along the central longitudinal axis A, through the collett 544, collett holder 508, and the cable tensioner 512, positioning the bushing in the bushing aperture 558 and extending the cable through the cable aperture 530. To tension the cable, the cable tension lever 354 is actuated from the first lever position L1 to the second lever position L2, sliding the cable tensioner 512 along the collett holder 508 from the first tensioner position T1, into the handle portion 502 against the tension bias member 542, to the second tensioner position T2. The cable is positioned through the radial groove 528 and wrapped about the circumferential groove 532 on the between the retention bushing 520 and the tension insert 522, securing the cable to the cable tensioner 512. The cable tension lever 534 is released, such that tension bias member 542 biases the cable tensioner 512 from the second tensioner position T2 towards the first tensioner position T1. The movement of the cable tensioner 512 towards the first tensioner position T1 applies a tension to the cable, forcing the bushing into the second fastener. The applied tension can be selected by actuating the cable tension lever 534 to the desired tension.

Figure 83:
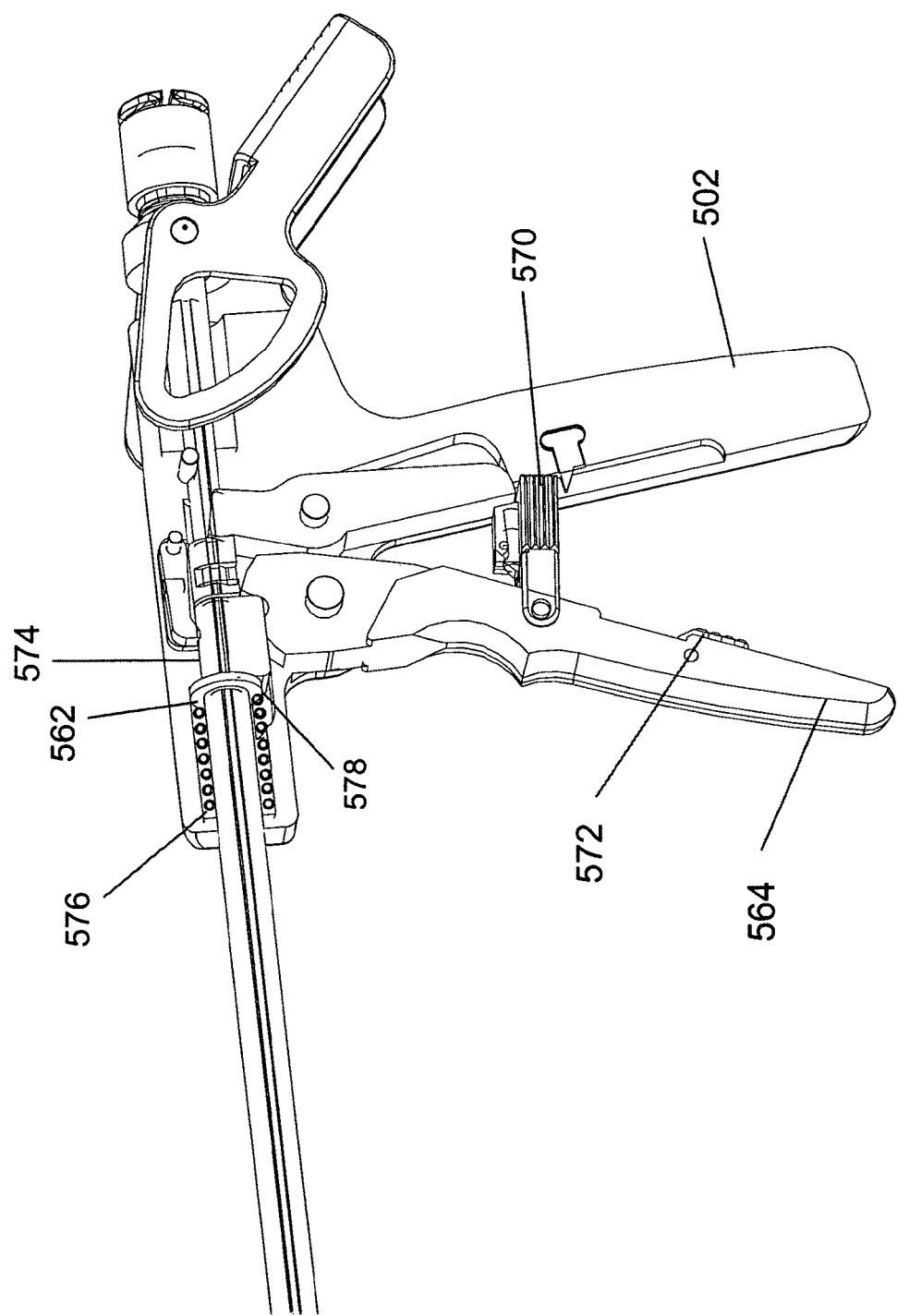
FIG. 83 depicts a partial isometric view showing the handle portion of the crimping mechanism of the medical device of FIG. 79.

Referring to FIGS. 79 and 83, the crimping mechanism 506 includes an outer tube 560 slidingly positioned over the collett holder 508. The outer tube 560 includes a first end 562 operably connected to a trigger 564 and a second end 566 connected to a collett closer 568. The trigger 1264 is pivotally mounted in the handle portion 502, such that the trigger 564 can be actuated from a first trigger position TR1 to a second trigger position TR2. A locking mechanism 570 prevents the trigger 564 from being actuated. The locking mechanism 570 is disengaged by rotating it away from the handle, where the locking mechanism is secured to the trigger with the locking pawl 572. (See also FIG. 80).

The operable connection between the first end of the outer tube 562 and the trigger 564 includes an outer tube ferrule 574 slidably positioned about the collett holder 408 and affixed to the first end of the outer tube 562. A tube bias member 576 is interposed between the handle portion 502 and the outer tube ferrule 574, such that the tube bias member 576 biases the outer tube ferrule 574 and the outer tube 560 into a first tube position P1. A tube washer 578 can be provided between the tube ferrule 574 and the bias member 576.

An actuation of the trigger 564 from a first trigger position TR1 to a second trigger position TR2 translates the outer tube ferrule 574 along the collett holder 1208 from the first tube position P1 to a second tube position P2. In the second tube position P2 a tube pawl 580 engages the outer tube ferrule 574, hold the outer tube ferrule in the second tub position P2.

Figure 85:
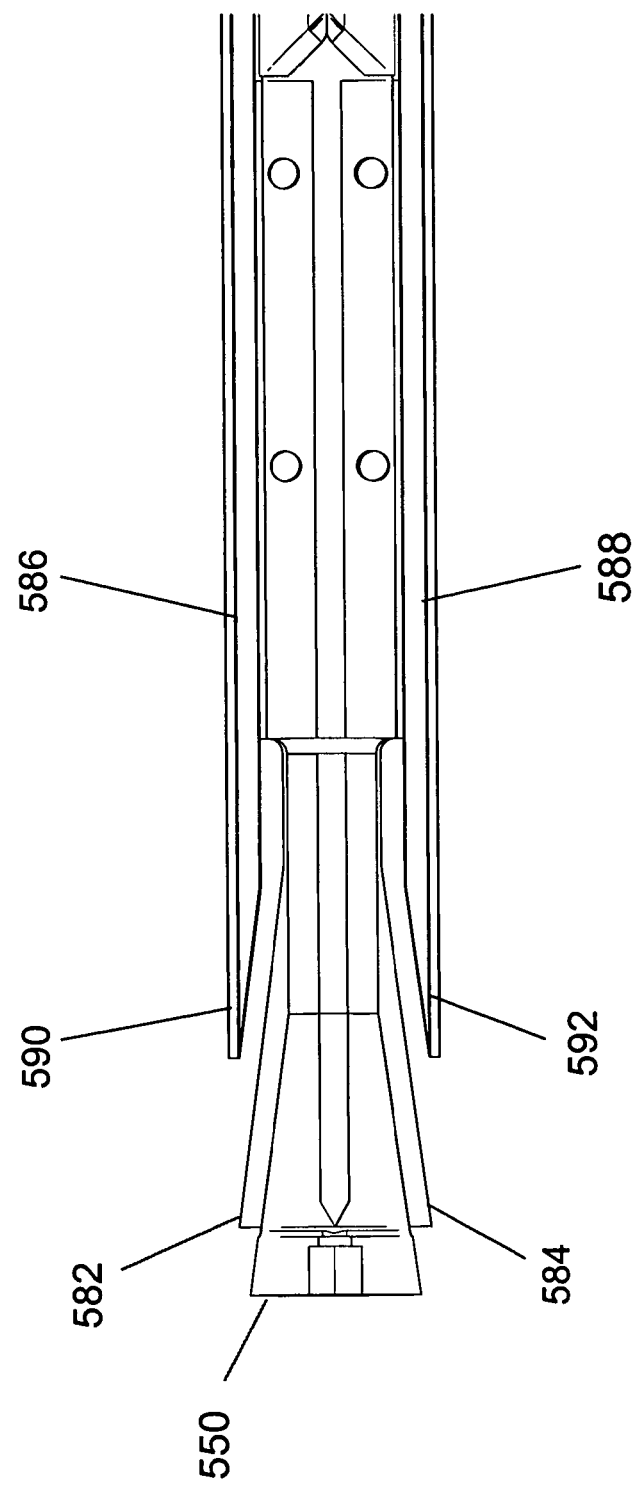
FIG. 85 depicts an isometric view of the cutting mechanism in the collett of the medical device of FIG. 79.

Referring to FIGS. 79 and 85, the collett closer 568 is positioned on the outer tube 560 proximal to the force application end portions 554 and 556 of the first and second collett arms 548 and 550. As the outer tube 560 is moved from the first tube position P1 to the second tube position P2, the collett closer 568 is moved over the force application end portions 554 and 556. The collett closer 568 includes inner tapered surfaces 582, such that the inner tapered surfaces 580 apply compressive forces to the force application end portions 554 and 556 as the collett closer 568 is moved over the force application end portions 554 and 556, closing the gap 552 there between.

In use, the trigger 564 is actuated from the first trigger position TR1 to the second trigger position TR2. The actuation of the trigger 564 slides the outer tube 560 along the collett holder 508 from the first tube position P1 to the second tube position P2, moving collett closer 568 about the force application end portions 554 and 556 of the first and second collett arms 548 and 550. The inner tapered surfaces 580 of the collett closer 568 apply compressive forces to the first and second force application end portions 554 and 556, closing the gap 552 there between.

Figure 84:
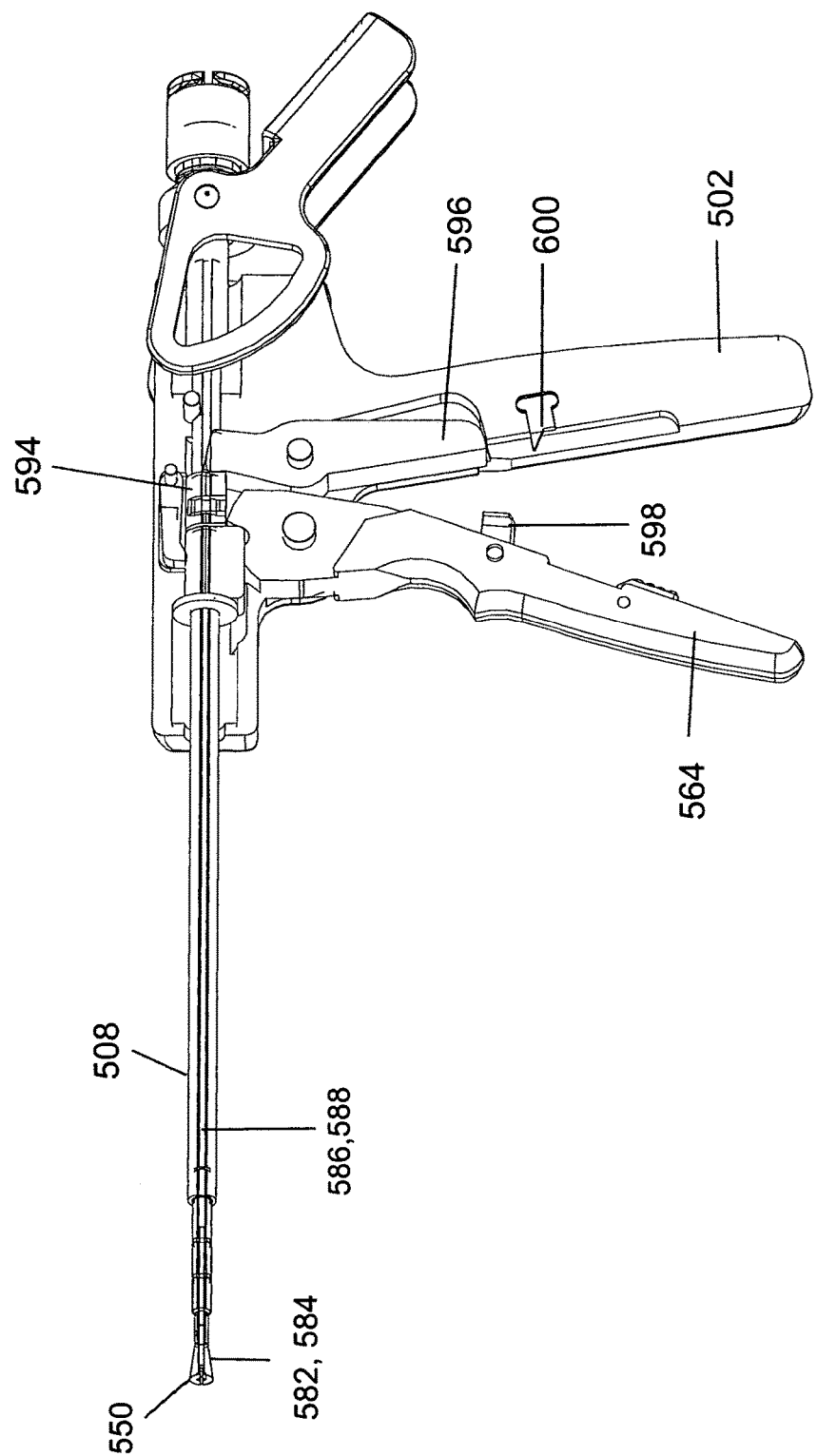
FIG. 84 depicts a partial isometric view showing the cutting mechanism of the medical device of FIG. 79.
Figure 86:
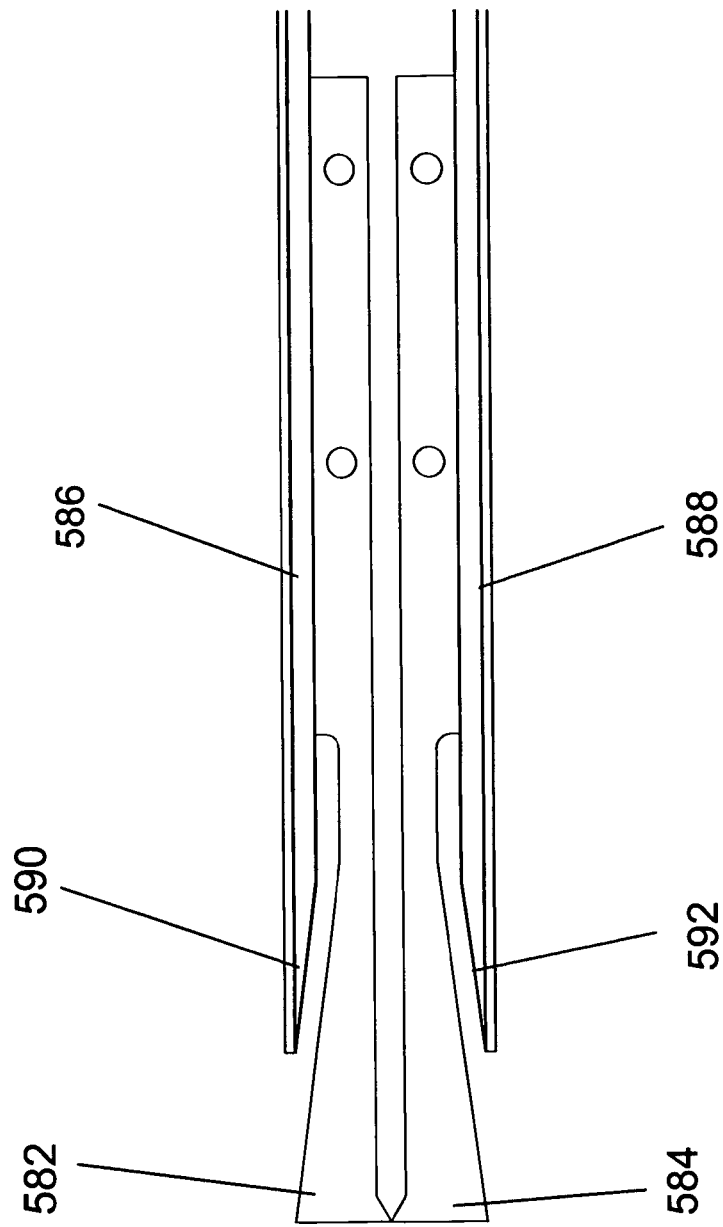
FIG. 86 depicts the cutting wedge of the medical device of FIG. 79.

Referring to FIGS. 84-86, the crimping mechanism 506 can further include a cutting mechanism. The cutting mechanism includes a pair of cut off cams 582 and 584 positioned in the collett gap 552. A pair of wedges 586 and 588 are slidingly positioned along and on opposite sides of the collett 550 and the collett holder 508. Each of the wedges 586 and 588 include tapered ends 590 and 592 positioned proximal to the cut off arms, such that when the wedges are moved from a first wedge position W1 to a second wedge position W2, the tapered ends 590 and 592 compress the cut off cams 582 and 584 together, cutting the cable.

The handle 502 further includes a wedge pusher 594 slidingly positioned about the collett holder 508, adjacent to second ends 594 and 596 of wedges 586 and 588. The wedge pusher 594 is slidable from a first position to a second position, such that the wedges 586 and 588 are moved from the first wedge position W1 to the second wedge position W2. A rocker 596 is pivotally connected to the handle 502, such that an actuation of the rocker 596 from a first rocker position R1 to a second rocker position R2, slides the wedge pusher 594 from the first position to the second position, moving wedges 586 and 588 from the first wedge position W1 to the second wedge position W2

Figure 87:
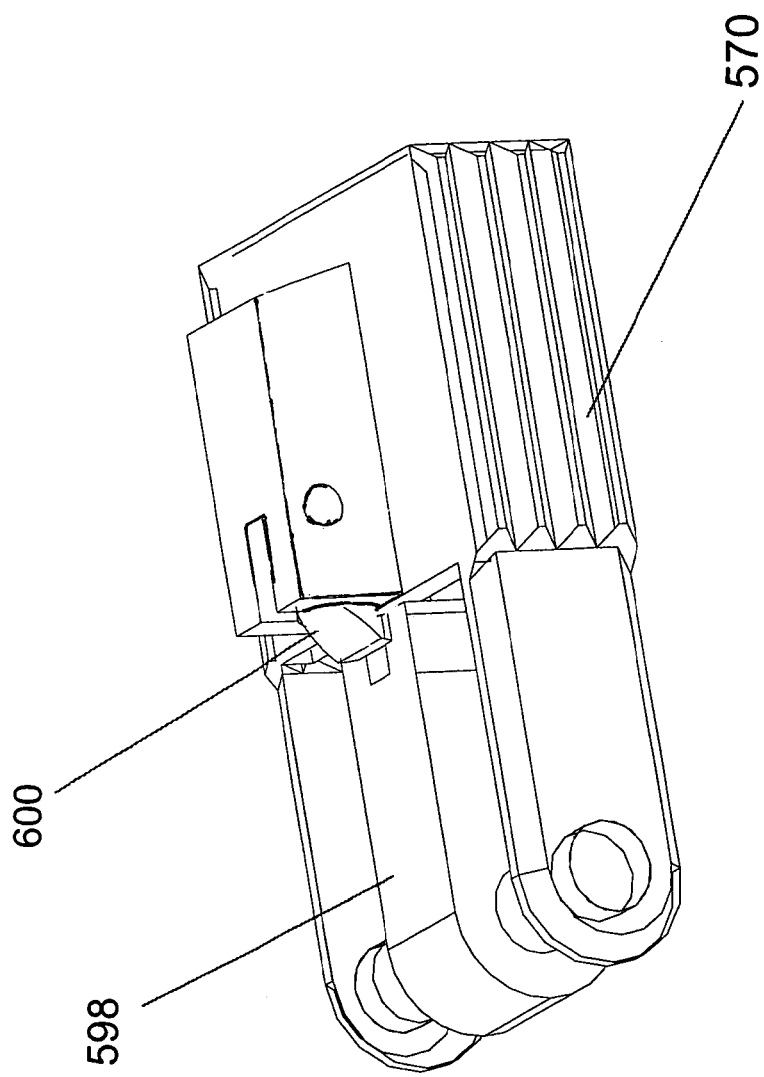
FIG. 87 depicts a safety lock of the medical device of FIG. 79.

Referring to FIGS. 84 and 87, the locking mechanism 570 includes a rocker kicker 598 pivotally affixed therein. The rocker kicker 598 is biasedly connected to the locking mechanism 570, being held in a closed position by a pin 600. When the trigger 564 is actuated from the first trigger position TR1 to the second trigger position TR2, the release 602 engages the pin 600, releasing the rocker kicker 590.

The trigger 564 is released, allowing the trigger 564 to move from the second trigger position TR2 to the first trigger position TR1. To actuate the cutting mechanism, the trigger is again moved from the first trigger position TR1 to the second trigger position TR2, such that the rocker kicker 598 engages the rocker 596, pivoting the rocker 596 from the first rocker position R1 to the second rocker position. The rocker 596 slides the wedge pusher 594 from the first position to the second position, moving wedges 586 and 588 from the first wedge position W1 to the second wedge position W2, such that, the tapered ends 590 and 592 compress the cut off cams 582 and 584 together, cutting the cable. The trigger 564 can then be released, releasing the crimped fastener.

It is also contemplated that the system and medical device of the present invention may be disposable or may be sterilized after use and reused.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia *lata*, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include biodegradable plates, porcine or bovine patches, metallic fasteners, compliant bearings for one or more compartments of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled Apparatus and Method for Use in Positioning a Suture Anchor, discloses devices for controlling the placement depth of a fastener. Also, U.S. Patent Application Publication No. 2003/0181800 discloses methods of securing body tissue with a robotic mechanism. The above-mentioned patent and application are hereby incorporated by reference. Another introducer or cannula which may be used with the present invention is the VersaStepe System by Tyco® Healthcare.

The present invention may also be utilized with minimally invasive surgery techniques disclosed in U.S. Patent Application Publication No. 2003/0181800 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

In addition, intramedullary fracture fixation and comminuted fracture fixation may be achieved with the devices and methods of the present invention. For example, a plate or rod may be positioned within or against the fractured bone. A fastener may be driven through or about the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention. All references cited herein are expressly incorporated by reference in their entirety.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A method for stabilizing a bone in a body of a subject, comprising:
   introducing, into the body of the subject, a curved segment of an elongate, fastener placement rod, such that a leading end of the curved segment at least partially circumnavigates the bone;
   providing, at the leading end of the curved segment of the fastener placement rod, a fastener at the bone;
   securing the fastener with respect to the bone, wherein the fastener is secured with respect to the bone utilizing at least one flexible line;
   passing the flexible line from the fastener through at least a portion of the bone to a separate securing point within the body, wherein the passing step is performed utilizing a gripper at a leading end of an elongate gripper rod which pulls the flexible line from the fastener and at least through the portion of the bone to the separate securing point within the body, wherein the elongate fastener placement rod and elongate gripper rod extend from a hand-held guidance and positioning device; and
   forming a hole through the portion of the bone prior to the pulling step, wherein the hole forming step is performed by an elongate drill rod extending from the hand-held guidance and positioning device,
wherein:
   the bone is a first bone,
   the flexible line is provided attached to the fastener at the first bone, and
   the method includes a step of passing the flexible line from the fastener and at least through the portion of the first bone, through at least a portion of a second bone to a separate securing point within the body, thereby stabilizing at least the first and second bones with respect to each other.

2. The method of claim 1, further comprising securing the at least one flexible line at the separate securing point by a second fastener.

3. The method of claim 2, wherein the step of securing the at least one flexible line at the separate securing point by the second fastener comprises crimping the second fastener to the flexible line.

4. The method of claim 3, wherein the crimping step comprises introducing a crimping mechanism extending from an elongate rod of a crimping tool through an incision in the body and adjacent to the second fastener.

5. The method of claim 1, wherein the at least one flexible line comprises a suture.

6. The method of claim 1, wherein the at least one flexible line comprises a cable.

7. The method of claim 1, wherein the elongate gripper rod and elongate drill rod are guided by a guide tube extending from the hand-held guidance and positioning device.

8. The method of claim 1, wherein the elongate gripper rod extends from the hand-held guidance and positioning device along an axis that runs adjacent to or through the leading end of the curved segment of the fastener placement rod.

9. The method of claim 1, wherein the first bone is a first vertebra and the second bone is a second vertebra.

10. The method of claim 1, wherein the first bone is a first spinous process and the second bone is a second spinous process.

11. The method of claim 1, wherein the method includes a step of passing the flexible line from the fastener and at least through the portion of the first bone, through at least a portion of a second bone, and through at least a portion of a third bone to the separate securing point within the body, thereby stabilizing at least the first, second and third bones with respect to each other.

12. The method of claim 1, wherein the passing step further comprises passing the flexible line through an implant.

13. The method of claim 1, wherein the first bone is a first side of a cervical spine and the second bone is a second side of the cervical spine.

14. The method of claim 1, wherein the method further comprises passing the flexible line through a tubular implant positioned between the first and second bones.

15. The method of claim 1, further comprising a step of tensioning at least a portion of the flexible line extending between the fastener and the separate securing point.

16. The method of claim 1, wherein the flexible line extends to or through a stabilization rod or plate.

17. A method for stabilizing a bone in a body of a subject, comprising:
connecting a flexible line and a fastener;
introducing a curved segment of an elongate, fastener placement rod into the body of the subject, such that a leading end of the curved segment at least partially circumnavigates the bone;
providing, at the leading end of the curved segment of the fastener placement rod, the fastener and the flexible line at a fastener placement point that is at the bone, the providing step including passing the fastener and attached flexible line through the curved segment of the elongate fastener placement rod to the leading end;
passing the attached flexible line from approximate the fastener placement point through at least a portion of the bone to a securing point, wherein the passing step is performed utilizing a gripper at a leading end of an elongate gripper rod to pull the attached flexible line from approximate the fastener placement point through at least the portion of the bone to the securing point, wherein the elongate fastener placement rod and the elongate gripper rod extend from a hand-held guidance and positioning device;
forming a hole through the portion of the bone prior to the passing step, wherein the hole forming step is performed by an elongate drill rod extending from the hand-held guidance and positioning device;
tensioning the flexible line between the fastener placement point and the securing point; and
securing the flexible line at the securing point.

18. The method of claim 17 wherein the elongate gripper rod and the elongate drill rod are guided by a guide tube extending from the hand-held guidance and positioning device.

* * * * *